United States Patent
Frederick et al.

(10) Patent No.: US 10,383,951 B2
(45) Date of Patent: *Aug. 20, 2019

(54) METHODS OF USING OX40 LIGAND ENCODING POLYNUCLEOTIDES

(71) Applicant: ModernaTX, Inc., Cambridge, MA (US)

(72) Inventors: Joshua P. Frederick, Charlestown, MA (US); Ailin Bai, Newton, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/225,989

(22) Filed: Dec. 19, 2018

(65) Prior Publication Data
US 2019/0114090 A1    Apr. 18, 2019

Related U.S. Application Data

(63) Continuation of application No. 16/207,575, filed on Dec. 3, 2018, which is a continuation of application No. 15/996,140, filed on Jun. 1, 2018, now Pat. No. 10,143,723, which is a continuation of application No. PCT/US2016/068552, filed on Dec. 23, 2016.

(60) Provisional application No. 62/290,413, filed on Feb. 2, 2016, provisional application No. 62/387,168, filed on Dec. 23, 2015.

(51) Int. Cl.
| | | |
|---|---|---|
| *A61K 48/00* | (2006.01) | |
| *A61K 38/17* | (2006.01) | |
| *A61P 35/00* | (2006.01) | |
| *A61K 45/06* | (2006.01) | |
| *C07K 14/705* | (2006.01) | |

(52) U.S. Cl.
CPC ............ *A61K 48/00* (2013.01); *A61K 38/177* (2013.01); *A61K 45/06* (2013.01); *A61P 35/00* (2018.01); *C07K 14/70575* (2013.01)

(58) Field of Classification Search
None
See application file for complete search history.

(56) References Cited

U.S. PATENT DOCUMENTS

| | | | |
|---|---|---|---|
| 10,143,723 B2 | 12/2018 | Frederick et al. | |
| 10,172,808 B2* | 1/2019 | Frederick | A61K 48/00 |
| 2011/0244026 A1 | 10/2011 | Guild et al. | |
| 2012/0065252 A1 | 3/2012 | Schrum et al. | |
| 2014/0200261 A1 | 7/2014 | Hoge et al. | |
| 2016/0331844 A1* | 11/2016 | Fotin-Mleczek | A61K 39/39558 |
| 2018/0207295 A1 | 7/2018 | Fotin-Mleczek et al. | |
| 2018/0318385 A1 | 11/2018 | Frederick et al. | |

FOREIGN PATENT DOCUMENTS

| | | |
|---|---|---|
| EP | 2700708 A2 | 2/2014 |
| WO | 2015/007871 A2 | 1/2015 |
| WO | 2015048744 A2 | 4/2015 |
| WO | 2016170176 A1 | 10/2016 |
| WO | 2017112943 A1 | 6/2017 |
| WO | 2017191274 A2 | 11/2017 |
| WO | 2017201325 A1 | 11/2017 |
| WO | 2017201352 A1 | 11/2017 |

OTHER PUBLICATIONS

Andarini, S. et al., "Adenovirus Vector-Mediated in Vivo Gene Transfer of OX40 Ligand to Tumor Cells Enhances Antitumor Immunity of Tumor-Bearing Hosts", Cancer Research, vol. 64(9): 3281-3287(2004).
Cawood R. et al., "Use of tissue-specific microRNA to control pathology of wild-type adenovirus without attenuation of its ability to kill cancer cells," PLOS Pathogens, vol. 5 (5): e1000440, (2005).
Dannull, J. et al., "Enhancing the immunostimulatory function of dendritic cells by transfection with mRNA encoding OX40 ligand," Blood, vol. 105 (8):3206-3213 (2005).
Database Geneseq [Online] Mar. 12, 2015 (Mar. 12, 2015),"Human TNFSF4 gene, SEQ ID 11.", XP002767824, retrieved from EBI accession No. GSN:BBT93694 Database accession No. BBT93694 Sequence NCBI (2014, Reference Sequence: NM_003326.4).
International Preliminary Report on Patentability, PCT/US2016/068552, dated Jun. 26, 2018, 9 pages.
International Search Report and Written Opinion, PCT/US2016/068552, dated Mar. 21, 2017, 14 pages.
Kormann, M.S. et al., "Expression of therapeutic proteins after delivery of chemically modified mRNA in mice," Nature Biotechnology, vol. 29(2):154-159 (2011).
Kron, M. et al., "miRNA-mediated silencing in hepatocytes can increase adaptive immune responses to adenovirus vector-delivered transgenic antigens," Molecular Therapy, vol. 19(8):1547-1557 (2011).
Lennox, KA, et al., "Chemical modification and design of anti-miRNA oligonucleotides," Gene Therapy, vol. 18 (12):1111-1120 (2011).
Pichard, V. et al., "Specific Micro RNA-Regulated TetR-KRAB Transcriptional Control of Transgene Expression in Viral Vector-Transduced Cells", PLOS One, vol. 7(12):e51952 (2012).
Rotondaro, L. et al., "Efficiency of different viral promoters in directing gene expression in mammalian cells: effect of 3'-untranslated sequences," Gene, vol. 168(2):195-198 (1996).
Sahin, U. et al., "mRNA-based therapeutics—developing a new class of drugs," Nature Reviews Drug Discovery, vol. 13(10):759-780 (2014).

(Continued)

*Primary Examiner* — J. E. Angell
(74) *Attorney, Agent, or Firm* — Nelson Mullins Riley & Scarborough LLP; Amy E. Mandragouras, Esq.; Ariana D. Harris

(57) ABSTRACT

The disclosure relates to compositions and methods for the preparation, manufacture and therapeutic use of polynucleotide molecules comprising an mRNA encoding an OX40L polypeptide. Also provided is a method for activating T cells or increasing the number of NK cells in a subject in need thereof.

22 Claims, 31 Drawing Sheets

Specification includes a Sequence Listing.

(56) References Cited

OTHER PUBLICATIONS

Singh, R. et al., "Nanoengineering artificial lipid envelopes around adenovirus by self-assembly," ACS Nano, vol. 2 (5):1040-1050 (2008).
Smirnov, D.A. et al., "ATM Gene mutations result in both recessive and dominant expression phenotypes of genes and microRNAs", The American Journal of Human Genetics, vol. 83: 243-253 (2008).
Suzuki, T. et al., "miR-122a-Regulated Expression of a Suicide Gene Prevents Hepatotoxicity Without Altering Antitumor Effects in Suicide Gene Therapy," Molecular Therapy, vol. 16(10): 1719-1726 (2008).
Van Der Jeught, K. et al., "Targeting the tumor microenvironment to enhance antitumor immune responses," Oncotarget, vol. 6(3): 1359-1381(2014).
Vinuesa, C. et al., "Logic and Extent of miRNA-Mediated Control of Autoimmune Gene Expression", Int Rev Immunol., vol. 28(3-4):112-138 (2009).
Wang. Y. et al "Systemic delivery of modified mRNA encoding herpes simplex virus 1 thymidine kinase for targeted cancer gene therapy," Molecular Therapy, Nature Publishing Group, GB, vol. 21(2):358-367 (2012).
U.S. Appl. No. 16/207,575, filed Dec. 3, 2018, Joshua P. Frederick.
U.S. Appl. No. 15/996,140, filed Jun. 1, 2018, Joshua P. Frederick.
U.S. Appl. No. 16/207,641, filed Dec. 3, 2018, Joshua P. Frederick.
U.S. Appl. No. 14/041,011, filed Sep. 30, 2013, Stephen G. Hoge.
U.S. Appl. No. 15/996,140, Oct. 3, 2018.
U.S. Appl. No. 15/996,140, Sep. 20, 2018.
U.S. Appl. No. 14/041,011, Jan. 22, 2018.
U.S. Appl. No. 14/041,011, Sep. 16, 2016.
U.S. Appl. No. 14/041,011, Feb. 2, 2016.
U.S. Appl. No. 14/041,011, Apr. 22, 2015.
U.S. Appl. No. 16/207,575, Jan. 8, 2019.

\* cited by examiner

LNP-mediated cell surface expression of mOX40L in B16F10

OX40L

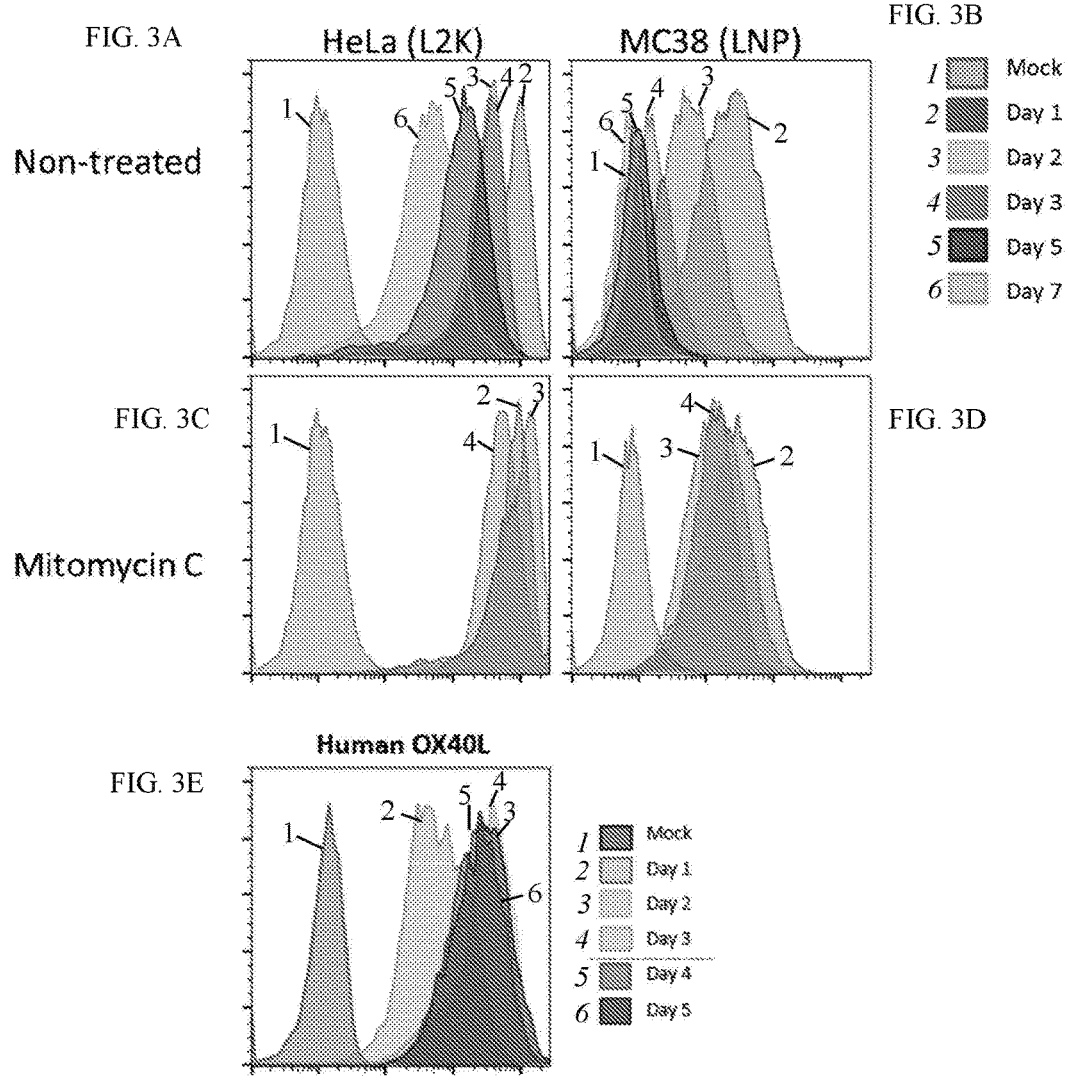

mOX40L or hOX40L expression from modRNA on B16F10 tumor cells or HeLa cells elicits T-cell IL2 response Luciferase flux in tumor and liver:

Absolute protein quantification by ELISA

Detected cell surface expression by flow

OX40L mRNA mediated increase in NK cells in the A20 TME

METHODS OF USING OX40 LIGAND ENCODING POLYNUCLEOTIDES

RELATED APPLICATIONS

This application is a Continuation of U.S. Continuation application Ser. No. 16/207,575 filed on Dec. 3, 2018, which is a continuation of Ser. No. 15/996,140 filed on Jun. 1, 2018, now patented under U.S. Pat. No. 10,143,723, issued on Dec. 4, 2018, which is a Continuation of Application PCT/US2016/068552 filed on Dec. 23, 2016. Application PCT/US2016/068552 claims the benefit of U.S. Provisional Application 62/387,168 filed on Dec. 23, 2015 and U.S. Provisional Application 62/290,413 filed on Feb. 2, 2016. The entire contents of the above-referenced patent applications are incorporated herein by this reference.

REFERENCE TO SEQUENCE LISTING SUBMITTED ELECTRONICALLY

The instant application contains a Sequence Listing which has been submitted in ASCII format via EFS-Web and is hereby incorporated by reference in its entirety. Said ASCII copy, created on Dec. 19, 2018, is named MDN_705PCCN3_Sequence_Listing and is 59611 bytes in size.

BACKGROUND

Cancer is a disease characterized by uncontrolled cell division and growth within the body. In the United States, roughly a third of all women and half of all men will experience cancer in their lifetime. Polypeptides are involved in every aspect of the disease including cancer cell biology (carcinogenesis, cell cycle suppression, DNA repair and angiogenesis), treatment (immunotherapy, hormone manipulation, enzymatic inhibition), and/or diagnosis and determination of cancer type (molecular markers for breast, prostate, colon and cervical cancer for example). With the host of undesired consequences brought about by standard treatments such as chemotherapy and radiotherapy used today, genetic therapy for the manipulation of disease-related peptides and their functions provides a more targeted approach to disease diagnosis, treatment and management. However, gene therapy poses multiple challenges including undesirable immune response and safety concern due to the incorporation of the gene at random locations within the genome.

Various methods of treating cancer are under development. For example, dendritic cell (DC) vaccines have been studied as a possible anti-cancer therapy. However, DC vaccines require multiple steps of isolating DCs from a subject, ex vivo manipulation of DCs to prime the cells for tumor antigen presentation, and subsequent administration of the manipulated DCs back into the subject. Further, it is reported that the overall clinical response rates for DC vaccines remain low and the ability of DC vaccines to induce cancer regression remains low. See, e.g., Kalkinski et al., "Dendritic cell-based therapeutic cancer vaccines: what we have and what we need," *Future Oncol.* 5(3):379-390 (2009).

BRIEF SUMMARY

The present disclosure relates to compositions and methods for activating an immune response in a subject. One aspect of the disclosure provides a method of activating T cells in a subject in need thereof comprising administering to the subject an effective amount of a polynucleotide comprising an mRNA encoding an OX40L polypeptide. In another aspect, the activated T cells reduce or decrease the size of a tumor or inhibit growth of a tumor in the subject.

Another aspect of the disclosure provides a method of increasing the number of Natural Killer (NK) cells in a subject in need thereof comprising administering to the subject an effective amount of a polynucleotide comprising an mRNA encoding an OX40L polypeptide. In another aspect, the increased NK cells reduce or decrease the size of a tumor or inhibit growth of a tumor in the subject.

In some embodiments, the disclosure provides a method for activating T cells and increasing the number of NK cells in a subject in need thereof comprising administering to the subject an effective amount of a polynucleotide comprising an mRNA encoding an OX40L polypeptide.

In another embodiment, administering to the subject an effective amount of a polynucleotide comprising an mRNA encoding an OX40L polypeptide further induces IL-2 release. In another embodiment, administering to the subject an effective amount of a polynucleotide comprising an mRNA encoding an OX40L polypeptide further induces IL-4 release. In another embodiment, administering to the subject an effective amount of a polynucleotide comprising an mRNA encoding an OX40L polypeptide further induces IL-21 release.

In some embodiments, administering to the subject an effective amount of a polynucleotide comprising an mRNA encoding an OX40L polypeptide induces T cell proliferation. In other embodiments, administering to the subject an effective amount of a polynucleotide comprising an mRNA encoding an OX40L polypeptide induces T cell infiltration in the tumor or increases the number of tumor infiltrating T cells. In certain embodiments, administering to the subject an effective amount of a polynucleotide comprising an mRNA encoding an OX40L polypeptide induces a memory T cell response. In some embodiments, the activated T cells comprise CD4$^+$ T cells. In other embodiments the activated T cells comprise CD8$^+$ T cells. In other embodiments, the activated T cells comprise both CD4$^+$ T cell and CD8 T cells. In some embodiments, the number of NK cells is increased at least about two-fold, at least about three-fold, at least about four-fold, at least about five-fold, at least about six-fold, at least about seven-fold, at least about eight-fold, at least about nine-fold, or at least about ten-fold.

In some embodiments of the disclosure, the polynucleotide comprises at least one chemically modified nucleoside as described herein. In one embodiment, the at least one chemically modified nucleoside comprises two or more combinations thereof. In another embodiment, the at least one chemically modified nucleoside is selected from the group consisting of pseudouridine (ψ), N1-methylpseudouridine (m1ψ), 2-thiouridine (s2U), 4'-thiouridine, 5-methylcytosine, 2-thio-1-methyl-1-deaza-pseudouridine, 2-thio-1-methylpseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, and two or more combinations thereof.

In another embodiment of the disclosure, the nucleosides in the mRNA are chemically modified by at least 10%, at least 20%, at least 30%, at least 40%, at least 50%, at least 60%, at least 70%, at least 80%, at least 90%, at least 95%, at least 99%, or 100%. In another aspect, the chemically modified nucleosides in the mRNA are selected from the group consisting of uridine, adenine, cytosine, guanine, and any combination thereof.

In one embodiment, the uridine nucleosides in the mRNA are chemically modified by at least 10%, at least 20%, at least 30%, at least 40%, at least 50%, at least 60%, at least 70%, at least 80%, at least 90%, at least 95%, at least 99%, or 100%. In another embodiment, the adenine nucleosides in the mRNA are chemically modified by at least 10%, at least 20%, at least 30%, at least 40%, at least 50%, at least 60%, at least 70%, at least 80%, at least 90%, at least 95%, at least 99%, or 100%. In another embodiment, the cytosine nucleosides in the mRNA are chemically modified by at least 10%, at least 20%, at least 30%, at least 40%, at least 50%, at least 60%, at least 70%, at least 80%, at least 90%, at least 95%, at least 99%, or 100%. In another embodiment, the guanine nucleosides in mRNA are chemically modified by at least 10%, at least 20%, at least 30%, at least 40%, at least 50%, at least 60%, at least 70%, at least 80%, at least 90%, at least 95%, at least 99%, or 100%.

The present disclosure further provides a method of activating T cells in a subject in need thereof or increasing the number of NK cells in a subject in need thereof comprising administering to the subject an effective amount of a polynucleotide comprising an mRNA encoding an OX40L polypeptide, wherein the mRNA encoding the OX40L polypeptide is an open reading frame. In one aspect, the OX40L polypeptide comprises an amino acid sequence at least 50%, at least 60%, at least 70%, at least 80%, at least 85%, at least 90%, at least 95%, at least 99%, or 100% identical to a sequence listed in Table 1, wherein the amino acid sequence is capable of binding to an OX40 receptor.

Another aspect of the disclosure provides a method of activating T cells in a subject in need thereof or increasing the number of NK cells in a subject in need thereof comprising administering to the subject an effective amount of a polynucleotide comprising an mRNA encoding an OX40L polypeptide, wherein the polynucleotide further comprises a nucleic acid sequence comprising a miRNA binding site. In one embodiment, the miRNA binding site binds to miR-122. In a particular embodiment, the miRNA binding site binds to miR-122-3p or miR-122-5p.

In one aspect of the disclosure, the miRNA binding site comprises a nucleotide sequence at least 80%, at least 85%, at least 90%, at least 95%, or 100% identical to SEQ ID NO: 26, wherein the miRNA binding site binds to miR-122. In another aspect, the miRNA binding site comprises a nucleotide sequence at least 80%, at least 85%, at least 90%, at least 95%, or 100% identical to SEQ ID NO: 24, wherein the miRNA binding site binds to miR-122. In another aspect, the miRNA binding site comprises a nucleotide sequence that binds to SEQ ID NO: 22.

Another aspect of the disclosure provides a method of activating T cells in a subject in need thereof or increasing the number of NK cells in a subject in need thereof comprising administering to the subject an effective amount of a polynucleotide comprising an mRNA encoding an OX40L polypeptide, wherein the polynucleotide further comprises a 5' untranslated region (UTR). In some embodiments, the 5' UTR comprises a nucleic acid sequence at least 90%, 95%, 96%, 97%, 98%, 99%, or 100% identical to a sequence listed in Table 3.

In another aspect, the polynucleotide used in the methods of the disclosure further comprises a 3' UTR. In some embodiments, the 3' UTR comprises a nucleic acid sequence at least 90%, 95%, 96%, 97%, 98%, 99%, or 100% identical to a sequence listed in Table 4.

In another aspect of the disclosure, the miRNA binding site is inserted within the 3' UTR. In some aspects, the polynucleotide further comprises a spacer sequence between the open reading frame and the miRNA binding site. In one aspect, the spacer sequence comprises at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, or at least about 100 nucleotides.

In some embodiments of the disclosure, the polynucleotide further comprises a 5' terminal cap. In one embodiment, the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In another embodiment, the polynucleotide further comprises a 3' polyadenylation (polyA tail).

In some embodiments of the disclosure, the polynucleotide comprises at least two, at least three, at least four, at least five, at least six, at least seven, at least eight, at least nine, or at least ten miRNA binding sites.

In another embodiment, the polynucleotide is codon optimized. In one aspect, the polynucleotide is codon optimized for expression in a mammal. In a particular embodiment, the polynucleotide is codon optimized for expression in a human.

In some embodiments, the polynucleotide is in vitro transcribed (IVT). In other embodiments, the polynucleotide is chimeric. In other embodiments, the polynucleotide is circular.

Another aspect of the disclosure provides a method of activating T cells in a subject in need thereof or increasing the number of NK cells in a subject in need thereof comprising administering to the subject an effective amount of a polynucleotide comprising an mRNA encoding an OX40L polypeptide, wherein the OX40L polypeptide is fused to one or more heterologous polypeptides. In one aspect, the one or more heterologous polypeptides increase a pharmacokinetic property of the OX40L polypeptide In another aspect of the disclosure, the polynucleotide further comprises a second open reading frame encoding a second polypeptide.

In some embodiments of the present disclosure, the methods further comprise administering a second polynucleotide. In one embodiment, the second polynucleotide comprises a second open reading frame encoding a second polypeptide. In another embodiment, the second open reading frame is a second mRNA. In some embodiments, the second mRNA comprises at least one chemically modified nucleoside.

In another embodiment of the disclosure, the polynucleotide is formulated with a delivery agent. In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In one embodiment, the delivery agent is a lipid nanoparticle. In another embodiment, the lipid nanoparticle comprises the lipid selected from the group consisting of DLin-DMA, DLin-K-DMA, 98N12-5, C12-200, DLin-MC3-DMA, DLin-KC2-DMA, DODMA, PLGA, PEG, PEG-DMG, PEGylated lipids, amino alcohol lipids, KL22, and combinations thereof.

In some embodiments of the disclosure, the polynucleotide is formulated for in vivo delivery. In one aspect, the polynucleotide is formulated for subcutaneous, intravenous, intraperitoneal, intratumoral, intramuscular, intra-articular, intra-synovial, intrasternal, intrathecal, intrahepatic, intralesional, intracranial, intraventricular, oral, inhalation spray, topical, rectal, nasal, buccal, vaginal, intratumoral, or implanted reservoir intramuscular, subcutaneous, intratumoral, or intradermal delivery. In another aspect, the polynucleotide is administered subcutaneously, intravenously, intraperitoneally, intratumorally, intramuscularly, intra-articularly, intra-synovially, intrasternally, intrathecally, intrahepatically, intralesionally, intracranially, intraventricularly, orally, by inhalation spray, topically, rectally, nasally, buccally, vaginally or via an implanted reservoir.

In some embodiments, the methods of the present disclosure treat a cancer. In one aspect, the cancer is selected from the group consisting of adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

In some aspects of the disclosure, the polynucleotide is delivered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof.

In one aspect, the polynucleotide is administered intratumorally to the subject at a unit dose of at least about 10 μg, at least about 12.5 μg, or at least about 15 μg. In another aspect, the effective amount is between about 0.10 μg/kg and about 1000 mg/kg.

In a particular aspect of the disclosure, the number of NK cells is increased at least five-fold at 24 hours after the administration.

In another aspect, the tumor growth is inhibited at least about 40%, at least about 50%, at least about 60%, at least about 70%, at least about 80%, at least about 90%, at least about 95%, or about 100% after the administration compared to a control polynucleotide that does not encode an OX40L polypeptide.

In one aspect of the disclosure, the methods of the disclosure further comprise administering a PD-1 antagonist to the subject. In some aspects, the PD-1 antagonist is an antibody or an antigen-binding portion thereof that specifically binds to PD-1. In a particular aspect, the PD-1 antagonist is a monoclonal antibody. In some aspects, the PD-1 antagonist is selected from the group consisting of Nivolumab, Pembrolizumab, Pidilizumab, and any combination thereof.

In another aspect, the methods of the disclosure further comprise administering a PD-L1 antagonist to the subject. In some aspects, the PD-L1 antagonist is an antibody or an antigen-binding portion thereof that specifically binds to PD-L1. In a particular aspect, the PD-L1 antagonist is a monoclonal antibody. In some aspects, the PD-L1 antagonist is selected from the group consisting of Durvalumab, Avelumab, MEDI473, BMS-936559, Atezolizumab, and any combination thereof.

In another aspect, the methods of the disclosure further comprise administering a CTLA-4 antagonist to the subject. In some aspects, the CTLA-4 antagonist is an antibody or an antigen-binding portion thereof that specifically binds to CTLA-4. In a particular aspect, the CTLA-4 antagonist is a monoclonal antibody. In some aspects, the CTLA-4 antagonist is selected from the group consisting of Ipilimumab, Tremelimumab, and any combination thereof.

EMBODIMENTS

E1. A method of activating T cells in a subject in need thereof comprising administering to the subject an effective amount of a polynucleotide comprising an mRNA encoding an OX40L polypeptide, wherein the activated T cells reduce or decrease the size of a tumor or inhibit growth of a tumor.

E2. The method of embodiment E1 wherein the T cell activation comprises inducing T cell proliferation.

E3. The method of embodiment E1 or E2, wherein the T cells activation comprises inducing T cell infiltration in the tumor or increasing the number of tumor-infiltrating T cells.

E4. The method of any one of embodiments E1 to E3, wherein the T cell activation comprises inducing a memory T cell response.

E5. The method of any one of embodiments E1 to E4, wherein the activated T cells comprises $CD4^+$ T cells, $CD8^+$ T cells, or both.

E6. The method of any one of embodiments E1 to E5, wherein the administering further increases the number of NK cells in the subject.

E7. A method of increasing the number of Natural Killer (NK) cells in a subject in need thereof comprising administering to the subject an effective amount of a polynucleotide comprising an mRNA encoding an OX40L polypeptide, wherein the increased NK cells reduce or decrease the size of a tumor or inhibit growth of a tumor.

E8. The method of any one of embodiments E1 to E7, wherein the T cell activation comprises inducing IL-2 release, IL-4 release, IL-21, release, or any combination thereof.

E9. The method of any one of embodiments E6 to E8, wherein the number of NK cells is increased at least about two-fold, at least about three-fold, at least about four-fold, at least about five-fold, at least about six-fold, at least about seven-fold, at least about eight-fold, at least about nine-fold, or at least about ten-fold.

E10. The method of any one of embodiments E1 to E9, wherein the polynucleotide comprises at least one chemically modified nucleoside.

E11. The method of embodiment E10, wherein the at least one chemically modified nucleoside is selected from the group consisting of pseudouridine (ψ), N1-methylpseudouridine (m1ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, and two or more combinations thereof.

E12. The method of any one of embodiments E1 to E11, wherein the nucleosides in the mRNA are chemically modified by at least 10%, at least 20%, at least 30%, at least 40%, at least 50%, at least 60%, at least 70%, at least 80%, at least 90%, at least 95%, at least 99%, or 100%.

E13. The method of any one of embodiments E10 to E12, wherein the chemically modified nucleosides in the mRNA are selected from the group consisting of uridine, adenine, cytosine, guanine, and any combination thereof.

E14. The method of any one of embodiments E1 to E13, wherein the uridine nucleosides in the mRNA are chemically modified by at least 10%, at least 20%, at least 30%, at least 40%, at least 50%, at least 60%, at least 70%, at least 80%, at least 90%, at least 95%, at least 99%, or 100%.

E15. The method of any one of embodiments E1 to E14, wherein the adenine nucleosides in the mRNA are chemically modified by at least 10%, at least 20%, at least 30%, at least 40%, at least 50%, at least 60%, at least 70%, at least 80%, at least 90%, at least 95%, at least 99%, or 100%.

E16. The method of any one of embodiments E1 to E15, wherein the cytosine nucleosides in the mRNA are chemically modified by at least 10%, at least 20%, at least 30%, at least 40%, at least 50%, at least 60%, at least 70%, at least 80%, at least 90%, at least 95%, at least 99%, or 100%.

E17. The method of any one of embodiments E1 to E16, wherein the guanine nucleosides in mRNA are chemically modified by at least 10%, at least 20%, at least 30%, at least 40%, at least 50%, at least 60%, at least 70%, at least 80%, at least 90%, at least 95%, at least 99%, or 100%.

E18. The method of any one of embodiments E1 to E17, wherein the mRNA encoding the OX40L polypeptide is an open reading frame.

E19. The method of embodiment E18, wherein the OX40L polypeptide comprises an amino acid sequence at least 50%, at least 60%, at least 70%, at least 80%, at least 85%, at least 90%, at least 95%, at least 99%, or 100% identical to SEQ ID NO: 2, wherein the amino acid sequence is capable of binding to an OX40 receptor.

E20. The method of embodiment E18, wherein the OX40L polypeptide comprises an amino acid sequence at least 50%, at least 60%, at least 70%, at least 80%, at least 85%, at least 90%, at least 95%, at least 99%, or 100% identical to SEQ ID NO: 1, wherein the amino acid sequence is capable of binding to an OX40 receptor.

E21. The method of any one of embodiments E1 to E20, wherein the polynucleotide further comprises a nucleic acid sequence comprising a miRNA binding site.

E22. The method of embodiment E21, wherein the miRNA binding site binds to miR-122.

E23. The method of embodiment E21 or E22, wherein the miRNA binding site binds to miR-122-3p or miR-122-5p.

E24. The method of embodiment E23, wherein the miRNA binding site comprises a nucleotide sequence at least 80%, at least 85%, at least 90%, at least 95%, or 100% identical to SEQ ID NO: 26, wherein the miRNA binding site binds to miR-122.

E25. The method of embodiment E23, wherein the miRNA binding site comprises a nucleotide sequence at least 80%, at least 85%, at least 90%, at least 95%, or 100% identical to SEQ ID NO: 24, wherein the miRNA binding site binds to miR-122.

E26. The method of any one of embodiments E21 to E25, wherein the nucleotide sequence binds to SEQ ID NO: 22.

E27. The method of any one of embodiments E1 to E26, wherein the polynucleotide further comprises a 5' UTR.

E28. The method of embodiment E27, wherein the 5' UTR comprises a nucleic acid sequence at least 90%, 95%, 96%, 97%, 98%, 99%, or 100% identical to a sequence listed in Table 3.

E29. The method of any one of embodiments E1 to E28 which further comprises a 3' UTR.

E30. The method of embodiment E29, wherein the 3' UTR comprises a nucleic acid sequence at least 90%, 95%, 96%, 97%, 98%, 99%, or 100% identical to a sequence listed in Table 4A or 4B.

E31. The method of embodiment E29 or E30, wherein the miRNA binding site is inserted within the 3' UTR.

E32. The method of embodiment E31, wherein the polynucleotide further comprises a spacer sequence between the open reading frame and the miRNA binding site.

E33. The method of embodiment E32, wherein the spacer sequence comprises at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, or at least about 100 nucleotides.

E34. The method of any one of embodiments E1 to E33, wherein the polynucleotide further comprises a 5' terminal cap.

E35. The method of embodiment E34, wherein the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

E36. The method of any one of embodiments E1 to E35, wherein the polynucleotide further comprises a 3' polyA tail.

E37. The method of any one of embodiments E21 to E36, wherein the polynucleotide comprises at least two, at least three, at least four, at least five, at least six, at least seven, at least eight, at least nine, or at least ten miRNA binding sites.

E38. The methods of any one of embodiments E1 to E37, wherein the polynucleotide is codon optimized.

E39. The method of any one of embodiments E1 to E38, wherein the polynucleotide is in vitro transcribed (IVT).

E40. The method of any one of embodiments E1 to E38, wherein the polynucleotide is chimeric.

E41. The method of any one of embodiments E1 to E38, wherein the polynucleotide is circular.

E42. The method of any one of embodiments E1 to E41, wherein the OX40L polypeptide is fused to one or more heterologous polypeptides.

E43. The method of embodiment E42, wherein the one or more heterologous polypeptides increase a pharmacokinetic property of the OX40L polypeptide.

E44. The method of any one of embodiments E1 to E43, wherein the polynucleotide further comprises a second open reading frame encoding a second polypeptide.

E45. The method of any one of embodiments E1 to E43, further comprising administering a second polynucleotide.

E46. The method of embodiment E45, wherein the second polynucleotide comprises a second open reading frame encoding a second polypeptide.

E47. The method of any one of embodiments E44 to E46, wherein the second open reading frame is a second mRNA.

E48. The method of embodiment E47, wherein the second mRNA comprises at least one chemically modified nucleoside.

E49. The method of any one of embodiments E1 to E48, wherein the polynucleotide is formulated with a delivery agent.

E50. The method of embodiment E49, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E51. The method of embodiment E50, wherein the delivery agent is a lipid nanoparticle.

E52. The method of embodiment E51, wherein the lipid nanoparticle comprises the lipid selected from the group consisting of DLin-DMA, DLin-K-DMA, 98N12-5, C12-200, DLin-MC3-DMA, DLin-KC2-DMA, DODMA, PLGA, PEG, PEG-DMG, PEGylated lipids, amino alcohol lipids, KL22, and combinations thereof.

E53. The method of any one of embodiments E1 to E52, wherein the polynucleotide is formulated for in vivo delivery.

E54. The method of embodiment E53, wherein the polynucleotide is formulated for subcutaneous, intravenous, intraperitoneal, intratumoral, intramuscular, intra-articular, intra-synovial, intrasternal, intrathecal, intrahepatic, intralesional, intracranial, intraventricular, oral, inhalation spray, topical, rectal, nasal, buccal, vaginal, intratumoral, or implanted reservoir intramuscular, subcutaneous, intratumoral, or intradermal delivery.

E55. The method of any one of embodiments E1 to E53, wherein the polynucleotide is administered subcutaneously, intravenously, intraperitoneally, intratumorally, intramuscularly, intra-articularly, intra-synovially, intrasternally, intrathecally, intrahepatically, intralesionally, intracranially, intraventricularly, orally, by inhalation spray, topically, rectally, nasally, buccally, vaginally or via an implanted reservoir.

E56. The method of any one of embodiments E1 to E55, wherein the administration treats a cancer.

E57. The method of embodiment E56, wherein the cancer is selected from the group consisting of adrenal cortical cancer, advanced cancer, anal cancer, aplastic anemia, bile-duct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, hepatocellular carcinoma (HCC), non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor, secondary cancers caused by cancer treatment, and any combination thereof.

E58. The method of any one of embodiments E1 to E57, wherein the polynucleotide is delivered by a device comprising a pump, patch, drug reservoir, short needle device, single needle device, multiple needle device, micro-needle device, jet injection device, ballistic powder/particle delivery device, catheter, lumen, cryoprobe, cannula, microcanular, or devices utilizing heat, RF energy, electric current, or any combination thereof.

E59. The method of any one of embodiments E1 to E58, wherein the polynucleotide is administered intratumorally to the subject at a unit dose of at least about 10 µg, at least about 12.5 µg, or at least about 15 µg.

E60. The method of any one of embodiments E1 to E58, wherein the effective amount is between about 0.10 µg/kg and about 1000 mg/kg.

E61. The method of any one of embodiments E6 to E60, wherein the number of NK cells is increased at least five-fold at 24 hours after the administration.

E62. The method of any one of embodiments E1 to E61, wherein the tumor growth is inhibited at least about 40%, at least about 50%, at least about 60%, at least about 70%, at least about 80%, at least about 90%, at least about 95%, or about 100% after the administration compared to a control polynucleotide that does not encode an OX40L polypeptide.

E63. The method of any one of embodiments E1 to E62, further comprising administering a PD-1 antagonist to the subject.

E64. The method of embodiment E63, wherein the PD-1 antagonist is an antibody or antigen binding portion thereof that specifically binds to PD-1.

E65. The method of embodiment E63 or E64, wherein the PD-1 antagonist is a monoclonal antibody.

E66. The method of any one of embodiments E63 to E65, wherein the PD-1 antagonist is selected from the group consisting of Nivolumab, Pembrolizumab, Pidilizumab, and any combination thereof.

E67. The method of any one of embodiments E1 to E62, further comprising administering a PD-L1 antagonist to the subject.

E68. The method of embodiment E67, wherein the PD-L1 antagonist is an antibody that binds to PD-L1.

E69. The method of embodiment E67 or E68, wherein the PD-L1 antagonist is a monoclonal antibody.

E70. The method of any one of embodiments E67 to E69, wherein the PD-L1 antagonist is selected from the group consisting of Durvalumab, Avelumab, MEDI473, BMS-936559, Atezolizumab, and any combination thereof.

E71. The method of any one of embodiments E1 to E62, further comprising administering a CTLA-4 antagonist to the subject.

E72. The method of embodiment E71, wherein the CTLA-4 antagonist is an antibody or antigen binding portion thereof that specifically binds to CTLA-4.

E73. The method of embodiment E71 or E72, wherein the CTLA-4 antagonist is a monoclonal antibody.

E74. The method of any one of embodiments E71 to E73, wherein the CTLA-4 antagonist is selected from the group consisting of Ipilimumab, Tremelimumab, and any combination thereof.

BRIEF DESCRIPTION OF THE DRAWINGS/FIGURES

FIG. 1 shows an example of an OX40L encoding polynucleotide (mRNA). The mRNA can comprise a 5'cap, 5' UTR, an OFR (mRNA) encoding an OX40L polypeptide, a 3'UTR, a miR122 binding site, and a poly-A tail.

FIG. 2 shows expression of OX40L on the surface of B16F10 cells after treatment with a polynucleotide comprising an mRNA encoding an OX40L polypeptide. The left peaks represent the control (either mock-treated or treated with negative control mRNA (non-translatable version of the same mRNA containing multiple stop codons)). The right four peaks represent OX40L expression from the administration of 6.3 ng, 12.5 ng, 25 ng, or 50 ng OX40L mRNA.

FIG. 3A shows expression of OX40L on the surface of HeLa cells after treatment with a polynucleotide comprising an mRNA encoding an OX40L polypeptide; treatment was in the absence of mitomycin C. FIG. 3B show expression of OX40L on the surface of MC-38 cells after treatment with a polynucleotide comprising an mRNA encoding an OX40L polypeptide; treatment was in the absence of mitomycin C. Peak 1 in FIGS. 3A and 3B shows surface expression on mock treated cells. Peaks 2-6 show surface expression on days 1, 2, 3, 5, and 7 (respectively) after treatment with a polynucleotide comprising an mRNA encoding an OX40L polypeptide.

FIG. 3C shows expression of OX40L on the surface of HeLa cells after treatment with a polynucleotide comprising an mRNA encoding an OX40L polypeptide; treatment was in the presence of mitomycin C. FIG. 3D shows expression of OX40L on the surface of MC-38 cells after treatment with a polynucleotide comprising an mRNA encoding an OX40L polypeptide; treatment was in the presence of mitomycin C. Peak 1 in FIGS. 3C and 3D shows surface expression on mock treated cells. Peaks 2-6 show surface expression on days 1, 2, 3, 5, and 7 (respectively) after treatment with a polynucleotide comprising an mRNA encoding an OX40L polypeptide.

FIG. 3E shows expression of human OX40L on the surface of HeLa cells after treatment with a polynucleotide comprising an mRNA encoding an OX40L polypeptide. Peak 1 shows the surface expression on mock treated cells. Peaks 2-6 show surface expression on day 1, 2, 3, 4, and 5 (respectively) after treatment with a polynucleotide comprising an mRNA encoding an OX40L polypeptide.

FIG. 3F shows quantitation of mouse OX40L protein in cell lysate and cell culture supernatant after treatment of HeLa cells with a polynucleotide comprising an mRNA encoding an OX40L polypeptide. FIG. 3G shows quantitation of human OX40L protein in cell lysate and cell culture supernatant after treatment of HeLa cells with a polynucleotide comprising an mRNA encoding an OX40L polypeptide. The y-axis in FIGS. 3F and 3G shows the amount of protein as nanograms (ng) per well.

FIG. 4A shows a schematic drawing of the T-cell activation assay. OX40L-expressing B16F10 cells or HeLa cells were co-cultured with $CD4^+$ T-cells and anti-mouse CD3 antibody (B16F10 cells) or anti-human CD3 antibody and soluble anti-human CD28 (HeLa cells). IL-2 production was measured using ELISA as a correlate of T-cell activation. FIG. 4B shows results of the T-cell activation assay as measured by mouse IL-2. FIG. 4C shows results of the T-cell activation assay as measured by human IL-2. The y-axis shows mIL2 expression in ng/ml.

Figure 5:
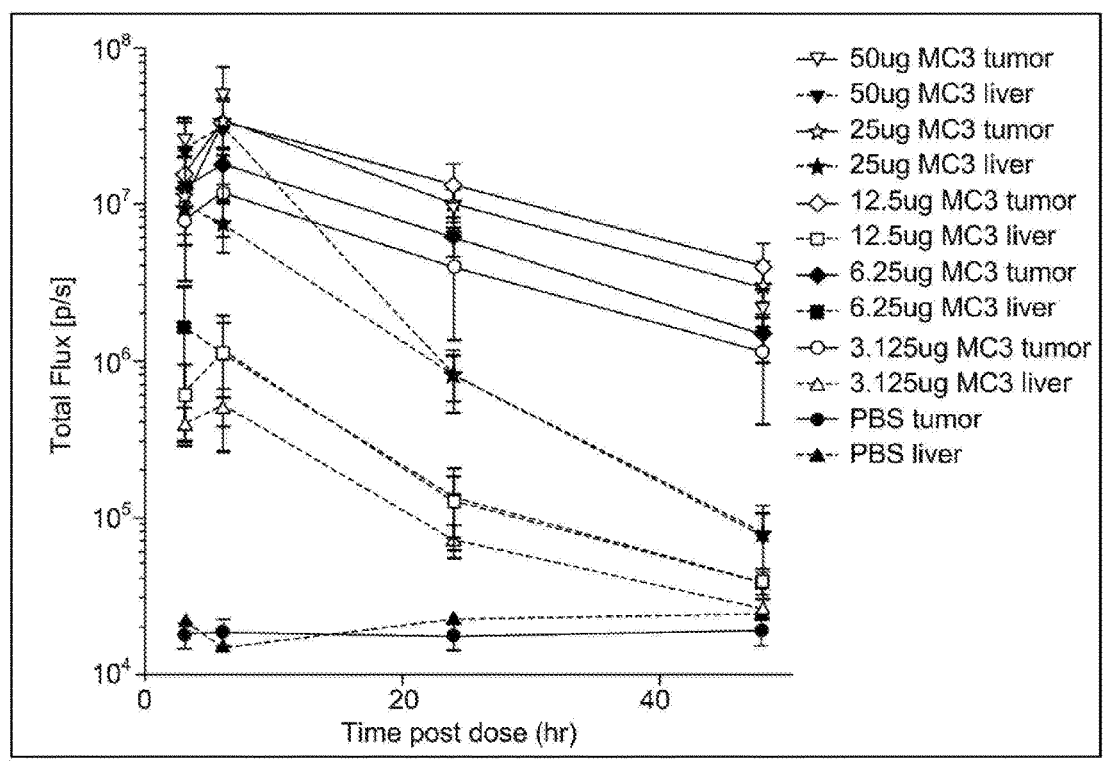

FIG. 5 shows luciferase flux levels in tumor tissue compared to liver tissue in animals treated with a polynucleotide comprising an mRNA encoding a luciferase polypeptide. Representative symbols are as follows. The open inverted triangle, open star, open diamond, shaded diamond, and open circle show the luciferase flux in tumor tissue after administration of 50 µg, 25 µg, 12.5 µg, 6.25 µg, and 3.125 µg of mOX40L_miR122 mRNA (respectively). The shaded inverted triangle, shaded star, open square, shaded square, and open triangle show the luciferase flux in liver tissue after administration of 50 µg, 25 µg, 12.5 µg, 6.25 µg, and 3.125 µg of mOX40L_miR122 mRNA (respectively). The shaded circle and shaded triangle show luciferase flux in tumor tissue (shaded circle) and liver tissue (shaded triangle) after administration of PBS control.

Figure 6:
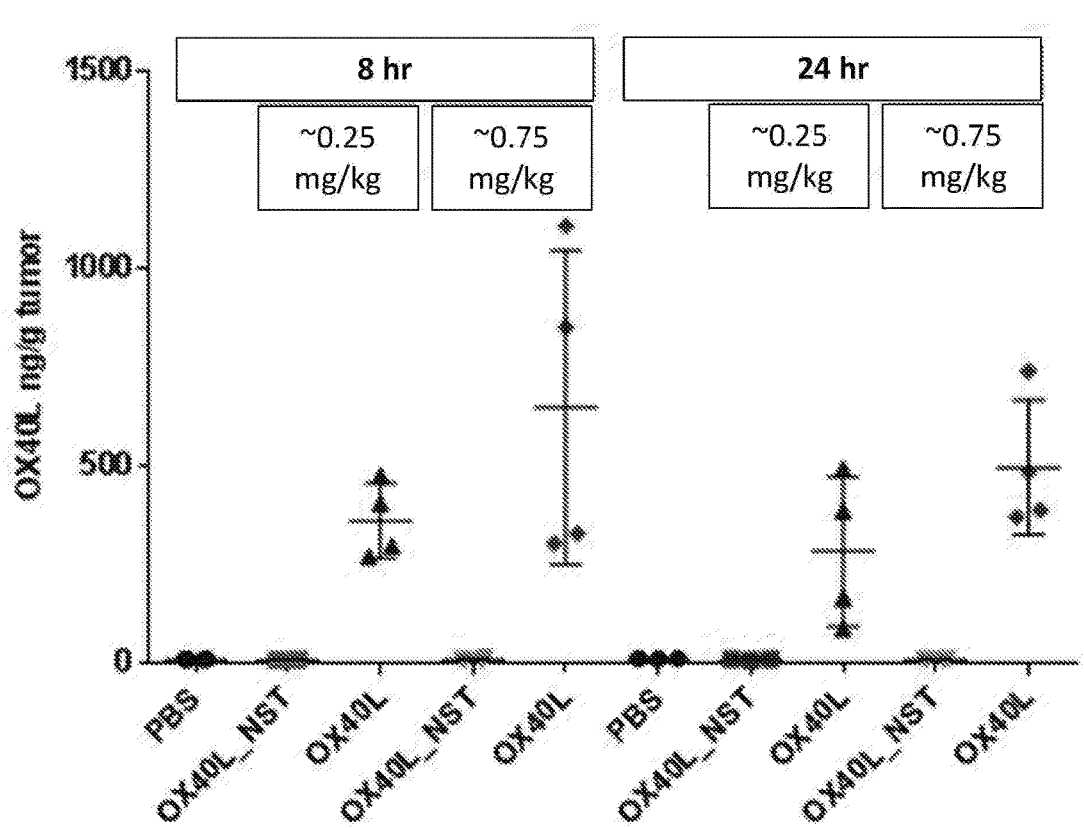

FIG. 6 shows the amount of OX40L polypeptide present in melanoma tumor tissue in animals treated with a polynucleotide comprising an mRNA encoding an OX40L polypeptide. The left panel shows 8 hours after treatment, and the right panel shows 24 hours after treatment.

Figure 7A:
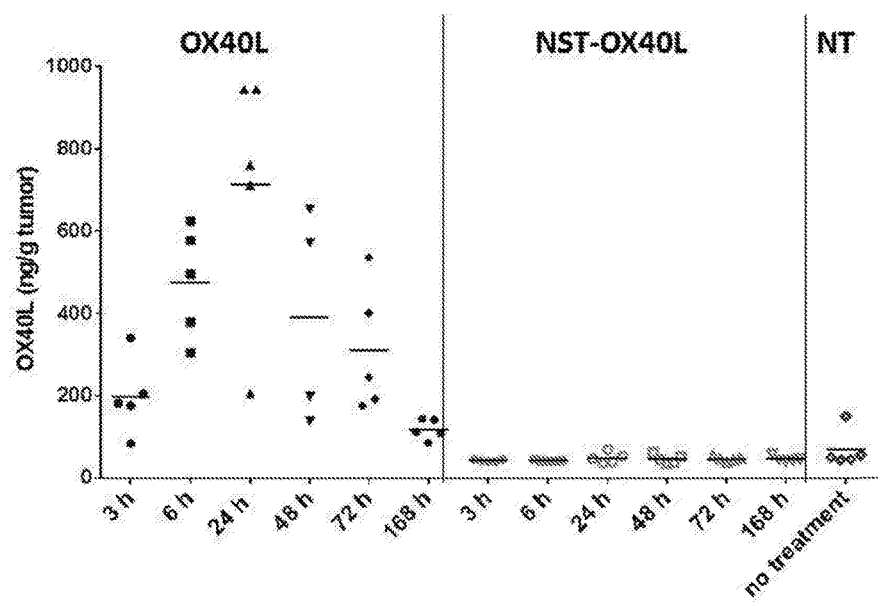
Figure 7B:
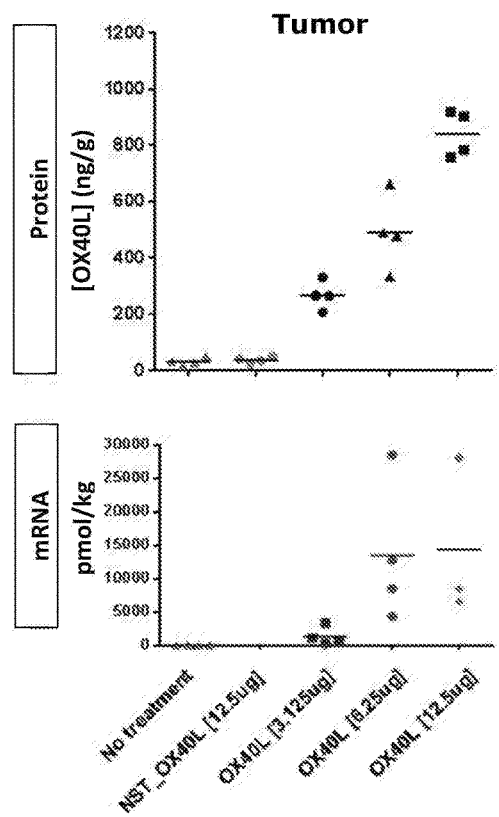
Figure 7C:
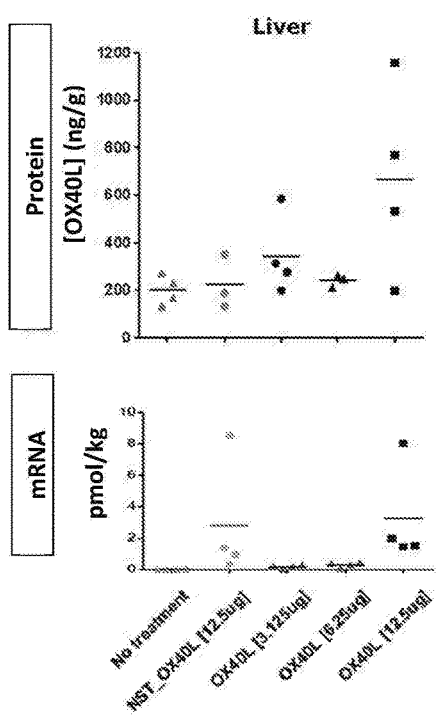
Figure 7D:
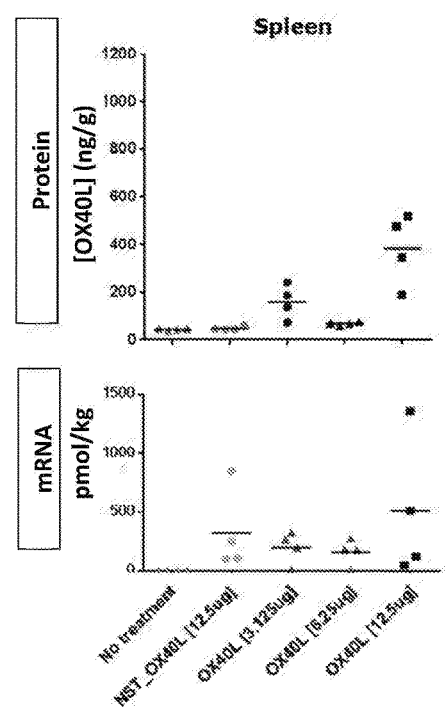

FIG. 7A shows the amount of OX40L polypeptide present in colon adenocarcinoma tumor tissue in animals treated with a polynucleotide comprising an mRNA encoding an OX40L polypeptide, a polynucleotide comprising an mRNA encoding a NST-OX40L (non translatable OX40L mRNA), or no treatment. The OX40L expression was measured at 3 hours, 6 hours, 24 hours, 48 hours, 72 hours, and 168 hours. FIG. 7B shows the amount of OX40L polypeptide (upper) and mRNA (lower) present in tumor tissue following administration of increasing doses of a polynucleotide comprising an mRNA encoding an OX40L polypeptide. FIG. 7C shows the amount of OX40L polypeptide (upper) and mRNA (lower) present in liver tissue following administration of the same polynucleotide. FIG. 7D shows the amount of OX40L polypeptide (upper) and mRNA (lower) present in spleen tissue following administration of the same polynucleotide.

Figure 8A:
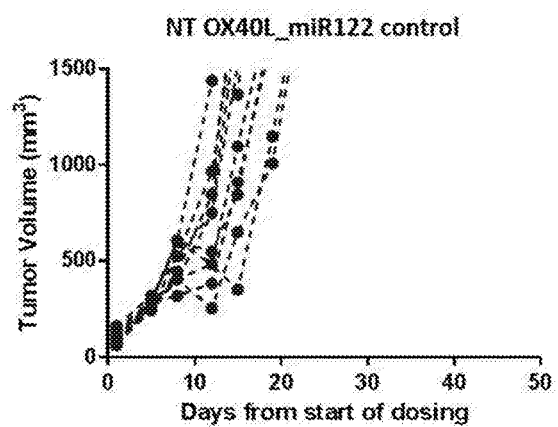
Figure 8B:
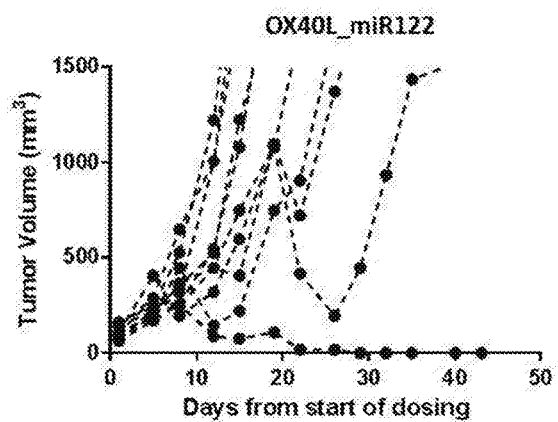
Figure 8C:
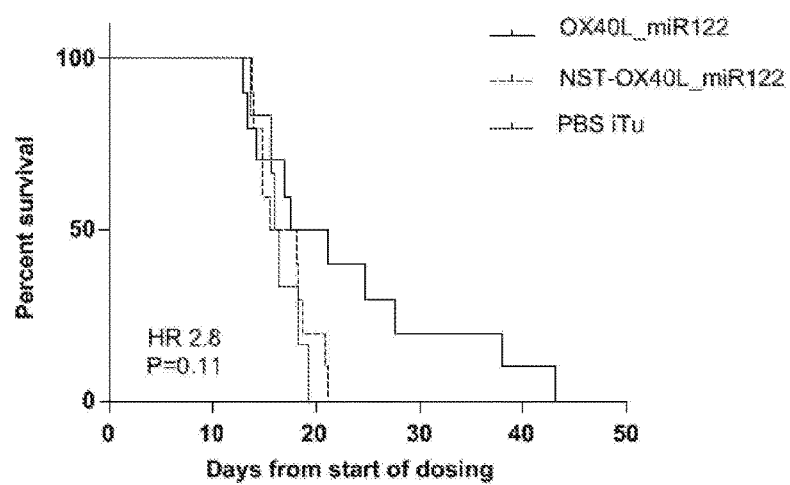

FIG. 8A-8C show the in vivo efficacy (as measured at Day 42) of administering a polynucleotide comprising an mRNA encoding an OX40L polypeptide in a colon adenocarcinoma model. FIG. 8A shows tumor growth for animals treated with a control mRNA (NT OX40L_miR122 control). FIG. 8B shows tumor growth for animals treated with a polynucleotide comprising an mRNA encoding an OX40L polypeptide (OX40L_miR122). FIG. 8C shows a Kaplan-Meier survival curve for all treatment groups. (OX40L_miR122, NST_OX40L_miR122, and PBS).

Figure 9A:
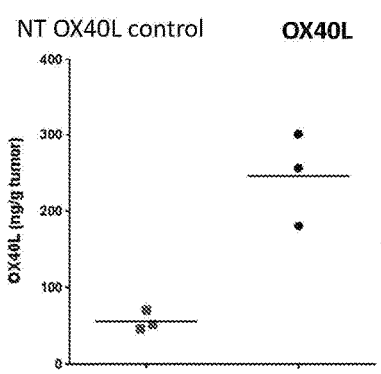
Figure 9B:
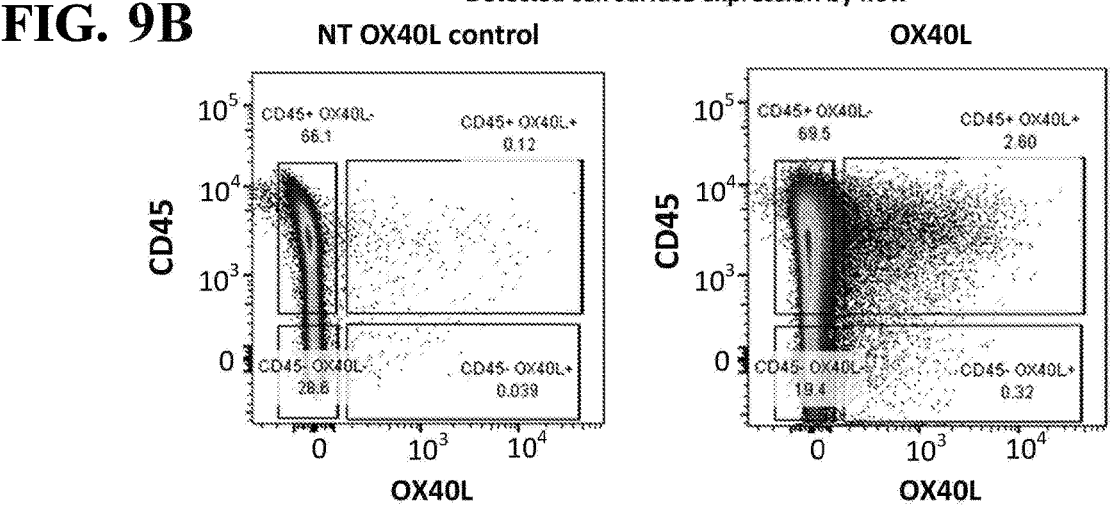
Figure 9C:
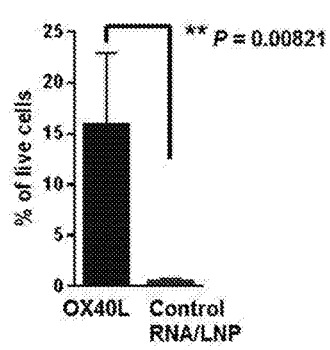

FIG. 9A-9C show OX40L expression in A20 B-cell lymphoma tumors in animals treated with a polynucleotide comprising an mRNA encoding an OX40L polypeptide. FIG. 9A shows OX40L expression quantitated in nanograms per gram of tumor tissue, as measured by ELISA. FIG. 9B shows OX40L expression on the cell surface of tumor cells, as measured by flow cytometry. FIG. 9C shows OX40L expression on the cell surface of tumor cells as measured by flow cytometry.

Figure 10A:
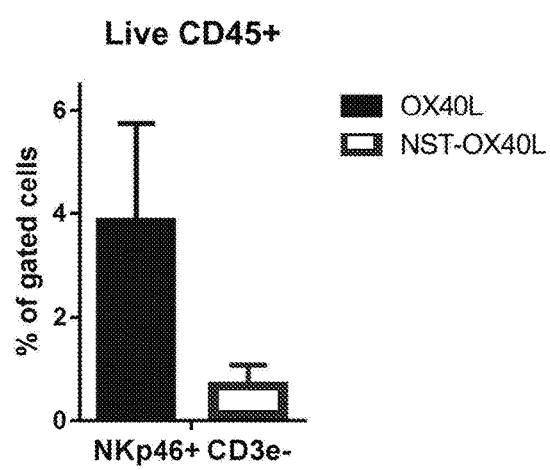
Figure 10B:
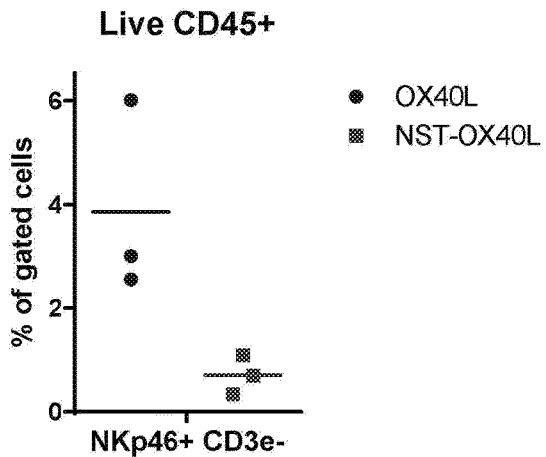

FIG. 10A-10B show Natural Killer (NK) cell infiltration into the tumor microenvironment in animals treated with a polynucleotide comprising an mRNA encoding an OX40L polypeptide. FIG. 10A shows the average percentage of live NK cells present in the tumor microenvironment. The left bar shows the percentage of the NK cells increased after administration of mOX40L_mRNA. The right bar shows the percentage of the NK cells increased after administration of NST_mOX40L_mRNA. FIG. 10B shows individual animal data from the same study.

Figure 11A:
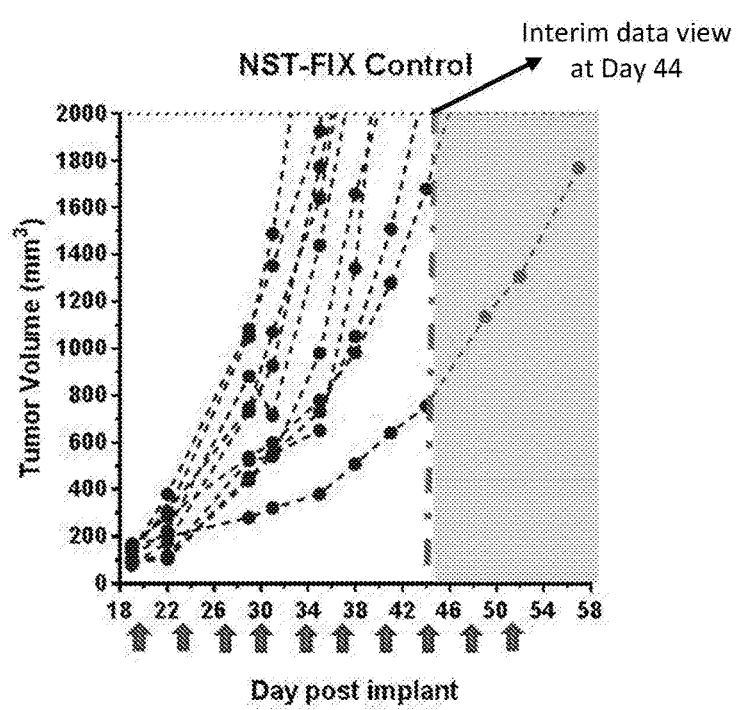
Figure 11B:
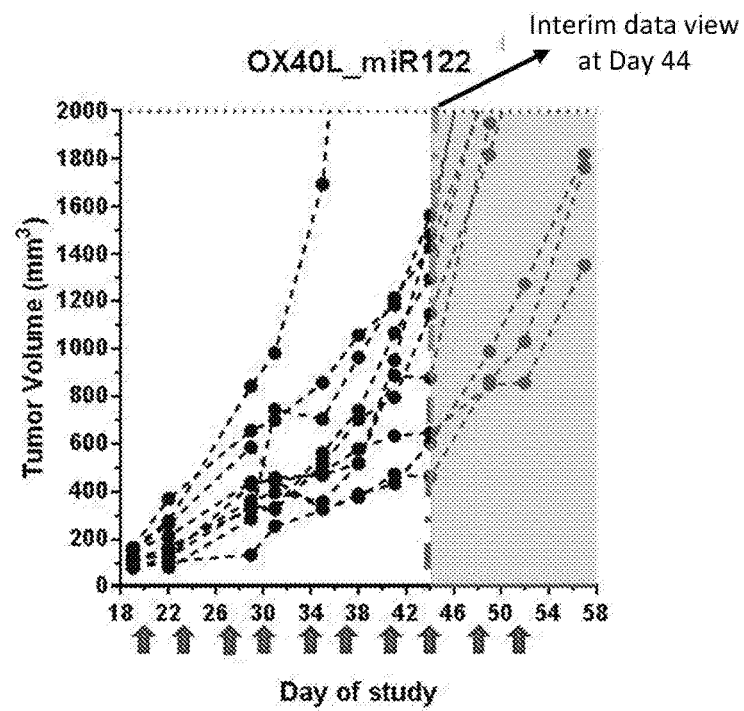
Figure 11C:
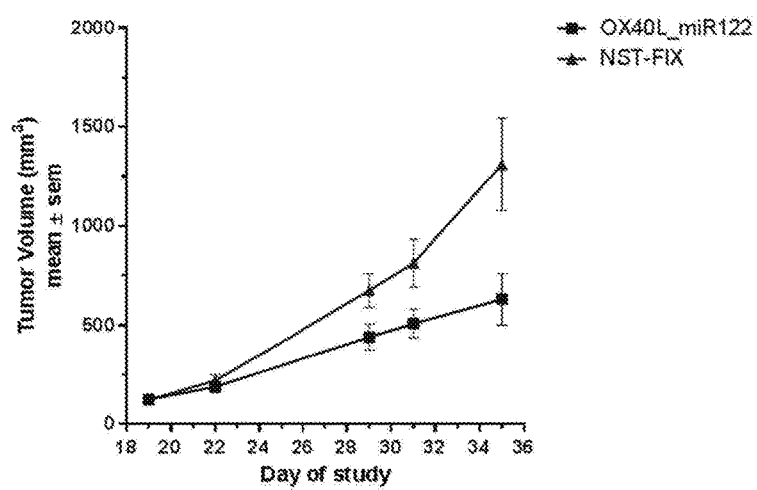
Figure 11D:
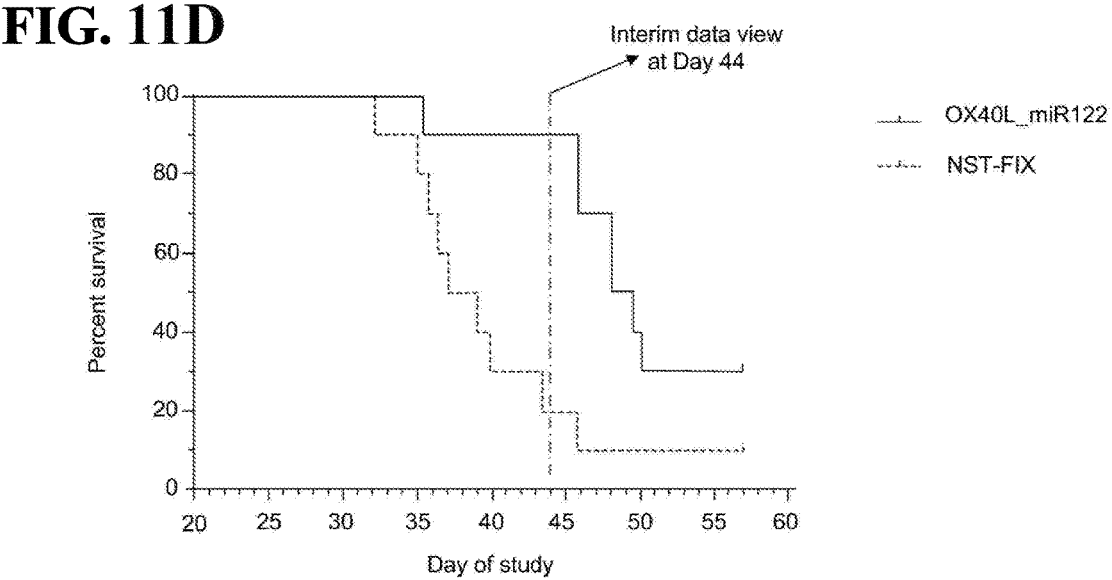

FIG. 11A-11D show in vivo efficacy of administering a polynucleotide comprising an mRNA encoding an OX40L polypeptide in a B-cell lymphoma tumor model. FIG. 11A shows tumor growth in animals treated with a control mRNA (NST-FIX control). FIG. 11B shows tumor growth in animals treated with a polynucleotide comprising an mRNA encoding an OX40L polypeptide (OX40L_miR122). FIG. 11C shows the average tumor volume for each group, as measured at Day 35. FIG. 11D shows Kaplan-Meier survival curves for each treatment group. The squares show the tumor volume after administration of OX40L_miR122. The triangles show the tumor volume after administration of NST-FIX (control).

Figures 12A, 12B:
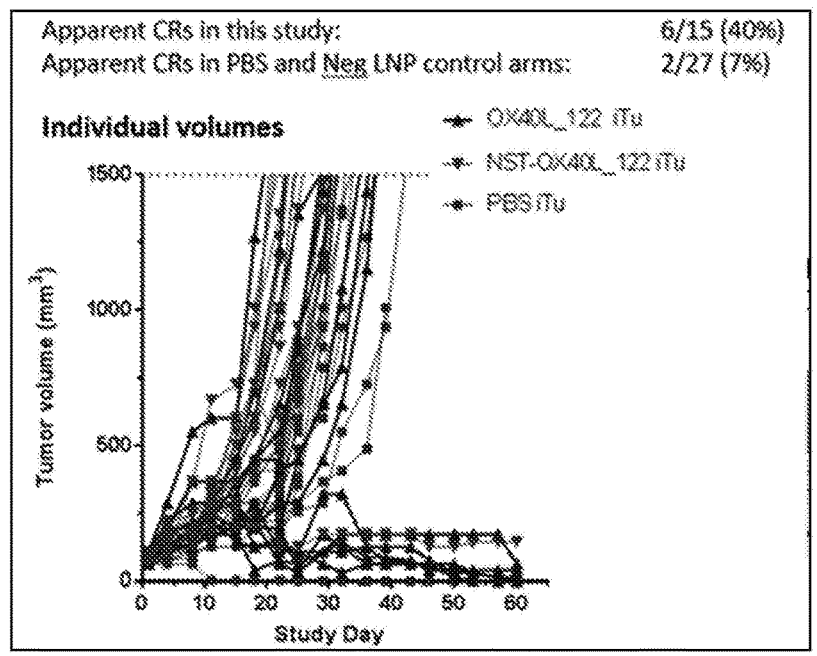

FIG. 12A. shows in vivo immune response after administering a polynucleotide comprising an mRNA encoding an OX40L polypeptide. Mice were inoculated with MC-38 colon adenocarcinoma cells. Once the tumors reached palpable size, mice were administered a polynucleotide comprising an mRNA encoding an OX40L polypeptide (OX40L_122; triangle), a control nonsense mRNA (NST-OX40L_122; inverted triangle), or PBS (square). Sixty days following administration of the polypeptide, mice were re-challenged with a second MC-38 tumor cell inoculation. FIG. 12A shows the individual animal tumor during the first period through Day 60. FIG. 12B shows the number of animals presenting with tumor growth 23 days after re-challenge.

Figure 13:
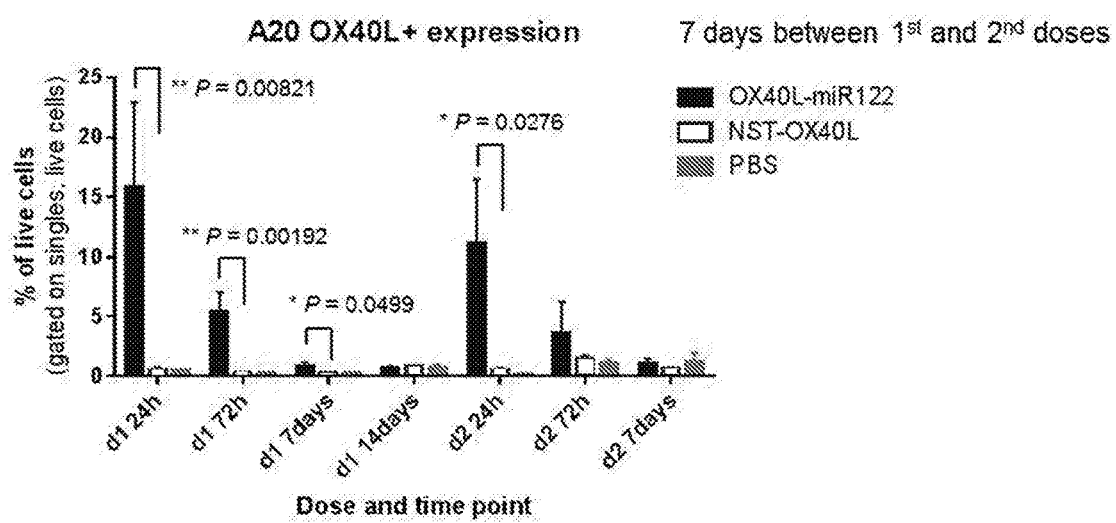

FIG. 13 shows OX40L expression in A20 tumors at various timepoints after a first and/or second dose of a polynucleotide comprising an mRNA encoding an OX40L polypeptide. Expression is shown at 24 hours, 72 hours, 7 days, and 14 days after administration of a first dose of the polynucleotide and 24 hours, 72 hours, and 7 days after administration of a second dose of the polynucleotide.

Figure 14A:
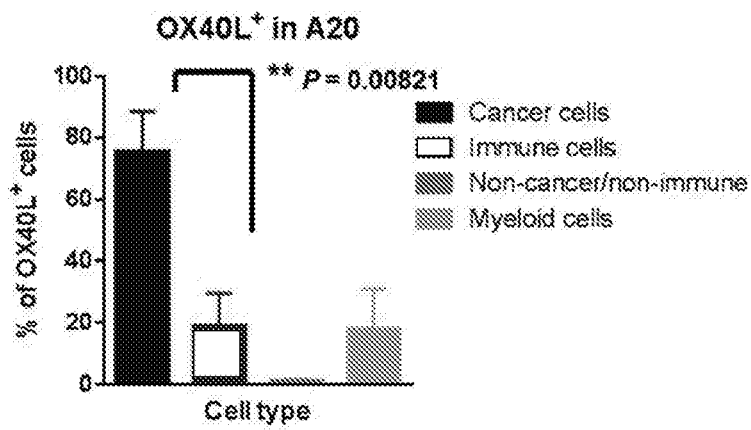
Figure 14B:
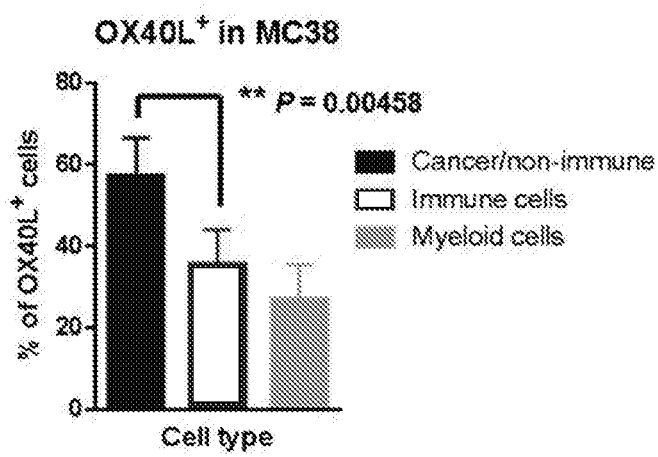
Figure 14C:
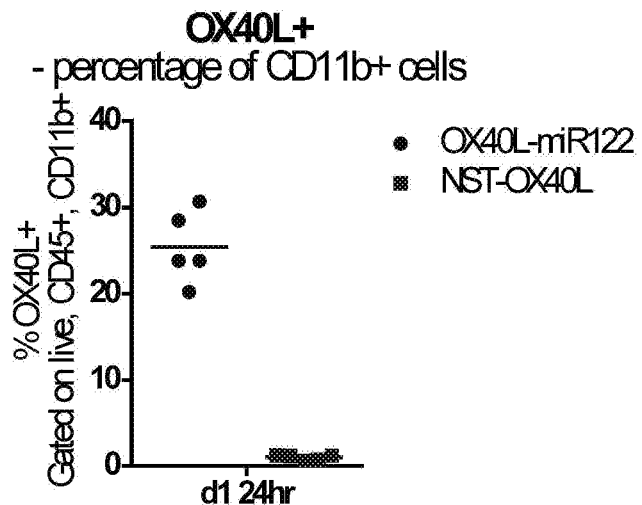

FIG. 14A-14C show different cell types present in the tumor microenvironment following administration of a polynucleotide comprising an mRNA encoding an OX40L polypeptide. FIG. 14A shows the percentage of OX40L-expressing cells in A20 tumors that are cancer cells, immune cells, non-cancer/non-immune cells, and cells of myeloid lineage. FIG. 14B shows the percentage of OX40L-expressing cells in MC38 tumors that are tumor cells, immune cells, and cells of myeloid lineage. FIG. 14C shows the percentage of myeloid cells in the tumor microenvironment that are OX40L-expressing cells following administration of the polynucleotide.

Figure 15A:
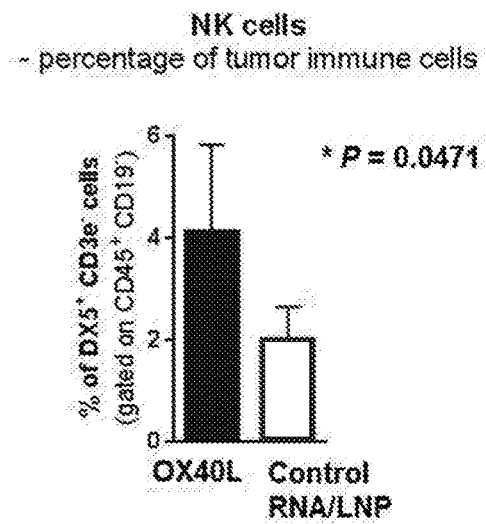
Figure 15B:
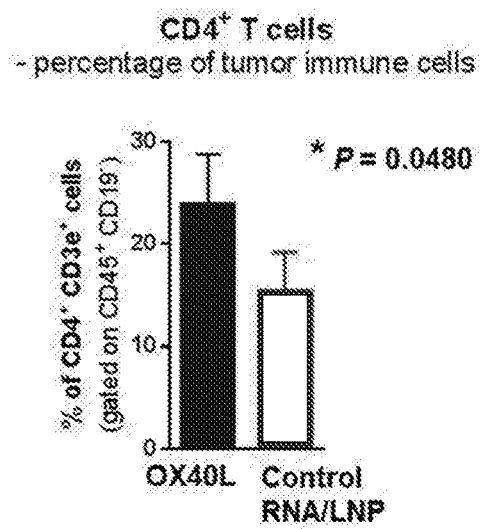
Figure 15C:
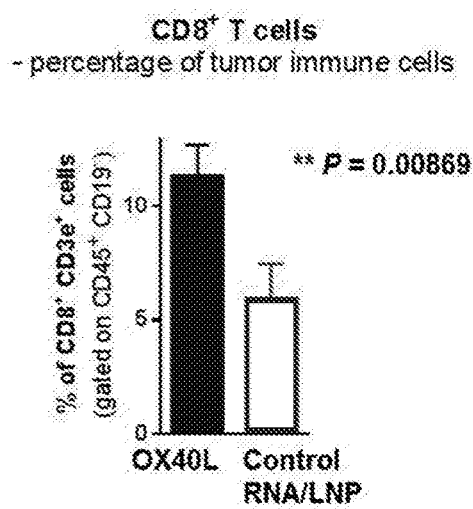
Figure 15D:
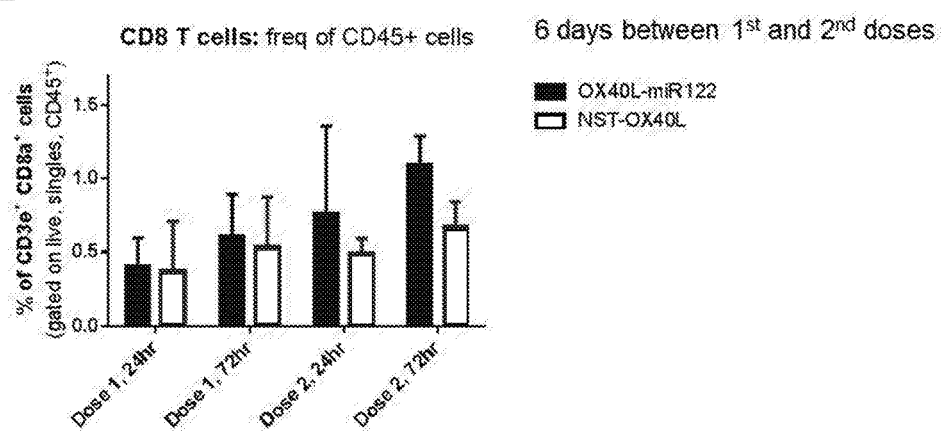

FIG. 15A-15D show the different types of immune cells that infiltrate the tumor microenvironment in A20 tumors following administration of a polynucleotide comprising an mRNA encoding an OX40L polypeptide. FIG. 15A shows the percentage of NK cells in the tumor infiltrate 24 hours after treatment, as detected by the DX5 marker. FIG. 15B shows the percentage of CD4$^+$ T-cells in the tumor infiltrate 14 days after treatment, as detected by the CD4 marker. FIG. 15C shows the percentage of CD8$^+$ T-cells in the tumor infiltrate 14 days after treatment, as detected by the CD8 marker. FIG. 15D shows the percentage of CD8$^+$ T-cells in the tumor infiltrate of MC38 tumors 24 and 72 hours after a first and second dose of a polynucleotide comprising an mRNA encoding an OX40L polypeptide.

Figure 16A:
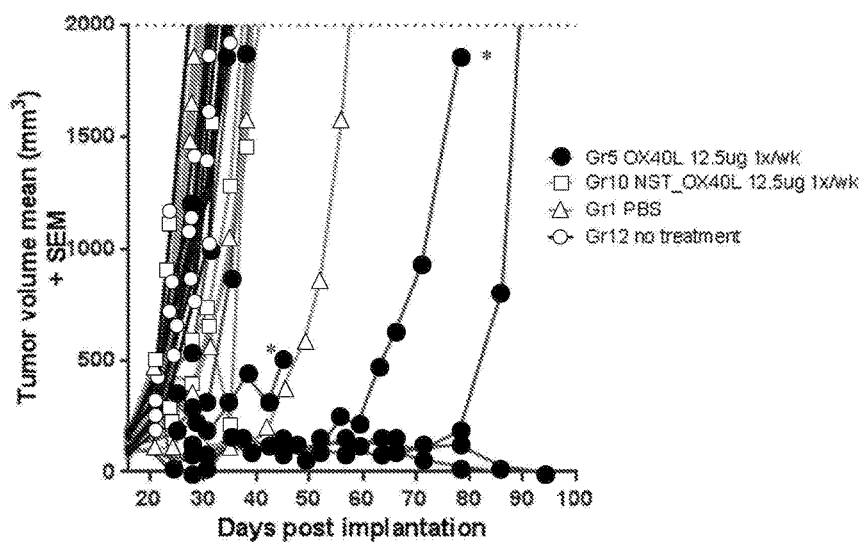
Figure 16B:
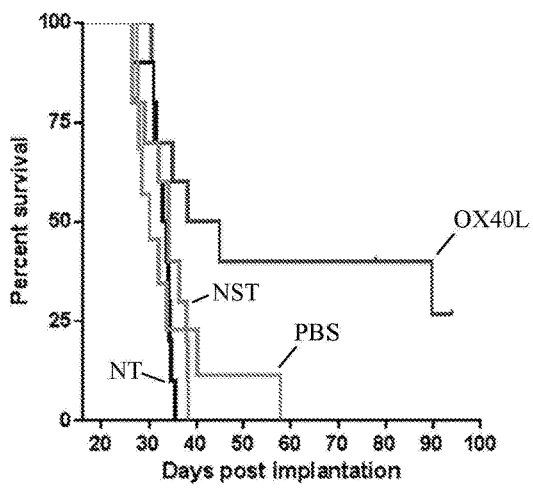

FIG. 16A-16B show in vivo efficacy of administration of a polynucleotide comprising an mRNA encoding an OX40L polypeptide in A20 tumors. FIG. 16A shows tumor volume (measured in mm$^3$) over time. Treatments are shown as follows: mOX40L_miR122 (filled circles); control mRNA (NST) (open squares); PBS (open triangles); and untreated (open circles). FIG. 16B shows a Kaplan-Meier survival curve for the same animals.

Figure 17A:
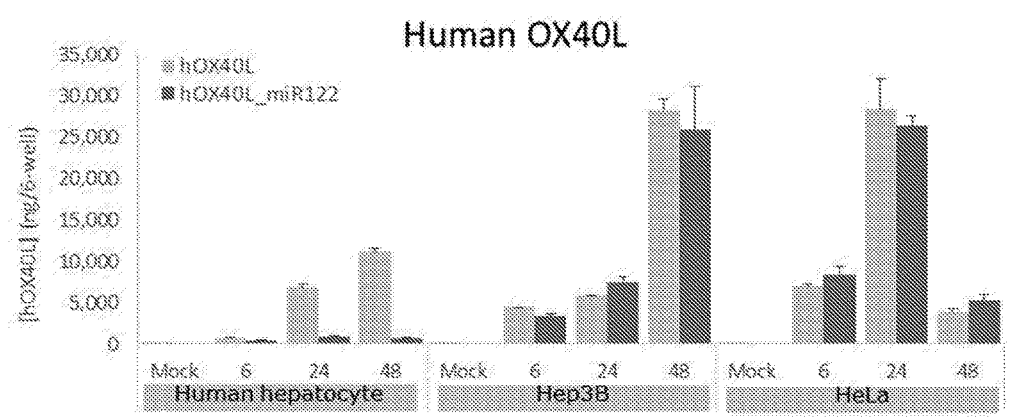
Figure 17B:
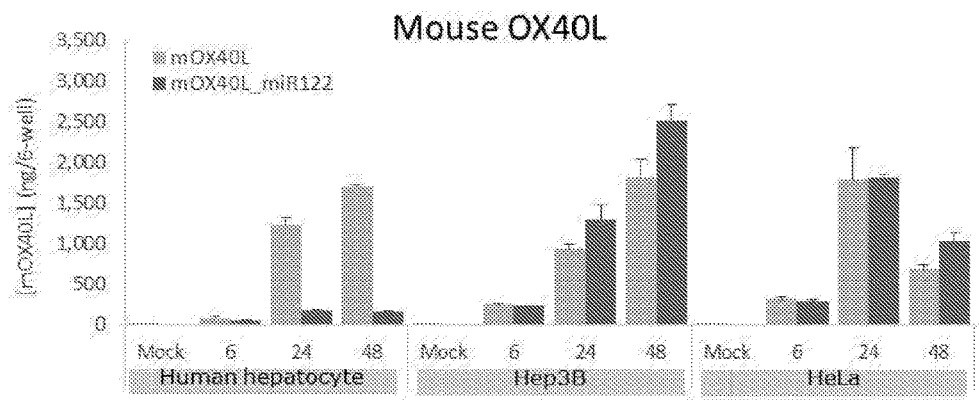

FIG. 17A-17B show expression of OX40L protein in primary human hepatocytes, human liver cancer cells (Hep3B), and human cervical carcinoma cells (HeLa) at 6 hours, 24 hours, and 48 hours post-transfection. FIG. 17A shows expression of human OX40L polypeptide as measured in nanograms per well. FIG. 17B shows expression of mouse OX40L polypeptide as measured in nanograms per well.

Figure 18A:
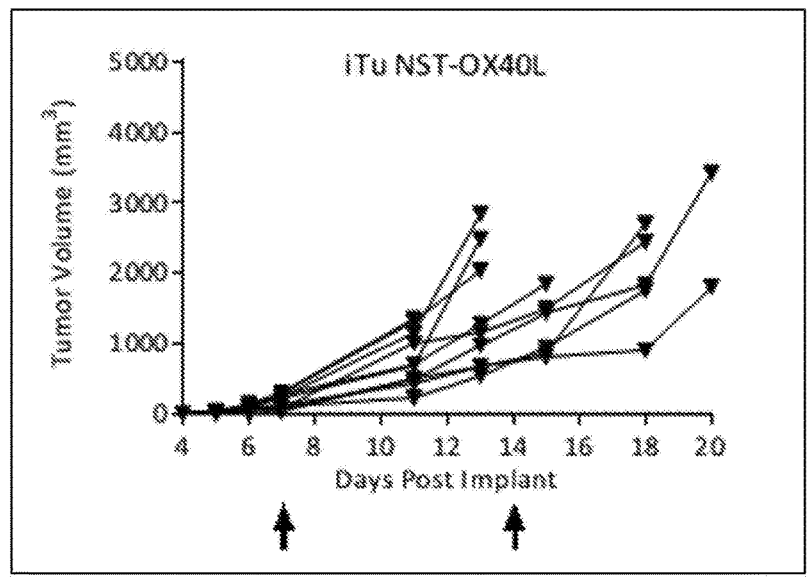
Figure 18B:
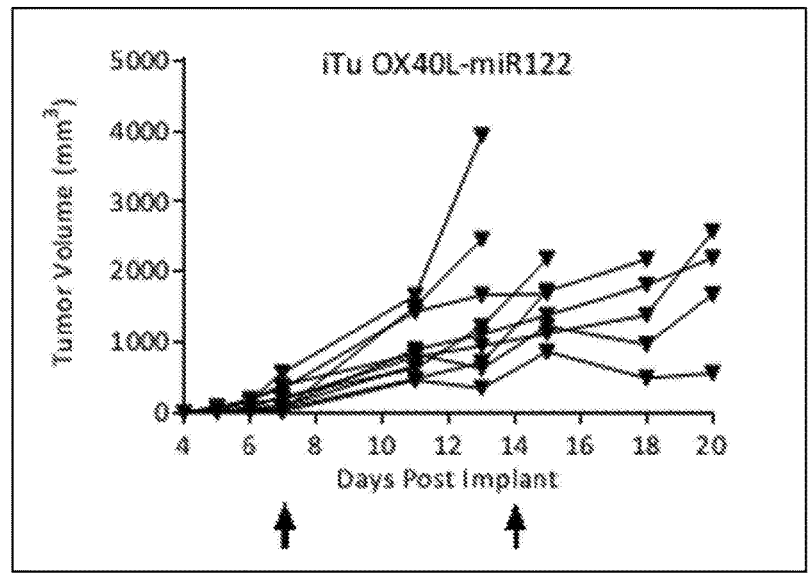
Figure 18C:
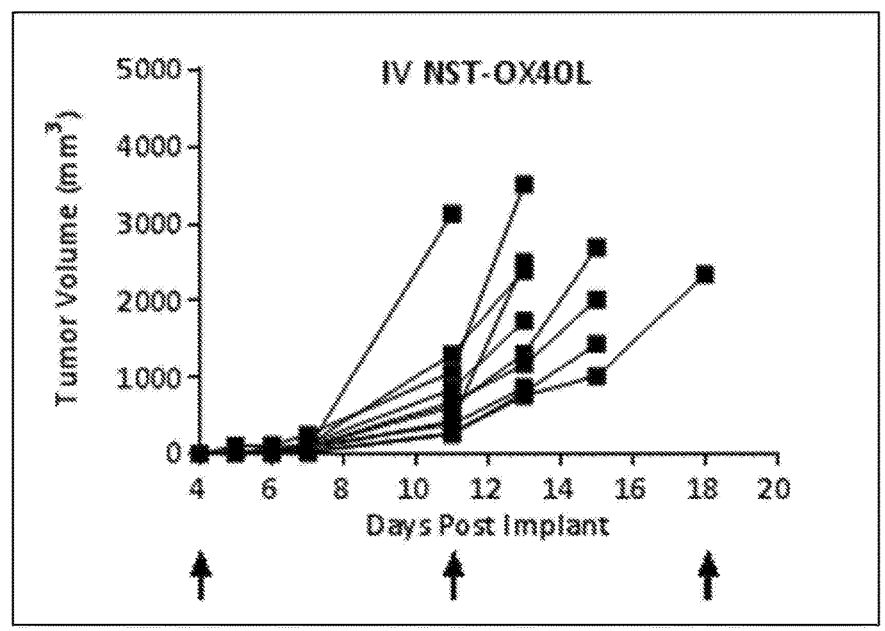
Figure 18D:
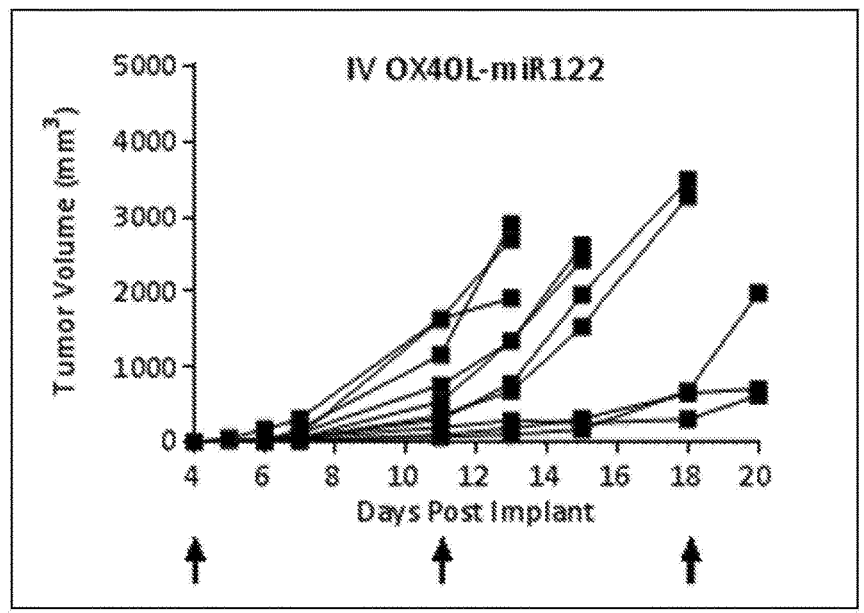
Figure 18E:
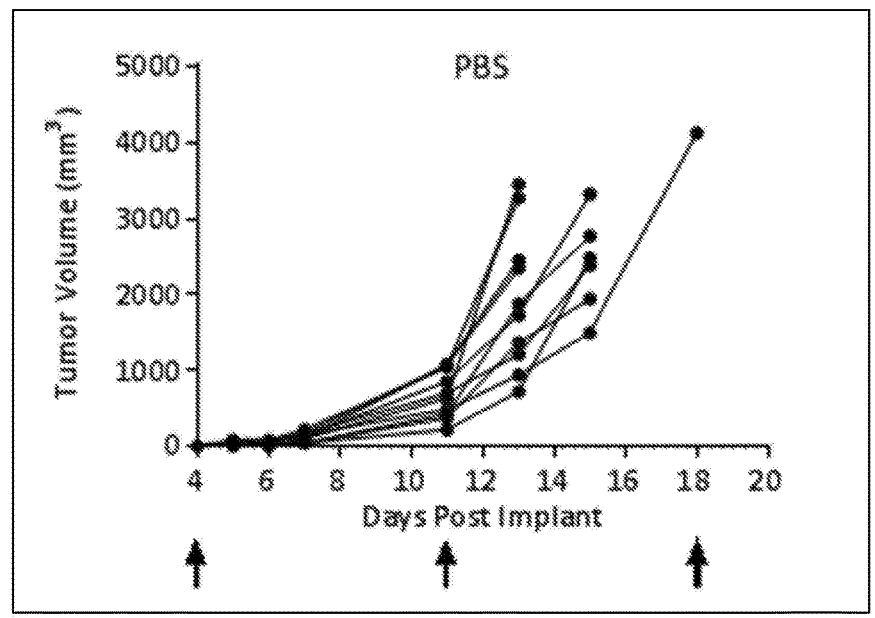

FIG. 18A-18E show in vivo anti-tumor efficacy of mOX40L_miR122 delivered intratumorally or intravenously. FIG. 18A shows tumor growth in animals treated intratumorally with control mRNA ("NST-OX40L") (arrows mark injection days). FIG. 18B shows tumor growth in animals treated intratumorally with mOX40L_miR122 mRNA ("OX40L-miR122") (arrows mark injection days). FIG. 18C shows tumor growth in animals treated intravenously with control mRNA ("NST-OX40L") (arrows mark injection days). FIG. 18D shows tumor growth in animals treated intravenously with mOX40L_miR122 mRNA ("OX40L-miR122") (arrows mark injection days). FIG. 18E shows tumor growth in animals treated intravenously with PBS (arrows mark injection days).

Figure 19:
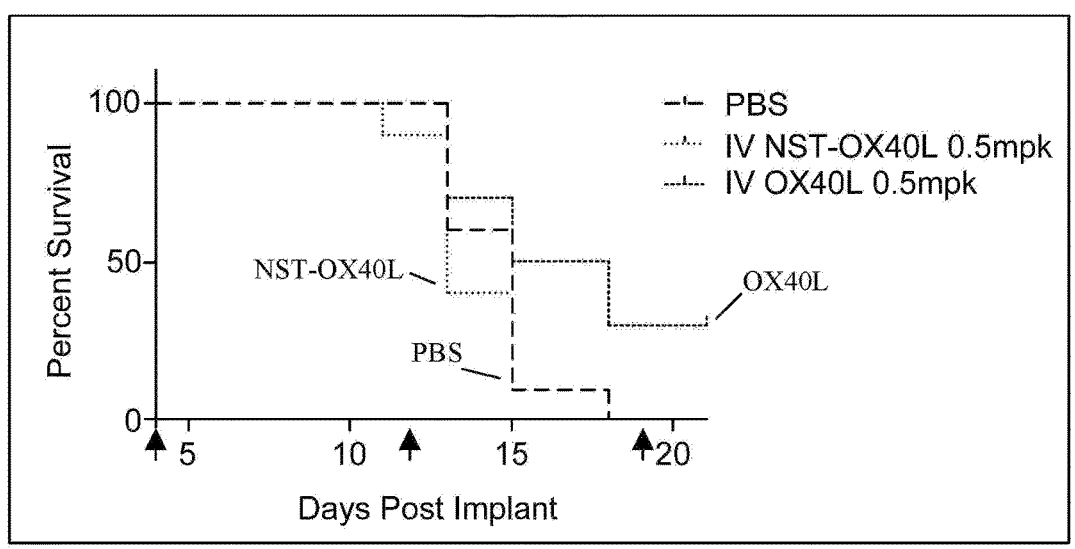

FIG. 19 shows survival curves for animals treated intravenously with PBS, negative control mRNA ("NST-OX40L"), or mOX40L-miR122 mRNA ("OX40L"). Dose days are indicated by arrows.

Figure 20A:
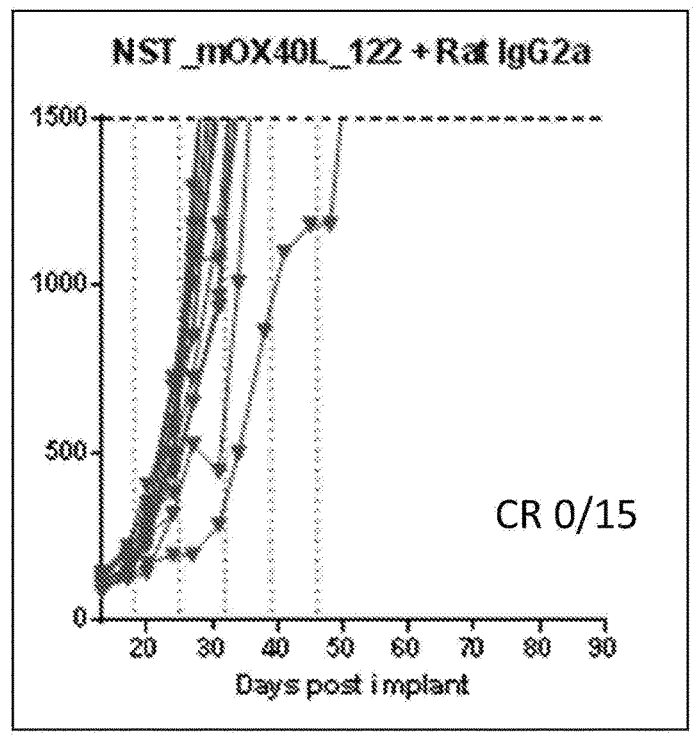
Figure 20B:
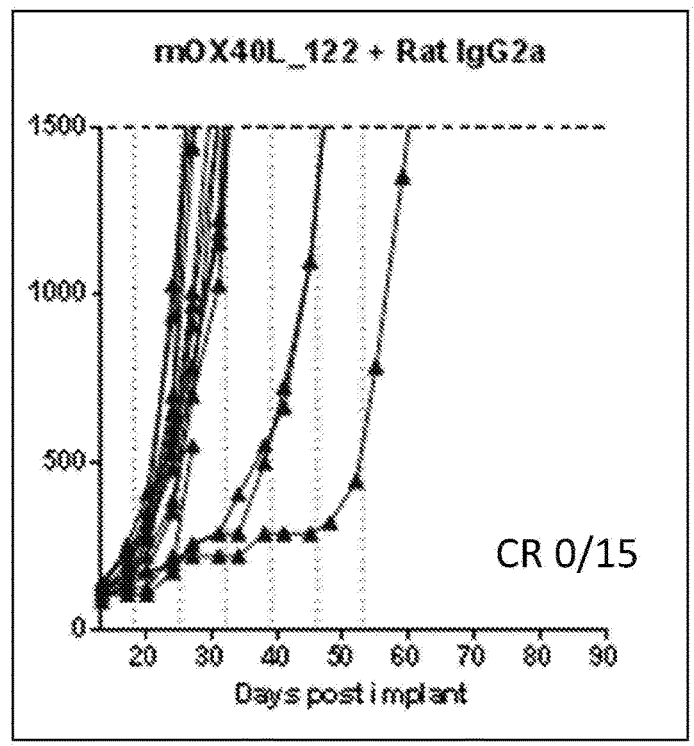
Figure 20C:
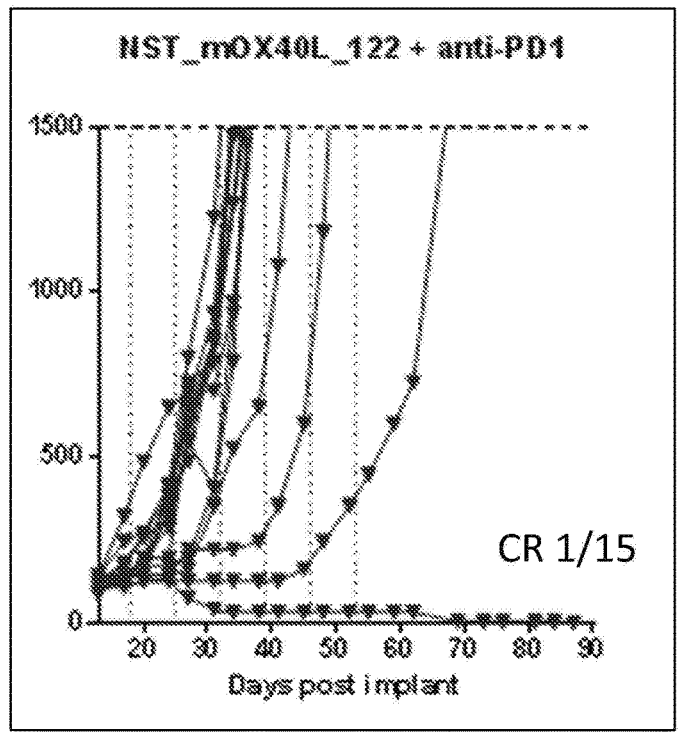
Figure 20D:
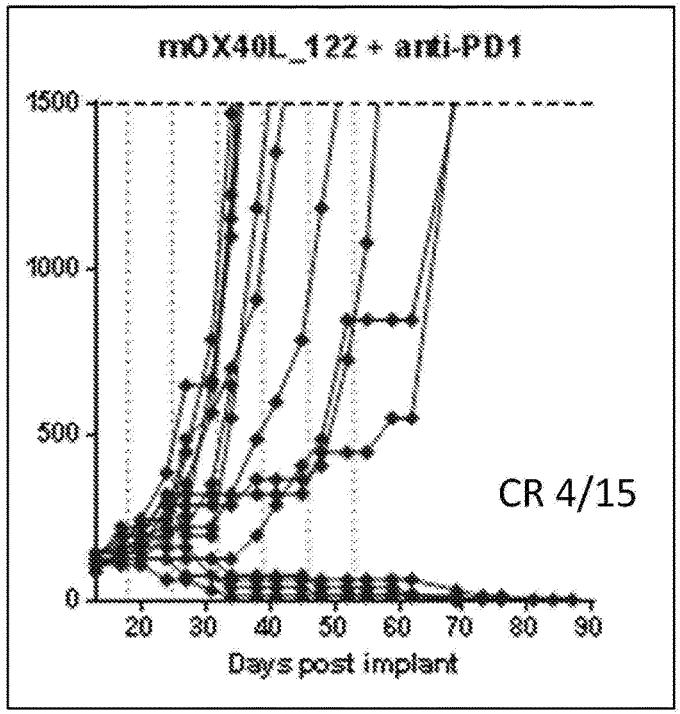
Figure 20E:
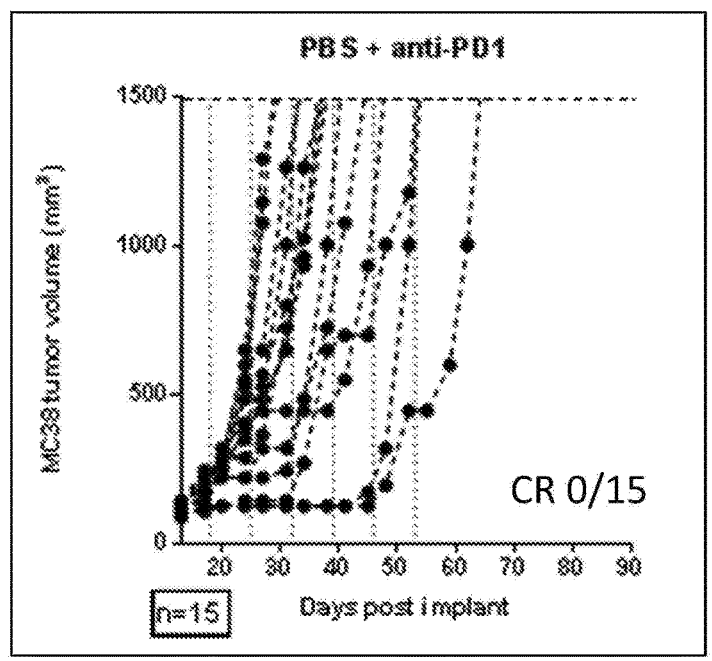
Figure 20F:
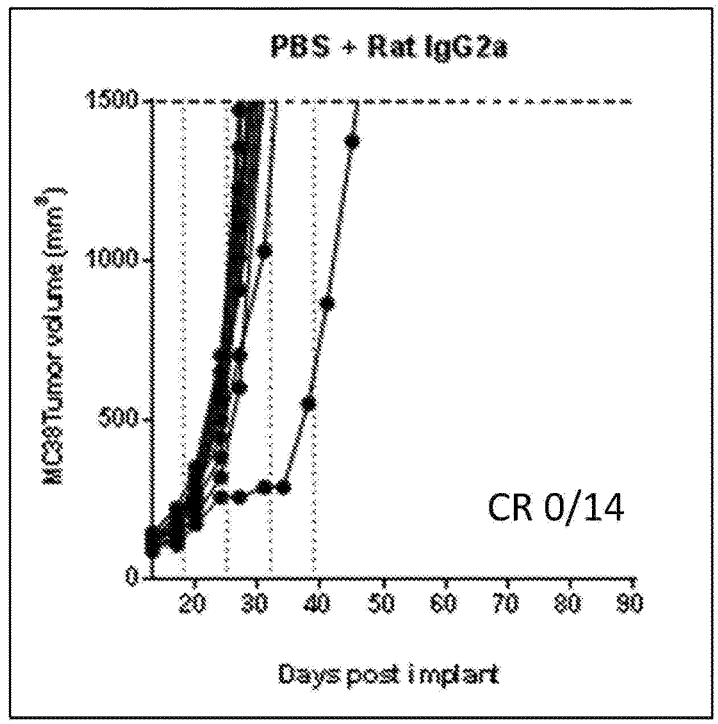

FIG. 20A-20F show in vivo anti-tumor efficacy of combination therapy comprising a polynucleotide comprising an mRNA encoding an OX40L polypeptide and an anti-PD-1 antibody. FIG. 20A shows tumor growth in animals treated with intratumoral injections of control mRNA ("NST_mOX40L_122") and control antibody ("Rat IgG2a"). FIG. 20B shows tumor growth in animals treated with intratumoral injections of mOX40L_miR122 ("mOX40L_122") and control antibody ("Rat IgG2a"). FIG. 20C shows tumor growth in animals treated with intratumoral injections of control mRNA ("NST_mOX40L_122") and anti-PD-1 antibody ("anti-PD-1"). FIG. 20D shows tumor growth in animals treated with intratumoral injections of mOX40L_miR122 ("mOX40L_122") and anti-PD-1 antibody ("anti-PD-1"). FIG. 20E shows tumor growth in animals treated with intratumoral injections of anti-PD-1 antibody and PBS. FIG. 20F shows tumor growth in animals treated with PBS and control antibody ("Rat IgG2a"). CR=complete responder.

Figure 21:
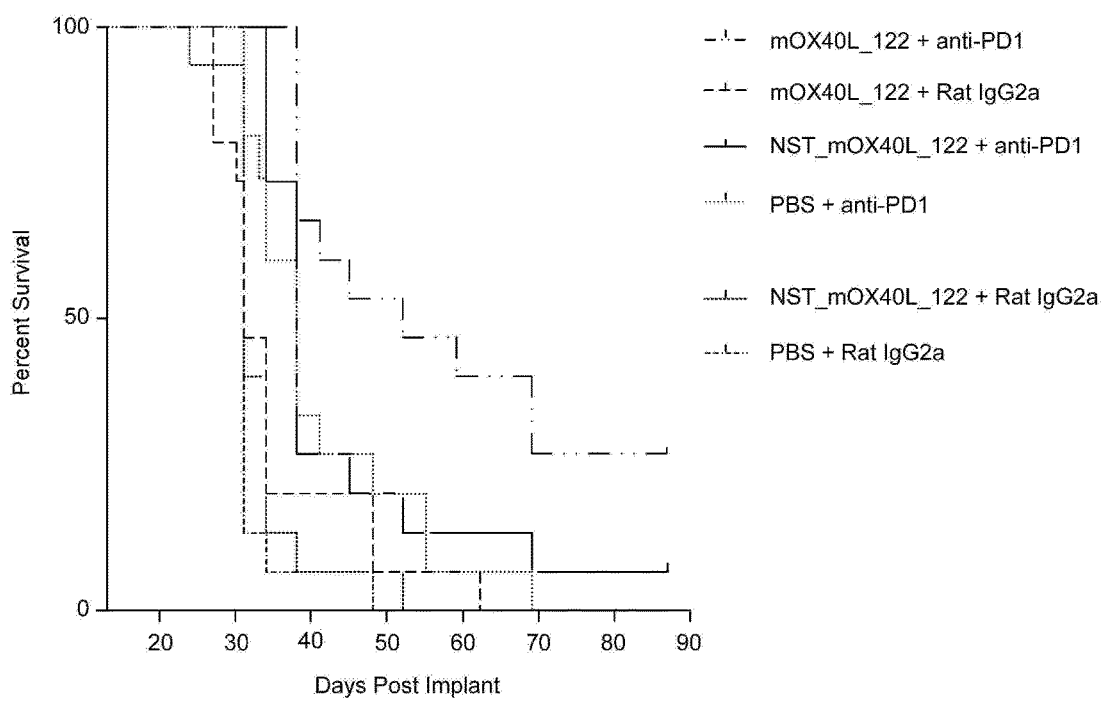

FIG. 21 shows survival curves for animals treated intratumorally with combination therapy comprising control mRNA and control antibody ("NST_mOX40L_122+Rat IgG2a"), mOX40L_miR122 and control antibody ("mOX40L_122+Rat IgG2a"), control mRNA and anti-PD-1 antibody ("NST_mOX40L_122+anti-PD-1"), mOX40L_miR122 and anti-PD-1 antibody ("mOX40L_122+anti-PD-1"), anti-PD-1 antibody and PBS ("PBS+anti-PD-1"), and PBS and control antibody ("PBS+Rat IgG2a").

Figure 22A:
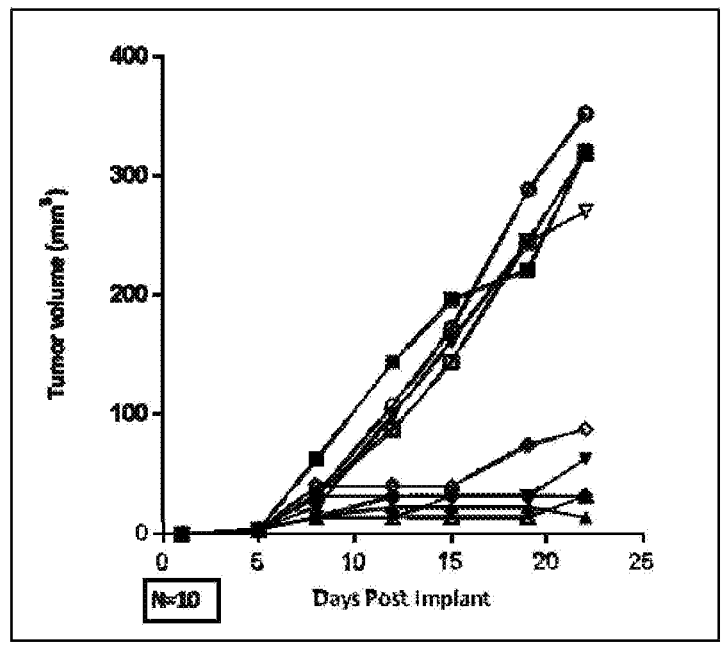
Figure 22B:
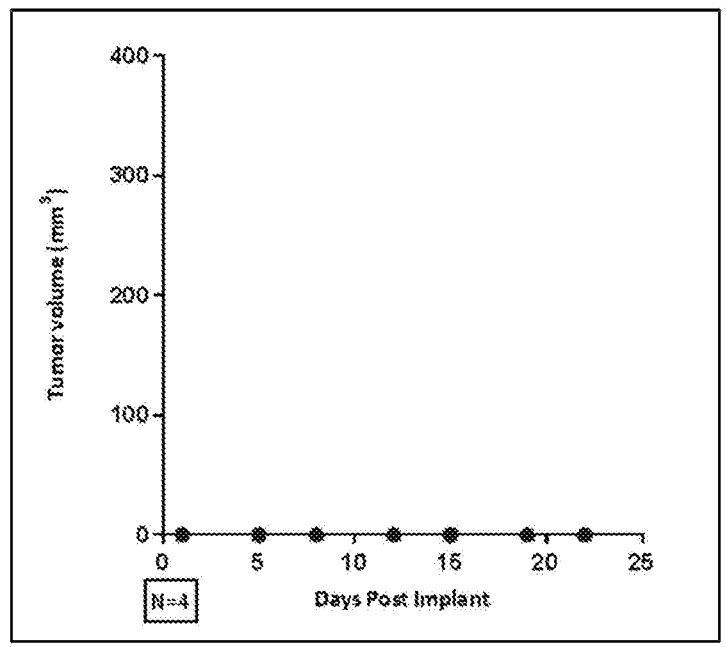

FIG. 22A-22B show a memory immune response in animals treated with combination therapy comprising a polynucleotide comprising an mRNA encoding an OX40L polypeptide and a miR122 binding site and an anti-PD-1 antibody. Animals were initially treated with intratumoral injections of mOX40L_miR122 and anti-PD-1 antibody as shown in FIG. 20D. Four animals identified as complete responders (CR) were re-challenged with MC38 tumor cells. FIG. 22A shows individual tumor growth in naïve animals challenged with MC38 tumor cells. FIG. 22B shows individual tumor growth in the four CR animals re-challenged with MC38 tumor cells.

DETAILED DESCRIPTION

The present application is directed to methods of activating T cells or increasing the number of Natural Killer (NK) cells in a subject using a polynucleotide comprising an mRNA encoding an OX40L polypeptide. The polynucleotide described herein can further reduce or decrease a size of a tumor or inhibit a tumor growth in a subject in need thereof by providing a polynucleotide comprising an mRNA which encodes an OX40L polypeptide.

The headings provided herein are not limitations of the various aspects or aspects of the disclosure, which can be defined by reference to the specification as a whole. Accordingly, the terms defined immediately below are more fully defined by reference to the specification in its entirety. Before describing the present disclosure in detail, it is to be understood that this disclosure is not limited to specific compositions or process steps, as such can vary.

I. Definitions

In order that the present disclosure can be more readily understood, certain terms are first defined. As used in this application, except as otherwise expressly provided herein, each of the following terms shall have the meaning set forth below. Additional definitions are set forth throughout the application.

The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. In general, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Amino acid substitution: The term "amino acid substitution" refers to replacing an amino acid residue present in a parent sequence (e.g., a consensus sequence) with another amino acid residue. An amino acid can be substituted in a parent sequence, for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally present at position n, and Y is the substituting amino acid residue. In other aspects, substitution patterns can be described according to the schema An(YZ), wherein A is the single letter code corresponding to the amino acid residue substituting the amino acid naturally present at position X, and Y and Z are alternative substituting amino acid residue, i.e., In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Conservative amino acid substitution: A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a tumor, an effective amount of an agent is, for example, an amount sufficient to reduce or decrease a size of a tumor or to inhibit a tumor growth, as compared to the response obtained without administration of the agent. The term "effective amount" can be used interchangeably with "effective dose," "therapeutically effective amount," or "therapeutically effective dose."

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988). Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

Immune Response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Isolated: As used herein, the term "isolated" refers to a substance or entity that has been separated from at least some of the components with which it was associated (whether in nature or in an experimental setting). Isolated substances (e.g., nucleotide sequence or protein sequence) can have varying levels of purity in reference to the substances from which they have been associated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A, C, T and U in the case of a synthetic DNA, or A, C, T, and U in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding RNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Nucleic Acid Sequence: The terms "nucleic acid sequence," "nucleotide sequence," or "polynucleotide" are used interchangeably and refer to a contiguous nucleic acid sequence. The sequence can be either single stranded or double stranded DNA or RNA, e.g., an mRNA.

The phrase "nucleotide sequence encoding" and variants thereof refers to the nucleic acid (e.g., an mRNA or DNA molecule) coding sequence that comprises a nucleotide sequence which encodes a polypeptide or functional fragment thereof as set forth herein. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single OX40L polypeptide or can be a multi-molecular complex such as a dimer, trimer or tetramer. They can also comprise single chain or multi-chain polypeptides. Most commonly disulfide linkages are found in multichain polypeptides. The term polypeptide can also apply to amino acid polymers in which one or more amino acid residues are an artificial chemical analogue of a corresponding naturally occurring amino acid.

Prophylaxis: As used herein, a "prophylaxis" refers to a measure taken to maintain health and prevent the spread of disease. An "immune prophylaxis" refers to a measure to produce active or passive immunity to prevent the spread of disease.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine ($\psi$m).

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the OX40 receptor.

Similarity: As used herein, the term "similarity" refers to the overall relatedness between polymeric molecules, e.g.

between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of a cancer treatment.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a hyper-proliferative disease, e.g., cancer. For example, "treating" cancer can refer to inhibiting survival, growth, and/or spread of a tumor. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified can, but does not always, refer to the wild type or native form of a biomolecule. Molecules can undergo a series of modifications whereby each modified molecule can serve as the "unmodified" starting molecule for a subsequent modification.

II. Methods of Use

The methods of the present disclosure provide for the use of a polynucleotide comprising an mRNA encoding an OX40L polypeptide.

Human OX40L was first identified on the surface of human lymphocytes infected with human T-cell leukemia virus type-I (HTLV-I) by Tanaka et al. (Tanaka et al., International Journal of Cancer (1985), 36(5):549-55). Human OX40L is a 34 kDa glycosylated type II transmembrane protein that exists on the surface of cells as a trimer. OX40L comprises a cytoplasmic domain (amino acids 1-23), a transmembrane domain (amino acids 24-50) and an extracellular domain (amino acids 51-183). OX40L is also referred to as Tumor Necrosis Factor Superfamily (ligand) Member 4 (TNFSF4), CD252, CD134L, Tax-Transcriptionally Activated Glycoprotein 1 (TXGP1), Glycoprotein 34 (GP34), and ACT-4-L.

Thus, the present disclosure provides a method of activating T cells in a subject in need thereof comprising administering to the subject a polynucleotide comprising an mRNA encoding an OX40L polypeptide. In one aspect, the activation of T cells in the subject is directed to an anti-tumor immune response in the subject. In another aspect, the activated T cells in the subject reduce or decrease the size of a tumor or inhibit the growth of a tumor in the subject. Activation of T cells can be measured using applications in the art such as measuring T cell proliferation; measuring cytokine production with enzyme-linked immunosorbant assays (ELISA) or enzyme-linked immunospot assays (ELISPOT); or detection of cell-surface markers associated with T cell activation (e.g., CD69, CD40L, CD137, CD25, CD71, CD26, CD27, CD28, CD30, CD154, and CD134) with techniques such as flow cytometry.

In some embodiments, the present disclosure provides a method of inducing T cell proliferation in a subject in need thereof comprising administering to the subject a polynucleotide comprising an mRNA encoding an OX40L polypeptide. In one aspect, the T cell proliferation in the subject is directed to an anti-tumor immune response in the subject. In another aspect, the T cell proliferation in the subject reduces or decreases the size of a tumor or inhibits the growth of a tumor in the subject. T cell proliferation can be measured using applications in the art such as cell counting, viability staining, optical density assays, or detection of cell-surface markers associated with T cell activation (e.g., CD69, CD40L, CD137, CD25, CD71, CD26, CD27, CD28, CD30, CD154, and CD134) with techniques such as flow cytometry.

In other embodiments, the present disclosure provides a method of inducing T cell infiltration in a tumor of a subject in need thereof comprising administering to the subject a polynucleotide comprising an mRNA encoding an OX40L polypeptide. In one aspect, the T cell infiltration in a tumor of the subject is directed to an anti-tumor immune response in the subject. In another aspect, the T cell infiltration in a tumor of the subject reduces or decreases the size of a tumor or inhibits the growth of a tumor in the subject. T cell infiltration in a tumor can be measured using applications in the art such as tissue sectioning and staining for cell markers, measuring local cytokine production at the tumor site, or detection of T cell-surface markers with techniques such as flow cytometry.

In other embodiments, the present disclosure provides a method of inducing a memory T cell response in a subject in need thereof comprising administering to the subject a polynucleotide comprising an mRNA encoding an OX40L polypeptide. In one aspect, the memory T cell response in the subject is directed to an anti-tumor immune response in the subject. In another aspect, the memory T cell response in the subject reduces or decreases the size of a tumor or inhibits the growth of a tumor in the subject. A memory T cell response can be measured using applications in the art such as measuring T cell markers associated with memory T cells, measuring local cytokine production related to memory immune response, or detecting memory T cell-surface markers with techniques such as flow cytometry.

In certain embodiments, the activated T cells by the present methods are $CD4^+$ cells, $CD8^+$ cells, $CD62^+$ (L-selectin$^+$) cells, $CD69^+$ cells, $CD40L^+$ cells, $CD137^+$ cells, CD25+ cells, CD71+ cells, CD26+ cells, CD27+ cells, CD28+ cells, CD30+ cells, CD45+ cells, CD45RA+ cells, CD45RO+ cells, CD11b+ cells, CD154+ cells, CD134+ cells, CXCR3+ cells, CCR4+ cells, CCR6+ cells, CCR7+ cells, CXCR5+ cells, Crth2+ cells, gamma delta T cells, or any combination thereof. In some embodiments, the activated T cells by the present methods are $Th_1$ cells. In other embodiments, the T cells activated by the present methods are $Th_2$ cells. In other embodiments, the T cells activated by the present disclosure are cytotoxic T cells.

In some embodiments, the infiltrating T cells by the present methods are CD4+ cells, CD8+ cells, CD62+ (L-selectin+) cells, CD69+ cells, CD40L+ cells, CD137+ cells, CD25+ cells, CD71+ cells, CD26+ cells, CD27+ cells, CD28+ cells, CD30+ cells, CD45+ cells, CD45RA+ cells, CD45RO+ cells, CD11b+ cells, CD154+ cells, CD134+ cells, CXCR3+ cells, CCR4+ cells, CCR6+ cells, CCR7+ cells, CXCR5+ cells, Crth2+ cells, gamma delta T cells, or any combination thereof. In some embodiments, the infiltrating T cells by the present methods are $Th_1$ cells. In other embodiments, the infiltrating T cells by the present methods are $Th_2$ cells. In other embodiments, the infiltrating T cells by the present disclosure are cytotoxic T cells.

In some embodiments, the memory T cells induced by the present methods are CD4+ cells, CD8+ cells, CD62+ (L-selectin+) cells, CD69+ cells, CD40L+ cells, CD137+ cells, CD25+ cells, CD71+ cells, CD26+ cells, CD27+ cells, CD28+ cells, CD30+ cells, CD45+ cells, CD45RA+ cells, CD45RO+ cells, CD11b+ cells, CD154+ cells, CD134+ cells, CXCR3+ cells, CCR4+ cells, CCR6+ cells, CCR7+ cells, CXCR5+ cells, Crth2+ cells, gamma delta T cells, or any combination thereof. In some embodiments, the memory T cells by the present methods are $Th_1$ cells. In other embodiments, the memory T cells by the present methods are $Th_2$ cells. In other embodiments, the memory T cells by the present disclosure are cytotoxic T cells.

The present disclosure further provides a method of increasing the number of Natural Killer (NK) cells in a subject in need thereof comprising administering a polynucleotide comprising an mRNA encoding an OX40L polypeptide. In one aspect, the increase in the number of NK cells in the subject is directed to an anti-tumor immune response in the subject. In another aspect, the increase in the number of NK cells in the subject reduces or decreases the size of a tumor or inhibits the growth of a tumor in the subject. Increases in the number of NK cells in a subject can be measured using applications in the art such as detection of NK cell-surface markers (e.g., CD335/NKp46; CD336/NKp44; CD337NPp30) or intracellular NK cell markers (e.g., perforin; granzymes; granulysin).

In certain embodiments, administration of the mRNA encoding an OX40L polypeptide increases the total number of NK cells in the subject compared to the number of NK cells in a subject who is not administered with the mRNA encoding an OX40L polypeptide. In other embodiments, administration of the mRNA encoding an OX40L polypeptide increases the total number of NK cells in the subject compared to a subject who is administered a dendritic cell transduced with the mRNA encoding an OX40L polypeptide. In other embodiments, administration of the mRNA encoding an OX40L polypeptide increases the number of NK cells in the subject within the tumor microenvironment compared to that of a subject who is not administered with the mRNA encoding the OX40L polypeptide. In other embodiments, administration of the mRNA encoding an OX40L polypeptide increases the number of NK cells in a subject within the tumor microenvironment compared to that of a subject who is administered a dendritic cell transduced with the mRNA encoding an OX40L polypeptide. In other embodiments, the concentration of NK cells within the tumor microenvironment is increased while the total number of NK cells in the subject remains the same.

In certain embodiments of the disclosure, the number of NK cells is increased at least about two-fold, at least about three-fold, at least about four-fold, at least about five-fold, at least about six-fold, at least about seven-fold, at least about eight-fold, at least about nine-fold, or at least about ten-fold compared to a control (e.g., saline or an mRNA without OX40L expression). In a particular embodiment, the number of NK cells is increased by the mRNA encoding an OX40L polypeptide at least about two-fold compared to a control (e.g., saline or an mRNA without OX40L expression).

The present disclosure further provides a method of increasing IL-2 in a subject in need thereof comprising administering a polynucleotide comprising an mRNA encoding an OX40L polypeptide to increase IL-2 in the subject in need thereof. In one aspect, the increase in IL-2 in the subject is directed to an anti-tumor immune response in the subject. In one embodiment, the increase in IL-2 expression by the polynucleotide comprising an mRNA encoding an OX40L polypeptide is at least about two-fold, at least about three-fold, at least about four-fold, at least about five-fold, or at least about six-fold higher than a control (e.g., PBS treated). The IL-2 expression can be measured using any available techniques, such as ELISA or ELISPOT assays.

In other aspects, the present disclosure provides a method of increasing IL-4 in a subject in need thereof comprising administering a polynucleotide comprising an mRNA encoding an OX40L polypeptide to increase IL-4 in the subject in need thereof. In one aspect, the increase in IL-4 in the subject is directed to an anti-tumor immune response in the subject. In one embodiment, the increase in IL-4 expression by the polynucleotide comprising an mRNA encoding an OX40L polypeptide is at least about two-fold, at least about three-fold, at least about four-fold, at least about five-fold, or at least about six-fold higher than a control (e.g., PBS treated). The IL-4 expression can be measured using any available techniques, such as ELISA or ELISPOT assays.

In other aspects, the present disclosure provides a method of increasing IL-21 in a subject in need thereof comprising administering a polynucleotide comprising an mRNA encoding an OX40L polypeptide to increase IL-21 in the subject in need thereof. In one aspect, the increase in IL-21 in the subject is directed to an anti-tumor immune response in the subject. In one embodiment, the increase in IL-21 expression by the polynucleotide comprising an mRNA encoding an OX40L polypeptide is at least about two-fold, at least about three-fold, at least about four-fold, at least about five-fold, or at least about six-fold higher than a control (e.g., PBS treated). The IL-21 expression can be measured using any available techniques, such as ELISA or ELISPOT assays.

The polynucleotide (e.g., mRNA) of the present disclosure can be administered in any route available, including, but not limited to, intratumoral, enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraperitoneal (into the peritoneum), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In other embodiments, the mRNA of the present disclosure is administered parenterally (e.g., includes subcutaneous, intravenous, intraperitoneal, intratumoral, intramuscular, intra-articular, intra-synovial, intrasternal, intrathecal, intrahepatic, intralesional and intracranial injection or infusion techniques), intraventricularly, orally, by inhalation spray, topically, rectally, nasally, buccally, vaginally or via an implanted reservoir.

The present disclosure also includes a method of activating T cells in a subject in need thereof comprising intratumorally administering a polynucleotide comprising an mRNA encoding an OX40L polypeptide. In certain embodiments, the intratumoral administration of the present mRNA can increase the efficacy of the anti-tumor effect (e.g., T cell activation) compared to other routes of administration.

The present disclosure also includes a method of inducing T cell proliferation in a subject in need thereof comprising intratumorally administering a polynucleotide comprising an mRNA encoding an OX40L polypeptide. In certain embodiments, the intratumoral administration of the present mRNA can increase the efficacy of the anti-tumor effect (e.g., T cell proliferation) compared to other routes of administration.

The present disclosure also includes a method of inducing T cell infiltration in a tumor in a subject in need thereof comprising intratumorally administering a polynucleotide comprising an mRNA encoding an OX40L polypeptide. In certain embodiments, the intratumoral administration of the present mRNA can increase the efficacy of the anti-tumor effect (e.g., T cell infiltration in a tumor) compared to other routes of administration.

The present disclosure also includes a method of inducing a memory T cells response in a subject in need thereof comprising intratumorally administering a polynucleotide comprising an mRNA encoding an OX40L polypeptide. In certain embodiments, the intratumoral administration of the present mRNA can increase the efficacy of the anti-tumor effect (e.g., memory T cell response) compared to other routes of administration.

The present disclosure also includes a method of increasing the number of NK cells in a subject in need thereof comprising intratumorally administering a polynucleotide comprising an mRNA encoding an OX40L polypeptide. In certain embodiments, the intratumoral administration of the present mRNA can increase the efficacy of the anti-tumor effect (e.g., NK cell increase) compared to other routes of administration. The mRNA of the present disclosure can be formulated specifically for the intratumoral delivery as shown elsewhere herein.

The present disclosure further provides a method of increasing IL-2 in a subject in need thereof comprising intratumorally administering a polynucleotide comprising an mRNA encoding an OX40L polypeptide to the subject. In one aspect, the increase in IL-2 in the subject is directed to an anti-tumor immune response in the subject.

The present disclosure further provides a method of increasing IL-4 in a subject in need thereof comprising intratumorally administering a polynucleotide comprising an mRNA encoding an OX40L polypeptide to the subject. In one aspect, the increase in IL-4 in the subject is directed to an anti-tumor immune response in the subject.

The present disclosure further provides a method of increasing IL-21 in a subject in need thereof comprising intratumorally administering a polynucleotide comprising an mRNA encoding an OX40L polypeptide to the subject. In one aspect, the increase in IL-21 in the subject is directed to an anti-tumor immune response in the subject.

The present disclosure also includes a method of activating T cells in a subject in need thereof comprising intraperitoneally administering a polynucleotide comprising an mRNA encoding an OX40L polypeptide. In certain embodiments, the intraperitoneal administration of the present mRNA can increase the efficacy of the anti-tumor effect (e.g., T cell activation) compared to other routes of administration.

The present disclosure also includes a method of inducing T cell proliferation in a subject in need thereof comprising intraperitoneally administering a polynucleotide comprising an mRNA encoding an OX40L polypeptide. In certain embodiments, the intraperitoneal administration of the present mRNA can increase the efficacy of the anti-tumor effect (e.g., T cell proliferation) compared to other routes of administration.

The present disclosure also includes a method of inducing T cell infiltration in a tumor in a subject in need thereof comprising intraperitoneally administering a polynucleotide comprising an mRNA encoding an OX40L polypeptide. In certain embodiments, the intraperitoneal administration of the present mRNA can increase the efficacy of the anti-tumor effect (e.g., T cell infiltration in a tumor) compared to other routes of administration.

The present disclosure also includes a method of inducing a memory T cells response in a subject in need thereof comprising intraperitoneally administering a polynucleotide comprising an mRNA encoding an OX40L polypeptide. In certain embodiments, the intraperitoneal administration of the present mRNA can increase the efficacy of the anti-tumor effect (e.g., memory T cell response) compared to other routes of administration.

The present disclosure also includes a method of increasing the number of NK cells in a subject in need thereof comprising intraperitoneal administering a polynucleotide comprising an mRNA encoding an OX40L polypeptide. In certain embodiments, the intraperitoneal administration of the present mRNA can increase the efficacy of the anti-tumor effect (e.g., NK cell increase) compared to other routes of administration. The mRNA of the present disclosure can be formulated specifically for the intraperitoneal delivery as shown elsewhere herein.

The present disclosure further provides a method of increasing IL-2 in a subject in need thereof comprising intraperitoneally administering a polynucleotide comprising an mRNA encoding an OX40L polypeptide to the subject. In one aspect, the increase in IL-2 in the subject is directed to an anti-tumor immune response in the subject.

The present disclosure further provides a method of increasing IL-4 in a subject in need thereof comprising intraperitoneally administering a polynucleotide comprising an mRNA encoding an OX40L polypeptide to the subject. In one aspect, the increase in IL-4 in the subject is directed to an anti-tumor immune response in the subject.

The present disclosure further provides a method of increasing IL-21 in a subject in need thereof comprising intraperitoneally administering a polynucleotide comprising an mRNA encoding an OX40L polypeptide to the subject. In one aspect, the increase in IL-21 in the subject is directed to an anti-tumor immune response in the subject.

The present disclosure also includes a method of activating T cells in a subject in need thereof comprising intravenously administering a polynucleotide comprising an mRNA encoding an OX40L polypeptide. In certain embodiments, the intravenous administration of the present mRNA can increase the efficacy of the anti-tumor effect (e.g., T cell activation) compared to other routes of administration.

The present disclosure also includes a method of inducing T cell proliferation in a subject in need thereof comprising intravenously administering a polynucleotide comprising an mRNA encoding an OX40L polypeptide. In certain embodiments, the intravenous administration of the present mRNA can increase the efficacy of the anti-tumor effect (e.g., T cell proliferation) compared to other routes of administration.

The present disclosure also includes a method of inducing T cell infiltration in a tumor in a subject in need thereof comprising intravenously administering a polynucleotide comprising an mRNA encoding an OX40L polypeptide. In certain embodiments, the intravenous administration of the present mRNA can increase the efficacy of the anti-tumor effect (e.g., T cell infiltration in a tumor) compared to other routes of administration.

The present disclosure also includes a method of inducing a memory T cell response in a subject in need thereof comprising intravenously administering a polynucleotide comprising an mRNA encoding an OX40L polypeptide. In certain embodiments, the intravenous administration of the present mRNA can increase the efficacy of the anti-tumor effect (e.g., memory T cell response) compared to other routes of administration.

The present disclosure also includes a method of increasing the number of NK cells in a subject in need thereof comprising intravenously administering a polynucleotide comprising an mRNA encoding an OX40L polypeptide. In certain embodiments, the intravenous administration of the present mRNA can increase the efficacy of the anti-tumor effect (e.g., NK cell increase) compared to other routes of administration. The mRNA of the present disclosure can be formulated specifically for the intravenous delivery as shown elsewhere herein.

The present disclosure further provides a method of increasing IL-2 in a subject in need thereof comprising intravenously administering a polynucleotide comprising an mRNA encoding an OX40L polypeptide to the subject. In one aspect, the increase in IL-2 in the subject is directed to an anti-tumor immune response in the subject.

The present disclosure further provides a method of increasing IL-4 in a subject in need thereof comprising intravenously administering a polynucleotide comprising an mRNA encoding an OX40L polypeptide to the subject. In one aspect, the increase in IL-4 in the subject is directed to an anti-tumor immune response in the subject.

The present disclosure further provides a method of increasing IL-21 in a subject in need thereof comprising intravenously administering a polynucleotide comprising an mRNA encoding an OX40L polypeptide to the subject. In one aspect, the increase in IL-21 in the subject is directed to an anti-tumor immune response in the subject.

The present disclosure further includes a method of activating T cells in a subject in need thereof comprising administering (e.g., intratumorally, intraperitoneally, or intravenously) a polynucleotide comprising an mRNA encoding an OX40L polypeptide as a monotherapy, i.e., without any other anti-cancer agent in combination. The present disclosure also provides a method of increasing the number of Natural Killer (NK) cells in a subject in need thereof comprising administering (e.g., intratumorally, intraperitoneally, or intravenously) a polynucleotide comprising an mRNA encoding an OX40L polypeptide as a monotherapy. Some embodiments of the disclosure also include a method of increasing IL-2, IL-4, IL-21, or any combination thereof in a subject in need thereof comprising administering (e.g., intratumorally, intraperitoneally, or intravenously) a polynucleotide comprising an mRNA encoding an OX40L polypeptide as a monotherapy.

In certain embodiments, the disclosure is directed to a method of activating T cells in a subject in need thereof comprising administering (e.g., intratumorally, intraperitoneally, or intravenously) a polynucleotide comprising an mRNA encoding an OX40L polypeptide in combination with one or more anti-cancer agents to the subject. In other embodiments, the disclosure includes a method of increasing the number of NK cells in a subject in need thereof comprising administering (e.g., intratumorally, intraperitoneally, or intravenously) a polynucleotide comprising an mRNA encoding an OX40L polypeptide in combination with one or more anti-cancer agents to the subject. Other embodiments of the disclosure also provides a method of increasing IL-2, IL-4, IL-21, or any combination thereof in a subject in need thereof comprising administering (e.g., intratumorally, intraperitoneally, or intravenously) a polynucleotide comprising an mRNA encoding an OX40L polypeptide with one or more anti-cancer agents to the subject. In some embodiments, the one or more anti-cancer agents are an mRNA. In certain embodiments, the one or more anti-cancer agents are an mRNA encoding a tumor antigen. In other embodiments, the one or more anti-cancer agents are not a tumor antigen or an mRNA encoding a tumor antigen.

In some embodiments, the one or more anti-cancer agents are an approved agent by the United States Food and Drug Administration. In other embodiments, the one or more anti-cancer agents are a pre-approved agent by the United States Food and Drug Administration.

In some aspects, the subject for the present methods has been treated with one or more standard of care therapies. In other aspects, the subject for the present methods has not been responsive to one or more standard of care therapies or anti-cancer therapies. In one aspect, the subject has been previously treated with a PD-1 antagonist prior to the polynucleotide of the present disclosure. In another aspect, the subject has been treated with a monoclonal antibody that binds to PD-1 prior to the polynucleotide of the present disclosure. In another aspect, the subject has been treated with an anti-PD-1 monoclonal antibody therapy prior to the polynucleotide of the present methods. In other aspects, the anti-PD-1 monoclonal antibody therapy comprises Nivolumab, Pembrolizumab, Pidilizumab, or any combination thereof. In another aspect, the subject has been treated with a monoclonal antibody that binds to PD-L1 prior to the polynucleotide of the present disclosure. In another aspect, the subject has been treated with an anti-PD-L1 monoclonal antibody therapy prior to the polynucleotide of the present methods. In other aspects, the anti-PD-L1 monoclonal antibody therapy comprises Durvalumab, Avelumab, MEDI473, BMS-936559, Atezolizumab, or any combination thereof.

In some aspects, the subject has been treated with a CTLA-4 antagonist prior to the polynucleotide of the present disclosure. In another aspect, the subject has been previously treated with a monoclonal antibody that binds to CTLA-4 prior to the polynucleotide of the present disclosure. In another aspect, the subject has been treated with an anti-CTLA-4 monoclonal antibody prior to the polynucleotide of the present disclosure. In other aspects, the anti-CTLA-4 antibody therapy comprises Ipilimumab or Tremelimumab.

In some aspects, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with a PD-1 antagonist. In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-1. In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an anti-PD-1 monoclonal antibody.

In one embodiment, the anti-PD-1 antibody (or an antigen-binding portion thereof) useful for the disclosure is pembrolizumab. Pembrolizumab (also known as "KEYTRUDA", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www-.cancer.gov/drugdictionary?cdrid=695789 (last accessed: Dec. 14, 2014). Pembrolizumab has been approved by the FDA for the treatment of relapsed or refractory melanoma and advanced NSCLC.

In another embodiment, the anti-PD-1 antibody useful for the disclosure is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223.

In other embodiments, the anti-PD-1 antibody is MEDI0680 (formerly AMP-514), which is a monoclonal antibody against the PD-1 receptor MEDI0680 is described, for example, in U.S. Pat. No. 8,609,089B2 or in http://www.cancer.gov/drugdictionary?cdrid=756047 (last accessed Dec. 14, 2014).

In certain embodiments, the anti-PD-1 antibody is BGB-A317, which is a humanized monoclonal antibody. BGB-A317 is described in U.S. Publ. No. 2015/0079109.

In certain embodiments, a PD-1 antagonist is AMP-224, which is a B7-DC Fc fusion protein. AMP-224 is discussed in U.S. Publ. No. 2013/0017199 or in http://www.cancer-.gov/publications/dictionaries/cancer-drug?cdrid=700595 (last accessed Jul. 8, 2015).

In other embodiments, the disclosure includes a method of increasing the number of NK cells in a subject in need thereof comprising administering to the subject (e.g., intratumorally, intraperitoneally, or intravenously) a polynucleotide comprising an mRNA encoding an OX40L polypeptide in combination with a PD-1 antagonist. In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-1. In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an anti-PD-1 monoclonal antibody. In other aspects, the anti-PD-1 monoclonal antibody comprises Nivolumab, Pembrolizumab, Pidilizumab, or any combination thereof.

In other embodiments, the disclosure includes a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with a PD-1 antagonist. In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-1. In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an anti-PD-1 monoclonal antibody. In other aspects, the anti-PD-1 monoclonal antibody comprises Nivolumab, Pembrolizumab, Pidilizumab, or any combination thereof.

In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-L1. In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an anti-PD-L1 monoclonal antibody. In other aspects, the anti-PD-L1 monoclonal antibody comprises Durvalumab, Avelumab, MEDI473, BMS-936559, Atezolizumab, or any combination thereof.

In certain embodiments, the anti-PD-L1 antibody useful for the disclosure is MSB0010718C (also called Avelumab; See US 2014/0341917) or BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149), MEDI4736 (also called Durvalumab; Khleif (2013) In: Proceedings from the European Cancer Congress 2013; Sep. 27-Oct. 1, 2013; Amsterdam, The Netherlands.

In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-L1. In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an anti-PD-L1 monoclonal antibody. In other aspects, the anti-PD-L1 monoclonal antibody comprises Durvalumab, Avelumab, MEDI473, BMS-936559, Atezolizumab, or any combination thereof.

In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to PD-L1. In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an anti-PD-L1 monoclonal antibody. In other aspects, the anti-PD-L1 monoclonal antibody comprises Durvalumab, Avelumab, MEDI473, BMS-936559, Atezolizumab, or any combination thereof.

In some aspects, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with a CTLA-4 antagonist. In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to CTLA-4. In another aspect, the disclosure is directed to a method of activating T cells in a subject in need thereof comprising administering to the subject (e.g., intratumorally, intraperitoneally, or intravenously) a polynucleotide comprising an mRNA encoding an OX40L polypeptide in combination with an anti-CTLA-4 monoclonal antibody. In other aspects, the anti-CTLA-4 monoclonal antibody comprises Ipilimumab or Tremelimumab, or any combination thereof. In some aspects, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with a CTLA-4 antagonist. In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to CTLA-4. In another aspect, the disclosure is directed to a method of increasing the number of NK cells in a subject in need thereof comprising administering to the subject (e.g., intratumorally, intraperitoneally, or intravenously) a polynucleotide comprising an mRNA encoding an OX40L polypeptide in combination with an anti-CTLA-4 monoclonal antibody. In other aspects, the anti-CTLA-4 monoclonal antibody comprises Ipilimumab or Tremelimumab, or any combination thereof.

In some aspects, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with a CTLA-4 antagonist. In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an antibody or antigen-binding portion thereof that specifically binds to CTLA-4. In another aspect, the disclosure is directed to a method of increasing IL-2, IL-4, IL-21, or any combination thereof in a subject in need thereof comprising administering to the subject (e.g., intratumorally, intraperitoneally, or intravenously) a polynucleotide comprising an mRNA encoding an OX40L polypeptide in combination with an anti-CTLA-4 monoclonal antibody.

An exemplary clinical anti-CTLA-4 antibody is the human mAb 10D1 (now known as ipilimumab and marketed as YERVOY®) as disclosed in U.S. Pat. No. 6,984,720. Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Thus, the administration of mRNA as referred to in the present disclosure is not in the form of a dendritic cell comprising an mRNA encoding an OX40L protein. Rather, the administration in the present disclosure is a direct administration of the mRNA encoding an OX40L polypeptide to the subject (e.g., to a tumor in a subject).

Diseases, Disorders and/or Conditions

In some embodiments, the polynucleotides (e.g., mRNA) encoding an OX40L polypeptide of the present disclosure can be used to reduce or decrease a size of a tumor or inhibit a tumor growth in a subject in need thereof.

In some embodiments, the tumor is associated with a disease, disorder, and/or condition. In a particular embodiment, the disease, disorder, and/or condition is a cancer. Thus, in one aspect, the administration of the polynucleotide (e.g., mRNA) encoding an OX40L polypeptide treats a cancer.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor at various stages. In certain embodiments, the cancer or tumor is stage 0, such that, e.g., the cancer or tumor is very early in development and has not metastasized. In some embodiments, the cancer or tumor is stage I, such that, e.g., the cancer or tumor is relatively small in size, has not spread into nearby tissue, and has not metastasized. In other embodiments, the cancer or tumor is stage II or stage III, such that, e.g., the cancer or tumor is larger than in stage 0 or stage I, and it has grown into neighboring tissues but it has not metastasized, except potentially to the lymph nodes. In other embodiments, the cancer or tumor is stage IV, such that, e.g., the cancer or tumor has metastasized. Stage IV can also be referred to as advanced or metastatic cancer.

In some aspects, the cancer can include, but is not limited to, adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment.

In some aspects, the tumor is a solid tumor. A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas include, e.g., acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum.

Additional cancers that can be treated include, e.g., Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

III. Compositions

Polynucleotides

The polynucleotide of the present application comprises an mRNA encoding an OX40L polypeptide. OX40L is the ligand for OX40 (CD134). OX40L has also been designated CD252 (cluster of differentiation 252), tumor necrosis factor (ligand) superfamily, member 4, tax-transcriptionally activated glycoprotein 1, TXGP1, or gp34.

Human OX40L is 183 amino acids in length and contains three domains: a cytoplasmic domain of amino acids 1-23; a transmembrane domain of amino acids 24-50, and an extracellular domain of amino acids 51-183.

In some embodiments, the polynucleotide comprises an mRNA encoding a mammalian OX40L polypeptide. In some embodiments, the mammalian OX40L polypeptide is a murine OX40L polypeptide. In some embodiments, the mammalian OX40L polypeptide is a human OX40L polypeptide. In some embodiments, the OX40L polypeptide comprises the amino acid sequence set forth in SEQ ID NO: 1. In another embodiment, the OX40L polypeptide comprises the amino acid sequence set forth in SEQ ID NO: 2.

In some embodiments, the OX40L polypeptide comprises an amino acid sequence at least 50%, at least 60%, at least 70%, at least 80%, at least 85%, at least 90%, at least 95%, at least 99%, or 100% identical to an amino acid sequence listed in Table 1 (e.g., selected from SEQ ID NOs: 1-3) or an amino acid sequence encoded by a nucleotide sequence listed in Table 1, wherein the amino acid sequence is capable of binding to an OX40 receptor.

In other embodiments, the OX40L polypeptide useful for the disclosure comprises an amino acid sequence listed in Table 1 with one or more conservative substitutions, wherein the conservative substitutions do not affect the binding of the OX40L polypeptide to an OX40 receptor, i.e., the amino acid sequence binds to the OX40 receptor after the substitutions.

In certain embodiments, the OX40L polypeptide comprises an amino acid sequence at least 50%, at least 60%, at least 70%, at least 80%, at least 85%, at least 90%, at least 95%, at least 99%, or 100% identical to an extracellular domain of OX40L (e.g., SEQ ID NO: 2), wherein the OX40L polypeptide binds to an OX40 receptor.

In other embodiments, a nucleotide sequence (i.e., mRNA) encoding an OX40L polypeptide comprises a sequence at least 50%, at least 60%, at least 70%, at least 80%, at least 85%, at least 90%, at least 95%, at least 99%, or 100% identical to a nucleic acid sequence listed in Table 1 (e.g., selected from SEQ ID NOs: 4-21).

TABLE 1

OX40L Polypeptide and Polynucleotide Sequences

| Encoded Polypeptide | Description | Sequence | SEQ ID NO: |
|---|---|---|---|
| OX40L (TNFSF4) | Amino acid sequence of tumor necrosis factor ligand superfamily member 4 isoform 1 [Homo sapiens] NP_003317 | MERVQPLEENVGNAARPRFERNKLLLVASVI QGLGLLLCFTYICLHFSALQVSHRYPRIQSI KVQFTEYKKEKGFILTSQKEDEIMKVQNNSVI INCDGFYLISLKGYFSQEVNISLHYQKDEEPL FQLKKVRSVNSLMVASLTYKDKVYLNVTTDNT SLDDFHVNGGELILIHQNPGEFCVL | SEQ ID NO: 1 183 aa |
| OX40L (TNFSF4) | Amino acid sequence of tumor necrosis factor ligand superfamily member 4 isoform 2 [Homo sapiens] NP_001284491 | MVSHRYPRIQSIKVQFTEYKKEKGFILTSQ KEDEIMKVQNNSVIINCDGFYLISLKGYFS QEVNISLHYQKDEEPLFQLKKVRSVNSLMV ASLTYKDKVYLNVTTDNTSLDDFHVNGGEL ILIHQNPGEFCVL | SEQ ID NO: 2 133 aa |
| OX40L (TNFSF4) | Amino acid sequence of tumor necrosis factor ligand superfamily member 4 [Mus musculus] NP_033478 | MEGEGVQPLDENLENGSRPRFKWKKTLRLVVS GIKGAGMLLCFIYVCLQLSSSPAKDPPIQRLR GAVTRCEDGQLFISSYKNEYQTMEVQNNSVVI KCDGLYIIYLKGSFFQEVKIDLHFREDHNPIS IPMLNDGRRIVFTVVASLAFKDKVYLTVNAPD TLCEHLQINDGELIVVQLTPGYCAPEGSYHST VNQVPL | SEQ ID NO: 3 198 aa |
| OX40L (TNFSF4) | Nucleotide sequence of TNFSF4 tumor necrosis factor (ligand) superfamily, member 4, open reading frame [Homo sapiens] | AUGGGAAAGGGUCCAACCCCUGGAAGAGAAUGUG GGAAAUGCAGCCAGGCCAAGAUUCGAGAGGAAC AAGCUAUUGCUGGUGGCCUCUGUAAUUCAGGGA CUGGGGCUGCUCCUGUGCUUCACCUACAUCUGC CUGCACUUCUCUGCUCUUCAGGUAUCACAUCGG UAUCCUCGAAUUCAAAGUAUCAAAGUACAAUUU ACCGAAUAUAAGAAGGAGAAAGGUUUCAUCCUC ACUUCCAAAAGGAGGAUGAAAUCAUGAAGGUG CAGAACAACUCAGUCAUCAUCAACUGUGAUGGG UUUUAUCUCAUCUCCCUGAAGGGCUACUUCUCC CAGGAAGUCAACAUUAGCCUUCAUUACCAGAAG GAUGAGGAGCCCCUCUUCCAACUGAAGAAGGUC AGGUCUGUCAACUCCUUGAUGGUGGCCUCUCUG ACUUACAAAGACAAAGUCUACUUGAAUGUGACC ACUGACAAUACCUCCCUGGAUGACUUCCAUGUG AAUGGCGGAGAACUGAUUCUUAUCCAUCAAAAU CCUGGUGAAUUCUGUGUCCUU | SEQ ID NO: 4 549 nts |
| OX40L (TNFSF4) | Nucleotide sequence of homo sapiens tumor necrosis factor (ligand) superfamily, member 4 (TNFSF4), transcript variant 1, mRNA NM_003326 | GGCCCUGGGACCUUUGCCUAUUUUCUGAUUGAU AGGCUUUGUUUUGUCUUUACCUCCUUCUUUCUG GGGAAAACUUCAGUUUUAUCGCACGUUCCCCUU UUCCAUAUCUUCAUCUUCCCUCUACCCAGAUUG UGAAGAUGGAAAGGGUCCAACCCCUGGAAGAGA AUGUGGGAAAUGCAGCCAGGCCAAGAUUCGAGA GGAACAAGCUAUUGCUGGUGGCCUCUGUAAUUC AGGGACUGGGGCUGCUCCUGUGCUUCACCUACA UCUGCCUGCACUUCUCUGCUCUUCAGGUAUCAC | SEQ ID NO: 5 3484 nts |

TABLE 1-continued

OX40L Polypeptide and Polynucleotide Sequences

| Encoded Polypeptide | Description | Sequence | SEQ ID NO: |
|---|---|---|---|
| | | AUCGGUAUCCUCGAAUUCAAAGUAUCAAAGUAC AAUUUACCGAAUAUAAGAAGGAGAAAGGUUUCA UCCUCACUUCCCAAAAGGAGGAUGAAAUCAUGA AGGUGCAGAACAACUCAGUCAUCAUCAACUGUG AUGGGUUUUAUCUCAUCUCCCUGAAGGGCUACU UCUCCCAGGAAGUCAACAUUAGCCUUCAUUACC AGAAGGAUGAGGAGCCCCUCUUCCAACUGAAG AAGGUCAGGUCUGUCAACUCCUUGAUGGUGGC CUCUCUGACUUACAAAGACAAAGUCUACUUGA AUGUGACCACUGACAAUACCUCCCUGGAUGAC UUCCAUGUGAAUGGCGGAGAACUGAUUCUUAU CCAUCAAAAUCCUGGUGAAUUCUGUGUCCUUU GAGGGGCUGAUGGCAAUAUCUAAAACCAGGCA CCAGCAUGAACACCAAGCUGGGGGUGGACAGG GCAUGGAUUCUUCAUUGCAAGUGAAGGAGCCU CCCAGCUCAGCCACGUGGGAUGUGACAAGAAG CAGAUCCUGGCCCUCCCGCCCCCACCCCUCAG GGAUAUUUAAAACUUAUUUUAUAUACCAGUUA AUCUUAUUUAUCCUAUAUUUUCUAAAUUGCC UAGCCGUCACACCCCAAGAUUGCCUUGAGCCU ACUAGGCACCUUUGUGAGAAAGAAAAAAUAGA UGCCUCUUCUUCAAGAUGCAUUGUUUCUAUUG GUCAGGCAAUUGUCAUAAUAAACUUAUGUCAU UGAAAACGGUACCUGACUACCAUUUGCUGGAA AUUUGACAUGUGUGUGGCAUUAUCAAAAUGAA GAGGAGCAAGGAGUGAAGGAGUGGGGUUAUGA AUCUGCCAAAGGUGGUAUGAACCAACCCCUGG AAGCCAAAGCGGCCUCUCCAAGGUUAAAUUGA UUGCAGUUUGCAUAUUGCCUAAAUUUAAACUU UCUCAUUUGGUGGGGUUCAAAAGAAGAAUCA GCUUGUGAAAAAUCAGGACUUGAAGAGAGCCG UCUAAGAAAUACCACGUGCUUUUUUCUUUAC CAUUUUGCUUUCCCAGCCUCCAAACAUAGUUA AUAGAAAUUUCCCUUCAAAGAACUGUCUGGGG AUGUGAUGCUUUGAAAAAUCUAAUCAGUGACU UAAGAGAGAUUUUCUUGUAUACAGGGAGAGUG AGAUAACUUAUUGUGAAGGGUUAGCUUUACUG UACAGGAUAGCAGGGAACUGGACAUCUCAGGG UAAAAGUCAGUACGGAUUUUAAUAGCCUGGGG AGGAAAACACAUUCUUUGCCACAGACAGGCAA AGCAACACAUGCUCAUCCUCCUGCCCUAUGCUG AGAUACGCACUCAGCUCCAUGUCUUGUACACA CAGAAACAUUGCUGGUUUCAAGAAAUGAGGUG AUCCUAUUAUCAAAUUCAAUCUGAUGUCAAAU AGCACUAAGAAGUUAUUGUGCCUUAUGAAAAA UAAUGAUCUCUGUCUAGAAAUACCAUAGACCA UAUAUAGUCUCACAUUGAUAAUUGAAACUAGA AGGGUCUAUAAUCAGCCUAUGCCAGGGCUUCA AUGGAAUAGUAUCCCCUUAUGUUUAGUUGAAA UGUCCCCUUAACUUGAUAUAAUGUGUUAUGCU UAUGGCGCUGUGGACAAUCUGAUUUUUCAUGU CAACUUUCCAGAUGAUUUGUAACUUCUCUGUG CCAAACCUUUUAUAAACAUAAAUUUUUGAGAU AUGUAUUUUAAAAUUGUAGCACAUGUUUCCCU GACAUUUUCAAUAGAGGAUACAACAUCACAGA AUCUUUCUGGAUGAUUCUGUGUUAUCAAGGAA UUGUACUGUGCUACAAUUAUCUCUAGAAUCUC CAGAAAGGUGGAGGGCUGUUCGCCCUUACACU AAAUGGUCUCAGUUGGAUUUUUUUUCCUGUU UUCUAUUUCCUCUUAAGUACACCUUCAACUAU AUUCCAUCCCUCUAUUUUAAUCUGUUAUGAA GGAAGGUAAAUAAAAAUGCUAAAUAGAAGAAA UUGUAGGUAAGGUAAGAGGAAUCAAGUUCUGA GUGGCUGCCAAGGCACUCACAGAAUCAUAAUC AUGGCUAAAUAUUUAUGGAGGGCCUACUGUGG ACCAGGCACUGGGCUAAAUACUUACAUUUACA AGAAUCAUUCUGAGACAGAUAUUCAAUGAUAU CUGGCUUCACUACUCAGAAGAUUGUGUGUGUG UUUGUGUGUGUGUGUGUGUAUUUCACUUU UUUGUUAUUGACCAUGUUCUGCAAAAUUGCAG UUACUCAGUGAGUGAUAUCCGAAAAGUAAAC GUUUAUGACUAUAGGUAAUAUUUAAGAAAUG CAUGGUUCAUUUUUAAGUUUGGAAUUUUUAUC UAUAUUUCUCACAGAUGUGCAGUGCACAUGCA GGCCUAAGUAUAUGUUGUGUGUGUUGUUUGUC |  |

TABLE 1-continued

OX40L Polypeptide and Polynucleotide Sequences

| Encoded Polypeptide | Description | Sequence | SEQ ID NO: |
|---|---|---|---|
| | | UUUGAUGUCAUGGUCCCCUCUCUUAGGUGCUC<br>ACUCGCUUUGGGUGCACCUGGCCUGCUCUUCC<br>CAUGUUGGCCUCUGCAACCACACAGGGAUAUU<br>UCUGCUAUGCACCAGCCUCACUCCACCUUCCU<br>UCCAUCAAAAAUAUGUGUGUGUGUCUCAGUCC<br>CUGUAAGUCAUGUCCUUCACAGGGAGAAUUAA<br>CCCUUCGAUAUACAUGGCAGAGUUUUGUGGGA<br>AAAGAAUUGAAUGAAAAGUCAGGAGAUCAGAA<br>UUUUAAAUUUGACUUAGCCACUAACUAGCCAU<br>GUAACCUUGGGAAAGUCAUUUCCCAUUUCUGG<br>GUCUUGCUUUUCUUUCUGUUAAAUGAGAGGAA<br>UGUUAAAUAUCUAACAGUUUAGAAUCUUAUGC<br>UUACAGUGUUAUCUGUGAAUGCACAUAUUAAA<br>UGUCUAUGUUCUUGUUGCUAUGAGUCAAGGAG<br>UGUAACCUUCUCCUUUACUAUGUUGAAUGUAU<br>UUUUUUCUGGACAAGCUUACAUCUUCCUCAGC<br>CAUCUUUGUGAGUCCUUCAAGAGCAGUUAUCA<br>AUUGUUAGUUAGAUAUUUCUAUUUAGAGAAU<br>GCUUAAGGGAUUCCAAUCCCGAUCCAAAUCAU<br>AAUUUGUUCUUAAGUAUACUGGGCAGGUCCCC<br>UAUUUUAAGUCAUAAUUUUGUAUUUAGUGCUU<br>UCCUGGCUCUCAGAGAGUAUUAAUAUUGAUAU<br>UAAUAAUAUAGUUAAUAGUAAUAUUGCUAUUU<br>ACAUGGAAACAAAUAAAAGAUCUCAGAAUUCA<br>CUAAAAAAAAAAA | |
| OX40L (TNFSF4) | Nucleotide sequence of *Mus musculus* tumor necrosis factor (ligand) superfamily, member 4 (Tnfsf4), mRNA NM_009452 | AUUGCUUUUUGUCUCCUGUUCUGGGACCUUUA<br>UCUUCUGACCCGCAGGCUUGACUUUGCCCUUA<br>UUGGCUCCUUUGUGGUGAAGAGCAGUCUUCCC<br>CCAGGUUCCCCGCCACAGCUGUAUCUCCUCUG<br>CACCCCGACUGCAGAGAUGGAAGGGGAAGGGG<br>UUCAACCCCUGGAUGAGAAUCUGGAAAACGGA<br>UCAAGGCCAAGAUUCAAGUGGAAGAAGACGCU<br>AAGGCUGGUGGUCUCUGGGAUCAAGGGAGCAG<br>GGAUGCUUCUGUGCUUCAUCUAUGUCUGCCUG<br>CAACUCUCUUCCUCUCCGGCAAAGGACCCUCC<br>AAUCCAAAGACUCAGAGGAGCAGUUACCAGAU<br>GUGAGGAUGGGCAACUAUUCAUCAGCUCAUAC<br>AAGAAUGAGUAUCAAACUAUGGAGGUGCAGAA<br>CAAUUCGGUUGUCAUCAAGUGCGAUGGGCUUU<br>AUAUCAUCUACCUGAAGGGCUCCUUUUUCCAG<br>GAGGUCAAGAUUGACCUUCAUUUCCGGGAGGA<br>UCAUAAUCCCAUCUCUAUUCCAAUGCUGAACG<br>AUGGUCAAGGAUUGUCUUCACUGUGGUGGCC<br>UCUUUGGCUUUCAAAGAUAAAGUUUACCUGAC<br>UGUAAAUGCUCCUGAUACUCUCUGCGAACACC<br>UCCAGAUAAAUGAUGGGGAGCUGAUUGUUGUC<br>CAGCUAACGCCUGGAUACUGUGCUCCUGAAGG<br>AUCUUACCACAGCACUGUGAACCAAGUACCAC<br>UGUGAAUUCCACUCUGAGGGUGGACGGGACAC<br>AGGUUCUUUCUCGAGAGAUGAGUGCAUCCU<br>GCUCAUGAGAUGUGACUGAAUGCAGAGCCUAC<br>CCUACUUCCUCACUCAGGGAUAUUUAAAUCAU<br>GUCUUACAUAACAGUUGACCUCUCAUUCCCAG<br>GAUUGCCUUGAGCCUGCUAAGAGCUGUUCUGG<br>GAAUGAAAAAAAAAAAUAAAUGUCUCUUCAAGA<br>CACAUUGCUUCUGUCGGUCAGAAGCUCAUCGU<br>AAUAAACAUCUGCCACUGAAAAAUGGCGCUUGA<br>UUGCUAUCUUCUAGAAUUUUGAUGUUGUCAAA<br>AGAAAGCAAAACAUGGAAAGGUGGUGUCCAC<br>CGGCCAGUAGGAGCUGGAGUGCUCUCUUCAAG<br>GUUAAGGUGAUAGAAGUUUACAUGUUGCCUAA<br>AACUGUCUCUCAUCUCAUGGGGGGCUUGGAAA<br>GAAGAUUACCCGUGGAAAGCAGGACUUGAAG<br>AUGACUGUUUAAGCAACAAGGUGCACUCUUUU<br>CCUGGCCCCUGAAUACACAUAAAAGACAACUU<br>CCUUCAAAGAACUACCUAGGGACUAUGAUACC<br>CACCAAAGAACCACGUCAGCGAUGCAAAGAAA<br>ACCAGGAGAGCUUUGUUUAUUUUGCAGAGUAU<br>ACGAGAGAUUUUACCCUGAGGGCUAUUUUUAU<br>UAUACAGGAUGAGAGUGAACUGGAUGUCUCAG<br>GAUAAAGGCCAAGAAGGAUUUUCACAGUCUG<br>AGCAAGACUGUUUUUGUAGGUUCUCUCUCCAA<br>AACUUUUAGGUAAAUUUUUGAUAAUUUAAAA<br>UUUUUAGUUAUAUUUUUGGACCAUUUUCAAUA | SEQ ID NO: 6<br>1609 nts |

TABLE 1-continued

OX40L Polypeptide and Polynucleotide Sequences

| Encoded Polypeptide | Description | Sequence | SEQ ID NO: |
|---|---|---|---|
| | | GAAGAUUGAAACAUUUCCAGAUGGUUUCAUAU<br>CCCCACAAG | |
| OX40L (TNFSF4) | Codon-optimized sequence 1 for ENSP 281834 | AUGGAGAGAGUGCAGCCCCUGGAGGAGAACGUG<br>GGCAACGCCGCCAGACCCAGAUUCGAGAGAAAC<br>AAGCUGCUGCUGGUGGCCAGCGUGAUCCAGGGC<br>CUGGGCCUGCUGCUGUGCUUCACCUACAUCUGC<br>CUGCACUUCAGCGCCCUGCAGGUGAGCCACAGA<br>UACCCCAGAAUCCAGAGCAUCAAGGUGCAGUUC<br>ACCGAGUACAAGAAGGAGAAGGGCUUCAUCCUG<br>ACCAGCCAGAAGGAGGACGAGAUCAUGAAGGUG<br>CAGAACAACAGCGUGAUCAUCAACUGCGACGGC<br>UUCUACCUGAUCAGCCUGAAGGGCUACUUCAGC<br>CAGGAGGUGAACAUCAGCCUGCACUACCAGAAG<br>GACGAGGAGCCCCUGUUCCAGCUGAAGAAGGUG<br>AGAAGCGUGAACAGCCUGAUGGUGGCCAGCCUG<br>ACCUACAAGGACAAGGUGUACCUGAACGUGACC<br>ACCGACAACACCAGCCUGGACGACUUCCACGUG<br>AACGGCGGCGAGCUGAUCCUGAUCCACCAGAAC<br>CCCGGCGAGUUCUGCGUGCUG | SEQ ID NO: 7<br>549 nts |
| OX40L (TNFSF4) | Codon-optimized sequence 2 for ENSP 281834 | AUGGAGCGUGUGCAGCCUCUUGAGGAGAAUGUG<br>GGAAAUGCAGCCCGGCCUCGAUUCGAACGUAAU<br>AAACUCCUGCUCGUGGCCUCCGUGAUCCAGGGU<br>CUCGGUUUAUUGCUGUGUUUUACCUAUAUAUGC<br>UUACACUUUAGUGCAUUACAGGUCUCACACCGG<br>UACCCUCGCAUUCAGUCUAUAAAAGUGCAGUUU<br>ACCGAGUAUAAGAAGGAGAAAGGUUUUAUACUG<br>ACUUCUCAGAAAGAGGACGAGAUCAUGAAGGUG<br>CAGAAUAAUAGCGUCAUUAUCAACUGCGAUGGA<br>UUCUAUCUAAUUUCCCUAAAGGGGUACUUCAGC<br>CAGGAGGUCAAUAUAUCACUGCACUAUCAAAAG<br>GACGAGGAGCCCCUGUUUCAACUGAAGAAAGUG<br>CGAUCAGUUAACUCUCUGAUGGUUGCCUCUCUG<br>ACCUAUAAGGACAAAGUCUACUUGAACGUGACA<br>ACUGACAACACCUCACUGGAUGACUUUCAUGUG<br>AAUGGGGGGAACUGAUUCUUAUCCAUCAGAAU<br>CCAGGAGAAUUCUGUGUGCUC | SEQ ID NO: 8<br>549 nts |
| OX40L (TNFSF4) | Codon-optimized sequence 3 for ENSP 281834 | AUGGAGCGGGUGCAGCCCCUGGAGGAGAAUGUG<br>GGCAAUGCUGCCCGGCCUCAGGUUUGAAAGAAAC<br>AAGCUGCUGCUGGUGGCCAGCGUCAUCCAGGGC<br>CUGGGCCUGCUGCUGUGCUUCACCUACAUCUGC<br>CUGCACUUCAGCGCCCUGCAGGUGAGCCACCGC<br>UACCCCCGCAUCCAGAGCAUCAAGGUGCAGUUC<br>ACAGAGUACAAGAAGGAGAAGGGCUUCAUCCUG<br>ACCAGCCAGAAGGAGGAUGAGAUCAUGAAGGUG<br>CAGAACAACAGCGUCAUCAUCAACUGUGAUGGC<br>UUCUACCUGAUCAGCCUGAAGGGCUACUUCAGC<br>CAGGAGGUGAACAUCAGCCUGCACUACCAGAAG<br>GAUGAGGAGCCCCUCUUCCAGCUGAAGAAGGUG<br>CGCUCUGUGAACAGCCUGAUGGUGGCCAGCCUG<br>ACCUACAAGGACAAGGUGUACCUGAAUGUGACC<br>ACAGACAACACCAGCCUGGAUGACUUCCACGUG<br>AAUGGAGGAGAGCUGAUCCUGAUCCACCAGAAC<br>CCUGGAGAGUUCUGUGUGCUG | SEQ ID NO: 9<br>549 nts |
| OX40L (TNFSF4) | Codon-optimized sequence 4 for ENSP 281834 | AUGGAGCGGGUGCAGCCCCUGGAGGAGAACGUG<br>GGCAACGCCGCCCGCCCGCGUUUUGAGCGAAAU<br>AAGUUACUGCUUGUUGCAUCUGUGAUACAGGGG<br>UUGGGUUUACUUCUUUGCUUUACAUAUAUUUGU<br>CUCCACUUUAGUGCGCUUCAGGUAUCCCAUCGG<br>UACCCGCGCAUCCAGUCAAUCAAGGUCCAGUUC<br>ACUGAAUAUAAAAGGAGAAAGGAUUCAUUCUG<br>ACUUCACAAAAGAGGACGAAAUCAUGAAAGUG<br>CAGAACAACUCUGUAAUUAUAAACUGCGAUGGG<br>UUCUAUCUGAUCAGUCUGAAGGGAUAUUUUAGC<br>CAGGAAGUAAAUAUUUCACUACAUUAUCAGAAG<br>GACGAAGAACCACUUUUUCAACUGAAGAAAGUC<br>CGGUCCGUGAACUCCCUGAUGGUUGCUAGCCUU<br>ACCUACAAGGAUAAAGUCUAUUUAAACGUCACA<br>ACAGAUAACACUAGCCUCGACGAUUUCCAUGUG<br>AACGGAGGUGAACUGAUAUUGAUCCAUCAAAAC<br>CCCGGCGAGUUCUGCGUUUUA | SEQ ID NO: 10<br>549 nts |

TABLE 1-continued

OX40L Polypeptide and Polynucleotide Sequences

| Encoded Polypeptide | Description | Sequence | SEQ ID NO: |
|---|---|---|---|
| OX40L (TNFSF4) | Codon-optimized sequence 5 for ENSP 281834 | AUGGAGCGGGUCCAGCCCCUCGAGGAGAACGUU GGUAAUGCCGCACGUCCCAGGUUUGAACGCAAC AAGCUGCUGUUGGUGGCCAGCGUCAUUCAGGGG CUGGGUUUGUUGCUGUGCUUCACUUACAUCUGU CUGCAUUUUAGUGCACUCCAGGUGUCCCACCGC UACCCCCGUAUCCAAUCCAUUAAAGUCCAAUUU ACCGAAUACAAAAAAGAGAAGGGUUUCAUUCUU ACCUCCCAGAAGGAGGAUGAAAUUAUGAAGGUG CAGAACAAUUCUGUUAUCAUCAACUGUGACGGA UUCUAUCUGAUUUCACUGAAGGGAUACUUUUCC CAGGAGGUGAACAUCAGUCUGCAUUAUCAGAAG GACGAAGAACCGCUUUUUCAACUGAAGAAGGUU AGGAGUGUGAACUCCUUAAUGGUAGCCAGCCUG ACAUAUAAGGACAAGGUAUAUCUGAACGUCACC ACUGAUAACACCUCUUUAGACGAUUUUCAUGUA AAUGGGGGAGAAUUGAUACUCAUUCACCAGAA UCCGGGUGAGUUUGUGUUCUG | SEQ ID NO: 11 549 nts |
| OX40L (TNFSF4) | Codon-optimized sequence 1 for ENSP 356691 | AUGGUGAGCCACAGAUACCCCAGAAUCCAGAGCA UCAAGGUGCAGUUCACCGAGUACAAGAAGGAGAA GGGCUUCAUCCUGACCAGCCAGAAGGAGGACGAG AUCAUGAAGGUGCAGAACAACAGCGUGAUCAUCA ACUGCGACGGCUUCUACCUGAUCAGCCUGAAGGG CUACUUCAGCCAGGAGGUGAACAUCAGCCUGCAC UACCAGAAGGACGAGGAGCCCCUGUUCCAGCUGA AGAAGGUGAGAAGCGUGAACAGCCUGAUGGUGGC CAGCCUGACCUACAAGGACAAGGUGUACCUGAAC GUGACCACCGACAACACCAGCCUGGACGACUUCC ACGUGAACGGCGGCGAGCUGAUCCUGAUCCACCA GAACCCCGGCGAGUUCUGCGUGCUG | SEQ ID NO: 12 399 nts |
| OX40L (TNFSF4) | Codon-optimized sequence 2 for ENSP 356691 | AUGGUUUCUCACCGUUACCCACGGAUCCAGUCUA UCAAGGUUCAGUUUACCGAGUACAAAAAGGAAAA AGGGUUCAUCCUCACCUCUCAGAAAGAGGACGAA AUCAUGAAGGUGCAGAAUAACUCUGUAAUCAUUA AUUGCGACGGUUUUUAUCUGAUUUCACUGAAGGG CUACUUUAGUCAGGAAGUUAAUAUAUGUUUGCAC UACCAAAAGGACGAGGAGCCUCUCUUCCAACUAA AAAAGGUAAGAUCCGUUAAUUCCCUUAUGGUGGC CUCCUUAACUUAUAAGGACAAGGUGUAUCUGAAU GUGACCACAGAUAACACAUCCCUGGACGACUUUC AUGUAAAUGGCGGCGAGUUAAUUCUGAUACACCA GAACCCCUGGCGAGUUCUGCGUGCUG | SEQ ID NO: 13 399 nts |
| OX40L (TNFSF4) | Codon-optimized sequence 3 for ENSP 356691 | AUGGUGAGCCACCGCUACCCCCGCAUCCAGAGCA UCAAGGUGCAGUUCACAGAGUACAAGAAGGAGAA GGGCUUCAUCCUGACCAGCCAGAAGGAGGAUGAG AUCAUGAAGGUGCAGAACAACAGCGUCAUCAUCA ACUGUGAUGGCUUCUACCUGAUCAGCCUGAAGGG CUACUUCAGCCAGGAGGUGAACAUCAGCCUGCAC UACCAGAAGGAUGAGGAGCCCCUCUUCCAGCUGA AGAAGGUGCGCUCUGUGAACAGCCUGAUGGUGGC CAGCCUGACCUACAAGGACAAGGUGUACCUGAAU GUGACCACAGACAACACCAGCCUGGAUGACUUCC ACGUGAAUGGAGGAGAGCUGAUCCUGAUCCACCA GAACCCUGGAGAGUUCUGUGUGCUG | SEQ ID NO: 14 399 nts |
| OX40L (TNFSF4) | Codon-optimized sequence 4 for ENSP 356691 | AUGGUGAGCCACCGGUACCCCCGGAUCCAGAGCA UCAAGGUGCAGUUCACCGAAUACAAGAAGGAGAA GGGUUUUAUCCUGACGAGCCAGAAGGAAGACGAG AUUAUGAAGGUCCAAAACAACUCAGUCAUCAUAA ACUGCGAUGAUUUUACCUGAUCUCUCUGAAAGG GUACUUCUCCCAGGAAGUGAAUAUUAGCUUGCAC UAUCAAAAAGAUGAGGAGCCUCUAUUCCAGCUCA AGAAGGUCAGAAGCGUCAAUAGUCUGAUGGUCGC AUCAUUAACCUAUAAAGACAAAGUAUAUCUAAAU GUGACGACAGACAAUCAUCCCUCGAUGAUUUUC ACGUCAACGGAGGCGAACUCAUUCUGAUCCACCA GAAUCCAGGGGAAUUUGCGUGCUG | SEQ ID NO: 15 399 nts |
| OX40L (TNFSF4) | Codon-optimized sequence 5 for ENSP 356691 | AUGGUCUCACACCGGUACCCCCGUAUCCAGAGUA UUAAGGUGCAAUUCACGGAGUAUAAAAAGAAAA GGGAUUCAUUCUGACGUCUCAGAAGGAAGAUGAG AUCAUGAAGGUCCAGAACAAUUCUGUGAUCAUUA AUUGCGAUGGAUUUUAUCUGAUUUCACUUAAAGG | SEQ ID NO: 16 399 nts |

TABLE 1-continued

OX40L Polypeptide and Polynucleotide Sequences

| Encoded Polypeptide | Description | Sequence | SEQ ID NO: |
|---|---|---|---|
| | | AUAUUUUUCCCAGGAGGUUAAUAUCAGUUUGCAC UAUCAGAAAGACGAGGAGCCAUUAUUCCAGCUGA AGAAGGUGAGAUCAGUGAAUAGCCUGAUGGUUGC GUCACUGACGUAUAAAGACAAAGUUUAUCUAAAC GUUACCACUGAUAAUACAUCCCUUGAUGAUUUUC AUGUGAACGGGGGUGAACUGAUCCUUAUACACCA GAACCCCGGAGAGUUCUGUGUGUUG | |
| OX40L (TNFSF4) | Codon-optimized sequence 1 for ENSP 439704 | AUGGUGAGCCACAGAUACCCCAGAAUCCAGAGCAU CAAGGUGCAGUUCACCGAGUACAAGAAGGAGAAG GGCUUCAUCCUGACCAGCCAGAAGGAGGACGAGA UCAUGAAGGUGCAGAACAACAGCGUGAUCAUCAA CUGCGACGGCUUCUACCUGAUCAGCCUGAAGGGC UACUUCAGCCAGGAGGUGAACAUCAGCCUGCACU ACCAGAAGGACGAGGAGCCCCUGUUCCAGCUGAA GAAGGUGAGAAGCGUGAACAGCCUGAUGGUGGCC AGCCUGACCUACAAGGACAAGGUGUACCUGAACG UGACCACCGACAACACCAGCCUGGACGACUUCCA CGUGAACGGCGGCGAGCUGAUCCUGAUCCACCAG AACCCCGGCGAGUUCUGCGUGCUG | SEQ ID NO: 17 399 nts |
| OX40L (TNFSF4) | Codon-optimized sequence 2 for ENSP 439704 | AUGGUGUCACACCGGUACCCUCGGAUCCAGUCUA UUAAAGUUCAAUUUACGGAGUACAAGAAAGAAAA AGGCUUUAUCCUUACAAGCCAAAAGGAAGACGAG AUCAUGAAAGUGCAAAACAACAGUGUGAUUAUAA AUUGUGAUGGCUUCUACCUUAUUAGUCUGAAGGG CUACUUUAGUCAGGAAGUCAAUAUUAGCCUACAC UACCAGAAAGACGAGGAGCCCCUCUUUCAACUGA AAAAGGUGCGCUCCGUGAAUUCGUUGAUGGUCGC CUCUCUGACCUACAAAGAUAAGGUGUAUCUUAAC GUUACUACCGACAAUACUAGUCUGGACGACUUUC ACGUCAACGGAGGCGAACUUAUUCUGAUCCACCA GAACCCCGGCGAAUUCUGCGUGCUG | SEQ ID NO: 18 399 nts |
| OX40L (TNFSF4) | Codon-optimized sequence 3 for ENSP 439704 | AUGGUGAGCCACCGCUACCCCCGCAUCCAGAGCA UCAAGGUGCAGUUCACAGAGUACAAGAAGGAGAA GGGCUUCAUCCUGACCAGCCAGAAGGAGGAUGAG AUCAUGAAGGUGCAGAACAACAGCGUCAUCAUCA ACUGUGAUGGCUUCUACCUGAUCAGCCUGAAGGG CUACUUCAGCCAGGAGGUGAACAUCAGCCUGCAC UACCAGAAGGAUGAGGAGCCCCUCUUCCAGCUGA AGAAGGUGCGCUCUGUGAACAGCCUGAUGGUGGC CAGCCUGACCUACAAGGACAAGGUGUACCUGAAU GUGACCACAGACAACACCAGCCUGGAUGACUUCC ACGUGAAUGGAGGAGAGCUGAUCCUGAUCCACCA GAACCCUGGAGAGUUCUGUGUGCUG | SEQ ID NO: 19 399 nts |
| OX40L (TNFSF4) | Codon-optimized sequence 4 for ENSP 439704 | AUGGUGAGCCACCGGUACCCCCGGAUCCAGAGCA UCAAGGUGCAGUUCACAGAGUACAAGAAGGAGAA GGGAUUUAUUCUCACAAGUCAGAAAGAAGAUGAG AUCAUGAAGGUUCAGAACAACUCAGUCAUUAUUA AUUGCGACGGAUUCUAUCUCAUUAGCCUCAAAGG CUAUUUCAGCCAGGAGGUCAAUAUCAGCCUGCAC UACCAGAAGGAUGAGGAACCUCUCUUUCAGCUGA AAAAGUCCGCUCUGUGAAUUCCCUCAUGGUCGC UUCCCUGACCUACAAGGAUAAAGUUUAUUUGAAC GUUACAACAGAUAAUACAUCGCUGGACGACUUCC AUGUGAAUGGUGGCGAACUAAUUCUAAUACACCA AAAUCCAGGCGAAUUUUGUGUCCUU | SEQ ID NO: 20 399 nts |
| OX40L (TNFSF4) | Codon-optimized sequence 5 for ENSP 439704 | AUGGUAUCCCAUAGAUACCCACGUAUUCAAAGCA UUAAGGUGCAGUUCACAGAGUACAAAAAGGAGAA GGGUUUCAUACUGACGUCACAGAAGGAGGACGAG AUAAUGAAGGUGCAGAAUAAUAGUGUGAUCAUCA AUUGUGAUGGAUUCUAUUUGAUCAGCCUCAAAGG UUAUUUCUCACAGGAAGUCAACAUUUCCCUGCAC UACCAGAAGGACGAAGCCUUUGUUUCAGCUGA AGAAGGUGCGCUCAGUGAACAGUUUGAUGGUAGC CUCCCUAACUUAUAAAGAUAAAGUUUAUCUGAAC GUGACAACCGAUAACACAUCCCUGGACGACUUUC ACGUCAAUGGAGGUGAGUUAAUCCUGAUCCAUCA GAAUCCCGGAGAAUUCUGCGUUCUU | SEQ ID NO: 21 399 nts |

In some embodiments, the mRNA useful for the methods comprises an open reading frame encoding an extracellular domain of OX40L. In other embodiments, the mRNA comprises an open reading frame encoding a cytoplasmic domain of OX40L. In some embodiments, the mRNA comprises an open reading frame encoding a transmembrane domain of OX40L. In certain embodiments, the mRNA comprises an open reading frame encoding an extracellular domain of OX40L and a transmembrane of OX40L. In other embodiments, the mRNA comprises an open reading frame encoding an extracellular domain of OX40L and a cytoplasmic domain of OX40L. In yet other embodiments, the mRNA comprises an open reading frame encoding an extracellular domain of OX40L, a transmembrane of OX40L, and a cytoplasmic domain of OX40L.

In some embodiments, the mRNA comprises a codon optimized sequence encoding an OX40L polypeptide, e.g., a codon optimized sequence from Table 1 (e.g., selected from SEQ ID NOs: 7-21).

In some embodiments, the polynucleotides comprise an mRNA encoding an OX40L polypeptide which is full length. In some embodiments, the polynucleotides comprise an mRNA encoding a human OX40L polypeptide which is 183 amino acids in length. In certain embodiments, the OX40L polypeptide can lack at least one, at least two, at least three, at least four, at least five, at least six, at least seven, at least eight, at least nine, at least 10, at least 14, or at least 15 amino acids at the N-terminus or C-terminus of the OX40L polypeptide.

In some embodiments, the polynucleotide (e.g., mRNA) of the present disclosure is structurally modified or chemically modified. As used herein, a "structural" modification is one in which two or more linked nucleosides are inserted, deleted, duplicated, inverted or randomized in a polynucleotide without significant chemical modification to the mRNA themselves. Because chemical bonds will necessarily be broken and reformed to effect a structural modification, structural modifications are of a chemical nature and hence are chemical modifications. However, structural modifications will result in a different sequence of nucleotides. For example, the mRNA "AUCG" can be chemically modified to "AU-5meC-G". The same mRNA can be structurally modified from "AUCG" to "AUCCG". Here, the dinucleotide "CC" has been inserted, resulting in a structural modification to the polynucleotide.

In some embodiments, the polynucleotide (e.g., mRNA) of the present disclosure, can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotide (e.g., mRNA) encoding an OX40L polypeptide can have a uniform chemical modification of two, three, or four of the same nucleoside type throughout the entire polynucleotide (e.g., mRNA) (such as all uridines and all cytosines, etc. are modified in the same way).

When the polynucleotide (e.g., mRNA) encoding an OX40L polypeptide of the present disclosure are chemically and/or structurally modified the mRNA can be referred to as "modified mRNA." Non-limiting examples of chemical modifications are described elsewhere herein.

microRNA Binding Sites

The polynucleotide (e.g., mRNA) encoding an OX40L polypeptide can further comprise one or more microRNA binding sites. microRNAs (or miRNA) are 19-25 nucleotides long noncoding RNAs that bind to the 3'UTR of nucleic acid molecules and down-regulate gene expression either by reducing nucleic acid molecule stability or by inhibiting translation.

By engineering microRNA target sequences into the polynucleotides (e.g., in a 3'UTR like region or other region) of the disclosure, one can target the molecule for degradation or reduced translation, provided the microRNA in question is available. In one embodiment, the miRNA binding site (e.g., miR-122 binding site) binds to the corresponding mature miRNA that is part of an active RNA-induced silencing complex (RISC) containing Dicer. In another embodiment, binding of the miRNA binding site to the corresponding miRNA in RISC degrades the mRNA containing the miRNA binding site or prevents the mRNA from being translated.

As used herein, the term "microRNA binding site" refers to a microRNA target site or a microRNA recognition site, or any nucleotide sequence to which a microRNA binds or associates. It should be understood that "binding" can follow traditional Watson-Crick hybridization rules or can reflect any stable association of the microRNA with the target sequence at or adjacent to the microRNA site.

Some microRNAs, e.g., miR-122, are abundant in normal tissue but are present in much lower levels in cancer or tumor tissue. Thus, engineering microRNA target sequences (i.e., microRNA binding site) into the polynucleotides encoding an OX40L polypeptide (e.g., in a 3'UTR like region or other region) can effectively target the molecule for degradation or reduced translation in normal tissue (where the microRNA is abundant) while providing high levels of translation in the cancer or tumor tissue (where the microRNA is present in much lower levels). This provides a tumor-targeting approach for the methods and compositions of the disclosure.

In some embodiments, the microRNA binding site (e.g., miR-122 binding site) is fully complementary to miRNA (e.g., miR-122), thereby degrading the mRNA fused to the miRNA binding site. In other embodiments, the miRNA binding site is not fully complementary to the corresponding miRNA. In certain embodiments, the miRNA binding site (e.g., miR-122 binding site) is the same length as the corresponding miRNA (e.g., miR-122). In other embodiments, the microRNA binding site (e.g., miR-122 binding site) is one nucleotide shorter than the corresponding microRNA (e.g., miR-122, which has 22 nts) at the 5' terminus, the 3' terminus, or both. In still other embodiments, the microRNA binding site (e.g., miR-122 binding site) is two nucleotides shorter than the corresponding microRNA (e.g., miR-122) at the 5' terminus, the 3' terminus, or both. In yet other embodiments, the microRNA binding site (e.g., miR-122 binding site) is three nucleotides shorter than the corresponding microRNA (e.g., miR-122) at the 5' terminus, the 3' terminus, or both. In some embodiments, the microRNA binding site (e.g., miR-122 binding site) is four nucleotides shorter than the corresponding microRNA (e.g., miR-122) at the 5' terminus, the 3' terminus, or both. In other embodiments, the microRNA binding site (e.g., miR-122 binding site) is five nucleotides shorter than the corresponding microRNA (e.g., miR-122) at the 5' terminus, the 3' terminus, or both. In some embodiments, the microRNA binding site (e.g., miR-122 binding site) is six nucleotides shorter than the corresponding microRNA (e.g., miR-122) at the 5' terminus, the 3' terminus, or both. In other embodiments, the microRNA binding site (e.g., miR-122 binding site) is seven nucleotides shorter than the corresponding microRNA (e.g., miR-122) at the 5' terminus or the 3' terminus. In other embodiments, the microRNA binding site (e.g., miR-122 binding site) is eight nucleotides shorter than the corresponding microRNA (e.g., miR-122) at the 5' terminus or the 3' terminus. In other embodiments, the microRNA binding site (e.g., miR-122 binding site) is nine nucleotides shorter than the corresponding microRNA (e.g., miR-122) at the 5' terminus or the 3' terminus. In other embodiments, the microRNA binding site (e.g., miR-122 binding site) is ten nucleotides shorter than the corresponding microRNA (e.g., miR-122) at the 5' terminus or the 3' terminus. In other embodiments, the microRNA binding site (e.g., miR-122 binding site) is eleven nucleotides shorter than the corresponding microRNA (e.g., miR-122) at the 5' terminus or the 3' terminus. In other embodiments, the microRNA binding site (e.g., miR-122 binding site) is twelve nucleotides shorter than the corresponding microRNA (e.g., miR-122) at the 5' terminus or the 3' terminus. The miRNA binding sites that are shorter than the corresponding miRNAs are still capable of degrading the mRNA incorporating one or more of the miRNA binding sites or preventing the mRNA from translation.

In some embodiments, the microRNA binding site (e.g., miR-122 binding site) has sufficient complementarity to miRNA (e.g., miR-122) so that a RISC complex comprising the miRNA (e.g., miR-122) cleaves the polynucleotide comprising the microRNA binding site. In other embodiments, the microRNA binding site (e.g., miR-122 binding site) has imperfect complementarity so that a RISC complex comprising the miRNA (e.g., miR-122) induces instability in the polynucleotide comprising the microRNA binding site. In another embodiment, the microRNA binding site (e.g., miR-122 binding site) has imperfect complementarity so that a RISC complex comprising the miRNA (e.g., miR-122) represses transcription of the polynucleotide comprising the microRNA binding site. In one embodiment, the miRNA binding site (e.g., miR-122 binding site) has one mismatch from the corresponding miRNA (e.g., miR-122). In another embodiment, the miRNA binding site has two mismatches from the corresponding miRNA. In other embodiments, the miRNA binding site has three mismatches from the corresponding miRNA. In other embodiments, the miRNA binding site has four mismatches from the corresponding miRNA. In some embodiments, the miRNA binding site has five mismatches from the corresponding miRNA. In other embodiments, the miRNA binding site has six mismatches from the corresponding miRNA. In certain embodiments, the miRNA binding site has seven mismatches from the corresponding miRNA. In other embodiments, the miRNA binding site has eight mismatches from the corresponding miRNA. In other embodiments, the miRNA binding site has nine mismatches from the corresponding miRNA. In other embodiments, the miRNA binding site has ten mismatches from the corresponding miRNA. In other embodiments, the miRNA binding site has eleven mismatches from the corresponding miRNA. In other embodiments, the miRNA binding site has twelve mismatches from the corresponding miRNA.

In certain embodiments, the miRNA binding site (e.g., miR-122 binding site) has at least about ten contiguous nucleotides complementary to at least about ten contiguous nucleotides of the corresponding miRNA (e.g., miR-122), at least about eleven contiguous nucleotides complementary to at least about eleven contiguous nucleotides of the corresponding miRNA, at least about twelve contiguous nucleotides complementary to at least about twelve contiguous nucleotides of the corresponding miRNA, at least about thirteen contiguous nucleotides complementary to at least about thirteen contiguous nucleotides of the corresponding miRNA, or at least about fourteen contiguous nucleotides complementary to at least about fourteen contiguous nucleotides of the corresponding miRNA. In some embodiments, the miRNA binding sites have at least about fifteen contiguous nucleotides complementary to at least about fifteen contiguous nucleotides of the corresponding miRNA, at least about sixteen contiguous nucleotides complementary to at least about sixteen contiguous nucleotides of the corresponding miRNA, at least about seventeen contiguous nucleotides complementary to at least about seventeen contiguous nucleotides of the corresponding miRNA, at least about eighteen contiguous nucleotides complementary to at least about eighteen contiguous nucleotides of the corresponding miRNA, at least about nineteen contiguous nucleotides complementary to at least about nineteen contiguous nucleotides of the corresponding miRNA, at least about twenty contiguous nucleotides complementary to at least about twenty contiguous nucleotides of the corresponding miRNA, or at least about twenty one contiguous nucleotides complementary to at least about twenty one contiguous nucleotides of the corresponding miRNA.

In some embodiments, the polynucleotides comprise an mRNA encoding an OX40L polypeptide and at least one miR122 binding site, at least two miR122 binding sites, at least three miR122 binding sites, at least four miR122 binding sites, or at least five miR122 binding sites. In one aspect, the miRNA binding site binds miR-122 or is complementary to miR-122. In another aspect, the miRNA binding site binds to miR-122-3p or miR-122-5p. In a particular aspect, the miRNA binding site comprises a nucleotide sequence at least 80%, at least 85%, at least 90%, at least 95%, or 100% identical to SEQ ID NO: 24, wherein the miRNA binding site binds to miR-122. In another particular aspect, the miRNA binding site comprises a nucleotide sequence at least 80%, at least 85%, at least 90%, at least 95%, or 100% identical to SEQ ID NO: 26, wherein the miRNA binding site binds to miR-122. These sequences are shown below in Table 2.

TABLE 2 miR-122 and miR-122 binding sites

| SEQ ID NO. | Description | Sequence |
|---|---|---|
| SEQ ID NO: 22 | miR-122 | CCUUAGCAGAGCUGUGGAGUGUGACAAUGGUGUUUGUG UCUAAACUAUCAAACGCCAUUAUCACACUAAAUAGCUA CUGCUAGGC |
| SEQ ID NO: 23 | miR-122-3p | AACGCCAUUAUCACACUAAAUA |

TABLE 2-continued miR-122 and miR-122 binding sites

| SEQ ID NO. | Description | Sequence |
|---|---|---|
| SEQ ID NO: 24 | miR-122-3p binding site | UAUUUAGUGUGAUAAUGGCGUU |
| SEQ ID NO: 25 | miR-122-5p | UGGAGUGUGACAAUGGUGUUUG |
| SEQ ID NO: 26 | miR-122-5p binding site | CAAACACCAUUGUCACACUCCA |

In some embodiments, a miRNA binding site (e.g., miR-122 binding site) is inserted in the polynucleotide of the disclosure in any position of the polynucleotide (e.g., 3' UTR); the insertion site in the polynucleotide can be anywhere in the polynucleotide as long as the insertion of the miRNA binding site in the polynucleotide does not interfere with the translation of the functional OX40L polypeptide in the absence of the corresponding miRNA (e.g., miR122); and in the presence of the miRNA (e.g., miR122), the insertion of the miRNA binding site in the polynucleotide and the binding of the miRNA binding site to the corresponding miRNA are capable of degrading the polynucleotide or preventing the translation of the polynucleotide. In one embodiment, a miRNA binding site is inserted in a 3'UTR of the polynucleotide.

In certain embodiments, a miRNA binding site is inserted in at least about 30 nucleotides downstream from the stop codon of the OX40L encoding mRNA. In other embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of the polynucleotide, e.g., the OX40L encoding mRNA. In other embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of the polynucleotide, e.g., the OX40L encoding mRNA.

IVT Polynucleotide Architecture

In some embodiments, the polynucleotide of the present disclosure comprising an mRNA encoding an OX40L polypeptide is an IVT polynucleotide. Traditionally, the basic components of an mRNA molecule include at least a coding region, a 5'UTR, a 3'UTR, a 5' cap and a poly-A tail. The IVT polynucleotides of the present disclosure can function as mRNA but are distinguished from wild-type mRNA in their functional and/or structural design features which serve, e.g., to overcome existing problems of effective polypeptide production using nucleic-acid based therapeutics.

The primary construct of an IVT polynucleotide comprises a first region of linked nucleotides that is flanked by a first flanking region and a second flaking region. This first region can include, but is not limited to, the encoded OX40L polypeptide. The first flanking region can include a sequence of linked nucleosides which function as a 5' untranslated region (UTR) such as the 5' UTR of any of the nucleic acids encoding the native 5' UTR of the polypeptide or a non-native 5'UTR such as, but not limited to, a heterologous 5' UTR or a synthetic 5' UTR. The IVT encoding an OX40L polypeptide can comprise at its 5 terminus a signal sequence region encoding one or more signal sequences. The flanking region can comprise a region of linked nucleotides comprising one or more complete or incomplete 5' UTRs sequences. The flanking region can also comprise a 5' terminal cap. The second flanking region can comprise a region of linked nucleotides comprising one or more complete or incomplete 3' UTRs which can encode the native 3' UTR of OX40L or a non-native 3' UTR such as, but not limited to, a heterologous 3' UTR or a synthetic 3' UTR. The flanking region can also comprise a 3' tailing sequence. The 3' tailing sequence can be, but is not limited to, a polyA tail, a polyA-G quartet and/or a stem loop sequence.

Bridging the 5' terminus of the first region and the first flanking region is a first operational region. Traditionally, this operational region comprises a Start codon. The operational region can alternatively comprise any translation initiation sequence or signal including a Start codon.

Bridging the 3' terminus of the first region and the second flanking region is a second operational region. Traditionally this operational region comprises a Stop codon. The operational region can alternatively comprise any translation initiation sequence or signal including a Stop codon. Multiple serial stop codons can also be used in the IVT polynucleotide. In some embodiments, the operation region of the present disclosure can comprise two stop codons. The first stop codon can be "TGA" or "UGA" and the second stop codon can be selected from the group consisting of "TAA," "TGA," "TAG," "UAA," "UGA" or "UAG."

The IVT polynucleotide primary construct comprises a first region of linked nucleotides that is flanked by a first flanking region and a second flaking region. As used herein, the "first region" can be referred to as a "coding region" or "region encoding" or simply the "first region." This first region can include, but is not limited to, the encoded polypeptide of interest. In one aspect, the first region can include, but is not limited to, the open reading frame encoding at least one polypeptide of interest. The open reading frame can be codon optimized in whole or in part. The flanking region can comprise a region of linked nucleotides comprising one or more complete or incomplete 5' UTRs sequences which can be completely codon optimized or partially codon optimized. The flanking region can include at least one nucleic acid sequence including, but not limited to, miR sequences, TERZAK™ sequences and translation control sequences. The flanking region can also comprise a 5' terminal cap 138. The 5' terminal capping region can include a naturally occurring cap, a synthetic cap or an optimized cap. The second flanking region can comprise a region of linked nucleotides comprising one or more complete or incomplete 3' UTRs. The second flanking region can be completely codon optimized or partially codon optimized. The flanking region can include at least one nucleic acid sequence including, but not limited to, miR sequences and translation control sequences. After the second flanking region the polynucleotide primary construct can comprise a 3' tailing sequence. The 3' tailing sequence can include a synthetic tailing region and/or a chain terminating nucleoside. Non-liming examples of a synthetic tailing region include a polyA sequence, a polyC sequence, or a polyA-G quartet. Non-limiting examples of chain terminating nucleosides include 2'-O methyl, F and locked nucleic acids (LNA).

Bridging the 5' terminus of the first region and the first flanking region is a first operational region. Traditionally this operational region comprises a Start codon. The operational region can alternatively comprise any translation initiation sequence or signal including a Start codon.

Bridging the 3' terminus of the first region and the second flanking region is a second operational region. Traditionally this operational region comprises a Stop codon. The operational region can alternatively comprise any translation initiation sequence or signal including a Stop codon. According to the present disclosure, multiple serial stop codons can also be used.

In some embodiments, the first and second flanking regions of the IVT polynucleotide can range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, 900, 1,000, 1,500, 2,000, 2,500, 3,000, 3,500, 4,000, 4,500, 5,000, 5,500 nucleotides or at least 30, 40, 45, 50, 55, 60, 70, 80, 90, 100, 120, 140, 160, 180, 200, 250, 300, 350, 400, 450, 500, 600, 700, 800, 900, 1,000, 1,500, 2,000, 2,500, 3,000, 3,500, 4,000, 4,500, 5,000, 5,500 nucleotides).

In some embodiments, the tailing sequence of the IVT polynucleotide can range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length can be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

In some embodiments, the capping region of the IVT polynucleotide can comprise a single cap or a series of nucleotides forming the cap. In this embodiment the capping region can be from 1 to 10, e.g. 2-9, 3-8, 4-7, 1-5, 5-10, or at least 2, or 10 or fewer nucleotides in length. In some embodiments, the cap is absent.

In some embodiments, the first and second operational regions of the IVT polynucleotide can range from 3 to 40, e.g., 5-30, 10-20, 15, or at least 4, or 30 or fewer nucleotides in length and can comprise, in addition to a Start and/or Stop codon, one or more signal and/or restriction sequences.

In some embodiments, the IVT polynucleotides can be structurally modified or chemically modified. When the IVT polynucleotides are chemically and/or structurally modified the polynucleotides can be referred to as "modified IVT polynucleotides."

In some embodiments, if the IVT polynucleotides are chemically modified they can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the IVT polynucleotides can have a uniform chemical modification of two, three, or four of the same nucleoside type throughout the entire polynucleotide (such as all uridines and all cytosines, etc. are modified in the same way).

In some embodiments, the IVT polynucleotides can include a sequence encoding a self-cleaving peptide, described herein, such as but not limited to the 2A peptide. The polynucleotide sequence of the 2A peptide in the IVT polynucleotide can be modified or codon optimized by the methods described herein and/or are known in the art. In some embodiments, this sequence can be used to separate the coding region of two or more polypeptides of interest in the IVT polynucleotide.

Chimeric Polynucleotide Architecture

In some embodiments, the polynucleotide of the present disclosure is a chimeric polynucleotide. The chimeric polynucleotides or RNA constructs disclosed herein maintain a modular organization similar to IVT polynucleotides, but the chimeric polynucleotides comprise one or more structural and/or chemical modifications or alterations which impart useful properties to the polynucleotide. As such, the chimeric polynucleotides which are modified mRNA molecules of the present disclosure are termed "chimeric modified mRNA" or "chimeric mRNA."

Chimeric polynucleotides have portions or regions which differ in size and/or chemical modification pattern, chemical modification position, chemical modification percent or chemical modification population and combinations of the foregoing.

Examples of parts or regions, where the chimeric polynucleotide functions as an mRNA and encodes OX40L, but is not limited to, untranslated regions (UTRs, such as the 5' UTR or 3' UTR), coding regions, cap regions, polyA tail regions, start regions, stop regions, signal sequence regions, and combinations thereof. Regions or parts that join or lie between other regions can also be designed to have subregions.

In some embodiments, the chimeric polynucleotides of the disclosure have a structure comprising Formula I.

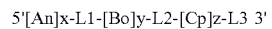     Formula I wherein:

each of A and B independently comprises a region of linked nucleosides;

either A or B or both A and B encode an OX40L polypeptide described elsewhere herein;

C is an optional region of linked nucleosides;

at least one of regions A, B, or C is positionally modified, wherein said positionally modified region comprises at least two chemically modified nucleosides of one or more of the same nucleoside type of adenosine, thymidine, guanosine, cytidine, or uridine, and wherein at least two of the chemical modifications of nucleosides of the same type are different chemical modifications;

n, o and p are independently an integer between 15-1000;

x and y are independently 1-20;

z is 0-5;

L1 and L2 are independently optional linker moieties, said linker moieties being either nucleic acid based or non-nucleic acid based; and L3 is an optional conjugate or an optional linker moiety, said linker moiety being either nucleic acid based or non-nucleic acid based.

In some embodiments, at least one of the regions of linked nucleosides of A comprises a sequence of linked nucleosides which can function as a 5' untranslated region (UTR). The sequence of linked nucleosides can be a natural or synthetic 5' UTR. As a non-limiting example, the chimeric polynucleotide can encode an OX40L polypeptide and the sequence of linked nucleosides of A can encode the native 5' UTR of the OX40L polypeptide or a non-heterologous 5' UTR such as, but not limited to a synthetic UTR.

In another embodiment, at least one of the regions of linked nucleosides of A is a cap region. The cap region can be located 5' to a region of linked nucleosides of A functioning as a 5'UTR. The cap region can comprise at least one cap such as, but not limited to, Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azido-guanosine, Cap2 and Cap4.

In some embodiments, the polynucleotide of the disclosure comprises a Cap1 5'UTR. In some embodiments, a polynucleotide comprising 5'UTR sequence, e.g., Cap1, for encoding an OX40L polypeptide disclosed herein increases expression of OX40L compared to polynucleotides encoding OX40L comprising a different 5'UTR (e.g., Cap0, ARCA, inosine, N1-methyl-guanosine, 2'fluoro-guanosine, 7-deaza-guanosine, 8-oxo-guanosine, 2-amino-guanosine, LNA-guanosine, 2-azido-guanosine, Cap2 or Cap4). In some embodiments, a polynucleotide comprises the Cap1 5'UTR, wherein the polynucleotide encodes an OX40L polypeptide. In some embodiments, polynucleotide comprising the Cap1 5'UTR, increases OX40L expression.

In some embodiments, at least one of the regions of linked nucleosides of B comprises at least one open reading frame of a nucleic acid sequence encoding an OX40L polypeptide. The nucleic acid sequence can be codon optimized and/or comprise at least one modification.

In some embodiments, at least one of the regions of linked nucleosides of C comprises a sequence of linked nucleosides which can function as a 3' UTR. The sequence of linked nucleosides can be a natural or synthetic 3' UTR. As a non-limiting example, the chimeric polynucleotide can encode an OX40L polypeptide and the sequence of linked nucleosides of C can encode the native 3' UTR of an OX40L polypeptide or a non-heterologous 3' UTR such as, but not limited to a synthetic UTR.

In some embodiments, at least one of the regions of linked nucleosides of A comprises a sequence of linked nucleosides which functions as a 5' UTR and at least one of the regions of linked nucleosides of C comprises a sequence of linked nucleosides which functions as a 3' UTR. In some embodiments, the 5' UTR and the 3' UTR can be from the same or different species. In another embodiment, the 5' UTR and the 3' UTR can encode the native untranslated regions from different proteins from the same or different species.

Chimeric polynucleotides, including the parts or regions thereof, of the present disclosure can be classified as hemimers, gapmers, wingmers, or blockmers.

As used herein, a "hemimer" is a chimeric polynucleotide comprising a region or part which comprises half of one pattern, percent, position or population of a chemical modification(s) and half of a second pattern, percent, position or population of a chemical modification(s). Chimeric polynucleotides of the present disclosure can also comprise hemimer subregions. In some embodiments, a part or region is 50% of one and 50% of another.

In some embodiments, the entire chimeric polynucleotide is 50% of one and 50% of the other. Any region or part of any chimeric polynucleotide of the disclosure can be a hemimer. Types of hemimers include pattern hemimers, population hemimers or position hemimers. By definition, hemimers are 50:50 percent hemimers.

As used herein, a "gapmer" is a chimeric polynucleotide having at least three parts or regions with a gap between the parts or regions. The "gap" can comprise a region of linked nucleosides or a single nucleoside which differs from the chimeric nature of the two parts or regions flanking it. The two parts or regions of a gapmer can be the same or different from each other.

As used herein, a "wingmer" is a chimeric polynucleotide having at least three parts or regions with a gap between the parts or regions. Unlike a gapmer, the two flanking parts or regions surrounding the gap in a wingmer are the same in degree or kind. Such similarity can be in the length of number of units of different modifications or in the number of modifications. The wings of a wingmer can be longer or shorter than the gap. The wing parts or regions can be 20, 30, 40, 50, 60 70, 80, 90 or 95% greater or shorter in length than the region which comprises the gap.

As used herein, a "blockmer" is a patterned polynucleotide where parts or regions are of equivalent size or number and type of modifications. Regions or subregions in a blockmer can be 50, 51, 52, 53, 54, 55, 56, 57, 58, 59, 60, 61 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 310, 320, 330, 340, 350, 360, 370, 380, 390, 400, 410, 420, 430, 440, 450, 460, 470, 480, 490 or 500, nucleosides long.

Chimeric polynucleotides, including the parts or regions thereof, of the present disclosure having a chemical modification pattern are referred to as "pattern chimeras." Pattern chimeras can also be referred to as blockmers. Pattern chimeras are those polynucleotides having a pattern of modifications within, across or among regions or parts.

Patterns of modifications within a part or region are those which start and stop within a defined region. Patterns of modifications across a part or region are those patterns which start in on part or region and end in another adjacent part or region. Patterns of modifications among parts or regions are those which begin and end in one part or region and are repeated in a different part or region, which is not necessarily adjacent to the first region or part.

The regions or subregions of pattern chimeras or blockmers can have simple alternating patterns such as ABAB [AB]n where each "A" and each "B" represent different chemical modifications (at least one of the base, sugar or backbone linker), different types of chemical modifications (e.g., naturally occurring and non-naturally occurring), different percentages of modifications or different populations of modifications. The pattern can repeat n number of times where n=3-300. Further, each A or B can represent from 1-2500 units (e.g., nucleosides) in the pattern. Patterns can also be alternating multiples such as AABBAABB[AABB]n (an alternating double multiple) or AAABBBAAABBB [AAABBB]n (an alternating triple multiple) pattern. The pattern can repeat n number of times where n=3-300.

Different patterns can also be mixed together to form a second order pattern. For example, a single alternating pattern can be combined with a triple alternating pattern to form a second order alternating pattern A'B'. One example would be [ABABAB][AAABBBAAABBB][ABABAB] [AAABBBAAABBB][ABABAB][AAABBBAAABBB], where [ABABAB] is A' and [AAABBBAAABBB] is B'. In like fashion, these patterns can be repeated n number of times, where n=3-300.

Patterns can include three or more different modifications to form an ABCABC[ABC]n pattern. These three component patterns can also be multiples, such as AABBCCAABBCC[AABBCC]n and can be designed as combinations with other patterns such as ABCABCAABBCCABCABCAABBCC, and can be higher order patterns.

Regions or subregions of position, percent, and population modifications need not reflect an equal contribution from each modification type. They can form series such as "1-2-3-4", "1-2-4-8", where each integer represents the number of units of a particular modification type. Alternatively, they can be odd only, such as "1-3-3-1-3-1-5" or even only "2-4-2-4-6-4-8" or a mixture of both odd and even number of units such as "1-3-4-2-5-7-3-3-4".

Pattern chimeras can vary in their chemical modification by degree (such as those described above) or by kind (e.g., different modifications).

Chimeric polynucleotides, including the parts or regions thereof, of the present disclosure having at least one region with two or more different chemical modifications of two or more nucleoside members of the same nucleoside type (A, C, G, T, or U) are referred to as "positionally modified" chimeras. Positionally modified chimeras are also referred to herein as "selective placement" chimeras or "selective placement polynucleotides". As the name implies, selective placement refers to the design of polynucleotides which, unlike polynucleotides in the art where the modification to any A, C, G, T or U is the same by virtue of the method of synthesis, can have different modifications to the individual As, Cs, Gs, Ts or Us in a polynucleotide or region thereof. For example, in a positionally modified chimeric polynucleotide, there can be two or more different chemical modifications to any of the nucleoside types of As, Cs, Gs, Ts, or Us. There can also be combinations of two or more to any two or more of the same nucleoside type. For example, a positionally modified or selective placement chimeric polynucleotide can comprise 3 different modifications to the population of adenines in the molecule and also have 3 different modifications to the population of cytosines in the construct—all of which can have a unique, non-random, placement.

Chimeric polynucleotides, including the parts or regions thereof, of the present disclosure having a chemical modification percent are referred to as "percent chimeras." Percent chimeras can have regions or parts which comprise at least 1%, at least 2%, at least 5%, at least 8%, at least 10%, at least 20%, at least 30%, at least 40%, at least 50%, at least 60%, at least 70%, at least 80%, at least 90%, at least 95%, or at least 99% positional, pattern or population of modifications. Alternatively, the percent chimera can be completely modified as to modification position, pattern, or population. The percent of modification of a percent chimera can be split between naturally occurring and non-naturally occurring modifications.

Chimeric polynucleotides, including the parts or regions thereof, of the present disclosure having a chemical modification population are referred to as "population chimeras." A population chimera can comprise a region or part where nucleosides (their base, sugar or backbone linkage, or combination thereof) have a select population of modifications. Such modifications can be selected from functional populations such as modifications which induce, alter or modulate a phenotypic outcome. For example, a functional population can be a population or selection of chemical modifications which increase the level of a cytokine. Other functional populations can individually or collectively function to decrease the level of one or more cytokines. Use of a selection of these like-function modifications in a chimeric polynucleotide would therefore constitute a "functional population chimera." As used herein, a "functional population chimera" can be one whose unique functional feature is defined by the population of modifications as described above or the term can apply to the overall function of the chimeric polynucleotide itself. For example, as a whole the chimeric polynucleotide can function in a different or superior way as compared to an unmodified or non-chimeric polynucleotide.

It should be noted that polynucleotides which have a uniform chemical modification of all of any of the same nucleoside type or a population of modifications produced by mere downward titration of the same starting modification in all of any of the same nucleoside type, or a measured percent of a chemical modification of all any of the same nucleoside type but with random incorporation, such as where all uridines are replaced by a uridine analog, e.g., pseudouridine or 5-methoxyuridine, are not considered chimeric polynucleotides. Likewise, polynucleotides having a uniform chemical modification of two, three, or four of the same nucleoside type throughout the entire polynucleotide (such as all uridines and all cytosines, etc. are modified in the same way) are not considered chimeric polynucleotides. One example of a polynucleotide which is not chimeric is the canonical pseudouridine/5-methyl cytosine modified polynucleotide. These uniform polynucleotides are arrived at entirely via in vitro transcription (IVT) enzymatic synthesis; and due to the limitations of the synthesizing enzymes, they contain only one kind of modification at the occurrence of each of the same nucleoside type, i.e., adenosine (A), thymidine (T), guanosine (G), cytidine (C) or uridine (U), found in the polynucleotide. Such polynucleotides can be characterized as IVT polynucleotides.

The chimeric polynucleotides of the present disclosure can be structurally modified or chemically modified. When the chimeric polynucleotides of the present disclosure are chemically and/or structurally modified the polynucleotides can be referred to as "modified chimeric polynucleotides."

The regions or parts of the chimeric polynucleotides can be separated by a linker or spacer moiety. Such linkers or spaces can be nucleic acid based or non-nucleosidic.

In some embodiments, the chimeric polynucleotides can include a sequence encoding a self-cleaving peptide described herein, such as, but not limited to, a 2A peptide. The polynucleotide sequence of the 2A peptide in the chimeric polynucleotide can be modified or codon optimized by the methods described herein and/or are known in the art.

Notwithstanding the foregoing, the chimeric polynucleotides of the present disclosure can comprise a region or part which is not positionally modified or not chimeric as defined herein. For example, a region or part of a chimeric polynucleotide can be uniformly modified at one or more A, T, C, G, or U, but the polynucleotides will not be uniformly modified throughout the entire region or part.

Chimeric polynucleotides of the present disclosure can be completely positionally modified or partially positionally modified. They can also have subregions which can be of any pattern or design.

In some embodiments, regions or subregions of the polynucleotides can range from absent to 500 nucleotides in length (e.g., at least 60, 70, 80, 90, 100, 110, 120, 130, 140, 150, 160, 170, 180, 190, 200, 250, 300, 350, 400, 450, or 500 nucleotides). Where the region is a polyA tail, the length can be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides to about 160 nucleotides are functional. The chimeric polynucleotides of the present disclosure which function as an mRNA need not comprise a polyA tail.

According to the present disclosure, chimeric polynucleotides which function as an mRNA can have a capping region. The capping region can comprise a single cap or a series of nucleotides forming the cap. In this embodiment the capping region can be from 1 to 10, e.g. 2-9, 3-8, 4-7, 1-5, 5-10, or at least 2, or 10 or fewer nucleotides in length. In some embodiments, the cap is absent.

The present disclosure contemplates chimeric polynucleotides which are circular or cyclic. As the name implies circular polynucleotides are circular in nature meaning that the termini are joined in some fashion, whether by ligation, covalent bond, common association with the same protein or other molecule or complex or by hybridization.

Chimeric polynucleotides, formulations and compositions comprising chimeric polynucleotides, and methods of making, using and administering chimeric polynucleotides are also described in International Patent Application No. PCT/US2014/53907.

In some embodiments, the chimeric polynucleotide encodes an OX40L polypeptide. In some embodiments, the chimeric polynucleotides of the disclosure comprise any one of the OX40L nucleic acid sequences listed in Table 1. In some embodiments the chimeric polynucleotide of the disclosure encodes any one of the OX40L polypeptides listed in Table 1.

Circular Polynucleotide

The polynucleotide (e.g., mRNA) encoding an OX40L polypeptide can be circular or cyclic. As used herein, "circular polynucleotides" or "circP" means a single stranded circular polynucleotide which acts substantially like, and has the properties of, an RNA. The term "circular" is also meant to encompass any secondary or tertiary configuration of the circP. Circular polynucleotides are circular in nature meaning that the termini are joined in some fashion, whether by ligation, covalent bond, common association with the same protein or other molecule or complex or by hybridization.

Circular polynucleotides, formulations and compositions comprising circular polynucleotides, and methods of making, using and administering circular polynucleotides are also disclosed in International Patent Application No. PCT/US2014/53904.

In some embodiments, the circular polynucleotide encodes an OX40L polypeptide. In some embodiments, the circular polynucleotides of the disclosure comprise any one of the OX40L nucleic acid sequences listed in Table 1. In some embodiments, the circular polynucleotides of the disclosure encode any one of the OX40L polypeptides listed in Table 1. In some embodiments, the circular polynucleotide increases OX40L expression.

Multimers of Polynucleotides

In some embodiments, multiple distinct chimeric polynucleotides and/or IVT polynucleotides can be linked together through the 3'-end using nucleotides which are modified at the 3'-terminus. Chemical conjugation can be used to control the stoichiometry of delivery into cells. This can be controlled by chemically linking chimeric polynucleotides and/or IVT polynucleotides using a 3'-azido terminated nucleotide on one polynucleotides species and a C5-ethynyl or alkynyl-containing nucleotide on the opposite polynucleotide species. The modified nucleotide is added post-transcriptionally using terminal transferase (New England Biolabs, Ipswich, Mass.) according to the manufacturer's protocol. After the addition of the 3'-modified nucleotide, the two polynucleotides species can be combined in an aqueous solution, in the presence or absence of copper, to form a new covalent linkage via a click chemistry mechanism as described in the literature.

In another example, more than two chimeric polynucleotides and/or IVT polynucleotides can be linked together using a functionalized linker molecule. For example, a functionalized saccharide molecule can be chemically modified to contain multiple chemical reactive groups (SH—, NH2-, N3, etc.) to react with the cognate moiety on a 3'-functionalized mRNA molecule (i.e., a 3'-maleimide ester, 3'-NHS-ester, alkynyl). The number of reactive groups on the modified saccharide can be controlled in a stoichiometric fashion to directly control the stoichiometric ratio of conjugated chimeric polynucleotides and/or IVT polynucleotides.

In some embodiments, the chimeric polynucleotides and/or IVT polynucleotides can be linked together in a pattern. The pattern can be a simple alternating pattern such as CD[CD]x where each "C" and each "D" represent a chimeric polynucleotide, IVT polynucleotide, different chimeric polynucleotides or different IVT polynucleotides. The pattern can repeat x number of times, where x=1-300. Patterns can also be alternating multiples such as CCDD[CCDD]x (an alternating double multiple) or CCCDDD[CCCDDD]x (an alternating triple multiple) pattern. The alternating double multiple or alternating triple multiple can repeat x number of times, where x=1-300.

Conjugates and Combinations of Polynucleotides

The polynucleotide (e.g., mRNA) encoding an OX40L polypeptide can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugation can result in increased stability and/or half-life and can be particularly useful in targeting the polynucleotides to specific sites in the cell, tissue or organism.

Polynucleotides Having Untranslated Regions (UTRs)

The polynucleotide (e.g., mRNA) encoding an OX40L polypeptide of the disclosure can further comprise a nucleotide sequence encoding one or more heterologous polypeptides. In one embodiment, the one or more heterologous polypeptides improve a pharmacokinetic property or pharmacodynamics property of the OX40L polypeptide or a polynucleotide encoding the polypeptide. In another embodiment, the one or more heterologous polypeptides comprise a polypeptide that can extend a half-life of the OX40L polypeptide In one embodiment, the mRNA encodes an extracellular portion of an OX40L polypeptide and one or more heterologous polypeptides.

In another embodiment, the mRNA encodes an extracellular region of an OX40L polypeptide and a heterologous polypeptide. In another embodiment, the mRNA encodes a fusion protein comprising an extracellular region of an OX40L polypeptide and a polypeptide that can extend a half-life of the OX40L polypeptide.

The polynucleotide (e.g., mRNA) encoding an OX40L polypeptide can further comprise one or more regions or parts which act or function as an untranslated region. By definition, wild type untranslated regions (UTRs) of a gene are transcribed but not translated. In mRNA, the 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. Tables 3 and 4 provide a listing of exemplary UTRs which can be utilized in the polynucleotides of the present disclosure.

5' UTR and Translation Initiation

In certain embodiments, the polynucleotide (e.g., mRNA) encoding an OX40L polypeptide further comprises a 5' UTR and/or a translation initiation sequence. Natural 5'UTRs bear features which play roles in translation initiation. They harbor signatures like Kozak sequences which are commonly known to be involved in the process by which the ribosome initiates translation of many genes. 5'UTR also have been known to form secondary structures which are involved in elongation factor binding.

By engineering the features typically found in abundantly expressed genes of specific target organs, one can enhance the stability and protein production of the polynucleotides of the disclosure. For example, introduction of 5' UTR of mRNA known to be upregulated in cancers, such as c-myc, could be used to enhance expression of a nucleic acid molecule, such as a polynucleotides, in cancer cells. Untranslated regions useful in the design and manufacture of polynucleotides include, but are not limited to, those disclosed in International Patent Publication No. WO 2014/164253 A2.

Shown in Table 3 is a listing of a 5'-untranslated region of the disclosure. Variants of 5' UTRs can be utilized wherein one or more nucleotides are added or removed to the termini, including A, U, C or G.

TABLE 3

5'-Untranslated Regions

| 5' UTR Identifier | Name/ Description | Sequence | SEQ ID NO. |
|---|---|---|---|
| 5UTR-001 | Upstream UTR | GGGAAAUAAGAGAGAAAAGAAGAGUAAGAAGAAAUAU AAGAGCCACC | SEQ ID NO: 27 |
| 5UTR-002 | Upstream UTR | GGGAGAUCAGAGAGAAAAGAAGAGUAAGAAGAAAUAU AAGAGCCACC | SEQ ID NO: 28 |
| 5UTR-003 | Upstream UTR | GGAAUAAAAGUCUCAACACAACAUAUACAAAACAAAC GAAUCUCAAGCAAUCAAGCAUUCUACUUCUAUUGCAG CAAUUUAAAUCAUUUCUUUUAAAGCAAAAGCAAUUUU CUGAAAAUUUUCACCAUUUACGAACGAUAGCAAC | SEQ ID NO: 29 |
| 5UTR-004 | Upstream UTR | GGGAGACAAGCUUGGCAUUCCGGUACUGUU GGUAAAGCCACC | SEQ ID NO: 30 |
| 5UTR-005 | Upstream UTR | GGGAGAUCAGAGAGAAAAGAAGAGUAAGAAGAAAUAU AAGAGCCACC | SEQ ID NO: 31 |
| 5UTR-006 | Upstream UTR | GGAAUAAAAGUCUCAACACAACAUAUACAAAACAAAC GAAUCUCAAGCAAUCAAGCAUUCUACUUCUAUUGCAG CAAUUUAAAUCAUUUCUUUUAAAGCAAAAGCAAUUUU CUGAAAAUUUUCACCAUUUACGAACGAUAGCAAC | SEQ ID NO: 32 |
| 5UTR-007 | Upstream UTR | GGGAGACAAGCUUGGCAUUCCGGUACUGUU GGUAAAGCCACC | SEQ ID NO: 33 |
| 5UTR-008 | Upstream UTR | GGGAAUUAACAGAGAAAAGAAGAGUAAGAAGAAAUAU AAGAGCCACC | SEQ ID NO: 34 |

TABLE 3-continued

5'-Untranslated Regions

| 5' UTR Identifier | Name/ Description | Sequence | SEQ ID NO. |
|---|---|---|---|
| 5UTR-009 | Upstream UTR | GGGAAAUUAGACAGAAAAGAAGAGUAAGAAGAAAUAU AAGAGCCACC | SEQ ID NO: 35 |
| 5UTR-010 | Upstream UTR | GGGAAAUAAGAGAGUAAAGAACAGUAAGAAGAAAUAU AAGAGCCACC | SEQ ID NO: 36 |
| 5UTR-011 | Upstream UTR | GGGAAAAAAGAGAGAAAAGAAGACUAAGAAGAAAUAU AAGAGCCACC | SEQ ID NO: 37 |
| 5UTR-012 | Upstream UTR | GGGAAAUAAGAGAGAAAAGAAGAGUAAGAAGAUAUAU AAGAGCCACC | SEQ ID NO: 38 |
| 5UTR-013 | Upstream UTR | GGGAAAUAAGAGACAAAACAAGAGUAAGAAGAAAUAU AAGAGCCACC | SEQ ID NO: 39 |
| 5UTR-014 | Upstream UTR | GGGAAAUUAGAGAGUAAAGAACAGUAAGUAGAAUUAA AAGAGCCACC | SEQ ID NO: 40 |
| 5UTR-015 | Upstream UTR | GGGAAAUAAGAGAGAAUAGAAGAGUAAGAAGAAAUAU AAGAGCCACC | SEQ ID NO: 41 |
| 5UTR-016 | Upstream UTR | GGGAAAUAAGAGAGAAAAGAAGAGUAAGAAGAAAAUU AAGAGCCACC | SEQ ID NO: 42 |
| 5UTR-017 | Upstream UTR | GGGAAAUAAGAGAGAAAAGAAGAGUAAGAAGAAAUUU AAGAGCCACC | SEQ ID NO: 43 |
| 5UTR-018 | Upstream UTR | GGGAAAUAAGAGAGAAAAGAAGAGUAAGAAGAAAUAU AAGAGCCACC | SEQ ID NO: 44 |

Other non-UTR sequences can also be used as regions or subregions within the polynucleotides. For example, introns or portions of introns sequences can be incorporated into regions of the polynucleotides. Incorporation of intronic sequences can increase protein production as well as polynucleotide levels.

Combinations of features can be included in flanking regions and can be contained within other features. For example, the ORF can be flanked by a 5' UTR which can contain a strong Kozak translational initiation signal and/or a 3' UTR which can include an oligo(dT) sequence for templated addition of a poly-A tail. 5'UTR can comprise a first polynucleotide fragment and a second polynucleotide fragment from the same and/or different genes such as the 5'UTRs described in US Patent Application Publication No. 20100293625.

These UTRs or portions thereof can be placed in the same orientation as in the transcript from which they were selected or can be altered in orientation or location. Hence a 5' or 3' UTR can be inverted, shortened, lengthened, made with one or more other 5' UTRs or 3' UTRs.

In some embodiments, the UTR sequences can be changed in some way in relation to a reference sequence. For example, a 3' or 5' UTR can be altered relative to a wild type or native UTR by the change in orientation or location as taught above or can be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' or 3' UTR can be used. As used herein, a "double" UTR is one in which two copies of the same UTR are encoded either in series or substantially in series. For example, a double beta-globin 3' UTR can be used as described in US Patent publication 20100129877.

In some embodiments, flanking regions can be heterologous. In some embodiments, the 5' untranslated region can be derived from a different species than the 3' untranslated region. The untranslated region can also include translation enhancer elements (TEE). As a non-limiting example, the TEE can include those described in US Application No. 20090226470.

3' UTR and the AU Rich Elements

In certain embodiments, the polynucleotide (e.g., mRNA) encoding an OX40L polypeptide further comprises a 3' UTR. 3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the disclosure comprises a binding site for regulatory proteins or microRNAs. In some embodiments, the 3'-UTR has a silencer region, which binds to repressor proteins and inhibits the expression of the mRNA. In other embodiments, the 3'-UTR comprises an AU-rich element. Proteins bind AREs to affect the stability or decay rate of transcripts in a localized manner or affect translation initiation. In other embodiments, the 3'-UTR comprises the sequence AAUAAA that directs addition of several hundred adenine residues called the poly(A) tail to the end of the mRNA transcript.

Table 4 shows a listing of 3'-untranslated regions useful for the mRNAs encoding an OX40L polypeptide. Variants of 3' UTRs can be utilized wherein one or more nucleotides are added or removed to the termini, including A, U, C or G.

TABLE 4A

Exemplary 3'-Untranslated Regions

| 3' UTR Identifier | Name/ Description | Sequence | SEQ ID NO. |
|---|---|---|---|
| 3UTR-001 | Creatine Kinase | GCGCCUGCCCACCUGCCACCGACUGCUGGAACCCAGCCA GUGGGAGGGCCUGGCCCACCAGAGUCCUGCUCCCUCACU CCUCGCCCCGCCCCCUGUCCCAGAGUCCCACCUGGGGGC UCUCUCCACCCUUCUCAGAGUUCCAGUUUCAACCAGAGU UCCAACCAAUGGGCUCCAUCCUCUGGAUUCUGGCCAAUG AAAUAUCUCCCUGGCAGGGUCCUCUUCUUUUCCCAGAGC UCCACCCCAACCAGGAGCUCUAGUUAAUGGAGAGCUCCC AGCACACUCGGAGCUUGUGCUUUGUCUCCACGCAAAGCG AUAAAUAAAAGCAUUGGUGGCCUUUGGUCUUUGAAUAAA GCCUGAGUAGGAAGUCUAGA | SEQ ID NO: 45 |
| 3UTR-002 | Myoglobin | GCCCCUGCCGCUCCCACCCCCACCCAUCUGGGCCCCGGG UUCAAGAGAGAGCGGGGUCUGAUCUCGUGUAGCCAUAUA GAGUUUGCUUCUGAGUGUCUGCUUUGUUUAGUAGAGGUG GGCAGGAGGAGCUGAGGGGCUGGGGCUGGGGUGUUGAAG UUGGCUUUGCAUGCCCAGCGAUGCGCCUCCCUGUGGGAU GUCAUCACCCUGGGAACCGGGAGUGGCCCUUGGCUCACU GUGUUCUGCAUGGUUUGGAUCUGAAUUAAUUGUCCUUUC UUCUAAAUCCCAACCGAACUUCUUCCAACCUCCAAACUG GCUGUAACCCCAAAUCCAAGCCAUUAACUACACCUGACA GUAGCAAUUGUCUGAUUAAUCACUGGCCCCUUGAAGACA GCAGAAUGUCCCUUUGCAAUGAGGAGGAGAUCUGGGCUG GGCGGGCCAGCUGGGGAAGCAUUUGACUAUCUGGAACUU GUGUGUGCCUCCUCAGGUAUGGCAGUGACUCACCUGGUU UUAAUAAAACAACCUGCAACAUCUCAUGGUCUUUGAAUA AAGCCUGAGUAGGAAGUCUAGA | SEQ ID NO: 46 |
| 3UTR-003 | α-actin | ACACACUCCACCUCCAGCACGCGACUUCUCAGGACGACG AAUCUUCUCAAUGGGGGGGCGGCUGAGCUCCAGCCACCC CGCAGUCACUUUCUUUGUAACAACUUCCGUUGCUGCCAU CGUAAACUGACACAGUGUUUAUAACGUGUACAUACAUUA ACUUAUUACCUCAUUUUGUUAUUUUUCGAAACAAAGCCC UGUGGAAGAAAAUGGAAAACUUGAAGAAGCAUUAAAGUC AUUCUGUUAAGCUGCGUAAAUGGUCUUUGAAUAAAGCCU GAGUAGGAAGUCUAGA | SEQ ID NO: 47 |
| 3UTR-004 | Albumin | CAUCACAUUUAAAAGCAUCUCAGCCUACCAUGAGAAUAA GAGAAAGAAAAUGAAGAUCAAAAGCUUAUUCAUCUGUUU UCUUUUUCGUUGGUGUAAAGCCAACACCCUGUCUAAAAA ACAUAAAUUUCUUUAAUCAUUUUGCCUCUUUUCUCUGU GCUUCAAUUAAUAAAAAAUGGAAAGAAUCUAAUAGAGUG GUACAGCACUGUUAUUUUUCAAAGAUGUGUUGCUAUCCU GAAAAUUCUGUAGGUUCUGUGGAAGUUCCAGUGUUCUCU CUUAUUCCACUUCGGUAGAGGAUUUCUAGUUUCUUGUGG GCUAAUUAAAUAAAUCAUUAAUACUCUUCUAAUGGUCUU UGAAUAAAGCCUGAGUAGGAAGUCUAGA | SEQ ID NO: 48 |
| 3UTR-005 | α-globin | GCUGCCUUCUGCGGGGCUUGCCUUCUGGCCAUGCCCUUC UUCUCUCCCUUGCACCUGUACCUCUUGGUCUUUGAAUAA AGCCUGAGUAGGAAGGCGGCCGCUCGAGCAUGCAUCUAG A | SEQ ID NO: 49 |
| 3UTR-006 | G-CSF | GCCAAGCCCUCCCCAUCCCAUGUAUUUAUCUCUAUUUAA UAUUUAUGUCUAUUUAAGCCUCAUAUUUAAAGACAGGGA AGAGCAGAACGGAGCCCCAGGCCUCUGUGUCCUUCCCUG CAUUUCUGAGUUUCAUUCUCCUGCCUGUAGCAGUGAGAA AAAGCUCCUGUCCUCCCAUCCCCUGGACUGGGAGGUAGA UAGGUAAAUACCAAGUAUUUAUUACUAUGACUGCUCCCC AGCCCUGGCUCUGCAAUGGGCACUGGGAUGAGCCGCUGU GAGCCCCUGGUCCUGAGGGUCCCCACCUGGGACCCUUGA GAGUAUCAGGUCUCCCACGUGGGAGACAAGAAAUCCCUG UUUAAUAUUUAAACAGCAGUGUUCCCCAUCUGGGUCCUU GCACCCCUCACUCUGGCCUCAGCCGACUGCACAGCGGCC CCUGCAUCCCCUUGGCUGUGAGGCCCCUGGACAAGCAGA GGUGGCCAGAGCUGGGAGGCAUGGCCCUGGGGUCCCACG AAUUUGCUGGGGAAUCUCGUUUUUCUUCUUAAGACUUUU GGGACAUGGUUUGACUCCCGAACAUCACCGACGCGUCUC CUGUUUUUCUGGGUGGCCUCGGGACACCUGCCCUGCCCC CACGAGGGUCAGGACUGUGACUCUUUUUAGGGCCAGGCA GGUGCCUGGACAUUUGCCUUGCUGGACGGGGACUGGGGA UGUGGGAGGGAGCAGACAGGAGGAAUCAUGUCAGGCCUG |  SEQ ID NO: 50 |

TABLE 4A-continued

Exemplary 3'-Untranslated Regions

| 3' UTR Identifier | Name/ Description | Sequence | SEQ ID NO. |
|---|---|---|---|
| | | UGUGUGAAAGGAAGCUCCACUGUCACCCUCCACCUCUUC ACCCCCCACUCACCAGUGUCCCCUCCACUGUCACAUUGU AACUGAACUUCAGGAUAAUAAAGUGUUUGCCUCCAUGGU CUUUGAAUAAAGCCUGAGUAGGAAGGCGGCCGCUCGAGC AUGCAUCUAGA | |
| 3UTR-007 | Col1a2; collagen, type I, alpha 2 | ACUCAAUCUAAAUUAAAAAAGAAAGAAAUUUGAAAAAAC UUUCUCUUUGCCAUUUCUUCUUCUUCUUUUUUAACUGAA AGCUGAAUCCUUCCAUUUCUUCUGCACAUCUACUUGCUU AAAUUGUGGGCAAAAGAGAAAAAGAAGGAUUGAUCAGAG CAUUGUGCAAUACAGUUUCAUUAACUCCUUCCCCCGCUC CCCCAAAAAUUUGAAUUUUUUUUUCAACACUCUUACACC UGUUAUGGAAAAUGUCAACCUUUGUAAGAAAACCAAAAU AAAAAUUGAAAAAUAAAAACCAUAAACAUUUGCACCACU UGUGGCUUUUGAAUAUCUUCCACAGAGGGAAGUUUAAAA CCCAAACUUCCAAAGGUUUAAACUACCUCAAAACACUUU CCCAUGAGUGUGAUCCACAUUGUUAGGUGCUGACCUAGA CAGAGAUGAACUGAGGUCCUUGUUUUGUUUUGUUCAUAA UACAAAGGUGCUAAUUAAUAGUAUUUCAGAUACUUGAAG AAUGUUGAUGGUGCUAGAAGAAUUUGAGAAGAAAUACUC CUGUAUUGAGUUGUAUCGUGUGGUGUAUUUUUUAAAAAA UUUGAUUUAGCAUUCAUAUUUUCCAUCUUAUUCCCAAUU AAAAGUAUGCAGAUUAUUUGCCCAAAUCUUCUUCAGAUU CAGCAUUUGUUCUUUGCCAGUCUCAUUUUCAUCUUCUUC CAUGGUUCCACAGAAGCUUUGUUUCUUGGGCAAGCAGAA AAAUUAAAUUGUACCUAUUUUGUAUAUGUGAGAUGUUUA AAUAAAUUGUGAAAAAAAUGAAAUAAAGCAUGUUUGGUU UUCCAAAAGAACAUAU | SEQ ID NO: 51 |
| 3UTR-008 | Col6a2; collagen, type VI, alpha 2 | CGCCGCCGCCCGGGCCCCGCAGUCGAGGGUCGUGAGCCC ACCCCGUCCAUGGUGCUAAGCGGGCCCGGGUCCCACACG GCCAGCACCGCUGCUCACUCGGACGACGCCCUGGGCCUG CACCUCUCCAGCUCCUCCCACGGGGUCCCCGUAGCCCCG GCCCCCGCCCAGCCCCAGGUCUCCCCAGGCCCUCCGCAG GCUGCCCGGCCUCCCUCCCCCUGCAGCCAUCCCAAGGCU CCUGACCUACCUGGCCCCUGAGCUCUGGAGCAAGCCCUG ACCCAAUAAAGGCUUUGAACCCAU | SEQ ID NO: 52 |
| 3UTR-009 | RPN1; ribophorin I | GGGGCUAGAGCCCUCUCCGCACAGCGUGGAGACGGGGCA AGGAGGGGGGUUAUUAGGAUUGGUGGUUUUGUUUUGCUU UGUUUAAAGCCGUGGGAAAAUGGCACAACUUUACCUCUG UGGGAGAUGCAACACUGAGAGCCAAGGGGUGGGAGUUGG GAUAAUUUUUAUAUAAAAGAAGUUUUUCCACUUUGAAUU GCUAAAAGUGGCAUUUUUCCUAUGUGCAGUCACCUCUCU CAUUUCUAAAAUAGGGACGUGGCCAGGCACGGUGGCUCA UGCCUGUAAUCCCAGCACUUUGGGAGGCCGAGGCAGGCG GCUCACGAGGUCAGGAGAUCGAGACUAUCCUGGCUAACA CGGUAAAACCCUGUCUCUACUAAAAGUACAAAAAAUUAG CUGGGCGUGGUGGUGGGCACCUGUAGUCCCAGCUACUCG GGAGGCUGAGGCAGGAGAAAGGCAUGAAUCCAAGAGGCA GAGCUUGCAGUGAGCUGAGAUCACGCCAUUGCACUCCAG CCUGGGCAACAGUGUUAAGACUCUGUCUCAAAUAUAAAU AAAUAAAUAAAUAAAUAAAUAAAUAAAAAUAAAGC GAGAUGUUGCCCUCAAA | SEQ ID NO: 53 |
| 3UTR-010 | LRP1; low density lipoprotein receptor-related protein 1 | GGCCCUGCCCCGUCGGACUGCCCCCAGAAAGCCUCCGC CCCCUGCCAGUGAAGUCCUUCAGUGAGCCCCUCCCCAGC CAGCCCUUCCCUGGCCCCGCCGGAUGUAUAAAUGUAAAA AUGAAGGAAUUACAUUUUAUAUGUGAGCGAGCAAGCCGG CAAGCGAGCACAGUAUUAUUUCUCCAUCCCCUCCCUGCC UGCUCCUUGGCACCCCAUGCUGCCUUCAGGGAGACAGG CAGGGAGGGCUUGGGGCUGCACCUCCUACCCUCCCACCA GAACGCACCCCACUGGGAGAGCUGGUGGUGCAGCCUUCC CCUCCCUGUAUAAGACACUUUGCCAAGGCUCUCCCCUCU CGCCCCAUCCCUGCUUGCCCGCUCCCACAGCUUCCUGAG GGCUAAUUCGGGAAGGGAGAGUUCUUUGCUGCCCCUGU CUGGAAGACGUGGCUCUGGGUGAGGUAGGCGGGAAAGGA UGGAGUGUUUUAGUUCUUGGGGGAGGCCACCCCAAACCC CAGCCCCAACUCCAGGGGCACCUAUGAGAUGGCCAUGCU CAACCCCCCUCCCAGACAGGCCCUCCCUGUCUCCAGGGC CCCCACCGAGGUUCCCAGGGCUGGAGACUUCCUCUGGUA | SEQ ID NO: 54 |

TABLE 4A-continued

Exemplary 3'-Untranslated Regions

| 3' UTR Identifier | Name/ Description | Sequence | SEQ ID NO. |
|---|---|---|---|
| | | AACAUUCCUCCAGCCUCCCCUCCCCUGGGGACGCCAAGG AGGUGGGCCACACCCAGGAAGGGAAAGCGGGCAGCCCCG UUUUGGGGACGUGAACGUUUUAAUAAUUUUUGCUGAAUU CCUUUACAACUAAAUAACACAGAUAUUGUUAUAAAUAAA AUUGU | |
| 3UTR-011 | Nnt1; cardio- trophin-like cytokine factor 1 | AUAUUAAGGAUCAAGCUGUUAGCUAAUAAUGCCACCUCU GCAGUUUUGGGAACAGGCAAAUAAAGUAUCAGUAUACAU GGUGAUGUACAUCUGUAGCAAAGCUCUUGGAGAAAAUGA AGACUGAAGAAAGCAAAGCAAAAACUGUAUAGAGAGAUU UUUCAAAAGCAGUAAUCCCUCAAUUUUAAAAAAGGAUUG AAAAUUCUAAAUGUCUUUCUGUGCAUAUUUUUGUGUUA GGAAUCAAAAGUAUUUUAUAAAAGGAGAAAGAACAGCCU CAUUUUAGAUGUAGUCCUGUUGGAUUUUUUAUGCCUCCU CAGUAACCAGAAAUGUUUUAAAAAACUAAGUGUUUAGGA UUUCAAGACAACAUUAUACAUGGCUCUGAAAUAUCUGAC ACAAUGUAAACAUUGCAGGCACCUGCAUUUUAUGUUUUU UUUUUCAACAAAUGUGACUAAUUUGAAACUUUUAUGAAC UUCUGAGCUGUCCCCUUGCAAUUCAACCGCAGUUUGAAU UAAUCAUAUCAAAUCAGUUUUAAUUUUUUAAAUUGUACU UCAGAGUCUAUAUUUCAAGGGCACAUUUUCUCACUACUA UUUUAAUACAUUAAAGGACUAAAUAAUCUUUCAGAGAUG CUGGAAACAAAUCAUUUGCUUUAUAUGUUUCAUUAGAAU ACCAAUGAAACAUACAACUUGAAAAUUAGUAAUAGUAUU UUUGAAGAUCCCAUUUCUAAUUGGAGAUCUCUUUAAUUU CGAUCAACUUAUAAUGUGUAGUACUAUAUUAAGUGCACU UGAGUGGAAUUCAACAUUUGACUAAUAAAAUGAGUUCAU CAUGUUGGCAAGUGAUGUGGCAAUUAUCUCUGGUGACAA AAGAGUAAAAUCAAAUAUUUCUGCCUGUUACAAAUAUCA AGGAAGACCUGCUACUAUGAAAUAGAUGACAUUAAUCUG UCUUCACUGUUUAUAAUACGGAUGGAUUUUUUUCAAAU CAGUGUGUGUUUUGAGGUCUUAUGUAAUUGAUGACAUUU GAGAGAAAUGGUGGCUUUUUUUAGCUACCUCUUUGUUCA UUUAAGCACCAGUAAAGAUCAUGUCUUUUUAUAGAAGUG UAGAUUUUCUUUGUGACUUUGCUAUCGUGCCUAAAGCUC UAAAUAUAGGUGAAUGUGUGAUGAAUACUCAGAUUAUUU GUCUCUCUAUAUAAUUAGUUUGGUACUAAGUUUCUCAAA AAAUUAUUAACACAUGAAAGACAAUCUCUAAACCAGAAA AAGAAGUAGUACAAAUUUUGUUACUGUAAUGCUCGCGUU UAGUGAGUUUAAAACACACAGUAUCUUUUGGUUUUAUAA UCAGUUUCUAUUUUGCUGUCCUGAGAUUAAGAUCUGUG UAUGUGUGUGUGUGUGUGUGCGUUUGUGUGUUAAAGC AGAAAAGACUUUUUUAAAAGUUUUAAGUGAUAAAUGCAA UUUGUUAAUUGAUCUUAGAUCACUAGUAAACUCAGGGCU GAAUUAUACCAUGUAUAUUCUAUUAGAAGAAAGUAAACA CCAUCUUUAUUCCUGCCCUUUUUCUUCUCUCAAAGUAGU UGUAGUUAUAUCUAGAAAGAAGCAAUUUUGAUUUCUUGA AAAGGUAGUUCCUGCACUCAGUUUAAACUAAAAAUAAUC AUACUUGGAUUUUAUUUAUUUUUUGUCAUAGUAAAAUUU UAAUUUAUAUAUUUUUAUUUAGUAUUAUCUUAUUCUU UGCUAUUUGCCAAUCCUUUGUCAUCAAUUGUGUUUAAAUG AAUUGAAAAUUCAUGCCCUGUUCAUUUUAUUUUACUUUA UUGGUUAGGAUAUUUAAAGGAUUUUGUAUAUAUAAUUU CUUAAAUUAAUAUUCCAAAAGGUUAGUGGACUUAGAUUA UAAAUUAUGGCAAAAAUCUAAAAACAACAAAAAUGAUUU UUAUACAUUCUAUUUCAUUAUUCCUCUUUUUCCAAUAAG UCAUACAAUUGGUAGAUAUGACUUAUUUUAUUUUUGUAU UAUUCACUAUAUCUUUAUGAUAUUUAAGUAUAAAUAAUU AAAAAAAUUUAUUGUACCUUAUAGUCUGUCACCAAAAAA AAAAAAUUAUCUGUAGGUAGUGAAAUGCUAAUGUUGAUU UGUCUUUAAGGGCUUGUUAACUAUCCUUUAUUUUCUCAU UUGUCUUAAAUUAGGAGUUUGUGUUUAAAUUACUCAUCU AAGCAAAAAAUGUAUAUAAAUCCCAUUACUGGGUAUAUA CCCAAAGGAUUAUAAAUCAUGCUGCUAUAAAGACACAUG CACACGUAUGUUUAUUGCAGCACUAUUCACAAUAGCAAA GACUUGGAACCAACCCAAAUGUCCAUCAAUGAUAGACUU GAUUAAGAAAAUGUGCACAUAUACACCAUGGAAUACUAU GCAGCCAUAAAAAGGAUGAGUUCAUGUCCUUUGUAGGG ACAUGGAUAAAGCUGGAAACCAUCAUUCUGAGCAAACUA UUGCAAGGACAGAAAACCAAACACUGCAUGUUCUCACUC AUAGGUGGGAAUUGAACAAUGAGAACACUUGGACACAAG GUGGGGAACACCACACACCAGGGCCUGUCAUGGGUGGG GGGAGUGGGGAGGGAUAGCAUUAGGAGAUAUACCUAAUG UAAAUGAUGAGUUAAUGGGUGCAGCACACCAACAUGGCA CAUGUAUACAUAUGUAGCAAACCUGCACGUUGUGCACAU | SEQ ID NO: 55 |

TABLE 4A-continued

Exemplary 3'-Untranslated Regions

| 3' UTR Identifier | Name/ Description | Sequence | SEQ ID NO. |
|---|---|---|---|
| | | GUACCCUAGAACUUAAAGUAUAAUUAAAAAAAAAAAGAA<br>AACAGAAGCUAUUUAUAAAGAAGUUAUUUGCUGAAAUAA<br>AUGUGAUCUUUCCCAUUAAAAAAAAUAAAGAAAUUUUGGG<br>GUAAAAAAACACAAUAUAUUGUAUUCUUGAAAAAUUCUA<br>AGAGAGUGGAUGUGAAGUGUUCUCACCACAAAAGUGAUA<br>ACUAAUUGAGGUAAUGCACAUAUUAAUUAGAAAGAUUUU<br>GUCAUUCCACAAUGUAUAUACUUAAAAAUAUGUUAUA<br>CACAAUAAAUACAUACAUUAAAAAAUAAGUAAAUGUA | |
| 3UTR-012 | Col6a1; collagen, type VI, alpha 1 | CCCACCCUGCACGCCGGCACCAAACCCUGUCCUCCCACC<br>CCUCCCCACUCAUCACUAAACAGAGUAAAAUGUGAUGCG<br>AAUUUCCCGACCAACCUGAUUCGCUAGAUUUUUUUUAA<br>GGAAAAGCUUGGAAAGCCAGGACACAACGCUGCUGCCUG<br>CUUUGUGCAGGGUCCUCCGGGGCUCAGCCCUGAGUUGGC<br>AUCACCUGCGCAGGGCCCUCUGGGGCUCAGCCCUGAGCU<br>AGUGUCACCUGCACAGGGCCCUCUGAGGCUCAGCCCUGA<br>GCUGGCGUCACCUGUGCAGGGCCCUCUGGGGCUCAGCCC<br>UGAGCUGGCCUCACCUGGGUUCCCCACCCCGGGCUCUCC<br>UGCCCUGCCCUCCUGCCCGCCCUCCCUCCUGCCUGCGCA<br>GCUCCUUCCUAGGCACCUCUGUGCUGCAUCCCACCAGC<br>CUGAGCAAGACGCCCUCUCGGGGCCUGUGCCGCACUAGC<br>CUCCCUCUCCUCUGUCCCCAUAGCUGGUUUUUCCCACCA<br>AUCCUCACCUAACAGUUACUUUACAAUUAAACUCAAAGC<br>AAGCUCUUCUCCUCAGCUUGGGGCAGCCAUUGGCCUCUG<br>UCUCGUUUUGGGAAACCAAGGUCAGGAGGCCGUUGCAGA<br>CAUAAAUCUCGGCGACUCGGCCCCGUCUCCUGAGGGUCC<br>UGCUGGUGACCGGCCUGGACCUUGGCCCUACAGCCCUGG<br>AGGCCGCUGCUGACCAGCACUGACCCCGACCUCAGAGAG<br>UACUCGCAGGGGCGCUGGCUGCACUCAAGACCCUCGAGA<br>UUAACGGUGCUAACCCCGUCUGCUCCUCCCUCCCGCAGA<br>GACUGGGGCCUGGACUGGACAUGAGAGCCCUUGGUGCC<br>ACAGAGGGCUGUGUCUUACUAGAAACAACGCAAACCUCU<br>CCUUCCUCAGAAUAGUGAUGUGUUCGACGUUUUAUCAAA<br>GGCCCCCUUUCUAUGUUCAUGUUAGUUUUGCUCCUUCUG<br>UGUUUUUUCUGAACCAUAUCCAUGUUGCUGACUUUUCC<br>AAAUAAAGGUUUUCACUCCUCUC | SEQ ID NO: 56 |
| 3UTR-013 | Calr; calreticulin | AGAGGCCUGCCUCCAGGGCUGGACUGAGGCCUGAGCGCU<br>CCUGCCGCAGAGCUGGCCGCGCCAAAUAAUGUCUCUGUG<br>AGACUCGAGAACUUUCAUUUUUUUCCAGGCUGGUUCGGA<br>UUUGGGGUGGAUUUUGGUUUUGUUCCCCUCCUCCACUCU<br>CCCCCACCCCCUCCCCGCCCUUUUUUUUUUUUUUUUUA<br>AACUGGUAUUUUAUCUUUGAUUCUCCUUCAGCCCCUCACC<br>CCUGGUUCUCAUCUUUCUUGAUCAACAUCUUUUCUUGCC<br>UCUGUCCCCUUCUCUCAUCUCUUAGCUCCCCUCCAACCU<br>GGGGGGCAGUGGUGUGGAGAAGCCACAGGCCUGAGAUUU<br>CAUCUGCUCUCCUUCCUGGAGCCCAGAGGAGGGCAGCAG<br>AAGGGGGUGGUGUCUCCAACCCCCCAGCACUGAGGAAGA<br>ACGGGGCUCUUCUCAUUUCACCCCUCCCUUUCUCCCCUG<br>CCCCCAGGACUGGGCCACUUCUGGGUGGGGCAGUGGGUC<br>CCAGAUUGGCUCACACUGAGAAUGUAAGAACUACAAACA<br>AAAUUUCUAUUAAAUUAAAUUUUGUGUCUCC | SEQ ID NO: 57 |
| 3UTR-014 | Col1a1; collagen, type I, alpha 1 | CUCCCUCCAUCCCAACCUGGCUCCCUCCCACCCAACCAA<br>CUUUCCCCCCAACCCGGAAACAGACAAGCAACCCAAACU<br>GAACCCCCUCAAAAGCCAAAAAAUGGGAGACAAUUUCAC<br>AUGGACUUUGGAAAAUAUUUUUUCCUUUGCAUUCAUCU<br>CUCAAACUUAGUUUUUAUCUUUGACCAACCGAACAUGAC<br>CAAAAACCAAAAGUGCAUUCAACCUUACCAAAAAAAAAA<br>AAAAAAAAGAAUAAAUAAAUAACUUUUUAAAAAAGGAA<br>GCUUGGUCCACUUGCUUGAAGACCCAUGCGGGGGUAAGU<br>CCCUUUCUGCCCGUUGGGCUUAUGAAACCCAAUGCUGC<br>CCUUUCUGCUCCUUUCUCCACACCCCCCUUGGGGCCUCC<br>CCUCCACUCCUUCCCAAAUCUGUCUCCCCAGAAGACACA<br>GGAAACAAUGUAUUGUCUGCCCAGCAAUCAAAGGCAAUG<br>CUCAAACACCCAAGUGGCCCCCACCCUCAGCCCGCUCCU<br>GCCCGCCCAGCACCCCAGGCCCUGGGGGACCUGGGGUU<br>CUCAGACUGCCAAAGAAGCCUUGCCAUCUGGCGCUCCCA<br>UGGCUCUUGCAACAUCUCCCCUUCGUUUUUGAGGGGGUC<br>AUGCCGGGGAGCCACCAGCCCCUCACUGGGUUCGGAGG<br>AGAGUCAGGAAGGGCCACGACAAAGCAGAAACAUCGGAU<br>UUGGGGAACGCGUGUCAAUCCCUUGUGCCGCAGGGCUGG<br>GCGGGAGAGACUGUUCUGUUCCUUGUGUAACUGUGUUGC<br>UGAAAGACUACCUCGUUCUUGUCUUGAUGUGUCACCGGG<br>GCAACUGCCUGGGGCGGGGAUGGGGGCAGGGUGGAAGC | SEQ ID NO: 58 |

TABLE 4A-continued

Exemplary 3'-Untranslated Regions

| 3' UTR Identifier | Name/ Description | Sequence | SEQ ID NO. |
|---|---|---|---|
| | | GGCUCCCCAUUUUAUACCAAAGGUGCUACAUCUAUGUGA UGGGUGGGUGGGGAGGGAAUCACUGGUGCUAUAGAAAU UGAGAUGCCCCCCCAGGCCAGCAAAUGUUCCUUUUUGUU CAAAGUCUAUUUUUAUUCCUUGAUAUUUUCUUUUUUUU UUUUUUUUUUUGUGGAUGGGGACUUGUGAAUUUUUCUAA AGGUGCUAUUUAACAUGGGAGGAGAGCGUGUGCGGUCC AGCCCAGCCCGCUGCUCACUUUCCACCCUCUCUCCACCU GCCUCUGGCUUCUCAGGCCUCUGCUCUCCGACCUCUCUC CUCUGAAACCCUCCUCCACAGCUGCAGCCCAUCCUCCCG GCUCCCUCCUAGUCUGUCCUGCGUCCUCUGUCCCCGGGU UUCAGAGACAACUUCCCAAAGCACAAAGCAGUUUUUCCC CCUAGGGGUGGGAGGAAGGCAAAAGACUCUGUACCUAUUU UGUAUGUGUAUAAUAAUUUUGAGAUGUUUUUAAUUAUUUU GAUUGCUGGAAUAAAGCAUGUGGAAAUGACCCAAACAUA AUCCGCAGUGGCCUCCUAAUUUCCUUCUUUGGAGUUGGG GGAGGGGUAGACAUGGGGAAGGGGCUUUGGGGUGAUGGG CUUGCCUUCCAUUCCUGCCCUUUCCUCCCCACUAUUCU CUUCUAGAUCCCUCCAUAACCCCACUCCCCUUUCUCUCA CCCUUCUUAUACCGCAAACCUUUCUACUUCCUCUUUCAU UUUCUAUUCUUGCAAUUUCCUUGCACCUUUUUCCAAAUCC UCUUCUCCCCUGCAAUACCAUACAGGCAAUCCACGUGCA CAACACACACACACACUCUUCACAUCUGGGGUUGUCCAA ACCUCAUACCCACUCCCCUUCAAGCCCAUCCACUCUCCA CCCCCUGGAUGCCCUGCACUUGGUGGCGGUGGGAUGCUC AUGGAUACUGGGAGGGUGAGGGGAGUGGAACCCGUGAGG AGGACCUGGGGGCCUCUCCUUGAACUGACAUGAAGGGUC AUCUGGCCUCUGCUCCCUUCUCACCCACGCUGACCUCCU GCCGAAGGAGCAACGCAACAGGAGAGGGGUCUGCUGAGC CUGGCGAGGGUCUGGGAGGGACCAGGAGGAAGGCGUGCU CCCUGCUCGCUGUCCUGGCCCUGGGGGAGUGAGGGAGAC AGACACCUGGGAGAGCUGUGGGGAAGGCACUCGCACCGU GCUCUUGGGAAGGAAGGAGACCUGGCCCUGCUCACCACG GACUGGGUGCCUCGACCUCCUGAAUCCCCAGAACACAAC CCCCCUGGGCUGGGGUGGUCUGGGGAACCAUCGUGCCCC CGCCUCCCGCCUACUCCUUUUUAAGCUU | |
| 3UTR-015 | Plod1; procollagen- lysine, 2- oxoglutarate 5- dioxygenase 1 | UUGGCCAGGCCUGACCCUCUUGGACCUUUCUUCUUUGCC GACAACCACUGCCCAGCAGCCUCUGGGACCUCGGGGUCC CAGGGAACCCAGUCCAGCCUCCUGGCUGUUGACUUCCCA UUGCUCUUGGAGCCACCAAUCAAAGAGAUUCAAAGAGAU UCCUGCAGGCCAGAGGCGGAACACUCUUUAUGGCUGGG GCUCUCCGUGGUGUUCUGGACCCAGCCCCUGGAGACACC AUUCACUUUUACUGCUUUGUAGUGACUCGUGCUCUCCAA CCUGUCUUCCUGAAAAACCAAGGCCCCCUUCCCCCACCU CUUCCAUGGGGUGAGACUUGAGCAGAACAGGGGCUUCCC CAAGUUGCCCAGAAAGACUGUCUGGGUGAGAAGCCAUGG CCAGAGCUUCUCCCAGGCACAGGUGUUGCACCAGGGACU UCUGCUUCAAGUUUUGGGGUAAAGACACCUGGAUCAGAC UCCAAGGGCUGCCCUGAGUCUGGGACUUCUGCCUCCAUG GCUGGUCAUGAGAGCAAACCGUAGUCCCCUGGAGACAGC GACUCCAGAGAACCUCUUGGGAGACAGAAGAGGCAUCUG UGCACAGCUCGAUCUUCUACUUGCCUGUGGGGAGGGGAG UGACAGGUCCACACACCACACUGGGUCACCCUGUCCUGG AUGCUCUGAAGAGAGGGACAGACCGUCAGAAACUGGAG AGUUUCUAUUAAAGGUCAUUUAAACCA | SEQ ID NO: 59 |
| 3UTR-016 | Nucb1; nucleobindin 1 | UCCUCCGGGACCCCAGCCCUCAGGAUUCCUGAUGCUCCA AGGCGACUGAUGGGCGCUGGAUGAAGUGGCACAGUCAGC UUCCCUGGGGGCUGGUGUCAUGUUGGGCUCCUGGGGCGG GGGCACGGCCUGGCAUUUCACGCAUUGCUGCCACCCCAG GUCCACCUGUCUCCACUUUCACAGCCUCCAAGUCUGUGG CUCUUCCCUUCUGUCCUCCGAGGGGCUUGCCUUCUCUCG UGUCCAGUGAGGUGCUCAGUGAUCGGCUUAACUUAGAGA AGCCCGCCCCUCCCCUUCUCCGUCUGUCCCAAGAGGGU CUGCUCUGAGCCUGCGUUCCUAGGUGGCUCGGCCUCAGC UGCCUGGGUUGUGGCCGCCCUAGCAUCCUGUAUGCCCAC AGCUACUGGAAUCCCCGCUGCUGCUCCGGGCCAAGCUUC UGGUUGAUUAAUGAGGGCAUGGGGUGGUCCCUCAAGACC UUCCCCUACCUUUUGUGGAACCAGUGAUGCCUCAAAGAC AGUGUCCCCUCCACAGCUGGGUGCCAGGGCAGGGGAUC CUCAGUAUAGCCGGUGAACCCUGAUACCAGGAGCCUGGG CCUCCCUGAACCCCUGGCUUCCAGCCAUUCAUCGCCAG CCUCCUCCUGGACCUCUGGCCCCCAGCCCCUUCCCCAC ACAGCCCCAGAAGGGUCCAGAGAGCUGACCCCACUCCAGG ACCUAGGCCCAGCCCCUCAGCCUCAUCUGGAGCCCCUGA | SEQ ID NO: 60 |

TABLE 4A-continued

Exemplary 3'-Untranslated Regions

| 3' UTR Identifier | Name/ Description | Sequence | SEQ ID NO. |
|---|---|---|---|
| | | AGACCAGUCCCACCCACCUUUCUGGCCUCAUCUGACACU GCUCCGCAUCCUGCUGUGUGUCCUGUUCCAUGUUCCGGU UCCAUCCAAAUACACUUUCUGGAACAAA | |
| 3UTR-017 | α-globin | GCUGGAGCCUCGGUGGCCAUGCUUCUUGCCCCUUGGGCC UCCCCCCAGCCCCUCCUCCCCUUCCUGCACCCGUACCCC CGUGGUCUUUGAAUAAAGUCUGAGUGGGCGGC | SEQ ID NO: 61 |
| 3UTR-018 | Downstream UTR | UAAUAGGCUGGAGCCUCGGUGGCCAUGCUUCUUGCCCCU UGGGCCUCCCCCCAGCCCCUCCUCCCCUUCCUGCACCCG UACCCCGUGGUCUUUGAAUAAAGUCUGAGUGGGCGGC | SEQ ID NO: 62 |

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NOS: 45-62 and any combination thereof. In a particular embodiment, the 3' UTR sequence further comprises a miRNA binding site, e.g., miR122 binding site. In other embodiments, a 3'UTR sequence useful for the disclosure comprises 3' UTR-018 (SEQ ID NO: 62).

In certain embodiments, the 3' UTR sequence comprises one or more miRNA binding sites, e.g., miR-122 binding sites, or any other heterologous nucleotide sequences therein, without disrupting the function of the 3' UTR. Some examples of 3' UTR sequences comprising a miRNA binding site are listed in Table 4B.

TABLE 4B

Exemplary 3' UTR with miRNA Binding Sites

| 3' UTR Identifier/ miRNA BS | Name/ Description | Sequence | SEQ ID NO. |
|---|---|---|---|
| 3UTR-018 + miR-122-5p binding site | Downstream UTR | UAAUAGGCUGGAGCCUCGGUGGCCAUGCUUCUUGCC CCUUGGGCCUCCCCCCAGCCCCUCCUCCCCUUCCUG CACCCGUACCCCCAAACACCAUUGUCACACUCCAG UGGUCUUUGAAUAAAGUCUGAGUGGGCGGC | SEQ ID NO: 63 |
| 3UTR-018 + miR-122-3p binding site | Downstream UTR | UAAUAGGCUGGAGCCUCGGUGGCCAUGCUUCUUGCC CCUUGGGCCUCCCCCCAGCCCCUCCUCCCCUUCCUG CACCCGUACCCCCUAUUUAGUGUGAUAAUGGCGUUG UGGUCUUUGAAUAAAGUCUGAGUGGGCGGC | SEQ ID NO: 64 |

*miRNA binding site is bolded and underlined.

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to the sequence set forth as SEQ ID NO: 63 or 64.

Regions Having a 5' Cap

The polynucleotide comprising an mRNA encoding an OX40L polypeptide can further comprise a 5' cap. The 5' cap useful for the OX40L encoding mRNA can bind the mRNA Cap Binding Protein (CBP), thereby increasing mRNA stability. The cap can further assist the removal of 5' proximal introns removal during mRNA splicing.

In some embodiments, the polynucleotide comprising an mRNA encoding an OX40L polypeptide of the present disclosure comprises a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, Mass.) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

In certain embodiments, the 5' cap comprises 2'-O-methylation of the ribose sugars of 5'-terminal and/or 5'-anteterminal nucleotides on the 2'-hydroxyl group of the sugar ring. In other embodiments, the caps for the OX40L encoding mRNA include cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs can be chemically (i.e. non-enzymatically) or enzymatically synthesized and/or linked to the polynucleotides of the disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' 0-Me-m7G(5')ppp(5')G). The 3'-O atom of the other, unmodified, guanine becomes linked to the 5'-terminal nucleotide of the capped polynucleotide. The N7- and 3'-O-methylated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5)ppp(5')G cap analog (See, e.g., the various cap analogs and the methods of synthesizing cap analogs described in Kore et al. Bioorganic & Medicinal Chemistry 2013 21:4570-4574). In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structure of nucleic acids produced by the endogenous, cellular transcription machinery, can lead to reduced translational competency and reduced cellular stability.

The OX40L encoding mRNA of the disclosure can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present disclosure are those which, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

In some embodiments, the polynucleotide comprising an mRNA encoding an OX40L polypeptide further comprises a poly A tail. In further embodiments, terminal groups on the poly-A tail can be incorporated for stabilization. In other embodiments, a poly-A tail comprises des-3' hydroxyl tails. The useful poly-A tails can also include structural moieties or 2'-Omethyl modifications as taught by Junjie Li, et al. (Current Biology, Vol. 15, 1501-1507, Aug. 23, 2005).

In one embodiment, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

Start Codon Region

In some embodiments, the polynucleotide comprising an mRNA encoding an OX40L polypeptide of the present disclosure further comprises regions that are analogous to or function like a start codon region.

In some embodiments, the translation of a polynucleotide initiates on a codon which is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11). As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11). Masking any of the nucleotides flanking a codon that initiates translation can be used to alter the position of translation initiation, translation efficiency, length and/or structure of a polynucleotide.

In some embodiments, a masking agent is used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11)).

In another embodiment, a masking agent is used to mask a start codon of a polynucleotide in order to increase the likelihood that translation will initiate on an alternative start codon. In some embodiments, a masking agent is used to mask a first start codon or alternative start codon in order to increase the chance that translation will initiate on a start codon or alternative start codon downstream to the masked start codon or alternative start codon.

In some embodiments, a start codon or alternative start codon is located within a perfect complement for a miR binding site. The perfect complement of a miR binding site can help control the translation, length and/or structure of the polynucleotide similar to a masking agent. As a non-limiting example, the start codon or alternative start codon is located in the middle of a perfect complement for a miR-122 binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide is removed from the polynucleotide sequence in order to have the translation of the polynucleotide begin on a codon which is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

Stop Codon Region

In some embodiments, the polynucleotide comprising an mRNA encoding an OX40L polypeptide of the present disclosure can further comprise at least one stop codon or at least two stop codons before the 3' untranslated region (UTR). The stop codon can be selected from UGA, UAA, and UAG. In some embodiments, the polynucleotides of the present disclosure include the stop codon UGA and one additional stop codon. In a further embodiment the addition stop codon can be UAA. In another embodiment, the polynucleotides of the present disclosure include three stop codons, four stop codons, or more.

Polynucleotide Comprising mRNA Encoding an OX40L Polypeptide

In certain embodiments, the polynucleotide comprising an mRNA encoding an OX40L polypeptide of the present disclosure comprises (i) an mRNA encoding an OX40L polypeptide, such as the sequences provided in Table 1 above, (ii) a miR-122 binding site, such as the sequences provided in Table 2 above, (iii) a 5' UTR, such as the sequences provided in Table 3 above, and (iv) a 3' UTR, such as the sequences provided in Table 4A or 4B above. In a particular embodiment, the polynucleotide of the present disclosure comprises a sequence set forth in Table 5A below (SEQ ID NO: 65).

TABLE 5A

Polynucleotides comprising an mRNA encoding an OX40L polypeptide and a miR-122 binding site

| SEQ ID NO. | Description | Sequence |
|---|---|---|
| SEQ ID NO: 65 | mRNA sequence: Human OX40L with 5'-UTR, 3'-UTR, and miR-122 biding site | GGGAAAUAAGAGAGAAAAGAAGAGUAAGAAGAAAUAUAAGAGCC ACCAUGGAAAGGGUCCAACCCCUGGAAGAGAAUGUGGGAAAUGC AGCCAGGCCAAGAUUCGAGAGGAACAAGCUAUUGCUGGUGGCCU CUGUAAUUCAGGGACUGGGGCUGCUCCUGUGCUUCACCUACAUC UGCCUGCACUUCUCUGCUCUUCAGGUAUCACAUCGGUAUCCUCG AAUUCAAAGUAUCAAAGUACAAUUUACCGAAUAUAAGAAGGAGA |

TABLE 5A-continued

Polynucleotides comprising an mRNA encoding an OX40L polypeptide
and a miR-122 binding site

| SEQ ID NO. | Description | Sequence |
|---|---|---|
| | | AAGGUUUCAUCCUCACUUCCCAAAAGGAGGAUGAAAUCAUGAAG<br>GUGCAGAACAACUCAGUCAUCAUCAACUGUGAUGGGUUUUAUCU<br>CAUCUCCCUGAAGGGCUACUUCUCCCAGGAAGUCAACAUUAGCC<br>UUCAUUACCAGAAGGAUGAGGAGCCCCUCUUCCAACUGAAGAAG<br>GUCAGGUCUGUCAACUCCUUGAUGGUGGCCUCUCUGACUUACAA<br>AGACAAAGUCUACUUGAAUGUGACCACUGACAAUACCUCCCUGG<br>AUGACUUCCAUGUGAAUGGCGGAGAACUGAUUCUUAUCCAUCAA<br>AAUCCUGGUGAAUUCUGUGUCCUUUGAUAAUAGGCUGGAGCCU<br>CGGUGGCCAUGCUUCUUGCCCCUUGGGCCUCCCCCCAGCCCCUC<br>CUCCCCUUCCUGCACCCGUACCCCCCAAACACCAUUGUCACACU<br>CCAGUGGUCUUUGAAUAAAGUCUGAGUGGGCGGC |

Additional polynucleotides comprising an mRNA, a miR-122 binding site, a 5' UTR, and a 3' UTR are shown below in Table 5B.

TABLE 5B

Additional polynucleotides comprising an mRNA and a miR-122 binding site

| SEQ ID NO. | Description | Sequence |
|---|---|---|
| SEQ ID NO: 66 | mRNA sequence: murine OX40L with 5'-UTR, 3'-UTR, and miR-122 binding site | GGGAAAUAAGAGAGAAAAGAAGAGUAAGAAGAAAUAUAAGAGCC<br>ACCAUGGAAGGGGAAGGGGUUCAACCCCUGGAUGAGAAUCUGGA<br>AAACGGAUCAAGGCCAAGAUUCAAGUGGAAGAAGACGCUAAGGC<br>UGGUGGUCUCUGGGAUCAAGGGAGCAGGGAUGCUUCUGUGCUUC<br>AUCUAUGUCUGCCUGCAACUCUCUUCCUCUCCGGCAAAGGACCC<br>UCCAAUCCAAAGACUCAGAGGAGCAGUUACCAGAUGUGAGGAUG<br>GGCAACUAUUCAUCAGCUCAUACAAGAAUGAGUAUCAAACUAUG<br>GAGGUGCAGAACAAUUCGGUUGUCAUCAAGUGCGAUGGGCUUUA<br>UAUCAUCUACCUGAAGGGCUCCUUUUUCCAGGAGGUCAAGAUUG<br>ACCUUCAUUUCCGGGAGGAUCAUAAUCCCAUCUCUAUUCCAAUG<br>CUGAACGAUGGUCGAAGGAUUGUCUUCACUGUGGUGGCCUCUUU<br>GGCUUUCAAAGAUAAAGUUUACCUGACUGUAAAUGCUCCUGAUA<br>CUCUCUGCGAACACCUCCAGAUAAAUGAUGGGGAGCUGAUUGUU<br>GUCCAGCUAACGCCUGGAUACUGUGCUCCUGAAGGAUCUUACC<br>ACAGCACUGUGAACCAAGUACCACUGUGAUAAUAGGCUGGAGCC<br>UCGGUGGCCAUGCUUCUUGCCCCUUGGGCCUCCCCCCAGCCCCU<br>CCUCCCCUUCCUGCACCCGUACCCCCCAAACACCAUUGUCACAC<br>UCCAGUGGUCUUUGAAUAAAGUCUGAGUGGGCGGC |
| SEQ ID NO: 67 | mRNA sequence: non-translatable FIX with 5'-UTR, 3'UTR and miR-122 binding site (NST-FIX) | GGGAAAUAAGAGAGAAAAGAAGAGUAAGAAGAAAUAUAAGACAG<br>CGCUCAACAUUGCCGAAUCGCCGGGACUCAUCACAAUCUGCCU<br>CUUGGGUUAUCUCUUGUCGGCAGAUACCUUCUUGGAUCACGAAA<br>ACGCGAACAAAAUUCUUAAUCGCCCGAAGCGGUAUAACUCCGGG<br>AAACUUGAGGAGUUUCAGGGCAAUCUUGAACGAGACGAGGAGAA<br>CUCCUUUGAGGAGGCGAGGGAAUUUGAAAACACAGAGCGAACAA<br>CGGAGUUUUGGAAGCAAUACGUAGGGGACCAGUCGAAUCCCCUC<br>AGGGGAUCUAAAGACAUCAAUAGCUACUGCCCGUUUGGGUUUGA<br>AGGGAAGAACUAGCUGACCAACAUCAAAAACGGACGCUAGCAGU<br>UUUGUAAGAACUCGGCUGACAAUAAGGUAGUCUCCACAGAGGGA<br>UACCGGCUGGCGGAGAACCAAAAAUCCGAGCCCGCAGUCCCGUU<br>CCCUUGGAGGAGCUCACAGACUAGCAAGUUGACGAGAGCGGAGA<br>CUGUAUUCCCCGACGACUACGUCAACAGCACCGAAGCCGAAACA<br>AUCCUCGAUAACAUCACGCAGAGCACUCAGUCCUUCAACUUUA<br>CGAGGGUCGUAGAGGACGCGAAACCCGGUCAGUUCCCCUGGCAG<br>GUAUUGAACGGAAAAGUCGCCUUUUGAGGUUCCAUUGUCAACGA<br>GAAGAUUGUCACAGCGGCACACUGCGUAGAAACAGGAAAAAUCA<br>CGGUAGCGGGAGAGCAUAACAUUGAAGAGACAGAGCACACGGAA<br>CAAAAGCGAAUCAUCAGAAUCAUUCCACACCAUAACUAUAACGC<br>GGCAAUCAAUAAGUACAAUCACGACAUCGCACUUUUGGAGCUUG<br>ACGAACCUUUGCUUAAUUCGUACGUCACCCCUAUUUGUAUUGCC<br>GACAAAGAGUAUACAAACAUCUUCUUGAAAUUCGGCUCCGGGUA<br>CGUAUCGGGCUGGGGCAGAUUCCAUAAGGGUAGAUCCGCACUGU<br>UGCAAUACCUCAGGCCCCUCGAUCGAGCCACUUGUCUGCGGUCC<br>ACCAAAUUCACAAUCUACAACAAUUUCUCGGGAUUCCAAGGGAG<br>AGAUAGCUGCCAGGGAGACUCAGGGGGUCCCCACACGGAAGUCG |

TABLE 5B-continued

Additional polynucleotides comprising an mRNA and a miR-122 binding site

| SEQ ID NO. | Description | Sequence |
|---|---|---|
| | | AGGGGACGUCAUUUCUGACGGGAAUUAUCUCGGGAGAGGCGAAG GGGAACAUCUACACUAAAUCACGGUUCAAUUGGAUCAAGGAAAA GACGAAACUCACGUGAUAAUAGGCUGGAGCCUCGGUGGCCAUGC UUCUUGCCCCUUGGGCCUCCCCCCAGCCCCUCCUCCCCUUCCUG CACCCGUACCCCGUGGUCUUUGAAUAAAGUCUGAGUGGGCGGC |
| SEQ ID NO: 68 | mRNA sequence: non-translatable OX40L with 5'-UTR, 3'UTR, and miR-122 binding site (NST OX40L) | GGGAAAUAAGAGAGAAAAGAAGAGUAAGAAGAAAUAUAAGAACC CGCAAGGAAGGGGAAGGGGUUCAACCCCUGGAAGAGAAUCUGGA AAACGGAUCAAGGCCAAGAUUCAAGAGGAAGAAGACGCUAAGGC UGGAGGUCUCUGGGAUCAAGGGAGCAGGGAAGCUUCUGAGCUUC AUCUAAGUCUGCCUGCAACUCUCUUCCUCUCCGGCAAAGGACCC UCCAAUCCAAAGACUCAGAGGAGCAGUUACCAGAAGAGAGGAAG GGCAACUAUUCAUCAGCUCAUACAAGAAAGAGUAUCAAACUAAG GAGGAGCAGAACAAUUCGGUUGUCAUCAAGAGCGAAGGGCUUUA UAUCAUCUACCUGAAGGGCUCCUUUUUCCAGGAGGUCAAGAUUG ACCUUCAUUUCCGGGAGGAUCAUAAUCCCAUCUCUAUUCCAAAG CUGAACGAAGGUCGAAGGAUUGUCUUCACUGAGGAGGCCUCUUU GGCUUUCAAAGAUAAAGUUUACCUGACUGUAAAAGCUCCUGAUA CUCUCUGCGAACACCUCCAGAUAAAAGAAGGGGAGCUGAUUGUU GUCCAGCUAACGCCUGGAUACUGAGCUCCUGAAGGAUCUUACC ACAGCACUGAGAACCAAGUACCACUGUGAUAAUAGGCUGGAGCC UCGGUGGCCAAGCUUCUUGCCCCUUGGGCCUCCCCCCAGCCCCU CCUCCCCUUCCUGCACCCGUACCCCCAAACACCAUUGUCACAC UCCAGUGGUCUUUGAAUAAAGUCUGAGUGGGCGGC |
| SEQ ID NO: 69 | mRNA sequence: Firefly luciferase with 5'-UTR, 3'-UTR, and miR-122 binding site | GGGAAAUAAGAGAGAAAAGAAGAGUAAGAAGAAAUAUAAGAGCC ACCAUGGAAGAUGCGAAGAACAUCAAGAAGGGACCUGCCCCGUU UUACCCUUUGGAGGACGGUACAGCAGGAGAACAGCUCCACAAGG CGAUGAAACGCUACGCCCUGGUCCCCGGAACGAUUGCGUUUACC GAUGCACAUAUUGAGGUAGACAUCACAUACGCAGAAUACUUCGA AAUGUCGGUGAGGCUGGCGGAAGCGAUGAAGAGAUAUGGUCUUA ACACUAAUCACCGCAUCGUGGUGUGUUCGGAGAACUCAUUGCAG UUUUUCAUGCCGGUCCUUGGAGCACUUUUCAUCGGGGUCGCAGU CGCGCCAGCGAACGACAUCUACAAUGAGCGGGAACUCUUGAAUA GCAUGGGAAUCUCCCAGCCGACGGUCGUGUUUGUCUCCAAAAAG GGGCUGCAGAAAAUCCUCAACGUGCAGAAGAAGCUCCCCAUUAU UCAAAAGAUCAUCAUUAUGGAUAGCAAGACAGAUUACCAAGGGU UCCAGUCGAUGUAUACCUUUGUGACAUCGCAUUUGCCGCCAGGG UUUAACGAGUAUGACUUCGUCCCCGAGUCAUUUGACAGAGAUA AAACCAUCGCGCUGAUUAUGAAUUCCUCGGGUAGCACCGGUUUG CCAAAGGGGGUGGCGUUGCCCCACCGCACUGCUUGUGUGCGGU CUCGCACGCUAGGGAUCCUAUCUUUGGUAAUCAGAUCAUUCCCG ACACAGCAAUCCUGUCCGUGGUACCUUUUCAUCACGGUUUUGGC AUGUUCACGACUCUCGGCUAUUUGAUUUGCGGUUUCAGGGUCGU ACUUAUGUAUCGGUUCGAGGAAGAACUGUUUUUUGAGAUCCUUGC AAGAUUACAAGAUCCAGUCGGCCCUCCUUGUGCCAACGCUUUUC UCAUUCUUUGCGAAAUCGACACUUAUUGAUAAGUAUGACCUUUC CAAUCUGCAUGAGAUUGCCUCAGGGGGAGCGCCGCUUAGCAAGG AAGUCGGGGAGGCAGUGGCCAAGCGCUUCCACCUUCCCGGAAUU CGGCAGGGAUACGGGCUCACGGAGACAACAUCCGCGAUCCUUAU CACGCCCGAGGGUGACGAUAAGCCGGGAGCCGUCGGAAAAGUGG UCCCCUUCUUUGAAGCCAAGGUCGUAGACCUCGACACGGGAAAA ACCCUCGGAGUGAACCAGAGGGGCGAGCUCUGCGUGAGAGGGCC GAUGAUCAUGUCAGGUUACGUGAAUAACCCUGAAGCGACGAAUG CGCUGAUCGACAAGGAUGGGUGGUUGCAUUCGGGAGACAUUGCC UAUUGGGAUGAGGAUGAGCACUUCUUUAUCGUAGAUCGACUUAA GAGCUUGAUCAAAUACAAAGGCUAUCAGGUAGCGCCUGCCGAGC UCGAGUCAAUCCUGCUCCAGCACCCCAACAUUUUCGACGCCGGA GUGGCCGGGUUGCCCGAUGACGACGCGGGUGAGCUGCCAGCGGC CGUGGUAGUCCUCGAACAUGGGAAAACAAUGACCGAAAAGGAGA UCGUGGACUACGUAGCAUCACAAGUGACGACUGCGAAGAAACUG AGGGGAGGGGUAGUCUUUGUGGACGAGGUCCCGAAAGGCUUGAC UGGGAAGCUUGACGCUCGCAAAAUCCGGGAAAUCCUGAUUAAGG CAAAGAAAGGCGGGAAAAUCGCUGUCGAUAAUAGGCUGGAGCC UCGGUGGCCAUGCUUCUUGCCCCUUGGGCCUCCCCCCAGCCCCU CCUCCCCUUCCUGCACCCGUACCCCCAAACACCAUUGUCACAC UCCAGUGGUCUUUGAAUAAAGUCUGAGUGGGCGGC |

In some embodiments, the polynucleotide of the disclosure comprises at least about 60%, at least about 70%, at least about 80%, at least about 90%, at least about 95%, at least about 96%, at least about 97%, at least about 98%, at least about 99% or about 100% identical to the polynucleotide sequence set forth as SEQ ID NO: 65 in Table 5A, wherein the protein encoded by the polynucleotide is capable of binding to the wild-type OX40 receptor.

In certain embodiments, the polynucleotide comprising an mRNA encoding an OX40L polypeptide of the present disclosure comprises (i) 5' cap provided above, (ii) 5' UTR, such as the sequences provided in Table 3 above, (iii) an open reading frame encoding an OX40L polypeptide, such as the sequences provided in Table 1 above, (iv) a stop codon, (v) a 3' UTR, such as the sequences provided in Table 4A or 4B above, and (vi) a poly-A tail provided above.

IV. Methods of Making Polynucleotides

The present disclosure also provides methods for making a polynucleotide disclosed herein or a complement thereof. In some aspects, a polynucleotide (e.g., an mRNA) disclosed herein, and encoding an OX40L polypeptide, can be constructed using in vitro transcription. In other aspects, a polynucleotide (e.g., an mRNA) disclosed herein, and encoding an OX40L polypeptide, can be constructed by chemical synthesis using an oligonucleotide synthesizer. In other aspects, a polynucleotide (e.g., an mRNA) disclosed herein, and encoding an OX40L polypeptide is made by using a host cell. In certain aspects, a polynucleotide (e.g., an mRNA) disclosed herein, and encoding an OX40L polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., an mRNA) encoding an OX40L polypeptide. The resultant mRNAs can then be examined for their ability to produce protein and/or produce a therapeutic outcome.

In Vitro Transcription-Enzymatic Synthesis

A polynucleotide disclosed herein can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate modified nucleic acids. See U.S. Publ. No. US20130259923.

The IVT system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein.

Any number of RNA polymerases or variants can be used in the synthesis of the polynucleotides of the present disclosure.

RNA polymerases can be modified by inserting or deleting amino acids of the RNA polymerase sequence. As a non-limiting example, the RNA polymerase is modified to exhibit an increased ability to incorporate a 2'-modified nucleotide triphosphate compared to an unmodified RNA polymerase (see International Publication WO2008078180 and U.S. Pat. No. 8,101,385).

Variants can be obtained by evolving an RNA polymerase, optimizing the RNA polymerase amino acid and/or nucleic acid sequence and/or by using other methods known in the art. As a non-limiting example, T7 RNA polymerase variants are evolved using the continuous directed evolution system set out by Esvelt et al. (Nature (2011) 472(7344): 499-503) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. Coli, Bacillus* DNA polymerase I, *Thermus aquaticus* (Taq) DNA polymerases, and the T7 RNA and DNA polymerases, is among the best studied of these families. Another large family is DNA polymerase α (pol α) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS, Vol. 91, 5695-5699 (1994)). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429.

In one aspect, the RNA polymerase which can be used in the synthesis of the polynucleotides described herein is a Syn5 RNA polymerase. (see Zhu et al. Nucleic Acids Research 2013). The Syn5 RNA polymerase was recently characterized from marine cyanophage Syn5 by Zhu et al. where they also identified the promoter sequence (see Zhu et al. Nucleic Acids Research 2013). Zhu et al. found that Syn5

RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-termini.

In one aspect, a Syn5 promoter can be used in the synthesis of the polynucleotides. As a non-limiting example, the Syn5 promoter can be 5'-ATTGGGCACCCGTAAGGG-3' as described by Zhu et al. (Nucleic Acids Research 2013).

In one aspect, a Syn5 RNA polymerase can be used in the synthesis of polynucleotides comprising at least one chemical modification described herein and/or known in the art. (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the disclosure.

Polymerase chain reaction (PCR) has wide applications in rapid amplification of a target gene, as well as genome mapping and sequencing. The key components for synthesizing DNA comprise target DNA molecules as a template, primers complementary to the ends of target DNA strands, deoxynucleoside triphosphates (dNTPs) as building blocks, and a DNA polymerase. As PCR progresses through denaturation, annealing and extension steps, the newly produced DNA molecules can act as a template for the next circle of replication, achieving exponentially amplification of the target DNA. PCR requires a cycle of heating and cooling for denaturation and annealing. Variations of the basic PCR include asymmetric PCR [Innis et al., PNAS, vol. 85, 9436-9440 (1988)], inverse PCR [Ochman et al., Genetics, vol. 120(3), 621-623, (1988)], reverse transcription PCR (RT-PCR) (Freeman et al., BioTechniques, vol. 26(1), 112-22, 124-5 (1999)). In RT-PCR, a single stranded RNA is the desired target and is converted to a double stranded DNA first by reverse transcriptase.

A variety of isothermal in vitro nucleic acid amplification techniques have been developed as alternatives or complements of PCR. For example, strand displacement amplification (SDA) is based on the ability of a restriction enzyme to form a nick. (Walker et al., PNAS, vol. 89, 392-396 (1992), the contents of which are incorporated herein by reference in their entirety)). A restriction enzyme recognition sequence is inserted into an annealed primer sequence. Primers are extended by a DNA polymerase and dNTPs to form a duplex. Only one strand of the duplex is cleaved by the restriction enzyme. Each single strand chain is then available as a template for subsequent synthesis. SDA does not require the complicated temperature control cycle of PCR.

Nucleic acid sequence-based amplification (NASBA), also called transcription mediated amplification (TMA), is also an isothermal amplification method that utilizes a combination of DNA polymerase, reverse transcriptase, RNAse H, and T7 RNA polymerase. [Compton, Nature, vol. 350, 91-92 (1991)]. A target RNA is used as a template and a reverse transcriptase synthesizes its complementary DNA strand. RNAse H hydrolyzes the RNA template, making space for a DNA polymerase to synthesize a DNA strand complementary to the first DNA strand which is complementary to the RNA target, forming a DNA duplex. T7 RNA polymerase continuously generates complementary RNA strands of this DNA duplex. These RNA strands act as templates for new cycles of DNA synthesis, resulting in amplification of the target gene.

Rolling-circle amplification (RCA) amplifies a single stranded circular polynucleotide and involves numerous rounds of isothermal enzymatic synthesis where O29 DNA polymerase extends a primer by continuously progressing around the polynucleotide circle to replicate its sequence over and over again. Therefore, a linear copy of the circular template is achieved. A primer can then be annealed to this linear copy and its complementary chain can be synthesized. [See Lizardi et al., Nature Genetics, vol. 19, 225-232 (1998)]. A single stranded circular DNA can also serve as a template for RNA synthesis in the presence of an RNA polymerase. (Daubendiek et al., JACS, vol. 117, 7818-7819 (1995)). An inverse rapid amplification of cDNA ends (RACE) RCA is described by Polidoros et al. A messenger RNA (mRNA) is reverse transcribed into cDNA, followed by RNAse H treatment to separate the cDNA. The cDNA is then circularized by CircLigase into a circular DNA. The amplification of the resulting circular DNA is achieved with RCA. (Polidoros et al., BioTechniques, vol. 41, 35-42 (2006)).

Any of the foregoing methods can be utilized in the manufacture of one or more regions of the polynucleotides of the present disclosure.

Assembling polynucleotides or nucleic acids by a ligase is also widely used. DNA or RNA ligases promote intermolecular ligation of the 5' and 3' ends of polynucleotide chains through the formation of a phosphodiester bond. Ligase chain reaction (LCR) is a promising diagnosing technique based on the principle that two adjacent polynucleotide probes hybridize to one strand of a target gene and couple to each other by a ligase. If a target gene is not present, or if there is a mismatch at the target gene, such as a single-nucleotide polymorphism (SNP), the probes cannot ligase. (Wiedmann et al., PCR Methods and Application, vol. 3 (4), s51-s64 (1994)). LCR can be combined with various amplification techniques to increase sensitivity of detection or to increase the amount of products if it is used in synthesizing polynucleotides and nucleic acids.

Several library preparation kits for nucleic acids are now commercially available. They include enzymes and buffers to convert a small amount of nucleic acid samples into an indexed library for downstream applications. For example, DNA fragments can be placed in a NEBNEXT® ULTRA™ DNA Library Prep Kit by NEWENGLAND BIOLABS® for end preparation, ligation, size selection, clean-up, PCR amplification and final clean-up.

Continued development is going on to improvement the amplification techniques. For example, U.S. Pat. No. 8,367,328 to Asada et al., teaches utilizing a reaction enhancer to increase the efficiency of DNA synthesis reactions by DNA polymerases. The reaction enhancer comprises an acidic substance or cationic complexes of an acidic substance. U.S.

Pat. No. 7,384,739 to Kitabayashi et al., teaches a carboxylate ion-supplying substance that promotes enzymatic DNA synthesis, wherein the carboxylate ion-supplying substance is selected from oxalic acid, malonic acid, esters of oxalic acid, esters of malonic acid, salts of malonic acid, and esters of maleic acid. U.S. Pat. No. 7,378,262 to Sobek et al., discloses an enzyme composition to increase fidelity of DNA amplifications. The composition comprises one enzyme with 3' exonuclease activity but no polymerase activity and another enzyme that is a polymerase. Both of the enzymes are thermostable and are reversibly modified to be inactive at lower temperatures.

U.S. Pat. No. 7,550,264 to Getts et al. teaches multiple round of synthesis of sense RNA molecules are performed by attaching oligodeoxynucleotides tails onto the 3' end of cDNA molecules and initiating RNA transcription using RNA polymerase. US Pat. Publication No. 2013/0183718 to Rohayem teaches RNA synthesis by RNA-dependent RNA polymerases (RdRp) displaying an RNA polymerase activity on single-stranded DNA templates. Oligonucleotides with non-standard nucleotides can be synthesized with enzymatic polymerization by contacting a template comprising non-standard nucleotides with a mixture of nucleotides that are complementary to the nucleotides of the template as disclosed in U.S. Pat. No. 6,617,106 to Benner.

Chemical Synthesis

Standard methods can be applied to synthesize an isolated polynucleotide sequence encoding an OX40L polypeptide. For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. 8,999,380, 8,710,200.

Purification

Purification of the polynucleotides (e.g., mRNA) encoding an OX40L polypeptide described herein can include, but is not limited to, polynucleotide clean-up, quality assurance and quality control. Clean-up can be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a polynucleotide such as a "purified polynucleotide" refers to one that is separated from at least one contaminant. As used herein, a "contaminant" is any substance which makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide (e.g., mRNA) encoding an OX40L polypeptide of the disclosure removes impurities that can reduce or remove an unwanted immune response, e.g., reducing cytokine activity.

In some embodiments, the polynucleotide (e.g., mRNA) encoding an OX40L polypeptide of the disclosure is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)). In some embodiments, a column chromatography (e.g., strong anion exchange HPLC, weak anion exchange HPLC, reverse phase HPLC (RP-HPLC), and hydrophobic interaction HPLC (HIC-HPLC), or (LCMS)) purified polynucleotide, which encodes an OX40L polypeptide disclosed herein increases expression of OX40L compared to polynucleotides encoding the OX40L polypeptide purified by a different purification method. In some embodiments, a column chromatography (e.g., strong anion exchange HPLC, weak anion exchange HPLC, reverse phase HPLC (RP-HPLC), and hydrophobic interaction HPLC (HIC-HPLC), or (LCMS)) purified polynucleotide encodes a mammalian OX40L polypeptide. In some embodiments, the purified polynucleotide encodes a murine OX40L polypeptide. In some embodiments, the purified polynucleotide encodes a human OX40L polypeptide. In some embodiments, the purified polynucleotide encodes a polypeptide comprising the amino acid sequence set forth in SEQ ID NO: 1. In some embodiments, the purified polynucleotide encodes a polypeptide comprising the amino acid sequence set forth in SEQ ID NO: 2.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC.

In another embodiment, the polynucleotides can be sequenced by methods including, but not limited to reverse-transcriptase-PCR.

V. Modifications

As used herein in a polynucleotide comprising an mRNA encoding an OX40L polypeptide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In a polypeptide, the term "modification" refers to a modification as compared to the canonical set of 20 amino acids.

The modifications can be various distinct modifications. In some embodiments, the regions can contain one, two, or more (optionally different) nucleoside or nucleotide (nucleobase) modifications. In some embodiments, a modified polynucleotide, introduced to a cell can exhibit reduced degradation in the cell, as compared to an unmodified polynucleotide. In other embodiments, the modification is in the nucleobase and/or the sugar structure. In yet other embodiments, the modification is in the backbone structure.

Chemical Modifications:

Some embodiments of the present disclosure provide a polynucleotide comprising an mRNA encoding an OX40L polypeptide, wherein the mRNA includes at least one chemical modification. In some embodiments, the chemical modification is selected from pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine), 5-methoxyuridine, and 2'-O-methyl uridine.

A "nucleoside" as used herein refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" as used herein refers to a nucleoside, including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphdioester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the polynucleotides of the present disclosure include, but are not limited to the following: 2-methylthio-N6-(cis-hydroxyisopentenyl)adenosine; 2-methylthio-N6-methyl adenosine; 2-methylthio-N6-threonyl carbamoyladenosine; N6-glycinylcarbamoyladenosine; N6-isopentenyladenosine; N6-methyl adenosine; N6-threonylcarbamoyladenosine; 1,2'-O-dimethyl adenosine; 1-methyladenosine; 2'-O-methyladenosine; 2'-O-ribosyladenosine (phosphate); 2-methyl adenosine; 2-methylthio-N6 isopentenyladenosine; 2-methylthio-N6-hydroxynorvalyl carbamoyl adenosine; 2'-O-methyladenosine; 2'-O-ribosyladenosine (phosphate); Isopentenyladenosine; N6-(cis-hydroxyisopentenyl)adenosine; N6,2'-O-dimethyl adenosine; N6,2'-O-dimethyladenosine; N6,N6,2'-O-trimethyladenosine; N6,N6-dimethyl adenosine; N6-acetyladenosine; N6-hydroxynorvalylcarbamoyl adenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl) adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2' O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl)cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-

Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl) cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methylguanosine; 7 (alkyl)guanine; 7 (deaza)guanine; 7 (methyl) guanine; 7-(alkyl)guanine; 7-(deaza)guanine; 7-(methyl) guanine; 8 (alkyl)guanine; 8 (alkynyl)guanine; 8 (halo) guanine; 8 (thioalkyl)guanine; 8-(alkenyl)guanine; 8-(alkyl) guanine; 8-(alkynyl)guanine; 8-(amino)guanine; 8-(halo) guanine; 8-(hydroxyl)guanine; 8-(thioalkyl)guanine; 8-(thiol)guanine; aza guanine; deaza guanine; N (methyl) guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl) pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methyl aminomethyl-2-selenouridine; 5-methylaminomethyl-2-thiouridine; 5-methyl aminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylaminocarbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylaminocarbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2' amino, 2' azido, 2'fluoro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio) pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4

(thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio) uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl)pseudouridine TP; (E)-5-(2-Bromo-vinyl)ara-uridine TP; (E)-5-(2-Bromo-vinyl)uridine TP; (Z)-5-(2-Bromo-vinyl)ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl)pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl)pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl)pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl)pseudouridine TP; 1-(4-Nitro-benzyl)pseudouridine TP; 1(4-Nitro-phenyl)pseudo-UTP; 1-(4-Thiomethoxybenzyl)pseudouridine TP; 1-(4-Trifluoromethoxybenzyl)pseudouridine TP; 1-(4-Trifluoromethylbenzyl)pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl)pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thiopseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2' amino, 2'azido, 2'fluoro-cytidine; 2' methyl, 2' amino, 2'azido, 2'fluoro-adenine; 2'methyl, 2' amino, 2'azido, 2'fluoro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl)isocarbostyrilyl; 3-(methyl)isocarbostyrilyl; 4-(fluoro)-6-(methyl)benzimidazole; 4-(methyl) benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazin1-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkylhydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl) isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-sub stituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-0H-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide comprising an mRNA encoding an OX40L polypeptide includes a combination of at least two (e.g., 2, 3, 4 or more) of the aforementioned modified nucleobases.

In some embodiments, modified nucleobases in the polynucleotide comprising an mRNA encoding an OX40L polypeptide are selected from the group consisting of pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine), 5-methoxyuridine and 2'-O-methyl uridine. In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, modified nucleobases in the polynucleotide comprising an mRNA encoding an OX40L polypeptide are selected from the group consisting of 1-methyl-pseudouridine (m1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide comprising an mRNA encoding an OX40L polypeptide comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide comprising an mRNA encoding an OX40L polypeptide comprises 1-methyl-pseudouridine (m1ψ) and 5-methyl-cytidine (m5C). In some embodiments, the polynucleotide comprising an mRNA encoding an OX40L polypeptide comprises 2-thiouridine (s2U). In some embodiments, the polynucleotide comprising an mRNA encoding an OX40L polypeptide comprises 2-thiouridine and 5-methyl-cytidine (m5C). In some embodiments, the polynucleotide comprising an mRNA encoding an OX40L polypeptide comprises methoxy-uridine (mo5U). In some embodiments, the polynucleotide comprising an mRNA encoding an OX40L polypeptide comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide comprising an mRNA encoding an OX40L polypeptide comprises 2'-O-methyl uridine and 5-methyl-cytidine (m5C). In some embodiments, the polynucleotide comprising an mRNA encoding an OX40L polypeptide comprises N6-methyl-adenosine (m6A). In some embodiments, the polynucleotide comprising an mRNA encoding an OX40L polypeptide comprises N6-methyl-adenosine (m6A) and 5-methyl-cytidine (m5C).

In some embodiments, the polynucleotide comprising an mRNA encoding an OX40L polypeptide is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenosine (m6A), and 2,6-Diaminopurine.

In some embodiments, a modified nucleobase is a modified guanine. Example nucleobases and nucleosides having a modified guanine include inosine (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, or 7-methyl-8-oxo-guanosine.

Other modifications which can be useful in the polynucleotides comprising an mRNA encoding an OX40L polypeptide of the present disclosure are listed in Table 6.

TABLE 6

Additional Modification types

| Name | Type |
| --- | --- |
| 2,6-(diamino)purine | Other |
| 1-(aza)-2-(thio)-3-(aza)-phenoxazin-1-yl | Other |
| 1,3-(diaza)-2-(oxo)-phenthiazin-1-yl | Other |
| 1,3-(diaza)-2-(oxo)-phenoxazin-1-yl | Other |
| 1,3,5-(triaza)-2,6-(dioxa)-naphthalene | Other |
| 2 (amino)purine | Other |
| 2,4,5-(trimethyl)phenyl | Other |
| 2' methyl, 2'amino, 2'azido, 2'fluro-cytidine | Other |
| 2' methyl, 2'amino, 2'azido, 2'fluro-adenine | Other |
| 2'methyl, 2'amino, 2'azido, 2'fluro-uridine | Other |
| 2'-amino-2'-deoxyribose | Other |
| 2-amino-6-Chloro-purine | Other |
| 2-aza-inosinyl | Other |
| 2'-azido-2'-deoxyribose | Other |
| 2'fluoro-2'-deoxyribose | Other |
| 2'-fluoro-modified bases | Other |
| 2'-O-methyl-ribose | Other |
| 2-oxo-7-aminopyridopyrimidin-3-yl | Other |
| 2-oxo-pyridopyrimidine-3-yl | Other |
| 2-pyridinone | Other |
| 3 nitropyrrole | Other |
| 3-(methyl)-7-(propynyl)isocarbostyrilyl | Other |
| 3-(methyl)isocarbostyrilyl | Other |
| 4-(fluoro)-6-(methyl)benzimidazole | Other |
| 4-(methyl)benzimidazole | Other |

TABLE 6-continued

Additional Modification types

| Name | Type |
| --- | --- |
| 4-(methyl)indolyl | Other |
| 4,6-(dimethyl)indolyl | Other |
| 5 nitroindole | Other |
| 5 substituted pyrimidines | Other |
| 5-(methyl)isocarbostyrilyl | Other |
| 5-nitroindole | Other |
| 6-(aza)pyrimidine | Other |
| 6-(azo)thymine | Other |
| 6-(methyl)-7-(aza)indolyl | Other |
| 6-chloro-purine | Other |
| 6-phenyl-pyrrolo-pyrimidin-2-on-3-yl | Other |
| 7-(aminoalkylhydroxy)-1-(aza)-2-(thio)-3-(aza)-phenthiazin-1-yl | Other |
| 7-(aminoalkylhydroxy)-1-(aza)-2-(thio)-3-(aza)-phenoxazin-1-yl | Other |
| 7-(aminoalkylhydroxy)-1,3-(diaza)-2-(oxo)-phenoxazin-1-yl | Other |
| 7-(aminoalkylhydroxy)-1,3-(diaza)-2-(oxo)-phenthiazin-1-yl | Other |
| 7-(aminoalkylhydroxy)-1,3-(diaza)-2-(oxo)-phenoxazin-1-yl | Other |
| 7-(aza)indolyl | Other |
| 7-(guanidiniumalkylhydroxy)-1-(aza)-2-(thio)-3-(aza)-phenoxazinl-yl | Other |
| 7-(guanidiniumalkylhydroxy)-1-(aza)-2-(thio)-3-(aza)-phenthiazin-1-yl | Other |
| 7-(guanidiniumalkylhydroxy)-1-(aza)-2-(thio)-3-(aza)-phenoxazin-1-yl | Other |
| 7-(guanidiniumalkylhydroxy)-1,3-(diaza)-2-(oxo)-phenoxazin-1-yl | Other |
| 7-(guanidiniumalkyl-hydroxy)-1,3-(diaza)-2-(oxo)-phenthiazin-1-yl | Other |
| 7-(guanidiniumalkylhydroxy)-1,3-(diaza)-2-(oxo)-phenoxazin-1-yl | Other |
| 7-(propynyl)isocarbostyrilyl | Other |
| 7-(propynyl)isocarbostyrilyl, propynyl-7-(aza)indolyl | Other |
| 7-deaza-inosinyl | Other |
| 7-substituted 1-(aza)-2-(thio)-3-(aza)-phenoxazin-1-yl | Other |
| 7-substituted 1,3-(diaza)-2-(oxo)-phenoxazin-1-yl | Other |
| 9-(methyl)-imidizopyridinyl | Other |
| aminoindolyl | Other |
| anthracenyl | Other |
| bis-ortho-(aminoalkylhydroxy)-6-phenyl-pyrrolo-pyrimidin-2-on-3-yl | Other |
| bis-ortho-substituted-6-phenyl-pyrrolo-pyrimidin-2-on-3-yl | Other |
| difluorotolyl | Other |
| hypoxanthine | Other |
| imidizopyridinyl | Other |
| inosinyl | Other |
| isocarbostyrilyl | Other |
| isoguanisine | Other |
| N2-substituted purines | Other |
| N6-methyl-2-amino-purine | Other |
| N6-substituted purines | Other |
| N-alkylated derivative | Other |
| napthalenyl | Other |
| nitrobenzimidazolyl | Other |
| nitroimidazolyl | Other |
| nitroindazolyl | Other |
| nitropyrazolyl | Other |
| nubularine | Other |
| O6-substituted purines | Other |
| O-alkylated derivative | Other |
| ortho-(aminoalkylhydroxy)-6-phenyl-pyrrolo-pyrimidin-2-on-3-yl | Other |
| ortho-substituted-6-phenyl-pyrrolo-pyrimidin-2-on-3-yl | Other |
| Oxoformycin TP | Other |
| para-(aminoalkylhydroxy)-6-phenyl-pyrrolo-pyrimidin-2-on-3-yl | Other |
| para-substituted-6-phenyl-pyrrolo-pyrimidin-2-on-3-yl | Other |
| pentacenyl | Other |
| phenanthracenyl | Other |
| phenyl | Other |
| propynyl-7-(aza)indolyl | Other |
| pyrenyl | Other |
| pyridopyrimidin-3-yl | Other |
| pyridopyrimidin-3-yl, 2-oxo-7-amino-pyridopyrimidin-3-yl | Other |
| pyrrolo-pyrimidin-2-on-3-yl | Other |
| pyrrolopyrimidinyl | Other |
| pyrrolopyrizinyl | Other |
| stilbenzyl | Other |
| substituted 1,2,4-triazoles | Other |
| tetracenyl | Other |
| tubercidine | Other |
| xanthine | Other |
| Xanthosine-5'-TP | Other |

TABLE 6-continued

Additional Modification types

| Name | Type |
| --- | --- |
| 2-thio-zebularine | Other |
| 5-aza-2-thio-zebularine | Other |
| 7-deaza-2-amino-purine | Other |
| pyridin-4-one ribonucleoside | Other |
| 2-Amino-riboside-TP | Other |
| Formycin A TP | Other |
| Formycin B TP | Other |
| Pyrrolosine TP | Other |
| 2'-OH-ara-adenosine TP | Other |
| 2'-OH-ara-cytidine TP | Other |
| 2'-OH-ara-uridine TP | Other |
| 2'-OH-ara-guanosine TP | Other |
| 5-(2-carbomethoxyvinyl)uridine TP | Other |
| N6-(19-Amino-pentaoxanonadecyl)adenosine TP | Other |

The polynucleotides comprising an mRNA encoding an OX40L polypeptide of the present disclosure can include any useful linker between the nucleosides. Such linkers, including backbone modifications are given in Table 7.

TABLE 7

Linker modifications

| Name | TYPE |
| --- | --- |
| 3'-alkylene phosphonates | Linker |
| 3'-amino phosphoramidate | Linker |
| alkene containing backbones | Linker |
| aminoalkylphosphoramidates | Linker |
| aminoalkylphosphotriesters | Linker |
| boranophosphates | Linker |
| —CH2-0-N(CH3)—CH2— | Linker |
| —CH2—N(CH3)—N(CH3)—CH2— | Linker |
| —CH2—NH—CH2— | Linker |
| chiral phosphonates | Linker |
| chiral phosphorothioates | Linker |
| formacetyl and thioformacetyl backbones | Linker |
| methylene (methylimino) | Linker |
| methylene formacetyl and thioformacetyl backbones | Linker |
| methyleneimino and methylenehydrazino backbones | Linker |
| morpholino linkages | Linker |
| —N(CH3)—CH2—CH2— | Linker |
| oligonucleosides with heteroatom internucleoside linkage | Linker |
| phosphinates | Linker |
| phosphoramidates | Linker |
| phosphorodithioates | Linker |
| phosphorothioate internucleoside linkages | Linker |
| phosphorothioates | Linker |
| phosphotriesters | Linker |
| PNA | Linker |
| siloxane backbones | Linker |
| sulfamate backbones | Linker |
| sulfide sulfoxide and sulfone backbones | Linker |
| sulfonate and sulfonamide backbones | Linker |
| thionoalkylphosphonates | Linker |
| thionoalkylphosphotriesters | Linker |
| thionophosphoramidates | Linker |

The polynucleotide comprising an mRNA encoding an OX40L polypeptide of the present disclosure can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase can be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present disclosure can be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs), hexitol nucleic acids (HNAs), or hybrids thereof. Additional modifications are described herein. Modified nucleic acids and their synthesis are disclosed in co-pending International Patent Publication No. WO2013052523.

In some embodiments, the polynucleotide comprising an mRNA encoding an OX40L polypeptide of the present disclosure does not substantially induce an innate immune response of a cell into which the mRNA is introduced. Features of an induced innate immune response include 1) increased expression of pro-inflammatory cytokines, 2) activation of intracellular PRRs (RIG-I, MDA5, etc, and/or 3) termination or reduction in protein translation.

Any of the regions of the polynucleotide comprising an mRNA encoding an OX40L polypeptide of the present disclosure can be chemically modified as taught herein or as taught in International Application Publication Number WO2013/052523 A1.

In some embodiments, a modified polynucleotide, e.g., mRNA comprising at least one modification described herein, of the disclosure encodes an OX40L polypeptide. In some embodiments, the modified polynucleotide, e.g., mRNA comprising at least one modification described herein, of the disclosure encodes a human OX40L polypeptide. In some embodiments, the modified polynucleotide, e.g., mRNA comprising at least one modification described herein, of the disclosure encodes a polypeptide comprising the amino acid sequence set forth in SEQ ID NO: 1. In some embodiments, the modified polynucleotide, e.g., mRNA comprising at least one modification described herein, of the disclosure encodes a polypeptide comprising the amino acid sequence set forth in SEQ ID NO: 2. In some embodiments, the modified polynucleotide, e.g., mRNA comprising at least one modification described herein, of the disclosure comprises the sequence set forth in SEQ ID NO: 65.

In some embodiments, the modified polynucleotide, e.g., mRNA comprising at least one modification described herein, of the disclosure encodes at least one OX40L mutant, a fragment, or variant thereof, e.g., an OX40L functional fragment comprising the extracellular domain of OX40L or a fragment of the extracellular domain of OX40L, the cytoplasmic domain of OX40L or a fragment of the cytoplasmic domain of OX40L, and/or the transmembrane domain of OX40L or a fragment of the transmembrane domain of OX40L.

In some embodiments, the modified polynucleotide, e.g., mRNA comprising at least one modification described herein, of the disclosure is selected from the OX40L nucleic acid sequences listed in Table 1 (e.g., selected from SEQ ID NOs: 4-21).

The polynucleotide comprising an mRNA encoding an OX40L polypeptide of the present disclosure can also include building blocks, e.g., modified ribonucleosides, and modified ribonucleotides, of polynucleotide molecules. For example, these building blocks can be useful for preparing the polynucleotides of the disclosure. Such building blocks are taught in International Patent Publication No. WO2013052523 and International Application Publication No. WO 2014/093924 A1.

Modifications on the Sugar

The modified nucleosides and nucleotides (e.g., building block molecules), which can be incorporated into a polynucleotide (e.g., RNA or mRNA, as described herein) comprising an mRNA encoding an OX40L polypeptide of the present disclosure, can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl) oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication No. WO2013052523 and International Patent Application No. PCT/US2013/75177.

Combinations of Modified Sugars, Nucleobases, and Internucleoside Linkages

The polynucleotides comprising an mRNA encoding an OX40L polypeptide of the disclosure can include a combination of modifications to the sugar, the nucleobase, and/or the internucleoside linkage. These combinations can include any one or more modifications described herein.

Examples of modified nucleotides and modified nucleotide combinations are provided below in Table 8. These combinations of modified nucleotides can be used to form the polynucleotides of the disclosure. Unless otherwise noted, the modified nucleotides can be completely substituted for the natural nucleotides of the polynucleotides of the disclosure. As a non-limiting example, the natural nucleotide uridine can be substituted with a modified nucleoside described herein. In another non-limiting example, the natural nucleotide uridine can be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker can be incorporated into the polynucleotides of the disclosure and such modifications are taught in International Patent Publication Nos. WO 2013/052523 and WO 2014/093924 A1.

TABLE 8

Combinations

| Modified Nucleotide | Modified Nucleotide Combination |
| --- | --- |
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

Additional examples of modified nucleotides and modified nucleotide combinations are provided below in Table 9.

TABLE 9

| Uracil | Cytosine | Adenine | Guanine |
|---|---|---|---|
| 5-methoxy-UTP | CTP | ATP | GTP |
| 5-Methoxy-UTP | N4Ac-CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4Ac-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Trifluoromethyl-CTP | ATP | GTP |
| 5-Methoxy-UTP | 5-Hydroxymethyl-CTP | ATP | GTP |
| 5-Methoxy-UTP | 5-Bromo-CTP | ATP | GTP |
| 5-Methoxy-UTP | N4-Ac-CTP | ATP | GTP |
| 5-Methoxy-UTP | 5-Iodo-CTP | ATP | GTP |
| 5-Methoxy-UTP | 5-Bromo-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | CTP | ATP | GTP |
| 5-Methoxy-UTP | CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | 5-Methyl-CTP | ATP | GTP |
| 5-Methoxy-UTP | CTP | Alpha-thio-ATP | GTP |
| 5-Methoxy-UTP | 5-Methyl-CTP | Alpha-thio-ATP | GTP |
| 5-Methoxy-UTP | CTP | ATP | Alpha-thio-GTP |
| 5-Methoxy-UTP | 5-Methyl-CTP | ATP | Alpha-thio-GTP |
| 5-Methoxy-UTP | CTP | N6-Me-ATP | GTP |
| 5-Methoxy-UTP | 5-Methyl-CTP | N6-Me-ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |

TABLE 9-continued

| Uracil | Cytosine | Adenine | Guanine |
|---|---|---|---|
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | 5-Ethyl-CTP | ATP | GTP |
| 5-Methoxy-UTP | 5-Methoxy-CTP | ATP | GTP |
| 5-Methoxy-UTP | 5-Ethynyl-CTP | ATP | GTP |
| 5-Methoxy-UTP | CTP | ATP | GTP |
| 5-Methoxy-UTP | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% 1-Methyl-pseudo-UTP | 5-Methyl-CTP | ATP | GTP |
| 50% 5-Methoxy-UTP + 50% 1-Methyl-pseudo-UTP | 5-Methyl-CTP | ATP | GTP |
| 25% 5-Methoxy-UTP + 75% 1-Methyl-pseudo-UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% 1-Methyl-pseudo-UTP | 75% 5-Methyl-CTP + 25% CTP | ATP | GTP |
| 75% 5-Methoxy-UTP + 25% 1-Methyl-pseudo-UTP | 50% 5-Methyl-CTP + 50% CTP | ATP | GTP |
| 75% 5-Methoxy-UTP + 25% 1-Methyl-pseudo-UTP | 25% 5-Methyl-CTP + 75% CTP | ATP | GTP |
| 50% 5-Methoxy-UTP + 50% 1-Methyl-pseudo-UTP | 75% 5-Methyl-CTP + 25% CTP | ATP | GTP |
| 50% 5-Methoxy-UTP + 50% 1-Methyl-pseudo-UTP | 50% 5-Methyl-CTP + 50% CTP | ATP | GTP |
| 50% 5-Methoxy-UTP + 50% 1-Methyl-pseudo-UTP | 25% 5-Methyl-CTP + 75% CTP | ATP | GTP |
| 25% 5-Methoxy-UTP + 75% 1-Methyl-pseudo-UTP | 75% 5-Methyl-CTP + 25% CTP | ATP | GTP |
| 25% 5-Methoxy-UTP + 75% 1-Methyl-pseudo-UTP | 50% 5-Methyl-CTP + 50% CTP | ATP | GTP |

TABLE 9-continued

| Additional combinations | | | |
|---|---|---|---|
| Uracil | Cytosine | Adenine | Guanine |
| 25% 5-Methoxy-UTP + 75% 1-Methyl-pseudo-UTP | 25% 5-Methyl-CTP + 75% CTP | ATP | GTP |
| 75% 5-Methoxy-UTP + 25% 1-Methyl-pseudo-UTP | CTP | ATP | GTP |
| 50% 5-Methoxy-UTP + 50% 1-Methyl-pseudo-UTP | CTP | ATP | GTP |
| 25% 5-Methoxy-UTP + 75% 1-Methyl-pseudo-UTP | CTP | ATP | GTP |
| 5-methoxy-UTP (In House) | CTP | ATP | GTP |
| 5-methoxy-UTP (Hongene) | CTP | ATP | GTP |
| 5-methoxy-UTP (Hongene) | 5-Methyl-CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 5-Methoxy-UTP | 5-Methyl-CTP | ATP | GTP |
| 75% 5-Methoxy-UTP + 25% UTP | 5-Methyl-CTP | ATP | GTP |
| 50% 5-Methoxy-UTP + 50% UTP | 5-Methyl-CTP | ATP | GTP |
| 25% 5-Methoxy-UTP + 75% UTP | 5-Methyl-CTP | ATP | GTP |
| 5-Methoxy-UTP | 75% 5-Methyl-CTP + 25% CTP | ATP | GTP |
| 5-Methoxy-UTP | 50% 5-Methyl-CTP + 50% CTP | ATP | GTP |
| 5-Methoxy-UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 75% 5-Methoxy-UTP + 25% UTP | 50% 5-Methyl-CTP + 50% CTP | ATP | GTP |
| 75% 5-Methoxy-UTP + 25% UTP | 25% 5-Methyl-CTP + 75% CTP | ATP | GTP |

TABLE 9-continued

| Uracil | Cytosine | Adenine | Guanine |
|---|---|---|---|
| 50% 5-Methoxy-UTP + 50% UTP | 75% 5-Methyl-CTP + 25% CTP | ATP | GTP |
| 50% 5-Methoxy-UTP + 50% UTP | 50% 5-Methyl-CTP + 50% CTP | ATP | GTP |
| 50% 5-Methoxy-UTP + 50% UTP | 25% 5-Methyl-CTP + 75% CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | CTP | ATP | GTP |
| 50% 5-Methoxy-UTP + 50% UTP | CTP | ATP | GTP |
| 25% 5-Methoxy-UTP + 75% UTP | CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | CTP | ATP | GTP |
| 25% 5-Methoxy-UTP + 75% UTP | 75% 5-Methyl-CTP + 25% CTP | ATP | GTP |

TABLE 9-continued

Additional combinations

| Uracil | Cytosine | Adenine | Guanine |
|---|---|---|---|
| 25% 5-Methoxy-UTP + 75% UTP | 50% 5-Methyl-CTP + 50% CTP | ATP | GTP |
| 25% 5-Methoxy-UTP + 75% UTP | 25% 5-Methyl-CTP + 75% CTP | ATP | GTP |
| 75% 5-Methoxy-UTP + 25% UTP | 75% 5-Methyl-CTP + 25% CTP | ATP | GTP |
| 5-Methoxy-UTP | 5-Fluoro-CTP | ATP | GTP |
| 5-Methoxy-UTP | 5-Phenyl-CTP | ATP | GTP |
| 5-Methoxy-UTP | N4-Bz-CTP | ATP | GTP |
| 5-Methoxy-UTP | CTP | N6-Isopentenyl-ATP | GTP |
| 5-Methoxy-UTP | N4-Ac-CTP | ATP | GTP |
| 25% 5-Methoxy-UTP + 75% UTP | 25% N4-Ac-CTP + 75% CTP | ATP | GTP |
| 25% 5-Methoxy-UTP + 75% UTP | 75% N4-Ac-CTP + 25% CTP | ATP | GTP |
| 75% 5-Methoxy-UTP + 25% UTP | 25% N4-Ac-CTP + 75% CTP | ATP | GTP |
| 75% 5-Methoxy-UTP + 25% UTP | 75% N4-Ac-CTP + 25% CTP | ATP | GTP |
| 5-Methoxy-UTP | 5-Hydroxymethyl-CTP | ATP | GTP |
| 25% 5-Methoxy-UTP + 75% UTP | 25% 5-Hydroxymethyl-CTP + 75% CTP | ATP | GTP |
| 25% 5-Methoxy-UTP + 75% UTP | 75% 5-Hydroxymethyl-CTP + 25% CTP | ATP | GTP |
| 75% 5-Methoxy-UTP + 25% UTP | 25% 5-Hydroxymethyl-CTP + 75% CTP | ATP | GTP |
| 75% 5-Methoxy-UTP + 25% UTP | 75% 5-Hydroxymethyl-CTP + 25% CTP | ATP | GTP |
| 5-Methoxy-UTP | N4-Methyl CTP | ATP | GTP |
| 25% 5-Methoxy-UTP + 75% UTP | 25% N4-Methyl CTP + 75% CTP | ATP | GTP |
| 25% 5-Methoxy-UTP + 75% UTP | 75% N4-Methyl CTP + 25% CTP | ATP | GTP |
| 75% 5-Methoxy-UTP + 25% UTP | 25% N4-Methyl CTP + 75% CTP | ATP | GTP |
| 75% 5-Methoxy-UTP + 25% UTP | 75% N4-Methyl CTP + 25% CTP | ATP | GTP |
| 5-Methoxy-UTP | 5-Trifluoromethyl-CTP | ATP | GTP |
| 25% 5-Methoxy-UTP + 75% UTP | 25% 5-Trifluoromethyl-CTP + 75% CTP | ATP | GTP |
| 25% 5-Methoxy-UTP + 75% UTP | 75% 5-Trifluoromethyl-CTP + 25% CTP | ATP | GTP |
| 75% 5-Methoxy-UTP + 25% UTP | 25% 5-Trifluoromethyl-CTP + 75% CTP | ATP | GTP |
| 75% 5-Methoxy-UTP + 25% UTP | 75% 5-Trifluoromethyl-CTP + 25% CTP | ATP | GTP |
| 5-Methoxy-UTP | 5-Bromo-CTP | ATP | GTP |
| 25% 5-Methoxy-UTP + 75% UTP | 25% 5-Bromo-CTP + 75% CTP | ATP | GTP |
| 25% 5-Methoxy-UTP + 75% UTP | 75% 5-Bromo-CTP + 25% CTP | ATP | GTP |
| 75% 5-Methoxy-UTP + 25% UTP | 25% 5-Bromo-CTP + 75% CTP | ATP | GTP |
| 75% 5-Methoxy-UTP + 25% UTP | 75% 5-Bromo-CTP + 25% CTP | ATP | GTP |
| 5-Methoxy-UTP | 5-Iodo-CTP | ATP | GTP |
| 25% 5-Methoxy-UTP + 75% UTP | 25% 5-Iodo-CTP + 75% CTP | ATP | GTP |
| 25% 5-Methoxy-UTP + 75% UTP | 75% 5-Iodo-CTP + 25% CTP | ATP | GTP |
| 75% 5-Methoxy-UTP + 25% UTP | 25% 5-Iodo-CTP + 75% CTP | ATP | GTP |
| 75% 5-Methoxy-UTP + 25% UTP | 75% 5-Iodo-CTP + 25% CTP | ATP | GTP |
| 5-Methoxy-UTP | 5-Ethyl-CTP | ATP | GTP |
| 25% 5-Methoxy-UTP + 75% UTP | 25% 5-Ethyl-CTP + 75% CTP | ATP | GTP |
| 25% 5-Methoxy-UTP + 75% UTP | 75% 5-Ethyl-CTP + 25% CTP | ATP | GTP |
| 75% 5-Methoxy-UTP + 25% UTP | 25% 5-Ethyl-CTP + 75% CTP | ATP | GTP |
| 75% 5-Methoxy-UTP + 25% UTP | 75% 5-Ethyl-CTP + 25% CTP | ATP | GTP |

TABLE 9-continued

Additional combinations

| Uracil | Cytosine | Adenine | Guanine |
|---|---|---|---|
| 5-Methoxy-UTP | 5-Methoxy-CTP | ATP | GTP |
| 25% 5-Methoxy-UTP + 75% UTP | 25% 5-Methoxy-CTP + 75% CTP | ATP | GTP |
| 25% 5-Methoxy-UTP + 75% UTP | 75% 5-Methoxy-CTP + 25% CTP | ATP | GTP |
| 75% 5-Methoxy-UTP + 25% UTP | 25% 5-Methoxy-CTP + 75% CTP | ATP | GTP |
| 75% 5-Methoxy-UTP + 25% UTP | 75% 5-Methoxy-CTP + 25% CTP | ATP | GTP |
| 5-Methoxy-UTP | 5-Ethynyl-CTP | ATP | GTP |
| 25% 5-Methoxy-UTP + 75% UTP | 25% 5-Ethynyl-CTP + 75% CTP | ATP | GTP |
| 25% 5-Methoxy-UTP + 75% UTP | 75% 5-Ethynyl-CTP + 25% CTP | ATP | GTP |
| 75% 5-Methoxy-UTP + 25% UTP | 25% 5-Ethynyl-CTP + 75% CTP | ATP | GTP |
| 75% 5-Methoxy-UTP + 25% UTP | 75% 5-Ethynyl-CTP + 25% CTP | ATP | GTP |
| 5-Methoxy-UTP | 5-Pseudo-iso-CTP | ATP | GTP |
| 25% 5-Methoxy-UTP + 75% UTP | 25% 5-Pseudo-iso-CTP + 75% CTP | ATP | GTP |
| 25% 5-Methoxy-UTP + 75% UTP | 75% 5-Pseudo-iso-CTP + 25% CTP | ATP | GTP |
| 75% 5-Methoxy-UTP + 25% UTP | 25% 5-Pseudo-iso-CTP + 75% CTP | ATP | GTP |
| 75% 5-Methoxy-UTP + 25% UTP | 75% 5-Pseudo-iso-CTP + 25% CTP | ATP | GTP |
| 5-Methoxy-UTP | 5-Formyl-CTP | ATP | GTP |
| 25% 5-Methoxy-UTP + 75% UTP | 25% 5-Formyl-CTP + 75% CTP | ATP | GTP |
| 25% 5-Methoxy-UTP + 75% UTP | 75% 5-Formyl-CTP + 25% CTP | ATP | GTP |
| 75% 5-Methoxy-UTP + 25% UTP | 25% 5-Formyl-CTP + 75% CTP | ATP | GTP |
| 75% 5-Methoxy-UTP + 25% UTP | 75% 5-Formyl-CTP + 25% CTP | ATP | GTP |
| 5-Methoxy-UTP | 5-Aminoallyl-CTP | ATP | GTP |
| 25% 5-Methoxy-UTP + 75% UTP | 25% 5-Aminoallyl-CTP + 75% CTP | ATP | GTP |
| 25% 5-Methoxy-UTP + 75% UTP | 75% 5-Aminoallyl-CTP + 25% CTP | ATP | GTP |
| 75% 5-Methoxy-UTP + 25% UTP | 25% 5-Aminoallyl-CTP + 75% CTP | ATP | GTP |
| 75% 5-Methoxy-UTP + 25% UTP | 75% 5-Aminoallyl-CTP + 25% CTP | ATP | GTP |

VI. Pharmaceutical Compositions

Formulation, Administration, Delivery and Dosing

The present disclosure provides use of a pharmaceutical composition comprising a polynucleotide which comprises an mRNA encoding an OX40L polypeptide to activate T cells in a subject in need thereof. The present disclosure further provides use of a pharmaceutical composition comprising a polynucleotide which comprises an mRNA encoding an OX40L polypeptide to increase the number of Natural Killer (NK) cells in a subject in need thereof. In some embodiments of the disclosure, the polynucleotide is formulated in compositions and complexes in combination with one or more pharmaceutically acceptable excipients. Pharmaceutical compositions can optionally comprise one or more additional active substances, e.g. therapeutically and/or prophylactically active substances. Pharmaceutical compositions of the present disclosure can be sterile and/or pyrogen-free. General considerations in the formulation and/or manufacture of pharmaceutical agents can be found, for example, in Remington: The Science and Practice of Pharmacy 21$^{st}$ ed., Lippincott Williams & Wilkins, 2005.

In some embodiments, compositions are administered to humans, human patients or subjects. For the purposes of the present disclosure, the phrase "active ingredient" generally refers to polynucleotides to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals.

In some embodiments, the polynucleotide of the present disclosure is formulated for subcutaneous, intravenous, intraperitoneal, intratumoral, intramuscular, intra-articular, intra-synovial, intrasternal, intrathecal, intrahepatic, intralesional, intracranial, intraventricular, oral, inhalation spray, topical, rectal, nasal, buccal, vaginal, intratumoral, or implanted reservoir intramuscular, subcutaneous, intratumoral, or intradermal delivery. In other embodiments, the polynucleotide is formulated for intratumoral, intraperitoneal, or intravenous delivery. In a particular embodiment, the polynucleotide of the present disclosure is formulated for intratumoral delivery.

Formulations of the pharmaceutical compositions described herein can be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition can comprise between 0.1% and 100%, e.g., between 0.5 and 50%, between 1-30%, between 5-80%, at least 80% (w/w) active ingredient.

Formulations

The polynucleotides comprising an mRNA encoding an OX40L polypeptide of the disclosure can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles, polymers, lipoplexes, core-shell nanoparticles, peptides, proteins, cells transfected with polynucleotides (e.g., for transplantation into a subject), hyaluronidase, nanoparticle mimics and combinations thereof. Accordingly, the formulations of the disclosure can include one or more excipients, each in an amount that together increases the stability of the polynucleotide, increases cell transfection by the polynucleotide, increases the expression of polynucleotides encoded protein, and/or alters the release profile of polynucleotide encoded proteins. Further, the polynucleotides of the present disclosure can be formulated using self-assembled nucleic acid nanoparticles.

Formulations of the pharmaceutical compositions described herein can be prepared by any method known or hereafter developed in the art of pharmacology. In general, such preparatory methods include the step of associating the active ingredient with an excipient and/or one or more other accessory ingredients.

A pharmaceutical composition in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered. For example, the composition can comprise between 0.1% and 99% (w/w) of the active ingredient. By way of example, the composition can comprise between 0.1% and 100%, e.g., between 0.5 and 50%, between 1-30%, between 5-80%, at least 80% (w/w) active ingredient.

In some embodiments, the formulations described herein contain at least one polynucleotide. As a non-limiting example, the formulations contain 1, 2, 3, 4 or 5 polynucleotides. In other embodiments, the polynucleotide of the disclosure is formulated for intratumoral delivery in a tumor of a patient in need thereof.

Pharmaceutical formulations can additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006). The use of a conventional excipient medium can be contemplated within the scope of the present disclosure, except insofar as any conventional excipient medium can be incompatible with a substance or its derivatives, such as by producing any undesirable biological effect or otherwise interacting in a deleterious manner with any other component(s) of the pharmaceutical composition.

In some embodiments, the particle size of the lipid nanoparticle is increased and/or decreased. The change in particle size can be able to help counter biological reaction such as, but not limited to, inflammation or can increase the biological effect of the modified mRNA delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients can optionally be included in the pharmaceutical formulations of the disclosure.

In some embodiments, the polynucleotides is administered in or with, formulated in or delivered with nanostructures that can sequester molecules such as cholesterol. Non-limiting examples of these nanostructures and methods of making these nanostructures are described in US Patent Publication No. US20130195759. Exemplary structures of these nanostructures are shown in US Patent Publication No. US20130195759, and can include a core and a shell surrounding the core.

Lipidoids

The polynucleotide comprising an mRNA encoding an OX40L polypeptide can be formulated with lipidoids. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA.

2010 107:1864-1869; Siegwart et al., Proc Natl Acad Sci USA. 2011 108:12996-3001).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010), the present disclosure describes their formulation and use in delivering polynucleotides.

Complexes, micelles, liposomes or particles can be prepared containing these lipidoids and therefore, can result in an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intraperitoneal, intratumoral, intramuscular, or subcutaneous routes.

In vivo delivery of nucleic acids can be affected by many parameters, including, but not limited to, the formulation composition, nature of particle PEGylation, degree of loading, polynucleotide to lipid ratio, and biophysical parameters such as, but not limited to, particle size (Akinc et al., Mol Ther. 2009 17:872-879). As an example, small changes in the anchor chain length of poly(ethylene glycol) (PEG) lipids can result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), and MD1, can be tested for in vivo activity.

The lipidoid referred to herein as "98N12-5" is disclosed by Akinc et al., Mol Ther. 2009 17:872-879.

The lipidoid referred to herein as "C12-200" is disclosed by Love et al., Proc Natl Acad Sci USA. 2010 107:1864-1869 and Liu and Huang, Molecular Therapy. 2010 669-670. The lipidoid formulations can include particles comprising either 3 or 4 or more components in addition to polynucleotides.

Lipidoids and polynucleotide formulations comprising lipidoids are described in International Patent Application No. PCT/US2014/097077.

Liposomes, Lipoplexes, and Lipid Nanoparticles

The polynucleotides of the disclosure can be formulated using one or more liposomes, lipoplexes, or lipid nanoparticles. In one embodiment, pharmaceutical compositions of the polynucleotides comprising an mRNA encoding an OX40L polypeptide include liposomes. Liposomes are artificially-prepared vesicles which can primarily be composed of a lipid bilayer and can be used as a delivery vehicle for the administration of pharmaceutical formulations. Liposomes can be of different sizes such as, but not limited to, a multilamellar vesicle (MLV) which can be hundreds of nanometers in diameter and can contain a series of concentric bilayers separated by narrow aqueous compartments, a small unicellular vesicle (SUV) which can be smaller than 50 nm in diameter, and a large unilamellar vesicle (LUV) which can be between 50 and 500 nm in diameter. Liposome design can include, but is not limited to, opsonins or ligands in order to improve the attachment of liposomes to unhealthy tissue or to activate events such as, but not limited to, endocytosis. Liposomes can contain a low or a high pH in order to improve the delivery of the pharmaceutical formulations.

The formation of liposomes can depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles are prepared by the methods, apparatus and devices described in US Patent Publication No. US20130177638, US20130177637, US20130177636, US20130177635, US20130177634, US20130177633, US20130183375, US20130183373 and US20130183372.

In one embodiment, pharmaceutical compositions described herein include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (as described in US20100324120) and liposomes which can deliver small molecule drugs such as, but not limited to, DOXIL® from Janssen Biotech, Inc. (Horsham, Pa.).

In one embodiment, pharmaceutical compositions described herein can include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations contain, but are not limited to, 48% cholesterol, 20% DSPC, 2% PEG-c-DMA, and 30% cationic lipid, where the cationic lipid can be 1,2-di stearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In other embodiments, formulations comprise a percentage of cholesterol selected from the group consisting of 28.5%, 31.5%, 33.5%, 36.5%, 37.0%, 38.5%, 39.0% and 43.5%. In some embodiments, formulations comprise from about 5.0% to about 10.0% DSPC and/or from about 7.0% to about 15.0% DSPC.

In one embodiment, pharmaceutical compositions include liposomes which are formed to deliver polynucleotides comprising an mRNA encoding an OX40L polypeptide. The polynucleotides can be encapsulated by the liposome and/or it can be contained in an aqueous core which can then be encapsulated by the liposome (see International Pub. Nos. WO2012031046, WO2012031043, WO2012030901 and WO2012006378 and US Patent Publication No. US20130189351, US20130195969 and US20130202684).

In another embodiment, liposomes are formulated for targeted delivery. As a non-limiting example, the liposome is formulated for targeted delivery to the liver. The liposome used for targeted delivery can include, but is not limited to, the liposomes described in and methods of making liposomes described in US Patent Publication No. US20130195967.

In another embodiment, the polynucleotides comprising an mRNA encoding an OX40L polypeptide is formulated in a cationic oil-in-water emulsion where the emulsion particle comprises an oil core and a cationic lipid which can interact with the polynucleotide anchoring the molecule to the emulsion particle (see International Pub. No. WO2012006380).

In one embodiment, the polynucleotides comprising an mRNA encoding an OX40L polypeptide is formulated in a water-in-oil emulsion comprising a continuous hydrophobic phase in which the hydrophilic phase is dispersed. As a non-limiting example, the emulsion can be made by the methods described in International Publication No. WO201087791.

In another embodiment, the lipid formulation includes at least cationic lipid, a lipid which can enhance transfection and a least one lipid which contains a hydrophilic head group linked to a lipid moiety (International Pub. No. WO2011076807 and U.S. Pub. No. 20110200582). In another embodiment, the polynucleotides comprising an mRNA encoding an OX40L polypeptide is formulated in a lipid vesicle which can have crosslinks between functionalized lipid bilayers (see U.S. Pub. No. 20120177724).

In one embodiment, the polylnucleotides are formulated in a liposome as described in International Patent Publication No. WO2013086526. The polynucleotides can be encapsulated in a liposome using reverse pH gradients and/or optimized internal buffer compositions as described in International Patent Publication No. WO2013086526.

In one embodiment, the polynucleotide pharmaceutical compositions are formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713)) and hyaluronan-coated liposomes (Quiet Therapeutics, Israel).

In one embodiment, the cationic lipid is a low molecular weight cationic lipid such as those described in US Patent Application No. 20130090372. In another embodiment, the polynucleotides comprising an mRNA encoding an OX40L polypeptide are formulated in a lipid vesicle which can have crosslinks between functionalized lipid bilayers.

In other embodiments, the polynucleotides comprising an mRNA encoding an OX40L polypeptide are formulated in a liposome comprising a cationic lipid. The liposome can have a molar ratio of nitrogen atoms in the cationic lipid to the phosphates in the polynucleotide (N:P ratio) of between 1:1 and 20:1 as described in International Publication No. WO2013006825. In another embodiment, the liposome can have a N:P ratio of greater than 20:1 or less than 1:1.

In one embodiment, the polynucleotides comprising an mRNA encoding an OX40L polypeptide are formulated in a lipid-polycation complex. The formation of the lipid-polycation complex can be accomplished by methods known in the art and/or as described in U.S. Pub. No. 20120178702. As a non-limiting example, the polycation includes a cationic peptide or a polypeptide such as, but not limited to, polylysine, polyornithine and/or polyarginine and the cationic peptides described in International Pub. No. WO2012013326 or US Patent Pub. No. US20130142818. In another embodiment, the polynucleotides are formulated in a lipid-polycation complex which can further include a non-cationic lipid such as, but not limited to, cholesterol or dioleoyl phosphatidylethanolamine (DOPE).

In one embodiment, the polynucleotides comprising an mRNA encoding an OX40L polypeptide are formulated in an aminoalcohol lipidoid. Aminoalcohol lipidoids which can be used in the present disclosure can be prepared by the methods described in U.S. Pat. No. 8,450,298.

The liposome formulation can be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200). In some embodiments, liposome formulations comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes is from about 5:1 to about 20:1, from about 10:1 to about 25:1, from about 15:1 to about 30:1 and/or at least 30:1.

In some embodiments, the ratio of PEG in the lipid nanoparticle (LNP) formulations is increased or decreased and/or the carbon chain length of the PEG lipid is modified from C14 to C18 to alter the pharmacokinetics and/or biodistribution of the LNP formulations. As a non-limiting example, LNP formulations contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG can be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid can be selected from any lipid known in the art such as, but not limited to, DLin-MC3-DMA, DLin-DMA, C12-200 and DLin-KC2-DMA.

In one embodiment, the polynucleotides comprising an mRNA encoding an OX40L polypeptide are formulated in a lipid nanoparticle such as those described in International Publication No. WO2012170930.

In another embodiment, the formulation comprising the polynucleotide is a nanoparticle which can comprise at least one lipid. The lipid can be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid is a cationic lipid such as, but not limited to, DLin-DMA, DLin-D-DMA, DLin-MC3-DMA, DLin-KC2-DMA, DODMA and amino alcohol lipids. The amino alcohol cationic lipid can be the lipids described in and/or made by the methods described in US Patent Publication No. US20130150625. As a non-limiting example, the cationic lipid can be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

In some embodiments, the polynucleotide of the disclosure is formulated in a lipid nanoparticle, wherein the polynucleotide comprises an mRNA encoding a polypeptide comprising the amino acid sequence set forth in SEQ ID NO: 1 or SEQ ID NO: 2. In some embodiments, the polynucleotide of the disclosure is formulated in a lipid nanoparticle, wherein the polynucleotide comprises the sequence set forth in SEQ ID NO: 65.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid:5-25% neutral lipid:25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005).

In one embodiment, the formulations of the disclosures include 25-75% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the disclosures include 35-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the disclosures include 45-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the disclosures include about 60% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the disclosures include about 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the disclosures include about 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the disclosures include about 40% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations of the disclosures include about 57.2% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the disclosures include about 57.5% of a cationic lipid selected from the PEG lipid is PEG-cDMA (PEG-cDMA is further discussed in Reyes et al. (J. Controlled Release, 107, 276-287 (2005)), about 7.5% of the neutral lipid, about 31.5% of the sterol, and about 3.5% of the PEG or PEG-modified lipid on a molar basis.

In some embodiments, lipid nanoparticle formulation consists essentially of a lipid mixture in molar ratios of about 20-70% cationic lipid:5-45% neutral lipid:20-55% cholesterol:0.5-15% PEG-modified lipid; e.g., in a molar ratio of about 20-60% cationic lipid:5-25% neutral lipid:25-55% cholesterol:0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578.

In one embodiment, the lipid nanoparticle formulations described herein comprise a cationic lipid, a PEG lipid and a structural lipid and optionally comprise a non-cationic lipid. As a non-limiting example, the lipid nanoparticle comprises about 40-60% of cationic lipid, about 5-15% of a non-cationic lipid, about 1-2% of a PEG lipid and about 30-50% of a structural lipid. As another non-limiting example, the lipid nanoparticle comprises about 50% cationic lipid, about 10% non-cationic lipid, about 1.5% PEG lipid and about 38.5% structural lipid. As yet another non-limiting example, the lipid nanoparticle comprises about 55% cationic lipid, about 10% non-cationic lipid, about 2.5% PEG lipid and about 32.5% structural lipid. In one embodiment, the cationic lipid is any cationic lipid described herein such as, but not limited to, DLin-KC2-DMA, DLin-MC3-DMA and L319.

In one embodiment, the lipid nanoparticle formulations described herein is 4 component lipid nanoparticles. The lipid nanoparticle can comprise a cationic lipid, a non-cationic lipid, a PEG lipid and a structural lipid. As a non-limiting example, the lipid nanoparticle can comprise about 40-60% of cationic lipid, about 5-15% of a non-cationic lipid, about 1-2% of a PEG lipid and about 30-50% of a structural lipid. As another non-limiting example, the lipid nanoparticle can comprise about 50% cationic lipid, about 10% non-cationic lipid, about 1.5% PEG lipid and about 38.5% structural lipid. As yet another non-limiting example, the lipid nanoparticle can comprise about 55% cationic lipid, about 10% non-cationic lipid, about 2.5% PEG lipid and about 32.5% structural lipid. In one embodiment, the cationic lipid can be any cationic lipid described herein such as, but not limited to, DLin-KC2-DMA, DLin-MC3-DMA and L319.

In one embodiment, the lipid nanoparticle formulations described herein comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In one embodiment, the cationic lipid is selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and US20130225836. In another embodiment, the cationic lipid can be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836. In yet another embodiment, the cationic lipid can be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115, formula I of US Patent Publication No US20130123338. As a non-limiting example, the cationic lipid can be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-10-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl]methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyl octyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-octylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In one embodiment, the lipid is a cleavable lipid such as those described in International Publication No. WO2012170889. In another embodiment, the lipid is a cationic lipid such as, but not limited to, Formula (I) of U.S. Patent Application No. US20130064894.

In one embodiment, the cationic lipid is synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354.

In another embodiment, the cationic lipid is a trialkyl cationic lipid. Non-limiting examples of trialkyl cationic lipids and methods of making and using the trialkyl cationic lipids are described in International Patent Publication No. WO2013126803.

In one embodiment, the LNP formulations of the polynucleotides contain PEG-c-DOMG at 3% lipid molar ratio. In another embodiment, the LNP formulations of the polynucleotides contain PEG-c-DOMG at 1.5% lipid molar ratio.

In one embodiment, the pharmaceutical compositions of the polynucleotides comprising an mRNA encoding an OX40L polypeptide include at least one of the PEGylated lipids described in International Publication No. WO2012099755.

In one embodiment, the LNP formulation contains PEG-DMG 2000 (1,2-dimyristoyl-sn-glycero-3-phophoethanolamine-N-[methoxy(polyethylene glycol)-2000). In one embodiment, the LNP formulation can contain PEG-DMG 2000, a cationic lipid known in the art and at least one other component. In another embodiment, the LNP formulation contains PEG-DMG 2000, a cationic lipid known in the art, DSPC and cholesterol. As a non-limiting example, the LNP formulation contains PEG-DMG 2000, DLin-DMA, DSPC and cholesterol. As another non-limiting example the LNP formulation contains PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294).

In one embodiment, the LNP formulation is formulated by the methods described in International Publication Nos. WO2011127255 or WO2008103276. As a non-limiting example, the polynucleotides comprising an mRNA encoding an OX40L polypeptide described herein are encapsulated in LNP formulations as described in WO2011127255 and/or WO2008103276.

In one embodiment, the polynucleotides comprising an mRNA encoding an OX40L polypeptide described herein are formulated in a nanoparticle to be delivered by a parenteral route as described in U.S. Pub. No. US20120207845.

In one embodiment, the polynucleotides comprising an mRNA encoding an OX40L polypeptide are formulated in a lipid nanoparticle made by the methods described in US Patent Publication No US20130156845 or International Publication No WO2013093648 or WO2012024526.

The lipid nanoparticles described herein can be made in a sterile environment by the system and/or methods described in US Patent Publication No. US20130164400.

In one embodiment, the LNP formulation is formulated in a nanoparticle such as a nucleic acid-lipid particle described in U.S. Pat. No. 8,492,359. As a non-limiting example, the lipid particle comprises one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle can be the polynucleotides described herein and/or are known in the art.

In one embodiment, the LNP formulation is formulated by the methods described in International Publication Nos. WO2011127255 or WO2008103276. As a non-limiting example, modified RNA described herein is encapsulated in LNP formulations as described in WO2011127255 and/or WO2008103276.

In one embodiment, LNP formulations described herein comprise a polycationic composition. As a non-limiting example, the polycationic composition is selected from formula 1-60 of US Patent Publication No. US20050222064. In another embodiment, the LNP formulations comprising a polycationic composition are used for the delivery of the modified RNA described herein in vivo and/or in vitro.

In one embodiment, the LNP formulations described herein additionally comprise a permeability enhancer molecule. Non-limiting permeability enhancer molecules are described in US Patent Publication No. US20050222064.

In one embodiment, the polynucleotide pharmaceutical compositions are formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713)) and hyaluronan-coated liposomes (Quiet Therapeutics, Israel).

In one embodiment, the polynucleotides comprising an mRNA encoding an OX40L polypeptide are formulated in a lyophilized gel-phase liposomal composition as described in US Publication No. US2012060293.

The nanoparticle formulations can comprise a phosphate conjugate. The phosphate conjugate can increase in vivo circulation times and/or increase the targeted delivery of the nanoparticle. Phosphate conjugates for use with the present disclosure can be made by the methods described in International Application No. WO2013033438 or US Patent Publication No. US20130196948. As a non-limiting example, the phosphate conjugates can include a compound of any one of the formulas described in International Application No. WO2013033438.

The nanoparticle formulation can comprise a polymer conjugate. The polymer conjugate can be a water soluble conjugate. The polymer conjugate can have a structure as described in U.S. Patent Application No. 20130059360. In one aspect, polymer conjugates with the polynucleotides comprising an mRNA encoding an OX40L polypeptide of the present disclosure can be made using the methods and/or segmented polymeric reagents described in U.S. Patent Application No. 20130072709. In another aspect, the polymer conjugate can have pendant side groups comprising ring moieties such as, but not limited to, the polymer conjugates described in US Patent Publication No. US20130196948.

The nanoparticle formulations can comprise a conjugate to enhance the delivery of nanoparticles of the present disclosure in a subject. Further, the conjugate can inhibit phagocytic clearance of the nanoparticles in a subject. In one aspect, the conjugate is a "self" peptide designed from the human membrane protein CD47 (e.g., the "self" particles described by Rodriguez et al (Science 2013 339, 971-975)). As shown by Rodriguez et al. the self peptides delayed macrophage-mediated clearance of nanoparticles which enhanced delivery of the nanoparticles. In another aspect, the conjugate is the membrane protein CD47 (e.g., see Rodriguez et al. Science 2013 339, 971-975). Rodriguez et al. showed that, similarly to "self" peptides, CD47 can increase the circulating particle ratio in a subject as compared to scrambled peptides and PEG coated nanoparticles.

In one embodiment, the polynucleotides comprising an mRNA encoding an OX40L polypeptide of the present disclosure are formulated in nanoparticles which comprise a conjugate to enhance the delivery of the nanoparticles of the present disclosure in a subject. The conjugate can be the CD47 membrane or the conjugate can be derived from the CD47 membrane protein, such as the "self" peptide described previously. In another aspect the nanoparticle can comprise PEG and a conjugate of CD47 or a derivative thereof. In yet another aspect, the nanoparticle comprises both the "self" peptide described above and the membrane protein CD47.

In another aspect, a "self" peptide and/or CD47 protein is conjugated to a virus-like particle or pseudovirion, as described herein for delivery of the polynucleotides of the present disclosure.

In another embodiment, pharmaceutical compositions comprising the polynucleotides comprising an mRNA encoding an OX40L polypeptide of the present disclosure and a conjugate which can have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443.

The nanoparticle formulations can be a carbohydrate nanoparticle comprising a carbohydrate carrier and a polynucleotide. As a non-limiting example, the carbohydrate carrier includes, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121).

Nanoparticle formulations of the present disclosure can be coated with a surfactant or polymer in order to improve the delivery of the particle. In one embodiment, the nanoparticle is coated with a hydrophilic coating such as, but not limited to, PEG coatings and/or coatings that have a neutral surface charge. The hydrophilic coatings can help to deliver nanoparticles with larger payloads such as, but not limited to, polynucleotides within the central nervous system. As a non-limiting example nanoparticles comprising a hydrophilic coating and methods of making such nanoparticles are described in US Patent Publication No. US20130183244.

In one embodiment, the lipid nanoparticles of the present disclosure are hydrophilic polymer particles. Non-limiting examples of hydrophilic polymer particles and methods of making hydrophilic polymer particles are described in US Patent Publication No. US20130210991.

In another embodiment, the lipid nanoparticles of the present disclosure are hydrophobic polymer particles. Lipid nanoparticle formulations can be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and can be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it can be terminally located at the terminal end of the lipid chain. The internal ester linkage can replace any carbon in the lipid chain.

In one embodiment, the internal ester linkage is located on either side of the saturated carbon.

In one embodiment, an immune response is elicited by delivering a lipid nanoparticle which can include a nanospecies, a polymer and an immunogen. (U.S. Publication No. 20120189700 and International Publication No. WO2012099805). The polymer can encapsulate the nanospecies or partially encapsulate the nanospecies. The immunogen can be a recombinant protein, a modified RNA and/or an OX40L polynucleotide described herein.

Lipid nanoparticles can be engineered to alter the surface properties of particles so the lipid nanoparticles can penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles can be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171). The transport of nanoparticles can be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier can be made as described in U.S. Pat. No. 8,241,670 or International Patent Publication No. WO2013110028.

The lipid nanoparticle engineered to penetrate mucus can comprise a polymeric material (i.e. a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material can be biodegradable and/or biocompatible. Non-limiting examples of biocompatible polymers are described in International Patent Publication No. WO2013116804. The polymeric material can additionally be irradiated. As a non-limiting example, the polymeric material can be gamma irradiated (See e.g., International App. No. WO201282165). Non-limiting examples of specific polymers include poly(caprolactone) (PCL), ethylene vinyl acetate polymer (EVA), poly(lactic acid) (PLA), poly (L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle can be coated or associated with a co-polymer such as, but not limited to, a block co-polymer (such as a branched polyether-polyamide block copolymer described in International Publication No. WO2013012476), and (poly (ethylene glycol))-(poly(propylene oxide))-(poly(ethylene glycol)) triblock copolymer (see e.g., US Publication 20120121718 and US Publication 20100003337 and U.S. Pat. No. 8,263,665). The co-polymer can be a polymer that is generally regarded as safe (GRAS) and the formation of the lipid nanoparticle can be in such a way that no new chemical entities are created. For example, the lipid nanoparticle can comprise poloxamers coating PLGA nanoparticles without forming new chemical entities which are still able to rapidly penetrate human mucus (Yang et al. Angew. Chem. Int. Ed. 2011 50:2597-2600). A non-limiting scalable method to produce nanoparticles which can penetrate human mucus is described by Xu et al. (See e.g., J Control Release 2013, 170(2):279-86).

The vitamin of the polymer-vitamin conjugate can be vitamin E. The vitamin portion of the conjugate can be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus can include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent can be embedded or enmeshed in the particle's surface or disposed (e.g., by coating, adsorption, covalent linkage, or other process) on the surface of the lipid nanoparticle. (see e.g., US Publication 20100215580 and US Publication 20080166414 and US20130164343).

In one embodiment, the mucus penetrating lipid nanoparticles comprises at least one polynucleotide described herein. The polynucleotide can be encapsulated in the lipid nanoparticle and/or disposed on the surface of the particle. The polynucleotide can be covalently coupled to the lipid nanoparticle. Formulations of mucus penetrating lipid nanoparticles can comprise a plurality of nanoparticles. Further, the formulations can contain particles which can interact with the mucus and alter the structural and/or adhesive properties of the surrounding mucus to decrease mucoadhesion which can increase the delivery of the mucus penetrating lipid nanoparticles to the mucosal tissue.

In another embodiment, the mucus penetrating lipid nanoparticles are a hypotonic formulation comprising a mucosal penetration enhancing coating. The formulation can be hypotonic for the epithelium to which it is being delivered. Non-limiting examples of hypotonic formulations can be found in International Patent Publication No. WO2013110028.

In one embodiment, in order to enhance the delivery through the mucosal barrier the polynucleotide formulation comprises or is a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9).

In one embodiment, the polynucleotide is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132).

In one embodiment such formulations are also constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133).

In one embodiment, the polynucleotides comprising an mRNA encoding an OX40L polypeptide of the disclosure are formulated as a solid lipid nanoparticle. A solid lipid nanoparticle (SLN) can be spherical with an average diameter between 10 to 1000 nm. SLN possess a solid lipid core matrix that can solubilize lipophilic molecules and can be stabilized with surfactants and/or emulsifiers. In a further embodiment, the lipid nanoparticle can be a self-assembly lipid-polymer nanoparticle (see Zhang et al., ACS Nano, 2008, 2 (8), pp 1696-1702). As a non-limiting example, the SLN can be the SLN described in International Patent Publication No. WO2013105101. As another non-limiting example, the SLN can be made by the methods or processes described in International Patent Publication No. WO2013105101.

Liposomes, lipoplexes, or lipid nanoparticles can be used to improve the efficacy of the polynucleotides comprising an mRNA encoding an OX40L polypeptide as these formulations can be able to increase cell transfection by the polynucleotides; and/or increase the translation of encoded OX40L. One such example involves the use of lipid encapsulation to enable the effective systemic delivery of polyplex plasmid DNA (Heyes et al., Mol Ther. 2007 15:713-720). The liposomes, lipoplexes, or lipid nanoparticles can also be used to increase the stability of the polynucleotide.

In one embodiment, the polynucleotides comprising an mRNA encoding an OX40L polypeptide of the present disclosure are formulated for controlled release and/or targeted delivery. As used herein, "controlled release" refers to a pharmaceutical composition or compound release profile that conforms to a particular pattern of release to effect a therapeutic outcome. In one embodiment, the polynucleotides are encapsulated into a delivery agent described herein and/or known in the art for controlled release and/or targeted delivery. As used herein, the term "encapsulate" means to enclose, surround or encase. As it relates to the formulation of the compounds of the disclosure, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the disclosure can be enclosed, surrounded or encased within the delivery agent. "Partially encapsulation" means that less than 10, 10, 20, 30, 40 50 or less of the pharmaceutical composition or compound of the disclosure can be enclosed, surrounded or encased within the delivery agent. Advantageously, encapsulation can be determined by measuring the escape or the activity of the pharmaceutical composition or compound of the disclosure using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the disclosure are encapsulated in the delivery agent.

In one embodiment, the controlled release formulation includes, but is not limited to, tri-block co-polymers. As a non-limiting example, the formulation includes two different types of tri-block co-polymers (International Pub. No. WO2012131104 and WO2012131106).

In another embodiment, the polynucleotides comprising an mRNA encoding an OX40L polypeptide is encapsulated into a lipid nanoparticle or a rapidly eliminated lipid nanoparticle and the lipid nanoparticles or a rapidly eliminated lipid nanoparticle can then be encapsulated into a polymer, hydrogel and/or surgical sealant described herein and/or known in the art. As a non-limiting example, the polymer, hydrogel or surgical sealant is PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, or COSEAL® (Baxter International, Inc Deerfield, Ill.).

In another embodiment, the lipid nanoparticle is encapsulated into any polymer known in the art which can form a gel when injected into a subject. As another non-limiting example, the lipid nanoparticle is encapsulated into a polymer matrix which can be biodegradable.

In one embodiment, the polynucleotides comprising an mRNA encoding an OX40L polypeptide formulation for controlled release and/or targeted delivery also includes at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the polynucleotide controlled release and/or targeted delivery formulation comprise at least one degradable polyester which can contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

In one embodiment, the polynucleotide controlled release and/or targeted delivery formulation comprising at least one polynucleotide comprises at least one PEG and/or PEG related polymer derivatives as described in U.S. Pat. No. 8,404,222.

In another embodiment, the polynucleotide controlled release delivery formulation comprising at least one polynucleotide is the controlled release polymer system described in US20130130348.

In one embodiment, the polynucleotide comprising an mRNA encoding an OX40L polypeptide of the present disclosure is encapsulated in a therapeutic nanoparticle. Therapeutic nanoparticles can be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211. In another embodiment, therapeutic polymer nanoparticles can be identified by the methods described in US Pub No. US20120140790.

In one embodiment, the polynucleotides comprising an mRNA encoding an OX40L polypeptide are formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle comprises a polymer and a therapeutic agent such as, but not limited to, the polynucleotides comprising an mRNA encoding an OX40L polypeptide of the present disclosure (see International Pub No. 2010075072 and US Pub No. US20100216804, US20110217377 and US20120201859). In another non-limiting example, the sustained release formulation comprises agents which permit persistent bioavailability such as, but not limited to, crystals, macromolecular gels and/or particulate suspensions (see US Patent Publication No US20130150295).

In one embodiment, the polynucleotides comprising an mRNA encoding an OX40L polypeptide can be formulated to be target specific. As non-limiting examples, the therapeutic nanoparticles include a corticosteroid (see International Pub. No. WO2011084518). As a non-limiting example, the therapeutic nanoparticles are formulated in nanoparticles described in International Pub No. WO2008121949, WO2010005726, WO2010005725, WO2011084521 and US Pub No. US20100069426, US20120004293 and US20100104655.

In one embodiment, the nanoparticles of the present disclosure comprise a polymeric matrix. As a non-limiting example, the nanoparticle comprises two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer includes PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In yet another embodiment, the diblock copolymer is a high-X diblock copolymer such as those described in International Patent Publication No. WO2013120052.

As a non-limiting example the therapeutic nanoparticle comprises a PLGA-PEG block copolymer (see US Pub. No. US20120004293 and U.S. Pat. No. 8,236,330). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923). In yet another non-limiting example, the therapeutic nanoparticle is a stealth nanoparticle or a target-specific stealth nanoparticle as described in US Patent Publication No. US20130172406.

In one embodiment, the therapeutic nanoparticle comprises a multiblock copolymer (See e.g., U.S. Pat. Nos. 8,263,665 and 8,287,910 and US Patent Pub. No. US20130195987).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253). The polynucleotides comprising an mRNA encoding an OX40L polypeptide of the present disclosure can be formulated in lipid nanoparticles comprising the PEG-PLGA-PEG block copolymer.

In one embodiment, the therapeutic nanoparticle comprises a multiblock copolymer (See e.g., U.S. Pat. Nos. 8,263,665 and 8,287,910 and US Patent Pub. No. US20130195987).

In one embodiment, the block copolymers described herein are included in a polyion complex comprising a non-polymeric micelle and the block copolymer. (See e.g., U.S. Pub. No. 20120076836).

In one embodiment, the therapeutic nanoparticle comprises at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the therapeutic nanoparticles comprise at least one poly(vinyl ester) polymer. The poly(vinyl ester) polymer can be a copolymer such as a random copolymer. As a non-limiting example, the random copolymer has a structure such as those described in International Application No. WO2013032829 or US Patent Publication No US20130121954. In one aspect, the poly(vinyl ester) polymers can be conjugated to the polynucleotides described herein.

In one embodiment, the therapeutic nanoparticle comprises at least one diblock copolymer. The diblock copolymer can be, but is not limited to, a poly(lactic) acid-poly(ethylene)glycol copolymer (see e.g., International Patent Publication No. WO2013044219). As a non-limiting example, the therapeutic nanoparticle are used to treat cancer (see International publication No. WO2013044219).

In one embodiment, the therapeutic nanoparticles comprise at least one cationic polymer described herein and/or known in the art.

In one embodiment, the therapeutic nanoparticles comprise at least one amine-containing polymer such as, but are not limited to polylysine, polyethylene imine, poly(amidoamine) dendrimers, poly(beta-amino esters) (See e.g., U.S. Pat. No. 8,287,849) and combinations thereof.

In another embodiment, the nanoparticles described herein comprise an amine cationic lipid such as those described in International Patent Application No. WO2013059496. In one aspect the cationic lipids have an amino-amine or an amino-amide moiety.

In one embodiment, the therapeutic nanoparticles comprise at least one degradable polyester which can contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters can include a PEG conjugation to form a PEGylated polymer.

In another embodiment, the therapeutic nanoparticle includes a conjugation of at least one targeting ligand. The targeting ligand can be any ligand known in the art such as, but not limited to, a monoclonal antibody. (Kirpotin et al, Cancer Res. 2006 66:6732-6740).

In one embodiment, the therapeutic nanoparticle is formulated in an aqueous solution which can be used to target cancer (see International Pub No. WO2011084513 and US Pub No. US20110294717).

In one embodiment, the polynucleotides comprising an mRNA encoding an OX40L polypeptide is formulated using the methods described by Podobinski et al in U.S. Pat. No. 8,404,799.

In one embodiment, the polynucleotides comprising an mRNA encoding an OX40L polypeptide is encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222. The synthetic nanocarriers can be formulated using methods known in the art and/or described herein. As a non-limiting example, the synthetic nanocarriers can be formulated by the methods described in International Pub Nos. WO2010005740, WO2010030763 and WO201213501 and US Pub. Nos. US20110262491, US20100104645, US20100087337 and US2012024422. In another embodiment, the synthetic nanocarrier formulations can be lyophilized by methods described in International Pub. No. WO2011072218 and U.S. Pat. No. 8,211,473. In yet another embodiment, formulations of the present disclosure, including, but not limited to, synthetic nanocarriers, can be lyophilized or reconstituted by the methods described in US Patent Publication No. US20130230568.

In one embodiment, the synthetic nanocarriers contain reactive groups to release the polynucleotides described herein (see International Pub. No. WO20120952552 and US Pub No. US20120171229).

In one embodiment, the synthetic nanocarriers contain an immunostimulatory agent to enhance the immune response from delivery of the synthetic nanocarrier. As a non-limiting example, the synthetic nanocarrier can comprise a Th1 immunostimulatory agent which can enhance a Th1-based response of the immune system (see International Pub No. WO2010123569 and US Pub. No. US20110223201).

In one embodiment, the synthetic nanocarriers are formulated for targeted release. In one embodiment, the synthetic nanocarrier is formulated to release the polynucleotides at a specified pH and/or after a desired time interval. As a non-limiting example, the synthetic nanoparticle is formulated to release the polynucleotides after 24 hours and/or at a pH of 4.5 (see International Pub. Nos. WO2010138193 and WO2010138194 and US Pub Nos. US20110020388 and US20110027217).

In one embodiment, the synthetic nanocarriers are formulated for controlled and/or sustained release of the polynucleotides described herein. As a non-limiting example, the synthetic nanocarriers for sustained release are formulated by methods known in the art, described herein and/or as described in International Pub No. WO2010138192 and US Pub No. 20100303850.

In one embodiment, the polynucleotides comprising an mRNA encoding an OX40L polypeptide are formulated for controlled and/or sustained release wherein the formulation comprises at least one polymer that is a crystalline side chain (CYSC) polymer. CYSC polymers are described in U.S. Pat. No. 8,399,007.

In one embodiment, the polynucleotides comprising an mRNA encoding an OX40L polypeptide are encapsulated in, linked to and/or associated with zwitterionic lipids. Non-limiting examples of zwitterionic lipids and methods of using zwitterionic lipids are described in US Patent Publication No. US20130216607. In one aspect, the zwitterionic lipids can be used in the liposomes and lipid nanoparticles described herein.

In one embodiment, the polynucleotides comprising an mRNA encoding an OX40L polypeptide are formulated in colloid nanocarriers as described in US Patent Publication No. US20130197100.

In one embodiment, the nanoparticle is optimized for oral administration. The nanoparticle can comprise at least one cationic biopolymer such as, but not limited to, chitosan or a derivative thereof. As a non-limiting example, the nanoparticle can be formulated by the methods described in U.S. Pub. No. 20120282343.

In some embodiments, LNPs comprise the lipid KL52 (an amino-lipid disclosed in U.S. Application Publication No. 2012/0295832). Activity and/or safety (as measured by examining one or more of ALT/AST, white blood cell count and cytokine induction) of LNP administration can be improved by incorporation of such lipids. LNPs comprising KL52 can be administered intravenously and/or in one or more doses. In some embodiments, administration of LNPs comprising KL52 results in equal or improved mRNA and/or protein expression as compared to LNPs comprising MC3.

In some embodiments, polynucleotides comprising an mRNA encoding an OX40L polypeptide are delivered using smaller LNPs. Such particles can comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

In another embodiment, polynucleotides comprising an mRNA encoding an OX40L polypeptide are delivered using smaller LNPs which can comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers can include, but are not limited to a slit interdigitial micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy—Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Application Publication Nos. 2004/0262223 and 2012/0276209.

In one embodiment, the polynucleotides comprising an mRNA encoding an OX40L polypeptide of the present disclosure is formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In one embodiment, the polynucleotides comprising an mRNA encoding an OX40L polypeptide of the present disclosure are formulated in lipid nanoparticles created using microfluidic technology (see Whitesides, George M. The Origins and the Future of Microfluidics. Nature, 2006 442: 368-373; and Abraham et al. Chaotic Mixer for Microchannels. Science, 2002 295: 647-651). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651).

In one embodiment, the polynucleotides comprising an mRNA encoding an OX40L polypeptide can be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the polynucleotides comprising an mRNA encoding an OX40L polypeptide are formulated for delivery using the drug encapsulating microspheres described in International Patent Publication No. WO2013063468 or U.S. Pat. No. 8,440,614. The microspheres can comprise a compound of the formula (I), (II), (III), (IV), (V) or (VI) as described in International Patent Publication No. WO2013063468. In another aspect, the amino acid, peptide, polypeptide, lipids (APPL) are useful in delivering the polynucleotides of the disclosure to cells (see International Patent Publication No. WO2013063468).

In one embodiment, the polynucleotides comprising an mRNA encoding an OX40L polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles have a diameter from about 10 to 500 nm. In one embodiment, the lipid nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle is a limit size lipid nanoparticle described in International Patent Publication No. WO2013059922. The limit size lipid nanoparticle can comprise a lipid bilayer surrounding an aqueous core or a hydrophobic core; where the lipid bilayer can comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle can comprise a polyethylene glycol-lipid such as, but not limited to, DLPE-PEG, DMPE-PEG, DPPC-PEG and DSPE-PEG.

In one embodiment, the polynucleotides comprising an mRNA encoding an OX40L polypeptide is delivered, localized and/or concentrated in a specific location using the delivery methods described in International Patent Publication No. WO2013063530. As a non-limiting example, a subject can be administered an empty polymeric particle prior to, simultaneously with or after delivering the polynucleotides to the subject. The empty polymeric particle undergoes a change in volume once in contact with the subject and becomes lodged, embedded, immobilized or entrapped at a specific location in the subject.

In one embodiment, the polynucleotides comprising an mRNA encoding an OX40L polypeptide are formulated in an active substance release system (See e.g., US Patent Publication No. US20130102545). The active substance release system can comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In one embodiment, the polynucleotides comprising an mRNA encoding an OX40L polypeptide are formulated in a nanoparticle comprising an inner core comprising a non-cellular material and an outer surface comprising a cellular membrane. The cellular membrane can be derived from a cell or a membrane derived from a virus. As a non-limiting example, the nanoparticle is made by the methods described in International Patent Publication No. WO2013052167. As another non-limiting example, the nanoparticle described in International Patent Publication No. WO2013052167, is used to deliver the polynucleotides described herein.

In one embodiment, the polynucleotides comprising an mRNA encoding an OX40L polypeptide are formulated in porous nanoparticle-supported lipid bilayers (protocells). Protocells are described in International Patent Publication No. WO2013056132.

In one embodiment, the polynucleotides comprising an mRNA encoding an OX40L polypeptide described herein are formulated in polymeric nanoparticles as described in or made by the methods described in U.S. Pat. Nos. 8,420,123 and 8,518,963 and European Patent No. EP2073848B1. As a non-limiting example, the polymeric nanoparticle has a high glass transition temperature such as the nanoparticles described in or nanoparticles made by the methods described in U.S. Pat. No. 8,518,963. As another non-limiting example, the polymer nanoparticle for oral and parenteral formulations is made by the methods described in European Patent No. EP2073848B1.

In another embodiment, the polynucleotides comprising an mRNA encoding an OX40L polypeptide described herein are formulated in nanoparticles used in imaging. The nanoparticles can be liposome nanoparticles such as those described in US Patent Publication No US20130129636. As a non-limiting example, the liposome can comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., US Patent Publication No US20130129636).

In one embodiment, the nanoparticles which can be used in the present disclosure are formed by the methods described in U.S. Patent Application No. US20130130348.

The nanoparticles of the present disclosure can further include nutrients such as, but not limited to, those which deficiencies can lead to health hazards from anemia to neural tube defects (see e.g., the nanoparticles described in International Patent Publication No WO2013072929). As a non-limiting example, the nutrient is iron in the form of ferrous, ferric salts or elemental iron, iodine, folic acid, vitamins or micronutrients.

In one embodiment, the polynucleotides comprising an mRNA encoding an OX40L polypeptide are formulated in a swellable nanoparticle. The swellable nanoparticle can be, but is not limited to, those described in U.S. Pat. No. 8,440,231. As a non-limiting embodiment, the swellable nanoparticle is used for delivery of the polynucleotides of the present disclosure to the pulmonary system (see e.g., U.S. Pat. No. 8,440,231).

The polynucleotides comprising an mRNA encoding an OX40L polypeptide are formulated in polyanhydride nanoparticles such as, but not limited to, those described in U.S. Pat. No. 8,449,916.

The nanoparticles and microparticles of the present disclosure can be geometrically engineered to modulate macrophage and/or the immune response. In one aspect, the geometrically engineered particles can have varied shapes, sizes and/or surface charges in order to incorporated the polynucleotides of the present disclosure for targeted delivery such as, but not limited to, pulmonary delivery (see e.g., International Publication No WO2013082111). Other physical features the geometrically engineering particles can have include, but are not limited to, fenestrations, angled arms, asymmetry and surface roughness, charge which can alter the interactions with cells and tissues. As a non-limiting example, nanoparticles of the present disclosure are made by the methods described in International Publication No WO2013082111.

In one embodiment, the nanoparticles of the present disclosure are water soluble nanoparticles such as, but not limited to, those described in International Publication No. WO2013090601. The nanoparticles can be inorganic nanoparticles which have a compact and zwitterionic ligand in order to exhibit good water solubility. The nanoparticles can also have small hydrodynamic diameters (HD), stability with respect to time, pH, and salinity and a low level of non-specific protein binding.

In one embodiment the nanoparticles of the present disclosure are developed by the methods described in US Patent Publication No. US20130172406.

In one embodiment, the nanoparticles of the present disclosure are stealth nanoparticles or target-specific stealth nanoparticles such as, but not limited to, those described in US Patent Publication No. US20130172406. The nanoparticles of the present disclosure can be made by the methods described in US Patent Publication No. US20130172406.

In another embodiment, the stealth or target-specific stealth nanoparticles comprise a polymeric matrix. The polymeric matrix can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle is a nanoparticle-nucleic acid hybrid structure having a high density nucleic acid layer. As a non-limiting example, the nanoparticle-nucleic acid hybrid structure is made by the methods described in US Patent Publication No. US20130171646. The nanoparticle can comprise a nucleic acid such as, but not limited to, polynucleotides described herein and/or known in the art.

At least one of the nanoparticles of the present disclosure can be embedded in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523.

Hyaluronidase

The intramuscular, intratumoral, or subcutaneous localized injection of polynucleotides comprising an mRNA encoding an OX40L polypeptide can include hyaluronidase, which catalyzes the hydrolysis of hyaluronan. By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440). It is useful to speed their dispersion and systemic distribution of encoded proteins produced by transfected cells. Alternatively, the hyaluronidase can be used to increase the number of cells exposed to a polynucleotide of the disclosure administered intramuscularly, intratumorally, or subcutaneously.

Nanoparticle Mimics

The polynucleotides comprising an mRNA encoding an OX40L polypeptide can be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the polynucleotides of the disclosure can be encapsulated in a non-virion particle which can mimic the delivery function of a virus (see International Pub. No. WO2012006376 and US Patent Publication No. US20130171241 and US20130195968).

Nanotubes

The polynucleotides comprising an mRNA encoding an OX40L polypeptide can be attached or otherwise bound to at least one nanotube such as, but not limited to, rosette nanotubes, rosette nanotubes having twin bases with a linker, carbon nanotubes and/or single-walled carbon nanotubes, The polynucleotides can be bound to the nanotubes through forces such as, but not limited to, steric, ionic, covalent and/or other forces. Nanotubes and nanotube formulations comprising polynucleotides are described in International Patent Application No. PCT/US2014/027077.

Self-Assembled Nanoparticles

The polynucleotides comprising an mRNA encoding an OX40L polypeptide can be formulated in self-assembled nanoparticles. Nucleic acid self-assembled nanoparticles are described in International Patent Application No. PCT/US2014/027077, such as in paragraphs [000740]-[000743]. Polymer-based self-assembled nanoparticles are described in International Patent Application No. PCT/US2014/027077.

Self-Assembled Macromolecules

The polynucleotides comprising an mRNA encoding an OX40L polypeptide can be formulated in amphiphilic macromolecules (AMs) for delivery. AMs comprise biocompatible amphiphilic polymers which have an alkylated sugar backbone covalently linked to poly(ethylene glycol). In aqueous solution, the AMs self-assemble to form micelles. Non-limiting examples of methods of forming AMs and AMs are described in US Patent Publication No. US20130217753.

Inorganic Nanoparticles

The polynucleotides comprising an mRNA encoding an OX40L polypeptide can be formulated in inorganic nanoparticles (U.S. Pat. No. 8,257,745). The inorganic nanoparticles can include, but are not limited to, clay substances that are water swellable. As a non-limiting example, the inorganic nanoparticle include synthetic smectite clays which are made from simple silicates (See e.g., U.S. Pat. Nos. 5,585,108 and 8,257,745).

In some embodiments, the inorganic nanoparticles comprise a core of the polynucleotides disclosed herein and a polymer shell. The polymer shell can be any of the polymers described herein and are known in the art. In an additional embodiment, the polymer shell can be used to protect the polynucleotides in the core.

Semi-Conductive and Metallic Nanoparticles

The polynucleotides comprising an mRNA encoding an OX40L polypeptide can be formulated in water-dispersible nanoparticle comprising a semiconductive or metallic material (U.S. Pub. No. 20120228565) or formed in a magnetic nanoparticle (U.S. Pub. No. 20120265001 and 20120283503). The water-dispersible nanoparticles can be hydrophobic nanoparticles or hydrophilic nanoparticles.

In some embodiments, the semi-conductive and/or metallic nanoparticles can comprise a core of the polynucleotides disclosed herein and a polymer shell. The polymer shell can be any of the polymers described herein and are known in the art. In an additional embodiment, the polymer shell can be used to protect the polynucleotides in the core.

Surgical Sealants: Gels and Hydrogels

In some embodiments, the polynucleotides comprising an mRNA encoding an OX40L polypeptide are encapsulated into any hydrogel known in the art which forms a gel when injected into a subject. Surgical sealants such as gels and hydrogels are described in International Patent Application No. PCT/US2014/027077.

Suspension Formulations

In some embodiments, suspension formulations are provided comprising polynucleotides, water immiscible oil depots, surfactants and/or co-surfactants and/or co-solvents. Combinations of oils and surfactants can enable suspension formulation with polynucleotides. Delivery of polynucleotides in a water immiscible depot can be used to improve bioavailability through sustained release of mRNA from the depot to the surrounding physiologic environment and prevent polynucleotides degradation by nucleases.

In some embodiments, suspension formulations of mRNA are prepared using combinations of polynucleotides, oil-based solutions and surfactants. Such formulations can be prepared as a two-part system comprising an aqueous phase comprising polynucleotides and an oil-based phase comprising oil and surfactants. Exemplary oils for suspension formulations can include, but are not limited to sesame oil and Miglyol (comprising esters of saturated coconut and palm-kernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, CAPMUL®, labrasol, isopropyl myristate, and/or Span 80. In some embodiments, suspensions can comprise co-solvents including, but not limited to, ethanol, glycerol and/or propylene glycol.

Suspensions can be formed by first preparing polynucleotides formulation comprising an aqueous solution of polynucleotide and an oil-based phase comprising one or more surfactants. Suspension formation occurs as a result of mixing the two phases (aqueous and oil-based). In some embodiments, such a suspension can be delivered to an aqueous phase to form an oil-in-water emulsion. In some embodiments, delivery of a suspension to an aqueous phase results in the formation of an oil-in-water emulsion in which the oil-based phase comprising polynucleotides forms droplets that can range in size from nanometer-sized droplets to micrometer-sized droplets. In some embodiments, specific combinations of oils, surfactants, cosurfactants and/or co-solvents can be utilized to suspend polynucleotides in the oil phase and/or to form oil-in-water emulsions upon delivery into an aqueous environment.

In some embodiments, suspensions provide modulation of the release of polynucleotides into the surrounding environment. In such embodiments, polynucleotides release can be modulated by diffusion from a water immiscible depot followed by resolubilization into a surrounding environment (e.g. an aqueous environment).

In some embodiments, polynucleotides within a water immiscible depot (e.g. suspended within an oil phase) result in altered polynucleotides stability (e.g. altered degradation by nucleases).

In some embodiments, the polynucleotides comprising an mRNA encoding an OX40L polypeptide are formulated such that upon injection, an emulsion forms spontaneously (e.g. when delivered to an aqueous phase). Such particle formation can provide a high surface area to volume ratio for release of polynucleotides from an oil phase to an aqueous phase.

In some embodiments, the polynucleotides comprising an mRNA encoding an OX40L polypeptide are formulated in a nanoemulsion such as, but not limited to, the nanoemulsions described in U.S. Pat. No. 8,496,945. The nanoemulsions can comprise nanoparticles described herein. As a non-limiting example, the nanoparticles can comprise a liquid hydrophobic core which can be surrounded or coated with a lipid or surfactant layer. The lipid or surfactant layer can comprise at least one membrane-integrating peptide and can also comprise a targeting ligand (see e.g., U.S. Pat. No. 8,496,945).

Cations and Anions

Formulations of polynucleotides comprising an mRNA encoding an OX40L polypeptide can include cations or anions. In some embodiments, the formulations include metal cations such as, but not limited to, Zn2+, Ca2+, Cu2+, Mg+ and combinations thereof. As a non-limiting example, formulations include polymers and a polynucleotides complexed with a metal cation (See e.g., U.S. Pat. Nos. 6,265,389 and 6,555,525).

In some embodiments, cationic nanoparticles comprising combinations of divalent and monovalent cations are formulated with polynucleotides. Such nanoparticles can form spontaneously in solution over a given period (e.g. hours, days, etc). Such nanoparticles do not form in the presence of divalent cations alone or in the presence of monovalent cations alone. The delivery of polynucleotides in cationic nanoparticles or in one or more depot comprising cationic nanoparticles can improve polynucleotide bioavailability by acting as a long-acting depot and/or reducing the rate of degradation by nucleases.

Molded Nanoparticles and Microparticles

The polynucleotides comprising an mRNA encoding an OX40L polypeptide can be formulated in nanoparticles and/or microparticles. As an example, the nanoparticles and/or microparticles can be made using the PRINT® technology by LIQUIDA TECHNOLOGIES® (Morrisville, N.C.) (See, e.g., International Pub. No. WO2007024323).

In some embodiments, the nanoparticles comprise a core of the polynucleotides disclosed herein and a polymer shell. The polymer shell can be any of the polymers described herein and are known in the art. In an additional embodiment, the polymer shell can be used to protect the polynucleotides in the core.

In some embodiments, the polynucleotides comprising an mRNA encoding an OX40L polypeptide are formulated in microparticles. The microparticles can contain a core of the polynucleotides and a cortex of a biocompatible and/or biodegradable polymer. As a non-limiting example, the microparticles which can be used with the present disclosure can be those described in U.S. Pat. No. 8,460,709, U.S. Patent Publication No. US20130129830 and International Patent Publication No WO2013075068. As another non-limiting example, the microparticles can be designed to extend the release of the polynucleotides of the present disclosure over a desired period of time (see e.g, extended release of a therapeutic protein in U.S. Patent Publication No. US20130129830).

NanoJackets and NanoLiposomes

The polynucleotides comprising an mRNA encoding an OX40L polypeptide can be formulated in NanoJackets and NanoLiposomes by Keystone Nano (State College, Pa.). NanoJackets are made of compounds that are naturally found in the body including calcium, phosphate and can also include a small amount of silicates. Nanojackets can range in size from 5 to 50 nm and can be used to deliver hydrophilic and hydrophobic compounds such as, but not limited to, polynucleotides.

NanoLiposomes are made of lipids such as, but not limited to, lipids which naturally occur in the body. NanoLiposomes can range in size from 60-80 nm and can be used to deliver hydrophilic and hydrophobic compounds such as, but not limited to, polynucleotides. In one aspect, the polynucleotides comprising an mRNA encoding an OX40L polypeptide are formulated in a NanoLiposome such as, but not limited to, Ceramide NanoLiposomes.

Minicells

In one aspect, the polynucleotides comprising an mRNA encoding an OX40L polypeptide can be formulated in bacterial minicells. As a non-limiting example, bacterial minicells are those described in International Publication No. WO2013088250 or US Patent Publication No. US20130177499. The bacterial minicells comprising therapeutic agents such as polynucleotides described herein can be used to deliver the therapeutic agents to brain tumors.

Semi-Solid Compositions

In some embodiments, the polynucleotides comprising an mRNA encoding an OX40L polypeptide are formulated with a hydrophobic matrix to form a semi-solid composition. As a non-limiting example, the semi-solid composition or paste-like composition is made by the methods described in International Patent Publication No WO201307604. The semi-solid composition can be a sustained release formulation as described in International Patent Publication No WO201307604.

In another embodiment, the semi-solid composition further has a micro-porous membrane or a biodegradable polymer formed around the composition (see e.g., International Patent Publication No WO201307604).

The semi-solid composition using the polynucleotides comprising an mRNA encoding an OX40L polypeptide can have the characteristics of the semi-solid mixture as described in International Patent Publication No WO201307604 (e.g., a modulus of elasticity of at least $10^{-4}$ N·mm$^{-2}$, and/or a viscosity of at least 100 mPa·s).

Exosomes

In some embodiments, the polynucleotides comprising an mRNA encoding an OX40L polypeptide are formulated in exosomes. The exosomes can be loaded with at least one polynucleotide and delivered to cells, tissues and/or organisms. As a non-limiting example, the polynucleotides comprising an mRNA encoding an OX40L polypeptide can be loaded in the exosomes described in International Publication No. WO2013084000.

Silk-Based Delivery

In some embodiments, the polynucleotides comprising an mRNA encoding an OX40L polypeptide are formulated in a sustained release silk-based delivery system. The silk-based delivery system can be formed by contacting a silk fibroin solution with a therapeutic agent such as, but not limited to, the polynucleotides comprising an mRNA encoding an OX40L polypeptide. As a non-limiting example, the sustained release silk-based delivery system which can be used in the present disclosure and methods of making such system are described in US Patent Publication No. US20130177611.

Microparticles

In some embodiments, formulations comprising polynucleotides comprising an mRNA encoding an OX40L polypeptide comprise microparticles. The microparticles can comprise a polymer described herein and/or known in the art such as, but not limited to, poly(α-hydroxy acid), a polyhydroxy butyric acid, a polycaprolactone, a polyorthoester and a polyanhydride. The microparticle can have adsorbent surfaces to adsorb biologically active molecules such as polynucleotides. As a non-limiting example microparticles for use with the present disclosure and methods of making microparticles are described in US Patent Publication No. US2013195923 and US20130195898 and U.S. Pat. Nos. 8,309,139 and 8,206,749.

In another embodiment, the formulation is a microemulsion comprising microparticles and polynucleotides. As a non-limiting example, microemulsions comprising microparticles are described in US Patent Publication No. US2013195923 and US20130195898 and U.S. Pat. Nos. 8,309,139 and 8,206,749.

Amino Acid Lipids

In some embodiments, the polynucleotides comprising an mRNA encoding an OX40L polypeptide are formulated in amino acid lipids. Amino acid lipids are lipophilic compounds comprising an amino acid residue and one or more lipophilic tails. Non-limiting examples of amino acid lipids and methods of making amino acid lipids are described in U.S. Pat. No. 8,501,824.

In some embodiments, the amino acid lipids have a hydrophilic portion and a lipophilic portion. The hydrophilic portion can be an amino acid residue and a lipophilic portion can comprise at least one lipophilic tail.

In some embodiments, the amino acid lipid formulations are used to deliver the polynucleotides to a subject.

In another embodiment, the amino acid lipid formulations deliver a polynucleotide in releasable form which comprises an amino acid lipid that binds and releases the polynucleotides. As a non-limiting example, the release of the polynucleotides can be provided by an acid-labile linker such as, but not limited to, those described in U.S. Pat. Nos. 7,098,032, 6,897,196, 6,426,086, 7,138,382, 5,563,250, and 5,505,931.

Microvesicles

In some embodiments, the polynucleotides comprising an mRNA encoding an OX40L polypeptide are formulated in microvesicles. Non-limiting examples of microvesicles include those described in US Patent Publication No. US20130209544.

In some embodiments, the microvesicle is an ARRDC1-mediated microvesicles (ARMMs). Non-limiting examples of ARMMs and methods of making ARMMs are described in International Patent Publication No. WO2013119602.

Interpolyelectrolyte Complexes

In some embodiments, the polynucleotides comprising an mRNA encoding an OX40L polypeptide are formulated in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368.

Cyrstalline Polymeric Systems

In some embodiments, the polynucleotides comprising an mRNA encoding an OX40L polypeptide are formulated in crystalline polymeric systems. Crystalline polymeric systems are polymers with crystalline moieties and/or terminal units comprising crystalline moieties. Non-limiting examples of polymers with crystalline moieties and/or terminal units comprising crystalline moieties termed "CYC polymers," crystalline polymer systems and methods of making such polymers and systems are described in U.S. Pat. No. 8,524,259.

Excipients

Pharmaceutical formulations can additionally comprise a pharmaceutically acceptable excipient, which, as used herein, includes, but are not limited to, any and all solvents, dispersion media, diluents, or other liquid vehicles, dispersion or suspension aids, surface active agents, isotonic agents, thickening or emulsifying agents, preservatives, solid binders, lubricants, flavoring agents, stabilizers, antioxidants, osmolality adjusting agents, pH adjusting agents and the like, as suited to the particular dosage form desired. Various excipients for formulating pharmaceutical compositions and techniques for preparing the composition are known in the art (see *Remington: The Science and Practice of Pharmacy*, 21$^{st}$ Edition, A. R. Gennaro (Lippincott, Williams & Wilkins, Baltimore, Md., 2006). The use of a conventional excipient medium can be contemplated within the scope of the present disclosure, except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use for humans and for veterinary use. In some embodiments, an excipient can be approved by United States Food and Drug Administration. In some embodiments, an excipient can be of pharmaceutical grade. In some embodiments, an excipient can meet the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients can optionally be included in pharmaceutical compositions. The composition can also include excipients such as cocoa butter and suppository waxes, coloring agents, coating agents, sweetening, flavoring, and/or perfuming agents.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC® F. 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); amino acids (e.g., glycine); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives can include, but are not limited to, antioxidants, chelating agents, antimicrobial preservatives, antifungal preservatives, alcohol preservatives, acidic preservatives, and/or other preservatives. Oxidation is a potential degradation pathway for mRNA, especially for liquid mRNA formulations. In order to prevent oxidation, antioxidants can be added to the formulation. Exemplary antioxidants include, but are not limited to, alpha tocopherol, ascorbic acid, acorbyl palmitate, benzyl alcohol, butylated hydroxyanisole, EDTA, m-cresol, methionine, butylated hydroxytoluene, monothioglycerol, potassium metabisulfite, propionic acid, propyl gallate, sodium ascorbate, sodium bisulfite, sodium metabisulfite, thioglycerol and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

In some embodiments, the pH of polynucleotide solutions is maintained between pH 5 and pH 8 to improve stability. Exemplary buffers to control pH can include, but are not limited to sodium phosphate, sodium citrate, sodium succinate, histidine (or histidine-HCl), sodium carbonate, and/or sodium malate. In another embodiment, the exemplary buffers listed above can be used with additional monovalent counterions (including, but not limited to potassium). Divalent cations can also be used as buffer counterions; however, these are not preferred due to complex formation and/or mRNA degradation.

Exemplary buffering agents can also include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Exemplary additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Cryoprotectants for mRNA

In some embodiments, the polynucleotide formulations comprise cyroprotectants. As used herein, the term "cryoprotectant" refers to one or more agent that when combined with a given substance, helps to reduce or eliminate damage to that substance that occurs upon freezing. In some embodiments, cryoprotectants are combined with polynucleotides in order to stabilize them during freezing. Frozen storage of mRNA between −20° C. and −80° C. can be advantageous for long term (e.g. 36 months) stability of polynucleotide. In some embodiments, cryoprotectants are included in polynucleotide formulations to stabilize polynucleotide through freeze/thaw cycles and under frozen storage conditions. Cryoprotectants of the present disclosure can include, but are not limited to sucrose, trehalose, lactose, glycerol, dextrose, raffinose and/or mannitol. Trehalose is listed by the Food and Drug Administration as being generally regarded as safe (GRAS) and is commonly used in commercial pharmaceutical formulations.

Bulking Agents

In some embodiments, the polynucleotide formulations comprise bulking agents. As used herein, the term "bulking agent" refers to one or more agents included in formulations to impart a desired consistency to the formulation and/or stabilization of formulation components. In some embodiments, bulking agents are included in lyophilized polynucleotide formulations to yield a "pharmaceutically elegant" cake, stabilizing the lyophilized polynucleotides during long term (e.g. 36 month) storage. Bulking agents of the present disclosure can include, but are not limited to sucrose, trehalose, mannitol, glycine, lactose and/or raffinose. In some embodiments, combinations of cryoprotectants and bulking agents (for example, sucrose/glycine or trehalose/mannitol) can be included to both stabilize polynucleotides during freezing and provide a bulking agent for lyophilization.

Non-limiting examples of formulations and methods for formulating the polynucleotides of the present disclosure are also provided in International Publication No WO2013090648 filed Dec. 14, 2012.

Naked Delivery

The polynucleotides comprising an mRNA encoding an OX40L polypeptide can be delivered to a cell (e.g., to a tumor cell) naked. As used herein in, "naked" refers to delivering polynucleotides free from agents which promote transfection. For example, the polynucleotides delivered to the cell, e.g., tumor cell, can contain no modifications. The naked polynucleotides comprising an mRNA encoding an OX40L polypeptide can be delivered to the tumor cell using routes of administration known in the art, e.g., intratumoral administration, and described herein.

Parenteral and Injectable Administration

Liquid dosage forms for parenteral administration, e.g. intratumoral, include, but are not limited to, pharmaceutically acceptable emulsions, microemulsions, solutions, suspensions, syrups, and/or elixirs. In addition to active ingredients, liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

A pharmaceutical composition for parenteral administration, e.g., intratumoral administration, can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations, e.g., intratumoral, can be sterilized, for example, by filtration through a bacterial-retaining filter, and/or by incorporating sterilizing agents in the form of sterile solid compositions which can be dissolved or dispersed in sterile water or other sterile injectable medium prior to use.

Injectable formulations, e.g., intratumoral, can be for direct injection into a region of a tissue, organ and/or subject, e.g., tumor.

In order to prolong the effect of an active ingredient, it is often desirable to slow the absorption of the active ingredient from intratumoral injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide.

Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Dosage Forms

A pharmaceutical composition described herein can be formulated into a dosage form described herein, such as a topical, intranasal, intratracheal, or injectable (e.g., intravenous, intratumoral, intraocular, intravitreal, intramuscular, intracardiac, intraperitoneal, or subcutaneous).

Liquid Dosage Forms

Liquid dosage forms for parenteral administration (e.g., intratumoral) include, but are not limited to, pharmaceutically acceptable emulsions, microemulsions, solutions, suspensions, syrups, and/or elixirs. In addition to active ingredients, liquid dosage forms can comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions can be mixed with solubilizing agents such as CREMOPHOR®, alcohols, oils, modified oils, glycols, polysorbates, cyclodextrins, polymers, and/or combinations thereof.

Injectable

Injectable preparations (e.g., intratumoral), for example, sterile injectable aqueous or oleaginous suspensions can be formulated according to the known art and can include suitable dispersing agents, wetting agents, and/or suspending agents. Sterile injectable preparations can be sterile injectable solutions, suspensions, and/or emulsions in non-toxic parenterally acceptable diluents and/or solvents, for example, a solution in 1,3-butanediol. Among the acceptable vehicles and solvents that can be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it can be desirable to slow the absorption of the active ingredient from subcutaneous or intramuscular injection. This can be accomplished by the use of a liquid suspension of crystalline or amorphous material with poor water solubility. The rate of absorption of the polynucleotides then depends upon its rate of dissolution which, in turn, can depend upon crystal size and crystalline form. Alternatively, delayed absorption of a parenterally administered polynucleotides can be accomplished by dissolving or suspending the polynucleotides in an oil vehicle. Injectable depot forms are made by forming microencapsule matrices of the polynucleotides in biodegradable polymers such as polylactide-polyglycolide. Depending upon the ratio of polynucleotides to polymer and the nature of the particular polymer employed, the rate of polynucleotides release can be controlled. Examples of other biodegradable polymers include, but are not limited to, poly(orthoesters) and poly(anhydrides). Depot injectable formulations can be prepared by entrapping the polynucleotides in liposomes or microemulsions which are compatible with body tissues.

VII. Kits and Devices

Kits

The disclosure provides a variety of kits for conveniently and/or effectively carrying out methods of the present disclosure. Typically kits will comprise sufficient amounts and/or numbers of components to allow a user to perform multiple treatments of a subject(s) and/or to perform multiple experiments.

In one aspect, the present disclosure provides kits comprising the polynucleotides of the disclosure. In some embodiments, the kit comprises one or more polynucleotides.

The kits can be for protein production, comprising a polynucleotide comprising an mRNA encoding an OX40L polypeptide. The kit can further comprise packaging and instructions and/or a delivery agent to form a formulation composition. The delivery agent can comprise a saline, a buffered solution, a lipidoid or any delivery agent disclosed herein.

In some embodiments, the buffer solution includes sodium chloride, calcium chloride, phosphate and/or EDTA. In another embodiment, the buffer solution includes, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046). In a further embodiment, the buffer solution is precipitated or it is lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present disclosure provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present disclosure provides kits for protein production, comprising a polynucleotide comprising an mRNA encoding an OX40L polypeptide, wherein the polynucleotide exhibits reduced degradation by a cellular nuclease, and packaging and instructions.

Devices

The present disclosure provides for devices which can incorporate polynucleotides comprising an mRNA encoding an OX40L polypeptide. These devices contain in a stable formulation the reagents to synthesize a polynucleotide in a formulation available to be immediately delivered to a subject in need thereof, such as a human patient.

Devices for administration can be employed to deliver the polynucleotides comprising an mRNA encoding an OX40L polypeptide according to single, multi- or split-dosing regimens taught herein. Such devices are taught in, for example, International Publication No. WO 2013151666 A2.

Method and devices known in the art for multi-administration to cells, organs and tissues are contemplated for use in conjunction with the methods and compositions disclosed herein as embodiments of the present disclosure. These include, for example, those methods and devices having multiple needles, hybrid devices employing for example lumens or catheters as well as devices utilizing heat, electric current or radiation driven mechanisms.

According to the present disclosure, these multi-administration devices can be utilized to deliver the single, multi- or split doses contemplated herein. Such devices are taught for example in, International Publication No. WO 2013151666 A2.

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the disclosure (e.g., any nucleic acid or protein encoded thereby; any method of production; any method of use; etc.) can be excluded from any one or more claims, for any reason, whether or not related to the existence of prior art.

All cited sources, for example, references, patents, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. In Vitro Cell Surface Expression of an OX40L Polypeptide

Expression of an OX40L polypeptide was measured on the surface of cancer cells following treatment with a polynucleotide comprising an mRNA encoding an OX40L polypeptide.
A. Formulation of mOX40L_miR122

A polynucleotide comprising an mRNA encoding an OX40L polypeptide (murine OX40L) and further comprising a miRNA binding site (miR-122) was used in this example (mOX40L_miR122; SEQ ID NO: 66). The OX40L modified mRNA was formulated in lipid nanoparticles (LNP) as described herein. (Moderna Therapeutics, Cambridge, Mass.).
B. Analysis of OX40L Cell-Surface Expression Mouse melanoma cells (B16F10, ATCC No. CRL-6475; ATCC, Manassas, Va.) were seeded in 12-well plates at a density of 140,000 cells per well. Increasing doses of mOX40L_miR122 (SEQ ID NO: 66) formulated in LNPs were added to each well directly after seeding the cells. Doses of mOX40L_miR122 included 6.3 ng, 12.5 ng, 25 ng, or 50 ng mRNA per well. Control cells were either mock-treated or treated with negative control mRNA (non-translatable version of the same mRNA containing multiple stop codons).

Figure 1:
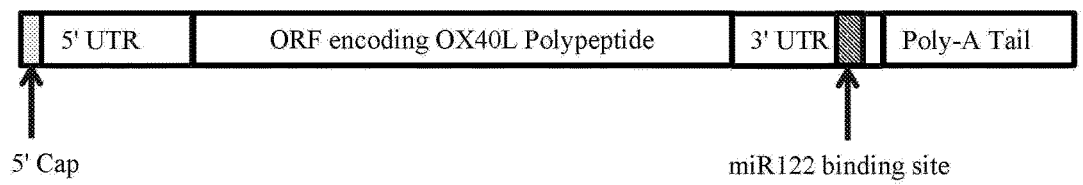
Figure 2:
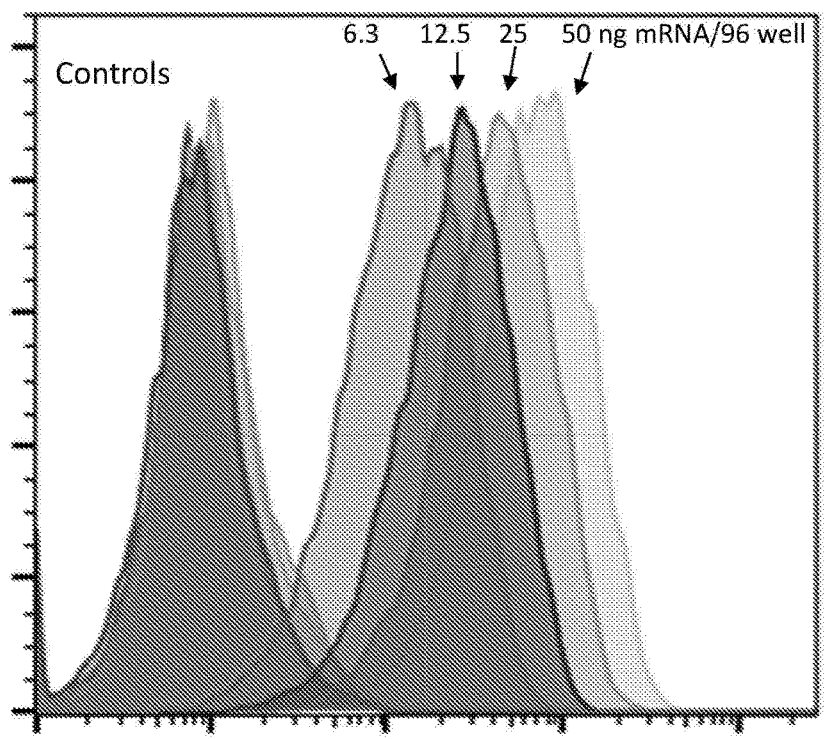

Following treatment, cell surface expression of OX40L was detected using flow cytometry. Cells were harvested by transferring the supernatants to a 96-well Pro-Bind U-bottom plate (Beckton Dickinson GmbH, Heidelberg, Germany). Cells from each well were then lifted with trypsin-free chelating solution, and stained with PE-conjugated anti-mouse OX40L antibody (R&D Systems, Minneapolis, Minn.) and visualized by flow cytometry. The results are shown in FIG. 2.
C. Results FIG. 2 shows a dose-dependent expression of OX40L on the surface of B16F10 cancer cells after treatment with OX40L modified mRNA. All four doses of mOX40L_miR122 generated significant OX40L expression on the cell surface compared to control samples.

These results show that administering an OX40L modified mRNA results in expression of an OX40L polypeptide on the surface of target cells.

Example 2: In Vitro Expression Kinetics of OX40L on Cell Surface

In this example, expression levels of an OX40L polypeptide on the surface of cancer cells were measured over time. Quantitation of OX40L protein expression was also measured.
A. Formulation of mOX40L_miR122

A polynucleotide comprising an mRNA encoding an OX40L polypeptide (murine OX40L or human OX40L) and further comprising a miRNA binding site (miR-122) was used in this example (mOX40L_miR122, SEQ ID NO: 66; hOX40L_miR122, SEQ ID NO: 65). The OX40L modified mRNA was formulated in either lipid nanoparticles (LNP) as described above in Example 1 or formulated in LIPOFECTAMINE 2000 (L2K) (ThermoFisher Scientific, Waltham, Mass.) according to the manufacturer's instructions.
B. Cell Lines Human cervical carcinoma cells (HeLa, ATCC No. CCL-2; ATCC, Manassas, Va.) were seeded at a density of 250,000 cells per well in 6-well plates. 24-hours post-seeding, L2K-formulated mOX40L_miR122 or hOX40L_miR122 containing 3 μg of mRNA was added to each well. The cells were treated with mOX40L_miR122 or hOX40L_miR122 in the presence or absence of 50 μg/ml mitomycin C 24 hours post-transfection.

Mouse colon adenocarcinoma cells (MC-38; Rosenberg et al., *Science* 233(4770):1318-21 (1986)) were seeded at a density of 300,000 cells per well in 6-well plates. LNP-formulated mOX40L_miR122 containing 3 μg of mRNA was added to each well 24 hours after seeding the cells. The MC-38 cells were treated with mOX40L_miR122 in the presence or absence of 25 μg/ml mitomycin C.

Figure 3F:
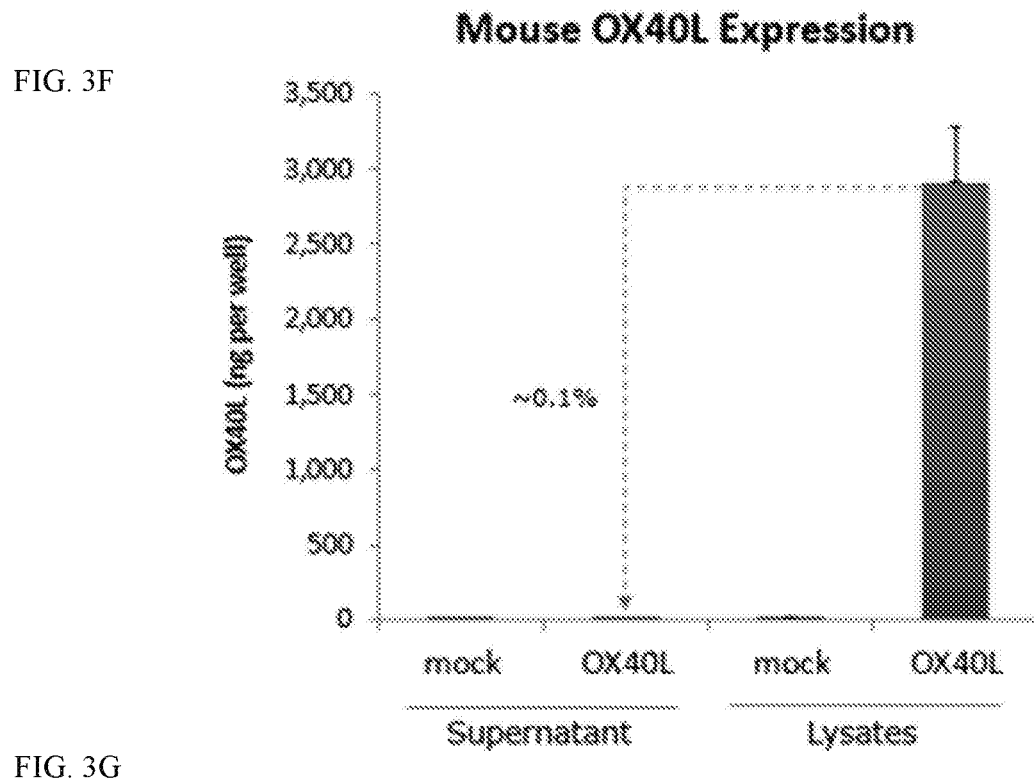
Figure 3G:
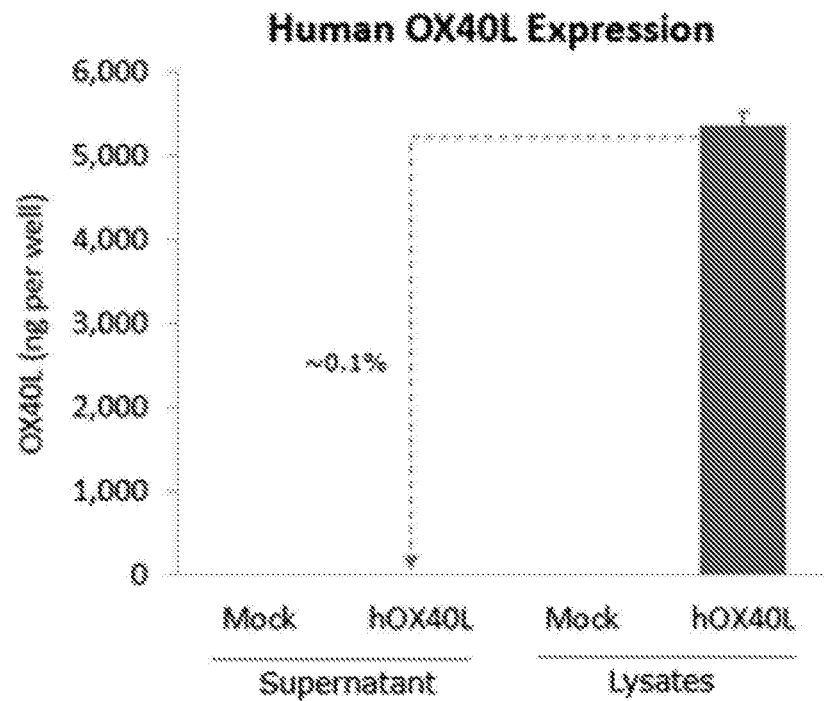

Control cells were mock-treated. Cell surface expression of OX40L was measured on Days 1, 2, 3, 5, and 7 following treatment with mOX40L_miR122 and Days 1, 2, 3, 4, and 5 following treatment with hOX40L_miR122. Cells were harvested and analyzed by flow cytometry as described above in Example 1. The results for cells treated with mOX40L_miR122 are shown in FIG. 3A-3D; the results for cells treated with hOX40L_miR122 are shown in FIG. 3E. Cell lysates and cell culture supernatants were also harvested and analyzed for OX40L protein expression (quantitated in nanograms per well). The results for mouse and human OX40L protein quantitation following treatments are shown in FIGS. 3F and 3G, respectively.

C. Results

FIG. 3A-3D shows that OX40L was detected on the surface of HeLa cells out to at least Day 7 after treatment with mOX40L_miR122. FIG. 3A-3D also shows that cell surface expression of OX40L on MC-38 cells treated with mOX40L_miR122 returned to baseline by Day 5 after treatment. In both cell lines, the gradual reduction in cell surface expression levels of OX40L over time was blocked by the presence of mitomycin C. FIG. 3E shows that human OX40L expression was detected on the surface of HeLa cells out to at least Day 5 after treatment with hOX40L_miR122.

No significant shedding of the OX40L polypeptide was detected in culture supernatants. This suggests that the OX40L expressed from mRNA was not actively shed from the cell surface, which was confirmed in FIGS. 3F and 3G. Twenty-four hours after treatment with mOX40L_miR122, hOX40L_miR122, or mock treatment, cell lysates were prepared using standard cell lysis buffers and methods for protein analysis. FIG. 3F and FIG. 3G show that both mOX40L_miR122 (FIG. 3F) and hOX40L_miR122 (FIG. 3G) produced proteins that were recognized by commercially available ELISAs. The majority of the expressed protein was associated with the cell lysate, with only approximately 0.1% of the produced protein detected in the supernatant of transfected cells.

These results show that treatment of cells with an OX40L modified mRNA results in expression of an OX40L polypeptide on the surface of target cells. These results also show that only minor amounts of protein are shed from transfected cells.

Example 3. In Vitro Biological Activity of OX40L

T-cell activation involves two concurrent cell signaling events: a primary signal from the T-cell receptor complex (e.g., CD3 stimulation) and a second signal from a costimulatory ligand-receptor interaction (e.g., OX40L/OX40R interaction). Kober et al., European Journal of Immunology 38:2678-2688 (2008). In this example, the costimulatory biological activity of OX40L expressed on the surface of cells treated with mOX40L_miR122 or hOX40L_miR122 was assessed.

A. Preparation of OX40L-Expressing Cells

Mouse melanoma cells (B16F10, ATCC No. CRL-6475; ATCC, Manassas, Va.) were seeded in 6-well plates at a density of 300,000 cells per well. Human cervical carcinoma cells (HeLa) were seeded in 6-well plates as described above. A polynucleotide comprising an mRNA encoding an OX40L polypeptide and further comprising a miR-122 binding site (mouse OX40L, mOX40L_miR122, SEQ ID NO: 66; human OX40L, hOX40L_miR122, SEQ ID NO: 65) was formulated in L2K as described above in Example 2. 24 hours after seeding the cells, formulations containing 3 µg of mOX40L_miR122 or hOX40L_miR122 mRNA were added to each well. Control cells were either mock-treated or treated with negative control mRNA (non-translatable version of the same mRNA except with no initiating codons). The cells were incubated for 24 hours at 37° C.

B. Preparation of Naïve CD4+ T-Cells

Spleens from C57BL/6 mice were removed and processed using standard techniques in the art to generate single cell suspensions of splenocytes. Total CD4+ T-cells were isolated from the splenocyte suspensions using a mouse CD4 T cell isolation kit (Miltenyi, San Diego, Calif.). Naïve human CD4+ T-cells were isolated from human peripheral blood mononuclear cells (PBMCs) by depleting non-CD4 cells using a commercially available magnetic bead T cell isolation kit.

Figure 4A:
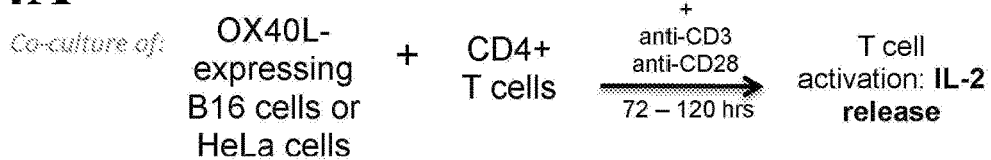
FIG. 4D shows the data from FIG. 4C with schematic diagram showing the addition of OX40L expressing cells to the naïve T-cell activation assay.
FIG. 4E shows a T-cell activation assay using pre-stimulated T-cells cultured in the presence or absence of OX40L expressing HeLa cells and in the presence or absence of anti-human CD3 antibody.

C. T-Cell Activation Assay 200,000 T-cells were added to each well of transfected B16F10 cells or HeLa cells in the presence of agonistic anti-mouse CD3 antibody (R&D Systems, Minneapolis, Minn.) or agonistic anti-human CD3 antibody and soluble anti-human CD28; and the cells were co-cultured for 72 hours (mouse) or 120 hours (human). A schematic of the assays is shown in FIG. 4A.

Figure 4B:
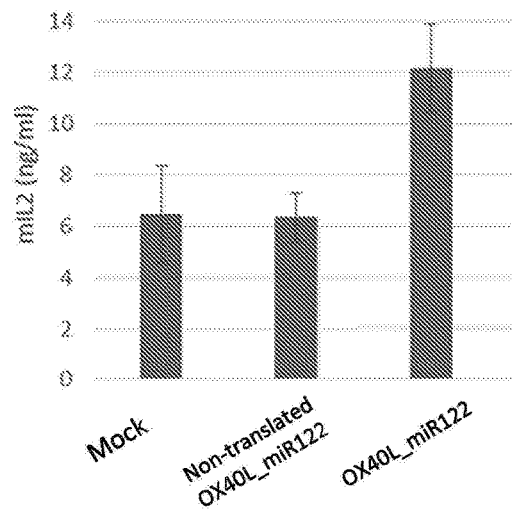

After co-culture with T-cells, mouse IL-2 production was measured using a mouse IL-2 ELISA. (mouse IL-2 DuoSet ELISA, R&D Systems, Minneapolis, Minn.). The amount of IL-2 produced by the CD4+ T-cells serves as an indicator of T-cell activation. Results are shown in FIG. 4B. Human IL-2 production was measured using a human IL-2 ELISA (human IL-2 DuoSet ELISA, R&D Systems, Minneapolis, Minn.). Results are shown in FIGS. 4C, 4D, and 4E.

D. Results

FIG. 4B shows that OX40L expression on the surface of B16F10 cells treated with mOX40L_miR122 elicits a T-cell IL-2 response in vitro. The mOX40L_miR122 mRNA induced about 12 ng/ml of IL2. B16F10 cells treated with non-translated negative control mRNA showed baseline levels of T-cell activation comparable to mock-treated cells (i.e., about 6 ng/ml of IL2). Therefore, the mOX40L_miR122 mRNA induced about two fold higher IL2 expression compared to a control (mock treated or non-translated mRNA).

Figure 4C:
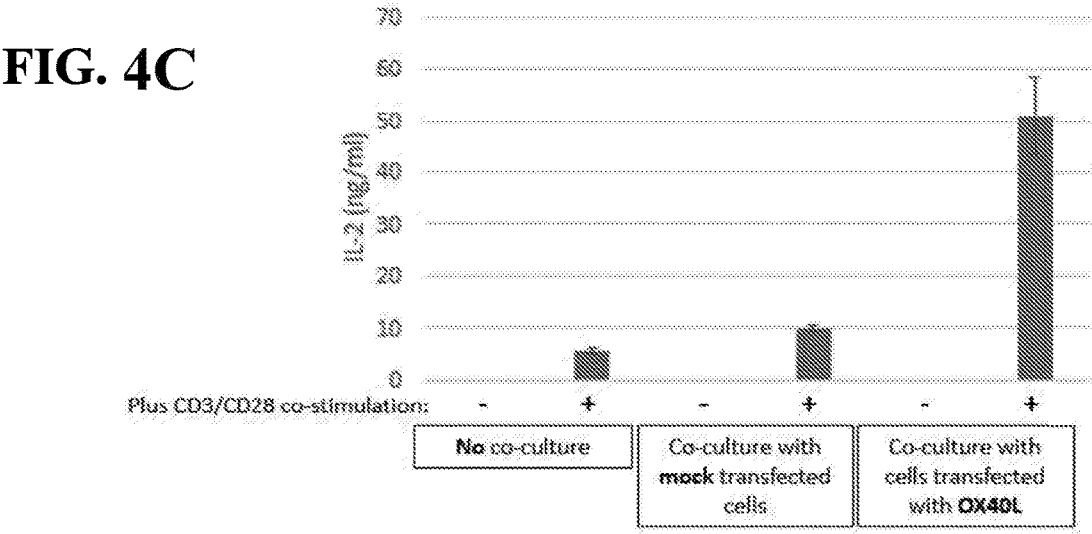
Figure 4D:
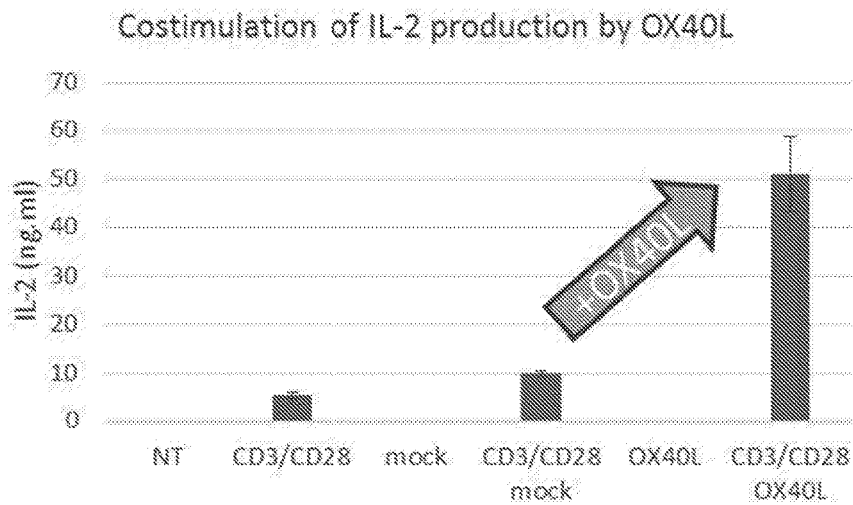
Figure 4E:
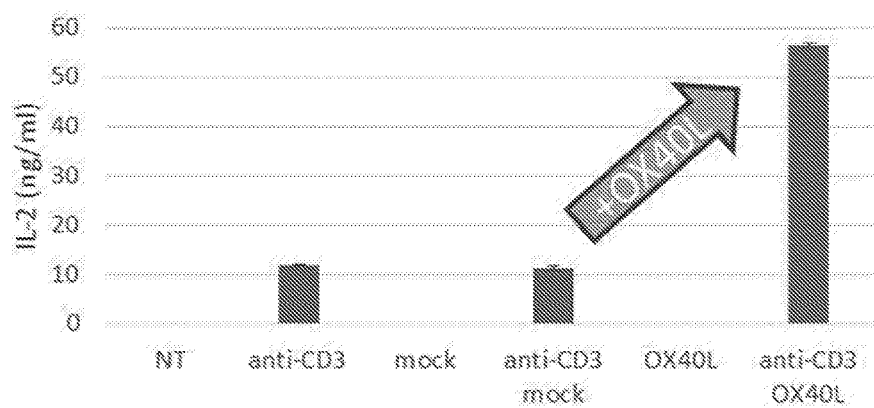

FIGS. 4C and 4D show that, in the presence of plate-coated anti-human CD3 antibody and soluble anti-human CD28 as the primary T-cell activators, co-culture with the OX40L_mRNA transfected HeLa cells greatly enhanced IL-2 production. Without OX40L expression, little to no IL-2 production was detected. FIG. 4E shows a similar level of increased human IL-2 production when the same experiment was performed with pre-stimulated (i.e., non-naïve) CD4+ T-cells.

These results show that the OX40L polypeptide is biologically active as a costimulatory molecule.

Example 4. In Vivo Expression Levels of Modified mRNA

To investigate in vivo expression levels of a polynucleotide comprising modified mRNA, a polynucleotide comprising an mRNA encoding luciferase and further comprising a miR-122 binding site was prepared (SEQ ID NO: 69). The luciferase modified mRNA was formulated in MC3 LNP. (US Publication no. US20100324120).

A. MC-38 Colon Adenocarcinoma Mouse Model

MC-38 colon adenocarcinoma tumors were established subcutaneously in C57BL/6 mice. (Rosenberg et al., *Science* 233(4770):1318-21 (1986)).

B. Treatment with Luciferase Modified mRNA

Once the MC-38 tumors reached approximately 200 mm$^3$, mice were treated with a single intratumoral dose of 3.125 µg, 6.25 µg, 12.5 µg, 25 µg, or 50 µg of luciferase modified mRNA (SEQ ID NO: 69; Cap1, G5 RP mRNA in 1.5% DMG MC3 LNP). Control animals were treated with intratumoral dose of PBS. 24 hours post-treatment, animals were anesthetized, injected with the luciferase substrate D-luciferin and the bioluminescence imaging (BLI) from living animals was evaluated in an IVIS imager 15 minutes later.

Signals from tumor tissue were obtained and compared with signals from liver tissue in the same animal. Results are shown in FIG. 5.

C. Results

FIG. 5 shows that the luciferase signal in tumor tissue was detected out to 48 hours post-dosing. FIG. 5 also shows that the three highest doses of modified mRNA (50 µg, 25 µg, and 12.5 µg) yielded comparable luciferase signals in tumor tissue. The 12.5 dose of modified mRNA yielded a high tumor signal with a lower liver (normal tissue) signal in the MC-38 colon carcinoma mouse model.

These results show that administration of a polynucleotide comprising a modified mRNA and a miRNA binding site preferentially targets tumor tissues over normal tissues.

Example 5. In Vivo Dose-Dependent Expression of OX40L in B16F10 Tumors

In vivo expression of OX40L was assessed in a B16F10 tumor model.

A. Preparation of OX40L modified mRNA

A polynucleotide comprising an mRNA encoding an OX40L polypeptide (murine OX40L) and further comprising a miRNA binding site (miR-122) was prepared (mOX40L_miR122; SEQ ID NO: 66). The OX40L modified mRNA was formulated in MC3 LNP as described in US20100324120. Negative control mRNA was also prepared (OX40L_NST, SEQ ID NO: 68; a non-translatable version of the same mRNA except no initiating codons).

B. Mouse Melanoma B16F10 Tumor Model

Subcutaneous B16F10 tumors were established in C57BL/6 mice. (Overwijk et al. *Current Protocols in Immunology* Ch. 20, Unit 20.1 (2001)).

Once the tumor size reached approximately 200 mm$^3$, animals were treated with a single intratumoral dose of mOX40L_miR122 (Cap1, G5 RP mRNA in 0.5 mol % DMG MC3 LNP) at a dose of 5 µg mRNA (approximately 0.25 mg/kg) or 15 µg mRNA (approximately 0.75 mg/kg). Control animals were treated with equivalent doses of negative control mRNA, OX40L_NST. Additional control animals were treated with PBS.

C. Measurement of OX40L in Tumor Tissue

Animals were sacrificed 8 hours and 24 hours after dosing. Tumor tissue was harvested and analyzed for expression of OX40L using a mouse OX40L ELISA assay (R&D Systems, Minneapolis, Minn.). Results are shown in FIG. 6 as the amount of OX40L present per gram of tumor tissue.

D. Results

FIG. 6 shows that a single intratumoral dose of 5 µg mOX40L_miR122 resulted in over 200 ng OX40L/g tumor tissue at both 8 hours and 24 hours post dosing. FIG. 6 also shows that a single intratumoral dose of 15 µg mOX40L_miR122 resulted in over 500 ng OX40L/g tumor tissue at both 8 hrs and 24 hours post-dosing.

In contrast, less than 100 ng OX40L was detectable in the liver of animals treated with the higher 15 µg dose of mOX40L_miR122.

These data show that administration of mOX40L_miR122 results in significant levels of OX40L polypeptide expression in the tumor tissue.

Example 6. In Vivo Expression of OX40L in MC-38 Tumors

In vivo expression of OX40L was assessed in a MC-38 tumor model.

A. Preparation of OX40L Modified mRNA

A polynucleotide comprising an mRNA encoding an OX40L polypeptide (murine OX40L) and further comprising a miRNA binding site (miR-122) was prepared (mOX40L_miR122; SEQ ID NO: 66). The OX40L modified mRNA was formulated in MC3 LNP as described above. A negative control mRNA was also prepared (non-translatable version of the same mRNA containing multiple stop codons; OX40L_NST; SEQ ID NO: 68).

B. MC-38 Colon Adenocarcinoma Mouse Model

MC-38 colon adenocarcinoma tumors were established subcutaneously in C57BL/6 mice. (Rosenberg et al., *Science* 233(4770):1318-21 (1986)).

Once the tumors reached a mean size of approximately 100 mm$^3$, animals were treated with a single intratumoral dose of mOX40L_miR122 (Cap1, G5 RP mRNA in 1.5 mol % DMG MC3 LNP) at a dose of 12.5 µg mRNA. Control animals were treated with an equivalent dose of negative control mRNA, OX40L_NST. Additional control animals were left untreated ("NT"). For dose-response experiments, animals were administered an intratumoral injection of 3.125, 6.25, or 12.5 µg mOX40L_miR122; control animals were left untreated or treated with 12.5 µg negative control mRNA.

C. Measurement of OX40L in Tumor Tissue

To measure OX40L expression over time, animals were sacrificed 3, 6, 24, 48, 72, and 168 hours after dosing. Tumor tissue was harvested and analyzed for expression of OX40L using ELISA (R&D Systems, Minneapolis, Minn.), as described above in Example 5. Results are shown in FIG. 7A as the amount of OX40L present per gram of tumor tissue.

To measure OX40L expression as a function of dose-response, animals were sacrificed 24 hours after dosing and tumor tissue was harvested for analysis as described above. Tumor tissue, liver tissue, and spleen tissue were analyzed for quantity of OX40L protein (FIG. 7B-7D, upper) and mRNA (FIG. 7B-7D, lower).

Tumor cells were also analyzed for expression of OX40L on the cell surface using flow cytometry (data not shown). Tumor tissue was minced and processed through cell strainers to prepare single cell suspensions. Cell suspensions were stained with PE-conjugated anti-mouse OX40L antibody (R&D Systems, Minneapolis, Minn.), and visualized by flow cytometry.

D. Results

FIG. 7A shows that a single intratumoral dose of 12.5 µg mOX40L_miR122 resulted in up to 1200 ng OX40L/g tumor tissue at 24 hours post dosing. The optical densities for two of the 24-hour OX40L-treated samples were above the standard range, resulting in underestimated values shown in FIG. 7A. FIG. 7A also shows OX40L expression was detectable in tumor tissue out to 168 hours (7 days) post dosing. In contrast, control treated animals showed no detectable OX40L in tumor tissue at any time point. FIG. 7B shows a dose-dependent increase in OX40L protein (upper) and mRNA (lower) in tumor tissue. FIGS. 7C and 7D show the presence of OX40L protein and mRNA in liver and spleen (respectively) are lower than the amounts present in the tumor tissue.

Flow cytometry results showed that approximately 6.5% of all live, tumor-associated cells were positive for OX40L expression (data not shown).

These data show that administration of mOX40L_miR122 results in significant levels of OX40L polypeptide expression in the tumor tissue.

Example 7. In Vivo Efficacy of OX40L Modified mRNA in a Colon Adenocarcinoma Model In vivo efficacy of a polynucleotide comprising an mRNA encoding an OX40L polypeptide was assessed.

A. Preparation of OX40L Modified mRNA

A polynucleotide comprising an mRNA encoding an OX40L polypeptide (murine OX40L) and further comprising a miRNA binding site (miR-122) was prepared as described above (mOX40L_miR122; SEQ ID NO: 66). A negative control mRNA was also prepared (non-translatable version of the same mRNA containing multiple stop codons; NT OX40L_miR122; SEQ ID NO: 68). Both modified mRNAs were formulated in MC3 LNP as described above.

B. MC-38 Colon Adenocarcinoma Mouse Model

MC-38 colon adenocarcinoma tumors were established subcutaneously in C57BL/6 mice as described above.

Fourteen days after tumor cell inoculation, animals were treated twice weekly for three weeks with an intratumoral dose of MC3 LNP-formulated modified mRNA (15 mRNA per dose). Control animals were treated with an equivalent dose and regimen of negative control mRNA, NT OX40L_miR122 (SEQ ID NO: 68).

Tumor volume was measured at the indicated time points using manual calipers. Tumor volume was recorded in cubic millimeters.

The in vivo efficacy study was carried out through Day 42 post-dosing. At the completion of the study, the full data sets were analyzed and presented in FIGS. 8A and 8B. Final Kaplan-Meier survival curves were prepared and are shown in FIG. 8C. Endpoints in the study were either death of the animal or a tumor volume reaching 1500 mm$^3$.

C. Results

FIG. 8A shows that administering a control modified mRNA had little effect on the tumor volume, as assessed at the study completion (Day 42 after the first dose). FIG. 8B shows that administering mOX40L_miR122 to the mice inhibited or slowed tumor growth in some animals and reduced or decreased the size of the tumor in some animals, as assessed at study completion (Day 42).

FIG. 8C shows that animals receiving mOX40L_miR122 had longer survival times as measured on Day 42 compared to control animals.

These data show that mOX40L_miR122 polynucleotides have anti-tumor efficacy when administered in vivo.

Example 8. In Vivo Expression of OX40L in A20 Tumors

Mouse models of B-cell lymphoma using the A20 cell line are useful for analyzing a tumor microenvironment. (Kim et al., Journal of Immunology 122(2):549-554 (1979); Donnou et al., Advances in Hematology 2012:701704 (2012)). Therefore, in vivo expression of OX40L and the tumor microenvironment were assessed in an A20 B-cell lymphoma tumor model.

A. Preparation of OX40L modified mRNA

A polynucleotide comprising an mRNA encoding an OX40L polypeptide (murine OX40L) and further comprising a miRNA binding site (miR-122) was prepared as described above (mOX40L_miR122; SEQ ID NO: 66). The OX40L modified mRNA was formulated in MC3 LNP as described above. A negative control mRNA was also prepared (non-translatable version of the same mRNA containing multiple stop codons; NT OX40L; SEQ ID NO: 68).

B. A20 B-Cell Lymphoma Tumor Model

B-cell lymphoma tumors were established subcutaneously in BALB/c mice. Mouse B-cell lymphoma cells (A20, ATCC No. TIB-208; ATCC, Manassas, Va.) were cultured according to the vendor's instructions. Cells were inoculated subcutaneously in BALB/c mice to generate subcutaneous tumors. Tumor was monitored for size and palpability.

Once the tumors reached a mean size of approximately 1300 mm$^3$, animals were separated into two groups. Group I was treated with a single intratumoral dose of mOX40L_miR122 (Cap1, G5 RP mRNA in 0.5 mol % DMG MC3 LNP) at a dose of 15 μg mRNA. Group II (controls) was treated with an equivalent dose of negative control mRNA, NT OX40L.

C. Measurement of OX40L in Tumor Tissue

Tumor tissue was harvested 24 hours after dosing and analyzed for expression of OX40L using ELISA (R&D Systems, Minneapolis, Minn.), as described above in Example 5. Results are shown in FIG. 9A as the amount of OX40L present per gram of tumor tissue.

A20 tumor cells were also analyzed for cell surface expression of OX40L. Tumor tissue was minced and processed through cell strainers to prepare single cell suspensions. Cells were stained with anti-mouse OX40L antibody (goat IgG polyclonal, PE conjugated; R&D Systems, Minneapolis, Minn.) and anti-mouse CD45 antibody (clone 30-F11, PE-Cy5 conjugated; eBioscience, San Diego, Calif.) to identify leukocytes (i.e., A20 cancer cells and infiltrating immune cells). The cells were subsequently analyzed by flow cytometry. Results are shown in FIGS. 9B and 9C.

D. Results

FIG. 9A shows that a single intratumoral dose of 15 μg mOX40L_miR122 resulted in up to 250 ng OX40L/g tumor tissue at 24 hours after dosing. In contrast, control treated animals showed less than 100 ng OX40L in tumor tissue 24 hours after dosing.

FIG. 9B shows that approximately 3% of all live, CD45$^+$ cells (i.e., tumor cells) expressed OX40L on the cell surface. In a similar experiment, approximately 15.8% total live cells from the tumor were found to express introduced OX40L, compared to less than 0.5% OX40L-positive live cells in tumors treated with the negative control mRNA (FIG. 9C).

These data show that administration of mOX40L_miR122 results in significant levels of OX40L polypeptide expression in the tumor tissue.

Example 9. In Vivo Pharmacodynamic Effects of OX40L

The ability of mOX40L_miR122 mediated OX40L expression to recruit natural killer (NK) cells to the tumor site was assessed.

A. A20 B-Cell Lymphoma Tumor Model

The B-cell lymphoma tumors described above in Example 8 were also assessed for NK cell infiltration following treatment. As described above, mice were treated with a single intratumoral dose of either mOX40L_miR122 or control NT OX40L_mRNA (15 dose; Cap1, G5 RP mRNA in 0.5 mol % DMG MC3 LNP). 24 hours after dosing, tumors were harvested as described above and processed through cell strainers to prepare single cell suspensions.

B. Natural Killer Cell Infiltration

Single cell suspensions were incubated with anti-mouse NKp46 antibody (clone 29A1.4, PerCP-eFluor® 710 conjugated; eBioscience, San Diego, Calif.), which is specific to the NK cell marker p46 (CD335), and anti-mouse CD3 antibody (clone 145-2C11, FITC conjugated; BioLegend, San Diego, Calif.), which is specific to T-cells. The cells were analyzed based on CD45+ expression for leukocyte, as well as NKp46 and CD3c expression using flow cytometry. NK cells are p46+ and CD3−. Results are shown in FIGS. 10A and 10B.

C. Results

FIG. 10A shows that animals treated with mOX40L_miR122 exhibited approximately 5-fold increase in the relative number of NK cells within A20 tumors 24 hours after dosing. FIG. 10B shows the individual animal data from the same study.

These results show that treatment with a polynucleotide comprising an mRNA encoding an OX40L polypeptide increased the number of NK cells within the tumor microenvironment.

Example 10. In Vivo Efficacy of OX40L Modified mRNA in a B-Cell Lymphoma Model

In vivo efficacy of mOX40L_miR122 was assessed in a B-cell lymphoma model.

A. Preparation of OX40L Modified mRNA

A polynucleotide comprising an mRNA encoding an OX40L polypeptide (murine OX40L) and further comprising a miRNA binding site (miR-122) was prepared as described above (mOX40L_miR122; SEQ ID NO: 66). A negative control mRNA was also prepared (non-translatable version of the Factor IX mRNA containing multiple stop codons; NST-FIX, SEQ ID NO: 67). Both modified mRNAs were formulated in the same manner (Cap1, G5 RP mRNA in 1.5 mol % DMG MC3 LNP).

B. A20 B-Cell Lymphoma Tumor Model

B-cell lymphoma tumors were established subcutaneously in BALB/c mice. Mouse B-cell lymphoma cells (A20, ATCC No. TIB-208; ATCC, Manassas, Va.) were cultured according to the vendor's instructions. Cells were inoculated subcutaneously in BALB/c mice to generate subcutaneous tumors. Tumor was monitored for size and palpability.

Once the tumors reached a mean size of approximately 100 mm$^3$, animals were separated into two groups. Group I was treated with repeated intratumoral doses of mOX40L_miR122 (Cap1, G5 RP mRNA in 1.5 mol % DMG MC3 LNP) at a dose of 12.5 mRNA. Group II (control) was treated with an equivalent dose of negative control mRNA, NST-FIX. Animals were dosed on Days 20, 23, 27, 30, 34, 37, 41, 44, 48, and 51. Results are shown in FIGS. 11A, 11B, 11C, and 11D.

The study was carried out through Day 57. Final Kaplan-Meier survival curves were prepared and are shown in FIG. 11D. Endpoints in the study were either death of the animal or a tumor volume reaching 2000 mm$^3$.

C. Results

FIG. 11A shows individual tumor growth in animals treated with control NST-FIX mRNA. FIG. 11B shows individual tumor growth in animals treated with mOX40L_miR122. Arrows represent dosing days. Multiple doses of a control modified mRNA had little effect on the tumor volume. In contrast, multiple doses of mOX40L_miR122 reduced or decreased the size of tumors in some animals or inhibited the growth of tumors in some animals.

FIG. 11C shows the average tumor size for each group as assessed at Day 35 of the study. These data show that administering mOX40L_miR122 reduced or inhibited tumor growth compared to treatment with control mRNA. The following formula was used to calculate the percentage of tumor growth inhibition (TGI) at Day 34 compared to Day 19:

TGI %=[(Vc−Vt)/Vc−Vo)]×100

Using the formula above and the data shown in FIG. 11C, the TGI % for mOX40L_miR122 was 57%. In other words, animals treated with mOX40L_miR122 showed 57% tumor growth inhibition between Days 19 and 34 compared to control treated animals.

FIG. 11D shows that animals receiving mOX40L_miR122 had longer survival times as measured on Day 42 compared to control animals.

These data show that mOX40L_miR122 polynucleotides have anti-tumor efficacy when administered in vivo.

Example 11. In Vivo Memory Immune Response mOX40L_miR122 was assessed for its ability to induce an adaptive (memory) immune response in the MC-38 adenocarcinoma model.

A. Preparation of OX40L Modified mRNA

A polynucleotide comprising an mRNA encoding an OX40L polypeptide (murine OX40L) and further comprising a miRNA binding site (miR-122) was prepared as described above (mOX40L_miR122; SEQ ID NO: 66). A negative control mRNA was also prepared (non-translatable version of the OX40L_mRNA containing multiple stop codons; NST-OX40L, SEQ ID NO: 68). Both modified mRNAs were formulated in the same manner (Cap1, G5 RP mRNA in 1.5 mol % DMG MC3 LNP).

B. MC-38 Colon Adenocarcinoma Model

MC-38 colon adenocarcinoma tumors were established subcutaneously in C57BL/6 mice as described above.

Seven days after tumor cell inoculation, animals were treated every three days (Q3D) for a maximum of 10 intratumoral doses of MC3 LNP-formulated modified mRNA (12.5 μg mRNA per dose). Control animals were treated with an equivalent dose and regimen of negative control mRNA, NT OX40L_miR122.

Tumor volume was measured at the indicated time points using manual calipers. Tumor volume was recorded in cubic millimeters. At Day 60 post-tumor inoculation, six apparent complete responder animals (CR) from the mOX40L_miR122 group were re-challenged with 5×10$^5$ MC-38 tumor cells; as a control, six naïve animals were also inoculated with 5×10$^5$ MC-38 cells. The results of the analysis are shown in FIGS. 12A and 13B.

C. Results

FIG. 12A shows individual tumor growth in animals treated with control NST-OX40L_mRNA, mOX40L_miR122, or PBS. FIG. 12A shows that 6 out of 15 animals administered mOX40L_miR122 (40%) exhibited a complete response with no significant tumor growth as measured on Day 60. In comparison, animals administered the negative control mRNA construct or PBS showed significant tumor growth through Day 60. (FIG. 12A). These results show that administering an mRNA encoding an OX40L polypeptide reduces or decreases the size of a tumor or inhibits the growth of a tumor.

At Day 60, six complete responders ("CR") from the mOX40L_miR122 group and six naïve control animals were re-challenged with MC-38 cells. FIG. 12B shows individual tumor growth in animals re-challenged with MC-38 cells. Animals previously administered mOX40L_miR122 showed no tumor growth (0/6 animals) for 23 days after re-challenge with tumor cells. In comparison, 67% (6/9 animals) of the animals in the naïve control group showed tumor growth at Day 23. These results show that administering an mRNA encoding an OX40L polypeptide induces a memory immune response with anti-tumor effects.

Example 12. Sustained In Vivo Expression of OX40L in A20 Tumors

In vivo expression of OX40L in the tumor microenvironment was assessed in an A20 B-cell lymphoma tumor model at various timepoints after one and/or two doses of a polynucleotide comprising an mRNA encoding an OX40L polypeptide.

A. Preparation of OX40L Modified mRNA

A polynucleotide comprising an mRNA encoding an OX40L polypeptide (murine OX40L) and further comprising a miRNA binding site (miR-122) was prepared as described above (mOX40L_miR122; SEQ ID NO: 66). The OX40L modified mRNA was formulated in MC3 LNP as described above. A negative control mRNA was also prepared (non-translatable version of the same mRNA containing multiple stop codons; NST-OX40L; SEQ ID NO: 68).

B. A20 B-Cell Lymphoma Tumor Model

B-cell lymphoma tumors were established as described above. Once the tumors reached a mean size of approximately 1300 mm$^3$, animals were separated into three groups. Group I was treated with a single intratumoral dose of mOX40L_miR122 (Cap1, G5 RP mRNA in 0.5 mol % DMG MC3 LNP) at a dose of 15 μg mRNA. Group II (control) was treated with an equivalent dose of negative control mRNA, NT OX40L. Group III was treated with an intratumoral injection of PBS. Each group also comprised a sub-group of animals that received a second dose of mRNA or PBS 7 days after the first dose.

C. Measurement of OX40L Expression

Live cells from A20 tumor cells were analyzed for cell surface expression of OX40L. Tumor tissue was minced and processed through cell strainers to prepare single cell suspensions. Live cells were stained with anti-mouse OX40L antibody (goat IgG polyclonal, PE conjugated; R&D Systems, Minneapolis, Minn.). The cells were subsequently analyzed by flow cytometry. Results are shown in FIG. 13.

D. Results

FIG. 13 shows statistically significant OX40L expression at 24 hours, 72 hours, and 7 days after a single dose of mOX40L_miR122. In particular, FIG. 13 shows that OX40L expression in A20 tumors is sustained at 72 hours and 7 days after a single dose of mOX40L_miR22. In animals receiving a second dose, statistically significant OX40L expression was detected 24 hours after the second dose of mOX40L_miR122.

These data show that administration of mOX40L_miR122 results in significant, sustained levels of OX40L polypeptide expression in the tumor tissue.

Example 13. Identity of Cell Types Expressing OX40L after mRNA Treatment

The identity of cell types expressing OX40L post-mRNA treatment within A20 and MC38 tumors was evaluated. A polynucleotide comprising an mRNA encoding an OX40L polypeptide (murine OX40L) and further comprising a miRNA binding site (miR-122) was prepared as described above. Mouse models of A20 tumors and MC38 tumors were established as described above.

A. Cell Differentiation by Flow Cytometry

Cells within A20 tumors were differentiated by CD19 and CD45 antibodies, which identify CD19-expressing B-lymphoma A20 cancer cells (CD19$^+$, CD45$^+$) from the non-cancer immune infiltrates (CD19$^-$, CD45$^+$) and the non-cancer/nonimmune cells (CD19$^-$, CD45$^-$), respectively. Results are shown in FIG. 14A. Cells within MC38 tumors were differentiated by CD45 marker to differentiate infiltrating host immune cells (CD45$^+$) from cancer cells and non-immune host cells (CD45$^-$). Results are shown in FIG. 14B. Immune infiltrate cells were differentiated with CD11b antibody. CD11b$^+$ immune infiltrate cells were separately analyzed for OX40L expression. Results are shown in FIG. 14C.

B. Results

FIG. 14A shows that in A20 tumors treated with mOX40L_miR122, 76% of the OX40L expressing cell population were the A20 tumor cells themselves, whereas approximately 19% of the OX40L positive cell population were infiltration immune cells within the A20 tumors. The population of OX40L expressing host immune cells was shown to be predominantly myeloid lineage cells, as determined by positive staining for CD11b. Of the CD11b$^+$ myeloid lineage cells in the A20 tumors, an average of 25.4% were positive for OX40L expression (FIG. 14C).

FIG. 14B shows that in MC38 tumors, the majority of OX40L positive cells were cancer cells (an average of 57.3%), while 35.6% of the positive cells were immune infiltrates, again primarily derived from myeloid lineage (CD45$^+$, CD11b$^+$).

These data show that administration of mOX40L_miR122 results in OX40L expression in a significant percentage of the tumor environment post-intratumoral mRNA administration, and that a majority of OX40L-expressing cells were cancer cells followed by myeloid immune cell infiltrates.

Example 14. Modulation of Immune Cell Populations within Tumors Treated with OX40L_mRNA Given the demonstrated activity of OX40L on innate immune natural killer (NK) cells and adaptive CD4+/CD8+ T cells, the objective of the following studies was to evaluate the pharmacodynamic effects of OX40L intratumoral treatment on tumor-associated immune cell populations. Mouse A20 and MC38 tumor models were established as described above.

A. Cell Differentiation by Flow Cytometry

A20 tumors were treated with a single 12.5 μg dose of mOX40L_miR122 or control mRNA (RNA/LNP) formulated in lipid nanoparticles. Tumor samples were initially analyzed 24 hours following treatment. NK cells were differentiated using an antibody against the mature NK cell surface marker, DX5. Results are shown in FIG. 15A. Other tumor samples were analyzed 14 days after treatment with mOX40L_miR122. CD4$^+$ and CD8$^+$ T-cells were identified using anti-mouse CD4 and anti-mouse CD8 antibodies, respectively. Results are shown in FIG. 15B-15C.

A similar experiment was performed in the MC38 tumor model. Mice with MC38 tumors were administered a single intratumoral injection of mOX40L_miR122 or NST-OX40L. In some animals a second dose of mRNA was administered 6 days after the first dose. Immune cell infiltrate was assessed for CD8$^+$ cells 24 hours and 72 hours after each dose of mRNA. Results are shown in FIG. 15D.

B. Results

FIG. 15A shows that 24 hours after administration of mOX40L_miR122 to A20 tumors, NK cells infiltration significantly increased in OX40L-dosed animals compared to controls. FIG. 15B-15C show that 14 days after administration of mOX40L_miR122 to A20 tumors, both CD4+ (FIG. 15B) and CD8+ (FIG. 15C) T-cell infiltration into the tumor microenvironment significantly increased compared to control tumor samples.

FIG. 15D shows a significant increase in infiltrating CD8+ T-cells 72 hours after a second dose of mOX40L_miR122 in MC38 tumors compared to control treated tumors.

These data from two tumor models demonstrate that administration of a polynucleotide comprising an mRNA encoding an OX40L polypeptide promotes increased numbers of both innate and adaptive immune cells within the tumor microenvironment.

Example 15. In Vivo Efficacy in A20 Tumors

In vivo efficacy was assessed in the A20 tumor model. A20 tumors were established as described above.

A. Tumor Treatment

Mice were treated with either 12.5 µg per dose mOX40L_miR122 in LNP, 12.5 µg per dose negative control mRNA designed not to be translated into protein in LNP (NST-OX40L), a PBS negative control, or left untreated. mRNA/LNPs and negative controls were dosed in a 25 µl volume directly into the A20 tumor lesions at a frequency of once every 7 days for up to 6 maximum doses. The tumor volumes of individual animals are shown in FIG. 16A (measured as mm³). A Kaplan-Meier survival curve of the same animals is shown in FIG. 16B. The x-axes of both graphs are Days post disease induction, i.e. subcutaneous cancer cell implantation.

B. Results

FIG. 16A shows that an increased number of animals treated with mOX40L_miR122 exhibited tumor growth inhibition compared to control animals. All of the control animals (30/30) were sacrificed by Day 60 post disease induction (primarily due to reaching the pre-determined tumor burden endpoint ≥2000 mm3). In contrast, 4/9 animals or 44% of the mOX40L_miR122-treated mice had not yet reached the tumor burden endpoint by Day 98.

FIG. 16B shows the survival benefit of mOX40L_miR122 treatment, in which 2 mice in the mOX40L_miR122 arm (as designated by asterisk* in FIG. 16A) and 1 from the PBS group were removed from the study due to tumor ulceration and not included in the survival estimate. By this criteria, 2/8 or 25% of the OX40L_mRNA treated animals were apparent complete responders by Day 98 post implantation compared to 0/29 of the control animals.

These data show the in vivo efficacy of administering a polynucleotide comprising an mRNA encoding an OX40L polypeptide (mOX40L_miR122) in the A20 tumor model.

Example 16. miR-122 Modulates OX40L Expression

The effects of incorporating a miR-122 binding site into the polynucleotide were assessed.

A. Preparation of OX40L Modified mRNA

A polynucleotide comprising an mRNA encoding an OX40L polypeptide (murine OX40L) and further comprising a miRNA binding site (miR-122) was prepared as described above (mouse OX40L, mOX40L_miR122, SEQ ID NO: 66; human OX40L, hOX40L_miR122, SEQ ID NO: 65). Polynucleotides comprising an mRNA encoding mouse OX40L polypeptide or human OX40L polypeptide, each without a miR-122 binding site, were also prepared to compare the effects of the presence of the miR-122 binding site.

B. Cell Transfections

Primary human hepatocytes, human liver cancer cells (Hep3B), and human cervical carcinoma cells (HeLa) were transfected with a polynucleotide comprising an mRNA encoding human OX40L polypeptide (hOX40L) or a polynucleotide comprising an mRNA encoding human OX40L polypeptide and further comprising a miR-122 binding site (hOX40L_miR122). Cells were analyzed for OX40L expression 6 hours, 24 hours, and 48 hours after transfection. Results are shown in FIG. 17A. The same experiment was also performed with mouse OX40L, as shown in FIG. 17B.

C. Results

FIG. 17A shows that incorporating a miR-122 binding site into the polynucleotide markedly reduced human OX40L expression in primary hepatocytes at later timepoints. Specifically, at 24 hours post-transfection, OX40L expression was reduced by 88% from 6,706 ng/well in cells treated with a hOX40L (no miR-122 binding site) to 814 ng/well in cells treated with hOX40L_miR122 (comprising a miR-122 binding site). At 48 hours post-transfection, OX40L expression was reduced by 94% from 11,115 ng/well to 698 ng/well in cells treated with a polynucleotide comprising a miR-122 binding site.

FIG. 17B shows similar results for mouse OX40L. Incorporating a miR-122 binding site into the polynucleotide reduced mouse OX40L expression in primary hepatocytes by 85% at 24 hours (from 1,237 ng/well to 182 ng/well) and by 91% at 48 hours (from 1,704 ng/well to 161 ng/well).

These data show that incorporating a microRNA binding site (miR-122) into a polynucleotide comprising an mRNA encoding an OX40L polypeptide reduces expression of the OX40L polypeptide in primary hepatocytes compared to a polynucleotide lacking a miR-122 binding site.

Example 17. In Vivo Activity of an OX40L-Encoding Polynucleotide Following Intravenous Administration A. Preparation of OX40L Modified mRNA A polynucleotide comprising an mRNA encoding an OX40L polypeptide (murine OX40L) and further comprising a miRNA binding site (miR-122) was prepared as described above (mOX40L_miR122; SEQ ID NO: 66). A negative control mRNA was also prepared (non-translatable version of the same mRNA containing multiple stop codons: NST_OX40L_122).

B. Acute Myeloid Leukemia (AML) Tumor Model

Acute myeloid leukemia (AML) tumors were established subcutaneously in mice. Mouse AML cells (P388D1 cells, ATCC No. CCL-46, ATCC, Manassas, Va.) were cultured according to the vendor's instructions. Cells were inoculated subcutaneously in DBA/2 mice to generate subcutaneous tumors. Tumors were monitored for size and palpability.

Once the tumors were established, animals were separated into five groups. Dosing for the intratumoral dosing groups was every 7 days (Q7D), beginning 7 days after tumor implantation. Group I was treated with intratumoral doses of mOX40L_miR122 at a dose of 12.5 µg mRNA (fixed dose). Group II was treated with intratumoral doses of control NST OX40L_122 mRNA at the same dosing regimen. Dosing for the intravenous dosing groups was every 7 days, beginning 4 days after tumor implantation. Group III was treated with intravenous doses of mOX40L_miR122 at a dose of 0.5 mg mRNA per kg body weight. Group IV was treated with intravenous doses of control mRNA at the same dosing regimen. Group V was treated with intravenous doses of PBS.

C. Results

Results are shown in FIG. 18A-18E and FIG. 19. FIG. 18A shows individual tumor growth in animals treated with intratumoral doses of control NST OX40L_122 mRNA. FIG. 18B shows individual tumor growth in animals treated with intratumoral doses of mOX40L_miR122 mRNA. FIG. 18C shows individual tumor growth in animals treated with intravenous control mRNA. FIG. 18D shows individual tumor growth in animals treated with intravenous doses of mOX40L_miR122 mRNA. FIG. 18E shows individual tumor growth in animals treated with intravenous doses of PBS (negative control).

These results show that both intratumoral and intravenous administration of a polynucleotide encoding an OX40L polypeptide comprising a miRNA binding site reduces or inhibits tumor growth compared to control mRNA or PBS treatment.

FIG. 19 shows the survival curves for animals treated with intravenous doses of mOX40L_miR122 compared to animals treated intravenously with control mRNA or PBS. These results show that intravenous dosing of mOX40L_miR122 increases survival in a mouse tumor model compared to survival of mice treated with a control mRNA.

Example 18. In Vivo Efficacy of Combination of an mRNA Encoding an OX40L Polypeptide, and an Anti-PD-1 Antibody A. Preparation of OX40L Modified mRNA and Anti-PD-1 Antibody A polynucleotide comprising an mRNA encoding an OX40L polypeptide (murine OX40L) and further comprising a miRNA binding site (miR-122) was prepared as described above (mOX40L_miR122; SEQ ID NO: 66). A negative control mRNA was also prepared (NST OX40L_122).

Anti-PD-1 monoclonal antibody (BioXcell BE0146, anti-mPD-1, clone RMP1-14, Lot No. 5792-599016J1) dosing solutions were prepared by diluting an aliquot of the stock (6.37 mg/mL) to 0.5 mg/mL in sterile PBS. The 0.5 mg/mL dosing solution provided the 5 mg/kg dosage in a dosing volume of 10 mL/kg. The anti-PD-1 dosing solution was prepared fresh daily and stored protected from light at 4° C.

Rat IgG2a (BioXcell BE0089, Rat IgG2a, clone 2A3, Lot No. 601416M1) dosing solutions were prepared by diluting an aliquot of the stock (7.38 mg/mL) to 0.5 mg/mL in sterile PBS. The 0.5 mg/mL dosing solution provided the 5 mg/kg dosage in a dosing volume of 10 mL/kg. The anti-PD-1 dosing solution was prepared fresh daily and stored protected from light at 4° C.

B. MC38 Colon Adenocarcinoma Model

MC-38 colon adenocarcinoma tumors were established subcutaneously in C57BL/6 mice as described above.

Once the tumors were established, animals were divided into groups and received intratumoral doses of one of the following combination therapies shown in the table below:

TABLE 10

Combination Dosing and Interval

| Group | Treatment | Dose | Interval |
|---|---|---|---|
| i | NST_OX40L_122 | 2.5 µg mRNA per dose | Q7D |
|  | Rat IgG2a antibody | 5 mg per kg | BIW × 2 |
| ii | mOX40L_miR122 | 2.5 µg mRNA per dose | Q7D |
|  | Rat IgG2a antibody | 5 mg per kg | BIW × 2 |
| iii | NST_OX40L_122 | 2.5 µg mRNA per dose | Q7D |
|  | Anti-PD-1 antibody | 5 mg per kg | BIW × 2 |
| iv | mOX40L_miR122 | 2.5 µg mRNA per dose | Q7D |
|  | Anti-PD-1 antibody | 5 mg per kg | BIW × 2 |
| v | PBS | NA | Q7D |
|  | Anti-PD-1 antibody | 5 mg per kg | BIW × 2 |
| vi | PBS | NA | Q7D |
|  | Rat IgG2a antibody | 5 mg per kg | BIW × 2 |

Mice received intratumoral doses of mRNA every 7 days (Q7D). Mice received intratumoral doses of antibody every two weeks (BIW×2).

C. Results

Results are shown in FIG. 20A-20E and FIG. 21. FIG. 20A shows individual tumor growth in animals treated with intratumoral doses of control NST OX40L_122 mRNA combined with intratumoral doses of control antibody. There were 0/15 complete responders (CR) in the control group. FIG. 20B shows individual tumor growth in animals treated with intratumoral doses of mOX40L_miR122 mRNA combined with intratumoral doses of control antibody. By Day 90 post-implantation, the CR was 0/15 for this group. FIG. 20C shows individual tumor growth in animals treated with intratumoral control mRNA combined with intratumoral doses of anti-PD-1 antibody. By Day 90 post-implantation, the CR was 2/15 for this group. FIG. 20D shows individual tumor growth in animals treated with intratumoral doses of mOX40L_miR122 mRNA combined with intratumoral doses of anti-PD-1 antibody. By Day 90 post-implantation, the CR was 6/15 for the dual combination group. FIG. 20E shows individual tumor growth in animals treated with intratumoral doses of PBS combined with intratumoral doses of anti-PD-1 antibody. By Day 90 post-implantation, the CR was 0/15 for this group. FIG. 20F shows individual tumor growth in animals treated with intratumoral doses of PBS combined with intratumoral doses of control antibody. By Day 90 post-implantation, the CR for this treatment group was 0/14.

These results show that combination therapy comprising a polynucleotide comprising an mRNA encoding an OX40L polypeptide and an immune checkpoint inhibitor, such as an anti-PD-1 antibody, is effective in vivo for inhibiting or reducing tumor growth in the MC38 mouse tumor model. The combination of mOX40L_miR122 with anti-PD-1 antibody showed synergistic in vivo anti-tumor efficacy. These results also show that lower doses of mRNA can be used in combination therapy.

FIG. 21 shows the survival curves for animals in the same treatment groups. These results show that combining intratumoral dosing of a modified OX40L_mRNA with intratumoral dosing of an anti-PD-1 antibody effectively increases survival in a mouse tumor model compared to control treatment groups.

Example 19. In Vivo Memory Immune Response Following Treatment with Combination Therapy Mice were treated with mOX40L_miR122 combined with anti-PD-1 antibody as described above in Example 18. At Day 90 post-tumor inoculation, four complete responder animals (CR) from the mOX40L_miR122+anti-PD-1 combination therapy group were re-challenged with $5 \times 10^5$ MC38 tumor cells. As a control, 10 naïve animals were also inoculated with $5 \times 10^5$ MC38 cells. The results of the analysis are shown in FIGS. 22A and 22B.

FIG. 22A shows individual tumor growth in naïve animals challenged with MC38 cells. Naïve mice began developing detectable tumors approximately 5 days after implantation, and tumors continued to grow during the study. FIG. 22B shows individual tumor growth in the complete responder animals previously given intratumoral doses of combination therapy of mOX40L_miR122 and anti-PD-1 antibody. The complete responder animals showed no tumor growth (0/4 animals) for 23 days after re-challenge with tumor cells. In contrast, naïve animals showed a high percentage of tumor growth. These results show that intratumoral dosing of an mRNA encoding an OX40L polypeptide combined with an anti-PD-1 antibody induces a memory immune response with anti-tumor effects.

Other Embodiments

It is to be understood that the words which have been used are words of description rather than limitation, and that changes can be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method for treating cancer in a subject by increasing the number of NK cells in vivo, comprising administering to the subject a lipid nanoparticle (LNP) encapsulated messenger RNA (mRNA) encoding a human OX40L polypeptide, thereby increasing the number of NK cells in vivo, to treat cancer in the subject.

2. The method of claim 1, wherein increasing NK cells results in one or more of: reduction or decrease in the size of a tumor, and inhibition of growth of a tumor.

3. The method of claim 1, wherein the mRNA comprises a 3' untranslated region (UTR) comprising at least one microRNA-122 (miR-122) binding site, wherein the miR-122 binding site is a miR-122-3p binding site or a miR-122-5-binding site.

4. The method of claim 3, wherein the miR-122-5p binding site comprises the nucleotide sequence as set forth in SEQ ID NO: 26.

5. The method of claim 1, wherein the human OX40L polypeptide comprises the amino acid sequence as set forth in SEQ ID NO: 1.

6. A method for treating cancer in a subject by increasing the number of NK cells in vivo, comprising administering to the subject a lipid nanoparticle (LNP) encapsulated messenger RNA (mRNA) encoding a human OX40L polypeptide, wherein the mRNA comprises an open reading frame comprising a nucleotide sequence at least 90% identical to SEQ ID NO: 4, thereby increasing the number of NK cells in vivo, to treat cancer in the subject.

7. The method of claim 6, wherein increasing NK cells results in one or more of: reduction or decrease in the size of a tumor, and inhibition of growth of a tumor.

8. The method of claim 6, wherein the open reading frame comprises the nucleotide sequence set forth in SEQ ID NO: 4.

9. The method of claim 6, wherein the mRNA comprises the nucleotide sequence as set forth in SEQ ID NO: 65 or a nucleotide sequence at least 90% identical to SEQ ID NO: 65.

10. The method of claim 6, wherein the lipid nanoparticle is administered intratumorally.

11. The method of claim 6, wherein the mRNA is fully modified with chemically-modified uridines.

12. The method of claim 6, wherein the mRNA comprises a 5' UTR comprising the nucleotide sequence as set forth in SEQ ID NO: 27, and a 3' UTR comprising the nucleotide sequence as set forth in SEQ ID NO: 63.

13. The method of claim 6, wherein the mRNA comprises a 3' UTR comprising at least one microRNA-122 (miR-122) binding site, wherein the miR-122 binding site is a miR-122-3p binding site or a miR-122-5-binding site.

14. The method of claim 13, wherein the miR-122-5p binding site comprises the nucleotide sequence as set forth in SEQ ID NO: 26.

15. A method for treating cancer in a subject by increasing the number of NK cells in vivo, comprising administering to the subject a lipid nanoparticle (LNP) encapsulated messenger RNA (mRNA) encoding a human OX40L polypeptide, wherein the mRNA comprises a nucleotide sequence at least 90% identical to SEQ ID NO: 65, thereby increasing the number of NK cells in vivo, to treat cancer in the subject.

16. The method of claim 15, wherein increasing NK cells results in one or more of: reduction or decrease in the size of a tumor, and inhibition of growth of a tumor.

17. The method of claim 15, wherein the mRNA comprises the nucleotide sequence as set forth in SEQ ID NO: 65.

18. The method of claim 15, wherein the lipid nanoparticle is administered intratumorally.

19. The method of claim 15, wherein the mRNA is fully modified with chemically-modified uridines.

20. The method of claim 15, wherein the mRNA comprises a 5' UTR comprising the nucleotide sequence as set forth in SEQ ID NO: 27, and a 3' UTR comprising the nucleotide sequence as set forth in SEQ ID NO: 63.

21. The method of claim 11, wherein the chemically-modified uridines are N1-methylpseudouridines (m1ψ).

22. The method of claim 19, wherein the chemically-modified uridines are N1-methylpseudouridines (m1ψ).

* * * * *

SEQUENCE LISTING

```
<160> NUMBER OF SEQ ID NOS: 69

<210> SEQ ID NO 1
<211> LENGTH: 183
<212> TYPE: PRT
<213> ORGANISM: Artificial Sequence
<220> FEATURE:
<223> OTHER INFORMATION: tumor necrosis factor ligand superfamily member
      4 isoform 1 [Homo sapiens]

<400> SEQUENCE: 1

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
```

180

<210> SEQ ID NO 2
<211> LENGTH: 133
<212> TYPE: PRT
<213> ORGANISM: Artificial Sequence
<220> FEATURE:
<223> OTHER INFORMATION: tumor necrosis factor ligand superfamily member
      4 isoform 2 [Homo sapiens]

<400> SEQUENCE: 2

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 3
<211> LENGTH: 198
<212> TYPE: PRT
<213> ORGANISM: Artificial Sequence
<220> FEATURE:
<223> OTHER INFORMATION: tumor necrosis factor ligand superfamily member
      4 [Mus musculus]

<400> SEQUENCE: 3

Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60

Gly Ala Val Thr Arg Cys Glu Asp Gly Gln Leu Phe Ile Ser Ser Tyr
65                  70                  75                  80

Lys Asn Glu Tyr Gln Thr Met Glu Val Gln Asn Asn Ser Val Val Ile
            85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
        115                 120                 125

Ile Pro Met Leu Asn Asp Gly Arg Arg Ile Val Phe Thr Val Val Ala
    130                 135                 140

Ser Leu Ala Phe Lys Asp Lys Val Tyr Leu Thr Val Asn Ala Pro Asp

```
145                 150                 155                 160
Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro Leu
        195

<210> SEQ ID NO 4
<211> LENGTH: 549
<212> TYPE: RNA
<213> ORGANISM: Artificial Sequence
<220> FEATURE:
<223> OTHER INFORMATION: TNFSF4 tumor necrosis factor (ligand)
      superfamily, member 4, open reading frame [Homo sapiens]

<400> SEQUENCE: 4
auggaaaggg uccaaccccu ggaagagaau gugggaaaug cagccaggcc aagauucgag      60
aggaacaagc uauugcuggu ggccucugua auucaggacu ggggcugcu ccugugcuuc     120 accuacaucu gccugcacuu cucugcucuu cagguaucac aucgguaucc ucgaauucaa    180
aguaucaaag uacaauuuac cgaauauaag aaggagaaag uuucauccu cacuucccaa     240 aaggaggaug aaaucaugaa ggugcagaac aacucaguca ucaucaacug gaugggguuu    300
uaucucaucu cccugaaggg cuacuucucc caggaaguca acauuagccu cauuaccag     360 aaggaugagg agccccucuu ccaacugaag aaggucaggu cugucaacuc cuugaugguy    420
gccucucuga cuuacaaaga caaagucuac uugaaugugu ccacgacaa uaccucccug    480 gaugacuucc augugaaugg cggagaacug auucuuaucc aucaaaaucc uggugaauuc    540
uguguccuu                                                           549

<210> SEQ ID NO 5
<211> LENGTH: 3484
<212> TYPE: RNA
<213> ORGANISM: Artificial Sequence
<220> FEATURE:
<223> OTHER INFORMATION: homo sapiens tumor necrosis factor (ligand)
      superfamily, member 4 (TNFSF4), transcript variant 1, mRNA

<400> SEQUENCE: 5
ggcccuggga ccuuugccua uuuucugauu gauaggcuuu guuugucuu uaccuccuuc      60 uuucggggga aaacuucagu uuuaucgcac guuccccuuu uccauaucuu caucuucccu    120
cuacccagau gugaagaug gaaagggucc aaccccugga agagaauguc ggaaaugcag    180
ccaggccaag auucgagagg aacaagcuau ugcuggugc cucuguaauu cagggacugg    240
ggcugcuccu gugcuucacc uacaucgcc ugcacuucuc ugcucuucag guaucauc      300 gguauccucg aauucaaagu aucaaaguac aaauuuaccga auauaagaag gagaaagguu    360
ucauccucac uucccaaaag gaggaugaaa ucaugaaggu gcagaacaac ucagucauca    420
ucaacuguga uggguuuuau cucaucuccc ugaagggcua cuucuccag gaagucaaca    480 uuagccuuca uuaccagaag gaugaggagc cccucuucca acugaagaag gucaggucug    540
ucaacuccuu gaugguggcc ucucugacu acaaagacaa agucuacuug aaugugacca    600
cugacaauac cucccuggau gacuuccaug ugaauggcgg agaacugauu cuuauccauc    660
aaaauccugg ugaauucugu guccuugag gggcugaugg caauaucuaa aaccaggcac    720
cagcaugaac accaagcugg ggguggacag ggcauggauu cuucauugca agugaaggag    780
```

```
ccucccagcu cagccacgug ggaugugaca agaagcagau ccuggcccuc ccgcccccac    840
cccucaggga uauuuaaaac uuauuuuaua uaccaguuaa ucuuauuuau ccuuauauuu    900
ucuaaauugc cuagccguca caccccaaga uugccuugag ccuacuaggc accuuuguga    960
gaaagaaaaa auagaugccu cuucuucaag augcauuguu ucuaugguc aggcaauugu    1020 cauaauaaac uuaugucauu gaaaacggua ccugacuacc auuugcugga aauuugacau    1080
guguguggca uuaucaaaau gaagaggagc aaggagugaa ggagugggu uaugaaucug    1140 ccaaaggugg uaugaaccaa ccccuggaag ccaaagcggc cucuccaagg uuaaauugau    1200
ugcaguuugc auauugccua aauuuaaacu uucauuug ugggggguuc aaaagaagaa    1260
ucagcuugug aaaaaucagg acuugaagag agccgucuaa gaaauaccac gugcuuuuu    1320 ucuuuaccau uuugcuuucc cagccuccaa acauaguuaa uagaaauuuc ccuucaaaga    1380
acugucuggg gaugugaugc uuugaaaaau cuaaucagug acuuaagaga gauuuucuug    1440
uauacaggga gagugagaua acuuauugu aagguuagc uuuacuguac aggauagcag    1500
ggaacuggac aucucagggu aaaagucagu acggauuuua uagccuggg gaggaaaaca    1560 cauucuuugc cacagacagg caaagcaaca caugcucauc cccugccua ugcugagaua    1620 cgcacucagc uccaugucuu guacacacag aaacauugcu gguuucaaga augagguga    1680 uccuauuauc aaauucaauc ugaugucaaa uagcacuaag aaguuaugu gccuuaugaa    1740 aaauaaugau cucugucuag aaauaccaua gaccauauau agucucacau ugauaauuga    1800
aacuagaagg gucuauaauc agccuaugcc agggcuucaa uggaauagua uccccuuaug    1860
uuuaguugaa augucccccuu aacuugauau aauguguuau gcuuauggcg cuguggacaa    1920
ucugauuuuu caugucaacu uuccagauga uuuguaacuu cucugugcca aaccuuuau    1980 aaacauaaau uuuugagaua uguauuuuaa auuguagca cauguuuccc ugacauuuc    2040 aauagaggau acaacaucac agaaucuuuc uggaugauuc uguguuauca aggaauugua    2100
cugugcuaca auuaucucua gaaucuccag aaagguggag ggcuguucgc ccuuacacua    2160
aauggucuca guuggauuuu uuuuuccugu uuucuauuuc cucuuaagua caccuucaac    2220
uauauuccca uccccucuauu uuaaucuguu augaaggaag guaaauaaaa augcuaaaua    2280
gaagaaauug uagguaaggu aagaggaauc aaguucgag uggcugccaa ggcacucaca    2340
gaaucauaau cauggcuaaa uauuuaugga gggccuacug uggaccaggc acugggcuaa    2400
auacuuacau uuacaagaau cauucugaga cagauauuca augauaucug gcuucacuac    2460
ucagaagauu gugugugugu uuguguguguu gugugugugu guauuucacu uuuuguuauu    2520
gaccauguuc ugcaaaauug caguuacuca gugagugaua uccgaaaaag uaaacguuua    2580
ugacuauagg uaauauuuaa gaaaaugcau gguucauuuu uaaguuugga auuuuuaucu    2640
auauuucuca cagaugugca gugcacaugc aggccuaagu auauguugug uguuguuu    2700 gucuuugaug ucauggucccc cucucuuagg ugcucacucg cuuugggugc accuggccug    2760
cucuucccau guuggccucu gcaaccacac agggauauuu cugcuaugca ccagccucac    2820
uccaccuucc uuccaucaaa aauaugugug ugugucucag ccccuguaag ucaugcccuu    2880
cacagggaga auuaacccuu cgauauacau ggcagaguuu ugggaaaaa gaauugaaug    2940 aaaagucagg agaucagaau uuuaaauuug acuuagccac uaacuagcca uguaaccuug    3000
ggaaagucau uucccauuuc uggqucugc uuuucuuucu guuaaugag aggaauguua    3060 aauaucuaac aguuuagaau cuuaugccuua caguuuauc ugaaugca cauauuaauu    3120 gucuauguuc uuguugcuau gagucaagga guguaaccuu cuccuuuacu auguugaaug    3180
```

```
uauuuuuuuc uggacaagcu uacaucuucc ucagccaucu uugugagucc uucaagagca    3240
guuaucaauu guuaguuaga uauuuucuau uuagagaaug cuuaagggau uccaaucccg    3300
auccaaauca uaauuuguuc uuaaguauac ugggcagguc cccuauuuua agucauaauu    3360
uuguauuuag gcuuuccug gcucucagag aguauuaaua uugauauuaa uaauauaguu    3420
aauaguaaua uugcuauuua cauggaaaca aauaaaagau cucagaauuc acuaaaaaaa    3480
aaaa                                                                 3484

<210> SEQ ID NO 6
<211> LENGTH: 1609
<212> TYPE: RNA
<213> ORGANISM: Artificial Sequence
<220> FEATURE:
<223> OTHER INFORMATION: Mus musculus tumor necrosis factor (ligand)
      superfamily, member 4 (Tnfsf4), mRNA

<400> SEQUENCE: 6
auugcuuuuu gucuccuguu cuggaccuuu uaucuucuga cccgcaggcu ugacuuugcc      60
cuuauuggcu ccuuuguggu gaagagcagu cuuccccag guuccccgcc acagcuguau     120
cuccucugca ccccgacugc agagauggaa ggggaagggg uucaaccccu ggaugagaau    180
cuggaaaacg gaucaaggcc aagauucaag uggaagaaga cgcuaaggcu ggugucucu     240 gggaucaagg gagcagggau gcuucugugc uucaucuaug ucugccugca cucucuucc     300 ucuccggcaa aggacccucc aauccaaaga cucagaggag caguuaccag augugaggau    360
gggcaacuau ucaucagcuc auacaagaau gaguaucaaa cuauggaggu gcagaacaau    420
ucgguuguca ucaagugcga ugggcuuuau aucaucuacc ugaagggcuc cuuuuccag    480 gaggucaaga uugaccuuca uuuccgggag gaucauaauc ccaucucuau uccaaugcug    540
aacgaugguc gaaggauugu cuucacugug guggccucuu uggcuuucaa agauaaaguu    600
uaccugacgu uaaaugcccc ugauacucuc ucgaacacc uccagauaaa ugauggggag    660
cugauuguug uccagcuaac gccuggauac ugugucccug aaggaucuua ccacagcacu    720
gugaaccaag uaccacugug aauuccacuc ugagggugga cgggacacag guucuuucuc    780
gagagagaug agugcauccu gcaugagaga ugugacugaa ugcagagccu acccuacuuc    840
cucacucagg gauauuuaaa ucaugucuua cauaacaguu gaccucucau ucccaggauu    900
gccuugagcc ugcuaagagc uguucuggga augaaaaaaa aauaaaugu cucuucaaga    960 cacaugcuuu cugucgguca gaagcucauc guaauaaaca ucugccacug aaaauggcgc   1020
uugauugcua ucuucuagaa uuuugauguu gucaaaagaa agcaaaacau ggaaagggug   1080
guguccaccg gccaguagga gcuggagugc ucucuucaag guuaagguga uagaaguuua   1140
cauguugccu aaaacugucu cucaucucau gggggcuug gaaagaagau uaccccgugg   1200
aaagcaggac uugaagauga cuguuuaagc aacaaggugc acucuuuccc uggcccuga    1260 auacacauaa aagacaacuu ccuucaaaga acuaccuagg gacuaugaua cccaccaaag   1320
aaccacguca gcgaugcaaa gaaaaccagg agagcuuugu uuauuugca gaguauacga    1380 gagauuuuac ccugagggcu auuuuuauua uacaggauga gagugaacug gaugucucag    1440
gauaaaggcc aagaaggauu uucacagauc ugagcaagac uguuuugua gguucucucu    1500 ccaaaacuuu uaggaaaauu uuugauaauu uuaaaauuuu uaguuauauu uuuggaccau    1560
uuucaauaga agauugaaac auuuccagau gguuucauau ccccacaag                1609
```

-continued

```
<210> SEQ ID NO 7
<211> LENGTH: 549
<212> TYPE: RNA
<213> ORGANISM: Artificial Sequence
<220> FEATURE:
<223> OTHER INFORMATION: Codon-optimized sequence 1 for ENSP 281834

<400> SEQUENCE: 7
auggagagag ugcagccccu ggaggagaac gugggcaacg ccgccagacc cagauucgag      60
agaaacaagc ugcugcuggu ggccagcgug auccagggcc ugggccugcu gcugugcuuc     120
accuacaucu gccugcacuu cagcgcccug caggugagcc acagauaccc cagaauccag     180
agcaucaagg ugcaguucac cgaguacaag aaggagaagg cuucauccu gaccagccag      240 aaggaggacg agaucaugaa ggugcagaac aacagcguga ucaucaacug cgacggcuuc     300
uaccugauca gccugaaggg cuacuucagc caggaggugu acaucagccu gcacuaccag     360
aaggacgagg agccccuguu ccagcugaag aaggugagaa gcgugaacag ccugauggug     420
gccagccuga ccuacaagga caaguguac cugaacguga ccaccgacaa caccagccug      480
gacgacuucc acgugaacgg cggcgagcug auccugaucc accagaaccc cggcgaguuc     540
ugcgugcug                                                              549

<210> SEQ ID NO 8
<211> LENGTH: 549
<212> TYPE: RNA
<213> ORGANISM: Artificial Sequence
<220> FEATURE:
<223> OTHER INFORMATION: Codon-optimized sequence 2 for ENSP 281834

<400> SEQUENCE: 8
auggagcgug ugcagccucu ugaggagaau gugggaaaug cagcccggcc ucgauucgaa      60
cguaauaaac uccugcucgu ggccuccgug auccaggguc ucgguuuauu gcuguguuuu     120
accuauauau gcuuacacuu uagugcauua caggucucac accgguaccc ucgcauucag     180
ucuauaaaag ugcaguuuac cgaguauaag aaggagaaag guuuuauacu gacuucucag     240
aaagaggacg agaucaugaa ggugcagaau aauagcguca uuaucaacug cgauggauuc     300
uaucuaauuu cccuaaaggg guacuucagc caggaggucau auauacacu gcacuaucaa     360 aaggacgagg agccccuguu ucaacugaag aaagugcgau caguuaacuc ucugaugguu     420
gccucucuga ccuauaagga caaagucuac uugaacguga caacugacaa cacccucacug    480 gaugacuuuc augugaaugg gggggaacug auucuuaucc aucagaauc aggagaauuc      540 ugugugcuc                                                              549

<210> SEQ ID NO 9
<211> LENGTH: 549
<212> TYPE: RNA
<213> ORGANISM: Artificial Sequence
<220> FEATURE:
<223> OTHER INFORMATION: Codon-optimized sequence 3 for ENSP 281834

<400> SEQUENCE: 9
auggagcggg ugcagccccu ggaggagaau gugggcaaug cugcccggcc cagguuugaa      60
agaaacaagc ugcugcuggu ggccagcguc auccagggcc ugggccugcu gcugugcuuc     120
accuacaucu gccugcacuu cagcgcccug caggugagcc accgcuaccc ccgcauccag     180
agcaucaagg ugcaguucac agaguacaag aaggagaagg cuucauccu gaccagccag      240 aaggaggaug agaucaugaa ggugcagaac aacagcguca ucaucaacug ugauggcuuc     300
```

| | |
|---|---|
| uaccugauca gccugaaggg cuacuucagc caggaggug a acaucagccu gcacuaccag | 360 |
| aaggaugagg agccccucuu ccagcugaag aaggugcgcu cugugaacag ccugaugggug | 420 |
| gccagccuga ccuacaagga caagguguac cugaauguga ccacagacaa caccagccug | 480 |
| gaugacuucc acgugaaugg aggagagcug auccugaucc accagaaccc uggagaguuc | 540 |
| ugugugcug | 549 |

<210> SEQ ID NO 10
<211> LENGTH: 549
<212> TYPE: RNA
<213> ORGANISM: Artificial Sequence
<220> FEATURE:
<223> OTHER INFORMATION: Codon-optimized sequence 4 for ENSP 281834

<400> SEQUENCE: 10

| | |
|---|---|
| auggagcggg ugcagccccu ggaggagaac gugggcaacg ccgcccgccc gcguuugag | 60 |
| cgaaauaagu uacugcuugu ugcaucugug uacaggggu uggguuuacu ucuuugcuuu | 120 |
| acauauauuu gucuccacuu uagugcgcuu cagguauccc aucggua ccc gcgcauccag | 180 |
| ucaaucaagg uccaguucac ugaauauaaa aaggagaaag gauucauucu gacuucacaa | 240 |
| aaagaggacg aaaucaugaa agugcagaac aacucuguaa uuauaaacug cgauggguuc | 300 |
| uaucugauca gucugaaggg auauuuuagc caggaaguaa auauuucacu acauuaucag | 360 |
| aaggacgaag aaccacuuuu ucaacugaag aaaguccggu ccgugaacuc ccugaugguu | 420 |
| gcuagccuua ccuacaagga uaaagucuau uuaaacguca caacagauaa cacuagccuc | 480 |
| gacgauuucc augugaacgg aggugaacug auauugaucc aucaaaaccc cggcgaguuc | 540 |
| ugcguuuua | 549 |

<210> SEQ ID NO 11
<211> LENGTH: 549
<212> TYPE: RNA
<213> ORGANISM: Artificial Sequence
<220> FEATURE:
<223> OTHER INFORMATION: Codon-optimized sequence 5 for ENSP 281834

<400> SEQUENCE: 11

| | |
|---|---|
| auggagcggg uccagcccu cgaggagaac guuggua aug ccgcacgucc caggguugaa | 60 |
| cgcaacaagc ugcuguuggu ggccagcguc auucagggc uggguuuguu gcugugcuuc | 120 |
| acuuacaucu gucugcauuu uagugcacuc cagguguccc accgcuaccc ccguauccaa | 180 |
| uccauuaaag uccaauuuac cgaauacaaa aagagaagg guucauucu uaccucccag | 240 |
| aaggaggaug aaauuaugaa ggugcagaac aauucuguua ucaucaacug ugacggauuc | 300 |
| uaucugauuu cacugaaggg auacuuuucc caggagguga acaucagucu gcauuaucag | 360 |
| aaggacgaag aaccgcuuuu ucaacugaag aagguuagga gugugaacuc cuuaaugggua | 420 |
| gccagccuga cauauaagga caagguauau cugaacguca ccacugauaa caccucuuua | 480 |
| gacgauuuuc augugaaugg gggagaauug auacucauuc accagaauccc gggugaguuu | 540 |
| uguguucug | 549 |

<210> SEQ ID NO 12
<211> LENGTH: 399
<212> TYPE: RNA
<213> ORGANISM: Artificial Sequence
<220> FEATURE:
<223> OTHER INFORMATION: Codon-optimized sequence 1 for ENSP 356691

<400> SEQUENCE: 12

```
auggugagcc acagauaccc cagaauccag agcaucaagg ugcaguucac cgaguacaag      60
aaggagaagg gcuucauccu gaccagccag aaggaggacg agaucaugaa ggugcagaac     120
aacagcguga ucaucaacug cgacggcuuc uaccugauca gccugaaggg cuacuucagc     180
caggagguga acaucagccu gcacuaccag aaggacgagg agccccuguu ccagcugaag     240
aaggugagaa gcgugaacag ccugauggug gccagccuga ccuacaagga caagguguac     300
cugaacguga ccaccgacaa caccagccug gacgacuucc acgugaacgg cggcgagcug     360
auccugaucc accagaaccc cggcgaguuc ugcgugcug                            399
```

<210> SEQ ID NO 13
<211> LENGTH: 399
<212> TYPE: RNA
<213> ORGANISM: Artificial Sequence
<220> FEATURE:
<223> OTHER INFORMATION: Codon-optimized sequence 2 for ENSP 356691

<400> SEQUENCE: 13

```
augguuucuc accguuaccc acggauccag ucuaucaagg uucaguuuac cgaguacaaa      60
aaggaaaaag gguucauccu caccucucag aaagaggacg aaaucaugaa ggugcagaau     120
aacucuguaa ucauuaauug cgacgguuuu uaucugauuu cacugaaggg cuacuuuagu     180
caggaaguua auauuaguuu gcacuaccaa aaggacgagg agccucucuu ccaacuaaaa     240
aagguaagau ccguuaauuc ccuuaugguu gccuccuuaa cuuauaagga caagguguau     300
cugaauguga ccacagauaa cacacccuug gacgacuuuc auguaaaugg cggcgaguua     360
auucugauac accagaaccc uggcgaguuc ugcgugcug                            399
```

<210> SEQ ID NO 14
<211> LENGTH: 399
<212> TYPE: RNA
<213> ORGANISM: Artificial Sequence
<220> FEATURE:
<223> OTHER INFORMATION: Codon-optimized sequence 3 for ENSP 356691

<400> SEQUENCE: 14

```
auggugagcc accgcuaccc ccgcauccag agcaucaagg ugcaguucac agaguacaag      60
aaggagaagg gcuucauccu gaccagccag aaggaggaug agaucaugaa ggugcagaac     120
aacagcguca ucaucaacug ugauggcuuc uaccugauca gccugaaggg cuacuucagc     180
caggagguga acaucagccu gcacuaccag aaggaugagg agccccucuu ccagcugaag     240
aaggugcgcu cugugaacag ccugauggug gccagccuga ccuacaagga caagguguac     300
cugaauguga ccacagacaa caccagccug gaugacuucc acgugaaugg aggagagcug     360
auccugaucc accagaaccc uggagaguuc ugugugcug                            399
```

<210> SEQ ID NO 15
<211> LENGTH: 399
<212> TYPE: RNA
<213> ORGANISM: Artificial Sequence
<220> FEATURE:
<223> OTHER INFORMATION: Codon-optimized sequence 4 for ENSP 356691

<400> SEQUENCE: 15

```
auggugagcc accgguaccc ccggauccag agcaucaagg ugcaguucac cgaauacaag      60
aaggagaagg guuuuauccu gacgagccag aaggaagacg agauuaugaa gguccaaaac     120
aacucaguca ucauaaacug cgauggauuu uaccugaucu cucugaaggg guacuucucc     180
```

```
caggaaguga auauuagcuu gcacuaucaa aaagaugagg agccucuauu ccagcucaag    240
aaggucagaa gcgucaauag ucgaugguc gcaucauuaa ccuauaaaga caaaguauau     300
cuaaauguga cgacagacaa uacaucccuc gaugauuuuc acgucaacgg aggcgaacuc    360
auucugaucc accagaaucc aggggaauuu ugcgugcug                           399
```

<210> SEQ ID NO 16
<211> LENGTH: 399
<212> TYPE: RNA
<213> ORGANISM: Artificial Sequence
<220> FEATURE:
<223> OTHER INFORMATION: Codon-optimized sequence 5 for ENSP 356691

<400> SEQUENCE: 16

```
auggcucac accgguaccc ccguauccag aguauuaagg ugcaauucac ggaguauaaa     60
aaagaaaagg gauucauucu gacgucucag aaggaagaug agaucaugaa ggnccagaac    120
aauucuguga ucauuaauug cgauggauuu uaucugauuu cacuuaaagg auauuuuucc    180
caggagguua auaucaguuu gcacuaucag aaagacgagg agccauuauu ccagcugaag    240
aaggugagau cagugaauag ccugaugguu gcgucacuga cguauaaaga caaaguuuau    300
cuaaacguua ccacugauaa uacaucccuu gaugauuuuc augugaacgg gggugaacug    360
auccuuauac accagaaccc cggagaguuc ugugucug                            399
```

<210> SEQ ID NO 17
<211> LENGTH: 399
<212> TYPE: RNA
<213> ORGANISM: Artificial Sequence
<220> FEATURE:
<223> OTHER INFORMATION: Codon-optimized sequence 1 for ENSP 439704

<400> SEQUENCE: 17

```
auggugagcc acagauaccc cagaauccag agcaucaagg ugcaguucac cgaguacaag    60
aaggagaagg gcuucauccu gaccagccag aaggaggacg agaucaugaa ggugcagaac    120
aacagcguga ucaucaacug cgacggcuuc uaccugauca gccugaaggg cuacuucagc    180
caggagguga caucagccu gcacuaccag aaggacgagg agccccguu ccagcugaag     240 aaggugagaa gcgugaacag ccugaugguq gccagccuga ccuacaagga caagguguac    300
cugaacguga ccaccgacaa caccagccug gacgacuucc acgugaacgg cggcgagcug    360
auccugaucc accagaaccc cggcgaguuc ugcgugcug                           399
```

<210> SEQ ID NO 18
<211> LENGTH: 399
<212> TYPE: RNA
<213> ORGANISM: Artificial Sequence
<220> FEATURE:
<223> OTHER INFORMATION: Codon-optimized sequence 2 for ENSP 439704

<400> SEQUENCE: 18

```
auggugucac accgguaccc ucggauccag ucuauuaaag uucaauuuac ggaguacaag    60
aaagaaaaag gcuuuauccu uacaagccaa aaggaagacg agaucaugaa agugcaaaac    120
aacaguguga uuauaaauug ugauggcuuc uaccuuauua gucugaaggg cuacuuuagu    180
caggaaguca auauuagccu acacuaccag aaagacgagg agcccucuuu ucaacugaaa    240
aaggugcgcu ccgugaauuc guugaugguc gccucucuga ccuacaagga uaagguguau    300
cuuaacguua cuaccgacaa uacuagucug gacgacuuuc acgucaacgg aggcgaacuu    360
auucugaucc accagaaccc cggcgaauuc ugcgugcug                           399
```

<210> SEQ ID NO 19
<211> LENGTH: 399
<212> TYPE: RNA
<213> ORGANISM: Artificial Sequence
<220> FEATURE:
<223> OTHER INFORMATION: Codon-optimized sequence 3 for ENSP 439704

<400> SEQUENCE: 19
auggugagcc accgcuaccc ccgcauccag agcaucaagg ugcaguucac agaguacaag    60
aaggagaagg gcuucauccu gaccagccag aaggaggaug agaucaugaa ggugcagaac   120
aacagcguca ucaucaacug ugauggcuuc uaccugauca gccugaaggg cuacuucagc   180
caggagguga acaucagccu gcacuaccag aaggaugagg agccccucuu ccagcugaag   240
aaggugcgcu cugugaacag ccugauggug gccagccuga ccuacaagga caagguguac   300
cugaauguga ccacagacaa caccagccug gaugacuucc acgugaaugg aggagagcug   360
auccugaucc accagaaccc uggagaguuc ugugugcug                          399

<210> SEQ ID NO 20
<211> LENGTH: 399
<212> TYPE: RNA
<213> ORGANISM: Artificial Sequence
<220> FEATURE:
<223> OTHER INFORMATION: Codon-optimized sequence 4 for ENSP 439704

<400> SEQUENCE: 20
auggugagcc accgguaccc ccggauccag agcaucaagg ugcaguucac agaguacaag    60
aaggagaagg gauuuauucu cacaagucag aaagaagaug agaucaugaa gguucagaac   120
aacucaguca uuauuaauug cgacggauuc uaucucauua gccugaaagg cuauuucagc   180
caggagguca auaucagccu gcacuaccag aaggaugagg aaccucucuu ucagcugaaa   240
aaaguccgcu cugugaauuc ccucaugguc gcucccuga ccuacaagga uaaaguuuau    300
uugaacguua caacagauaa uacaucgcug gacgacuucc augugaaugg uggcgaacua   360
auucuaauac accaaaaucc aggcgaauuu uguguccuu                          399

<210> SEQ ID NO 21
<211> LENGTH: 399
<212> TYPE: RNA
<213> ORGANISM: Artificial Sequence
<220> FEATURE:
<223> OTHER INFORMATION: Codon-optimized sequence 5 for ENSP 439704

<400> SEQUENCE: 21 auggauccc auagauaccc acguauucaa agcauuaagg ugcaguucac agaguacaaa     60
aaggagaagg guuucauacu gacgucacag aaggaggacg agauaaugaa ggugcagaau   120
aauaguguga ucaucaauug ugauggauuc uauugauca gccucaaagg uuauuucuca    180
caggaaguca acauuucccu gcacuaccag aaggacgaag agccuuuguu ucagcugaag   240
aaggugcgcu cagugaacag uuugauggua gcccucccuaa cuuauaaaga uaaaguuuau  300
cugaacguga caaccgauaa cacaucccug gacgacuuuc acgucaaugg aggugaguua   360
auccugaucc aucagaaucc cggagaauuc ugcguucuu                          399

<210> SEQ ID NO 22
<211> LENGTH: 85
<212> TYPE: RNA
<213> ORGANISM: Artificial Sequence
<220> FEATURE:

<223> OTHER INFORMATION: miR-122

<400> SEQUENCE: 22
ccuuagcaga gcuguggagu gugacaaugg uguuuguguc uaaacuauca aacgccauua    60
ucacacuaaa uagcuacugc uaggc                                        85

<210> SEQ ID NO 23
<211> LENGTH: 22
<212> TYPE: RNA
<213> ORGANISM: Artificial Sequence
<220> FEATURE:
<223> OTHER INFORMATION: miR-122-3p

<400> SEQUENCE: 23
aacgccauua ucacacuaaa ua                                           22

<210> SEQ ID NO 24
<211> LENGTH: 22
<212> TYPE: RNA
<213> ORGANISM: Artificial Sequence
<220> FEATURE:
<223> OTHER INFORMATION: miR-122-3p binding site

<400> SEQUENCE: 24
uauuuagugu gauaauggcg uu                                           22

<210> SEQ ID NO 25
<211> LENGTH: 22
<212> TYPE: RNA
<213> ORGANISM: Artificial Sequence
<220> FEATURE:
<223> OTHER INFORMATION: miR-122-5p

<400> SEQUENCE: 25
uggaguguga caaugguguu ug                                           22

<210> SEQ ID NO 26
<211> LENGTH: 22
<212> TYPE: RNA
<213> ORGANISM: Artificial Sequence
<220> FEATURE:
<223> OTHER INFORMATION: miR-122-5p binding site

<400> SEQUENCE: 26
caaacaccau ugucacacuc ca                                           22

<210> SEQ ID NO 27
<211> LENGTH: 47
<212> TYPE: RNA
<213> ORGANISM: Artificial Sequence
<220> FEATURE:
<223> OTHER INFORMATION: Upstream 5UTR-001

<400> SEQUENCE: 27
gggaaauaag agagaaaaga agaguaagaa gaaauauaag agccacc                47

<210> SEQ ID NO 28
<211> LENGTH: 47
<212> TYPE: RNA
<213> ORGANISM: Artificial Sequence
<220> FEATURE:
<223> OTHER INFORMATION: Upstream 5UTR-002

<400> SEQUENCE: 28
gggagaucag agagaaaaga agaguaagaa gaaauauaag agccacc                47

```
<210> SEQ ID NO 29
<211> LENGTH: 145
<212> TYPE: RNA
<213> ORGANISM: Artificial Sequence
<220> FEATURE:
<223> OTHER INFORMATION: Upstream 5UTR-003

<400> SEQUENCE: 29
ggaauaaaag ucucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gcaac                                         145

<210> SEQ ID NO 30
<211> LENGTH: 42
<212> TYPE: RNA
<213> ORGANISM: Artificial Sequence
<220> FEATURE:
<223> OTHER INFORMATION: Upstream 5UTR-004

<400> SEQUENCE: 30
gggagacaag cuuggcauuc cgguacuguu gguaaagcca cc                       42

<210> SEQ ID NO 31
<211> LENGTH: 47
<212> TYPE: RNA
<213> ORGANISM: Artificial Sequence
<220> FEATURE:
<223> OTHER INFORMATION: Upstream 5UTR-005

<400> SEQUENCE: 31
gggagaucag agagaaaaga agaguaagaa gaaauauaag agccacc                  47

<210> SEQ ID NO 32
<211> LENGTH: 145
<212> TYPE: RNA
<213> ORGANISM: Artificial Sequence
<220> FEATURE:
<223> OTHER INFORMATION: Upstream 5UTR-006

<400> SEQUENCE: 32
ggaauaaaag ucucaacaca acauauacaa aacaaacgaa ucucaagcaa ucaagcauuc     60
uacuucuauu gcagcaauuu aaaucauuuc uuuuaaagca aaagcaauuu ucugaaaauu    120
uucaccauuu acgaacgaua gcaac                                         145

<210> SEQ ID NO 33
<211> LENGTH: 42
<212> TYPE: RNA
<213> ORGANISM: Artificial Sequence
<220> FEATURE:
<223> OTHER INFORMATION: Upstream 5UTR-007

<400> SEQUENCE: 33
gggagacaag cuuggcauuc cgguacuguu gguaaagcca cc                       42

<210> SEQ ID NO 34
<211> LENGTH: 47
<212> TYPE: RNA
<213> ORGANISM: Artificial Sequence
<220> FEATURE:
<223> OTHER INFORMATION: Upstream 5UTR-008

<400> SEQUENCE: 34
```

```
gggaauuaac agagaaaaga agaguaagaa gaaauauaag agccacc        47

<210> SEQ ID NO 35
<211> LENGTH: 47
<212> TYPE: RNA
<213> ORGANISM: Artificial Sequence
<220> FEATURE:
<223> OTHER INFORMATION: Upstream 5UTR-009

<400> SEQUENCE: 35
gggaaauuag acagaaaaga agaguaagaa gaaauauaag agccacc        47

<210> SEQ ID NO 36
<211> LENGTH: 47
<212> TYPE: RNA
<213> ORGANISM: Artificial Sequence
<220> FEATURE:
<223> OTHER INFORMATION: Upstream 5UTR-010

<400> SEQUENCE: 36
gggaaauaag agaguaaaga acaguaagaa gaaauauaag agccacc        47

<210> SEQ ID NO 37
<211> LENGTH: 47
<212> TYPE: RNA
<213> ORGANISM: Artificial Sequence
<220> FEATURE:
<223> OTHER INFORMATION: Upstream 5UTR-011

<400> SEQUENCE: 37
gggaaaaaag agagaaaaga agacuaagaa gaaauauaag agccacc        47

<210> SEQ ID NO 38
<211> LENGTH: 47
<212> TYPE: RNA
<213> ORGANISM: Artificial Sequence
<220> FEATURE:
<223> OTHER INFORMATION: Upstream 5UTR-012

<400> SEQUENCE: 38
gggaaauaag agagaaaaga agaguaagaa gauauauaag agccacc        47

<210> SEQ ID NO 39
<211> LENGTH: 47
<212> TYPE: RNA
<213> ORGANISM: Artificial Sequence
<220> FEATURE:
<223> OTHER INFORMATION: Upstream 5UTR-013

<400> SEQUENCE: 39
gggaaauaag agacaaaaca agaguaagaa gaaauauaag agccacc        47

<210> SEQ ID NO 40
<211> LENGTH: 47
<212> TYPE: RNA
<213> ORGANISM: Artificial Sequence
<220> FEATURE:
<223> OTHER INFORMATION: Upstream 5UTR-014

<400> SEQUENCE: 40
gggaaauuag agaguaaaga acaguaagua gaauuaaaag agccacc        47

<210> SEQ ID NO 41
<211> LENGTH: 47
<212> TYPE: RNA
<213> ORGANISM: Artificial Sequence
```

```
<220> FEATURE:
<223> OTHER INFORMATION: Upstream 5UTR-015

<400> SEQUENCE: 41
gggaaauaag agagaauaga agaguaagaa gaaauauaag agccacc         47

<210> SEQ ID NO 42
<211> LENGTH: 47
<212> TYPE: RNA
<213> ORGANISM: Artificial Sequence
<220> FEATURE:
<223> OTHER INFORMATION: Upstream 5UTR-016

<400> SEQUENCE: 42
gggaaauaag agagaaaaga agaguaagaa gaaaauuaag agccacc         47

<210> SEQ ID NO 43
<211> LENGTH: 47
<212> TYPE: RNA
<213> ORGANISM: Artificial Sequence
<220> FEATURE:
<223> OTHER INFORMATION: Upstream 5UTR-017

<400> SEQUENCE: 43
gggaaauaag agagaaaaga agaguaagaa gaaauuuaag agccacc         47

<210> SEQ ID NO 44
<211> LENGTH: 47
<212> TYPE: RNA
<213> ORGANISM: Artificial Sequence
<220> FEATURE:
<223> OTHER INFORMATION: Upstream 5UTR-018

<400> SEQUENCE: 44
gggaaauaag agagaaaaga agaguaagaa gaaauauaag agccacc         47

<210> SEQ ID NO 45
<211> LENGTH: 371
<212> TYPE: RNA
<213> ORGANISM: Artificial Sequence
<220> FEATURE:
<223> OTHER INFORMATION: Creatine Kinase (3UTR-001)

<400> SEQUENCE: 45
gcgccugccc accugccacc gacugcugga acccagccag ugggagggcc uggcccacca    60
gaguccugcu cccucacucc ucgccccgcc cccuguccca gaucccacc uggggggcucu   120 cuccacccuu cucagaguuc caguuucaac cagaguucca accaaugggc ucauccucu    180 ggauucuggc caaugaaaua ucucccuggc agguccucu ucuuuuccca gagcuccacc    240
ccaaccagga gcucuaguua auggagagcu cccagcacac ucggagcuug ugcuuugucu    300
ccacgcaaag cgauaaauaa aagcauuggu ggccuuuggu cuuugaauaa agccugagua    360
ggaagucuag a                                                        371

<210> SEQ ID NO 46
<211> LENGTH: 568
<212> TYPE: RNA
<213> ORGANISM: Artificial Sequence
<220> FEATURE:
<223> OTHER INFORMATION: Myoglobin (3UTR-002)

<400> SEQUENCE: 46
gccccugccg cucccaccc cacccaucug ggccccgggu ucaagagaga gcggggucug     60
```

| | |
|---|---|
| aucucgugua gccauauaga guuugcuucu gagugucugc uuuguuuagu agaggugggc | 120 |
| aggaggagcu gagggggcugg ggcugggggug uugaaguugg cuuugcaugc ccagcgaugc | 180 |
| gccucccugu gggaugucau cacccuggga accgggagug gcccuuggcu cacuguguuc | 240 |
| ugcaugguuu ggaucugaau uaauugaccu uucuucuaaa ucccaaccga acuucuucca | 300 |
| accuccaaac uggcuguaac cccaaauccaa agccauuaac uacaccugac aguagcaauu | 360 |
| gucugauuaa ucacuggccc cuugaagaca gcagaaugac ccuuugcaau gaggaggaga | 420 |
| ucugggcugg gcgggccagc uggggaagca uuugacuauc uggaacuugu gugugccucc | 480 |
| ucagguaugg cagugacuca ccugguuuua auaaaacaac cugcaacauc ucauggucuu | 540 |
| ugaauaaagc cugaguagga agucuaga | 568 |

<210> SEQ ID NO 47
<211> LENGTH: 289
<212> TYPE: RNA
<213> ORGANISM: Artificial Sequence
<220> FEATURE:
<223> OTHER INFORMATION: alpha-actin (3UTR-003)

<400> SEQUENCE: 47

| | |
|---|---|
| acacacucca ccuccagcac gcgacuucuc aggacgacga aucuucucaa uggggggggcg | 60 |
| gcugagcucc agccaccccg cagucacuuu cuuuguaaca acuuccguug cugccaucgu | 120 |
| aaacugacac aguguuuaua acguguacau acauuaacuu auuaccucau uuuguuauuu | 180 |
| uucgaaacaa agcccugugg aagaaaaugg aaaacuugaa gaagcauuaa agucauucug | 240 |
| uuaagcugcg uaaauggucu uugaauaaag ccugaguagg aagucuaga | 289 |

<210> SEQ ID NO 48
<211> LENGTH: 379
<212> TYPE: RNA
<213> ORGANISM: Artificial Sequence
<220> FEATURE:
<223> OTHER INFORMATION: Albumin (3UTR-004)

<400> SEQUENCE: 48

| | |
|---|---|
| caucacauuu aaaagcaucu cagccuacca ugagaauaag agaaagaaaa ugaagaucaa | 60 |
| aagcuuauuc aucuguuuuu cuuuuucguu gguguaaagc caacacccug ucuaaaaaac | 120 |
| auaaauuucu uuaaucauuu ugccucuuuu cucugugcuu caauuaauaa aaaauggaaa | 180 |
| gaaucuaaua gagugguaca gcacuguuau uuuucaaaga uguguugcua ccugaaaaau | 240 |
| ucuguagguu cugugguagu uccagugauuc ucucuuauuc cacuucggua gaggauuucu | 300 |
| aguuucuugu gggcuaauua aauaaaucau uaauacucuu cuaauggucu uugaauaaag | 360 |
| ccugaguagg aagucuaga | 379 |

<210> SEQ ID NO 49
<211> LENGTH: 118
<212> TYPE: RNA
<213> ORGANISM: Artificial Sequence
<220> FEATURE:
<223> OTHER INFORMATION: alpha-globin (3UTR-005)

<400> SEQUENCE: 49

| | |
|---|---|
| gcugccuucu gcggggcuug ccuucuggcc augcccuucu ucucucccuu gcaccuguac | 60 |
| cucuuggucu uugaauaaag ccugaguagg aaggcggccg cucgagcaug caucuaga | 118 |

<210> SEQ ID NO 50
<211> LENGTH: 908

```
<212> TYPE: RNA
<213> ORGANISM: Artificial Sequence
<220> FEATURE:
<223> OTHER INFORMATION: G-CSF (3UTR-006)

<400> SEQUENCE: 50
gccaagcccu ccccauccca uguauuuauc ucuauuuaau auuuaugucu auuuaagccu      60
cauauuuaaa gacagggaag agcagaacgg agccccaggc cucuguqucc uucccugcau     120
uucugaguuu cauucuccug ccuguagcag ugagaaaaag cuccuguccu cccauccccu     180
ggacugggag guagauaggu aaauaccaag uauuuauuac uaugacugcu ccccagcccu     240
ggcucugcaa ugggcacugg gaugagccgc ugugagcccc uguccugag  guccccacc      300
ugggacccuu gagaguauca ggucucccac gugggagaca agaaaucccu guuuaauauu     360
uaaacagcag uguuccccau cugggucccuu gcaccccuca cucuggccuc agccgacugc    420
acagcggccc cugcaucccc uuggcuguga ggccccugga caagcagagg uggccagagc    480
ugggaggcau ggcccugggg ucccacgaau ugcugggga aucucguuuu cuucuuaag      540
acuuuggga caugguuuga cucccgaaca ucaccgacgc gucuccuguu uuucuggguuq     600
gccucgggac accugcccug cccccacgag ggucaggacu ugacucuuu uuagggccag    660
gcaggugccu ggacauuugc cuugcuggac ggggacuggg gaugugggag ggagcagaca    720
ggaggaauca ugucaggccu gugugugaaa ggaagcucca cugucacccu ccaccucuuc    780
accccccacu caccagugua ccccuccacug ucacauugua acugaacuuc aggauaauaa    840
aguguuugcc uccauggucu uugaauaaag ccugaguagg aaggcggccg cucgagcaug    900
caucuaga                                                              908

<210> SEQ ID NO 51
<211> LENGTH: 835
<212> TYPE: RNA
<213> ORGANISM: Artificial Sequence
<220> FEATURE:
<223> OTHER INFORMATION: Col1a2; collagen, type I, alpha 2 (3UTR-007)

<400> SEQUENCE: 51
acucaaucua aauuaaaaaa gaaagaaauu ugaaaaaacu uucucuuugc cauuucuucu      60
ucuucuuuuu uaacugaaag cugaauccuu ccauuucuuc ugcacaucua cuugcuuaaa    120
uugugggcaa aagagaaaaa gaaggauuga ucagagcauu gugcaauaca guucauuaa     180
cuccuucccc cgcuccccca aaaauuugaa uuuuuuuuuc aacacucuua caccuguuau    240
ggaaaauguc aaccuuugua agaaaaccaa aauaaaaauu gaaaaauaaa aaccauaaac    300
auuugcacca cuugugqcuu uugaauaucu ccacagagg gaaguuuaaa acccaaacuu     360
ccaaagguuu aaacuaccuc aaaacacuuu cccaugagug ugauccacau uguuaggugc    420
ugaccuagac agagaugaac ugaggguccuu guuuuguuuu guucauaaua caaaggugcu    480
aauuaauagu auuucagaua cuugaagaau guugauggu cuagaagaau uugagaagaa     540
auacuccugu auugaguugu aucgugugu guauuuuuua aaaauuuga uuuagcauuc     600
auauuuccca ucuuauuccc aauuaaaagu augcagauua uuugcccaaa ucuucuucag    660
auucagcauu uguucuuugc cagcucauu uucaucuucu ccauggguuc cacagaagcu    720
uuguuucuug ggcaagcaga aaauuaaauu uguaccuauu uuguauaugu gagauguuua    780
aauaaauugu gaaaaaaaug aaauaaagca uguuugguuu uccaaaagaa cauau         835

<210> SEQ ID NO 52
```

-continued

```
<211> LENGTH: 297
<212> TYPE: RNA
<213> ORGANISM: Artificial Sequence
<220> FEATURE:
<223> OTHER INFORMATION: Col6a2; collagen, type VI, alpha 2 (3UTR-008)

<400> SEQUENCE: 52
cgccgccgcc cgggccccgc agucgagggu cgugagccca ccccguccau ggugcuaagc     60
gggcccgggu cccacacggc cagcaccgcu gcucacucgg acgacgcccu gggccugcac    120
cucuccagcu ccucccacgg ggucccgua gccccggccc ccgcccagcc ccaggucucc     180
ccaggcccuc cgcaggcugc ccggccuccc uccccugca gccauccccaa ggcuccugac    240 cuaccuggcc ccugagcucu ggagcaagcc cugacccaau aaaggcuuug aacccau      297

<210> SEQ ID NO 53
<211> LENGTH: 602
<212> TYPE: RNA
<213> ORGANISM: Artificial Sequence
<220> FEATURE:
<223> OTHER INFORMATION: RPN1; ribophorin I (3UTR-009)

<400> SEQUENCE: 53
ggggcuagag cccucuccgc acagcgugga gacggggcaa ggaggggggu uauuaggauu     60
ggugguuuug uuuugcuuug uuuaaagccg ugggaaaaug gcacaacuuu accucugugg    120
gagaugcaac acugagagcc aaggggguggg aguuggauu auuuuauau aaaagaaguu     180 uuccacuuu gaauugcuaa aaguggcauu uuuccuaugu gcagucacuc cucucauuuc    240
uaaaauaggg acguggccag gcacgguggc ucaugccugu aaucccagca cuuugggagg    300
ccgaggcagg cggcucacga ggucaggaga ucgagacuau ccuggcuaac acgguaaaac    360
ccugucucua cuaaaaguac aaaaaauuag cugggcgugg uggugggcac cuguaguccc    420
agcuacucgg gaggcugagg caggagaaag gcaugaaucc aagaggcaga gcuugcagug    480
agcugagauc acgccauugc acuccagccu gggcaacagu guuaagacuc ugucucaaau    540
auaaauaaau aaauaaauaa auaaauaaau aaauaaaaau aaagcgagau guugcccuca    600
aa                                                                  602

<210> SEQ ID NO 54
<211> LENGTH: 785
<212> TYPE: RNA
<213> ORGANISM: Artificial Sequence
<220> FEATURE:
<223> OTHER INFORMATION: LRP1; low density lipoprotein receptor-related
      protein 1 (3UTR-010)

<400> SEQUENCE: 54
ggcccugccc cgucggacug ccccagaaa gccuccugcc cccugccagu gaaguccuuc      60
agugagcccc ucccagcca gcccuucccu ggccccgccg gauguauaaa uguaaaaaug    120
aaggaauuac auuuuauaug ugagcagca agccggcaag cgagcacagu auuauuucuc    180 caucccccucc cugccugcuc cuuggcaccc ccaugcugcc uucagggaga caggcaggga    240
gggcuugggg cugcaccucc uaccuccca ccagaacgca ccccacuggg agacuggug     300 gugcagccuu cccucccug uauaagacac uuugccaagg cucuccccuc ucgccccauc    360
ccugcuugcc cgcucccaca gcuuccugag ggcuaauucu gggaagggag aguucuuugc    420
ugccccuguc uggaagacgu ggcucugggu gagguaggcg ggaaggaug gaguguuuua    480 guucuugggg gaggccaccc caaaccccag ccccaacucc aggggcaccu augagauggc    540
```

| | |
|---|---|
| caugcucaac ccccucccca gacaggcccu cccugucucc agggccccca ccgagguucc | 600 |
| cagggcugga gacuuccucu gguaaacauu ccuccagccu ccccuccccu ggggacgcca | 660 |
| aggaggcuggg ccacacccag gaagggaaag cgggcagccc cguuuugggg acgugaacgu | 720 |
| uuuaauaauu uuugcugaau uccuuuacaa cuaaauaaca cagauauugu uauaaauaaa | 780 |
| auugu | 785 |

<210> SEQ ID NO 55
<211> LENGTH: 3001
<212> TYPE: RNA
<213> ORGANISM: Artificial Sequence
<220> FEATURE:
<223> OTHER INFORMATION: Nnt1; cardiotrophin-like cytokine factor 1
      (3UTR-011)

<400> SEQUENCE: 55

| | |
|---|---|
| auauuaagga ucaagcuguu agcuaauaau gccaccucug caguuugggg aacaggcaaa | 60 |
| uaaaguauca guauacaugg ugauguacau cuguagcaaa gcucuggag aaaaugaaga | 120 |
| cugaagaaag caaagcaaaa acuguauaga gagauuuuuc aaaagcagua auccccucaau | 180 |
| uuuaaaaaag gauugaaaau ucaaaugguc uuucugugca uauuuuugu guuaggaauc | 240 |
| aaaaguauuu uauaaaagga gaaagaacag ccucauuuua gaugauagucc uguuggauuu | 300 |
| uuuaugccuc cucaguaacc agaaaugoo uaaaaaacua aguguuuagg auuucaagac | 360 |
| aacauuauac augocucuga aauaucugac acaauguaaa cauugcaggc accugcauuu | 420 |
| uauguuuuuu uuucaacaa augugacuaa uuugaaacuu uuaugaaacuu cugagcuguc | 480 |
| cccuugcaau ucaaccgcag uuugaauuaa ucauaucaaa ucaguuuuuaa uuuuuuaaau | 540 |
| uguacuucag agucuauauu ucaagggcac auuuucucac uacuauuuua auacauuaaa | 600 |
| ggacuaaaua aucuuucaga gaugcuggaa acaaaucauu ugcuuuauau guuucauuag | 660 |
| aauaccaaug aaacauacaa cuugaaaauu aguaauagua uuuuugaaga ucccauuucu | 720 |
| aauuggagau cucuuuaauu ucgaucaacu uauaaugugu aguacauauu uaagugcacu | 780 |
| ugaguggaau ucaacauuug acuaauaaaa ugaguucauc auguuggcaa gugaugugggc | 840 |
| aauuaucucu ggugacaaaa gaguaaaauc aaauauuucu gccuguuaca auaucaagg | 900 |
| aagaccugcu acuaugaaau agaugacauu aaucugucuu cacguuuuau aauacggaug | 960 |
| gauuuuuuuu caaucaguug ugguguuuga ggucuuaugu aauugaugac auuugagaga | 1020 |
| aauggugggcu uuuuuagcu accucuuugu ucauuuaaagc accaguaaag aucaugucuu | 1080 |
| uuuauagaag guuagauuuu cuuugugacu uugcuaucgu gccuaaagcu cuaaauauag | 1140 |
| gugaaugugu gaugaauacu cagauuauuu gucucucuau auaauuaguu ugguacuaag | 1200 |
| uuucucaaaa aauuauuaac acaugaaaga caaucucuaa accagaaaaa gaaguaguac | 1260 |
| aaauuuugu acuguaaugc ucgcguuuag ugaguuaaaa acacacaguaa ucuuuugguu | 1320 |
| uuauaaucag uuucuauuuu gcugugccug agauuaagau cuguguaugu gugugugugu | 1380 |
| gugugugcgu uugugugua aagcagaaaa gacuuuuuua aaaguuuuaa gugauaaaaug | 1440 |
| caauuuguua auugaucuua gaucacuagu aaacucaggg cugaauuaua ccauguauau | 1500 |
| ucuauuagaa gaaaguaaac accaucuuua uuccugcccu uuuucuucuc ucaaaguagu | 1560 |
| uguaguuaua ucuagaaaga agcaauuuug auuucuugaa aagguaguuc cugcacucag | 1620 |
| uuuaaacuaa aaauaaucau acuuggauuu uauuuauuuu ugucauagua aaauuuuaa | 1680 |
| uuuauauaua uuuuuauuua guauuaucuu auucuuugcu auuugccaau ccuuugucau | 1740 |

| | |
|---|---|
| caauugmguu aaaugaauug aaaauucaug cccuguucau uuuauuuuac uuuauuggmu | 1800 |
| aggauauuua aaggauuuuu guauauauaa uuucuuaaau uaauauucca aaagguuagu | 1860 |
| ggacuuagau uauaaauuau ggcaaaaauc uaaaaacaac aaaaaugauu uuuauacauu | 1920 |
| cuauuucauu auuccucuuu uuccaauaag ucauacaauu gguagauaug acuuauuuua | 1980 |
| uuuuguauu auucacuaua ucuuuaugau auuuaaguau aaauaauuaa aaaauuuau | 2040 |
| uguaccuuau agucugucac caaaaaaaaa aaauuaucug uagguaguga aaugcuaaug | 2100 |
| uugauuuguc uuuaagggcu uguuaacuau ccuuuauuuu ucauuuguc uuaaauuagg | 2160 |
| aguuuguguu uaaauuacuc aucuaagcaa aaaauguaua uaaaucccau uacuggguau | 2220 |
| auacccaaag gauuauaaau caugcugcua uaaagacaca ugcacacgua uguuuauugc | 2280 |
| agcacuauuc acaauagcaa agacuuggaa ccaacccaaa uguccaucaa ugauagacuu | 2340 |
| gauuaagaaa augugcacau auacaccaug gaauacuaug cagccauaaa aaaggaugag | 2400 |
| uucauguccu uuguagggac auggauaaag cuggaaacca ucauucgag caaacuauug | 2460 |
| caaggacaga aaccaaaca cugcauguuc ucaucuaua gugggaauug aacaaugaga | 2520 |
| acacuuggac acaagguggg gaacaccaca caccagggcc ugucauggggg uggggggagu | 2580 |
| ggggagggau agcauuagga gauauaccua auguaaauga ugaguaaug ggucagcac | 2640 |
| accaacaugg cacaguaua cauaugaugc aaaaccugcac guuggugcaca uguacccuag | 2700 |
| aacuuaaagu uauaauuaaaa aaaaaaaagaa aacagaagcu auuauaaag aaguauuug | 2760 |
| cugaaauaaa ugugaucuuu cccauuaaaa aaauaaagaa auuuugggu aaaaaacac | 2820 |
| aauauauugu auucuugaaa aauucuaaga gagguggaugu gaaguguucu caccacaaaa | 2880 |
| gugauaacua auugagguaa ugcacauauu aauuagaaag auuuugucau uccacaaugu | 2940 |
| auauaaucuu aaaauaugu uauacacaau aaauacauac auuaaaaaaau aaguaaaugu | 3000 |
| a | 3001 |

<210> SEQ ID NO 56
<211> LENGTH: 1037
<212> TYPE: RNA
<213> ORGANISM: Artificial Sequence
<220> FEATURE:
<223> OTHER INFORMATION: Col6a1; collagen, type VI, alpha 1 (3UTR-012)

<400> SEQUENCE: 56

| | |
|---|---|
| cccacccugc acgccggcac caaacccugu ccucccaccc cucccacucc aucacuaaac | 60 |
| agaguaaaau gugaugcgaa uuuucccgac caaccugauu cgcuagauuu uuuuuaagga | 120 |
| aaagcuugga aagccaggac acaacgcugc ugccugcuuu gugcagggug cuccggggcu | 180 |
| cagcccugag uuggcaucac cugcgcaggg cccucgggg ucagcccug agcuagmguc | 240 |
| accugcacag ggccucuga ggcucagccc ugagcuggcg ucaccugugc agggcccucu | 300 |
| ggggcucagc ccugagcugg ccucaccugg guucccacc ccgggcucuc cugcccugcc | 360 |
| cuccugcccg ccucucccucc ugccugcgca gcuccuuccc uaggcaccuc ugugcugcau | 420 |
| cccaccagcc ugagcaagac gcccucucgg ggccugugcc gcacuagccu cccucuccuc | 480 |
| ugucccauca gcuggmuuuu cccaccaauc cucaccuaac aguuacuuua caauuaaacu | 540 |
| caaagcaagc ucuucccuc agcuuggggc agccauuggc cucugucucg uuuugggaaa | 600 |
| ccaaggucag gaggccguug cagacauaaa ucucggcgac ucggcccgu uccugagggg | 660 |
| uccugcugggu gaccggccug gaccuuggcc cuacagcccu ggaggccgcu gcugaccagc | 720 |
| acugacccccg accucagaga guacucgcag gggcgcuggc ugcacucaag acccucgaga | 780 |

```
uuaacggugc uaaccccguc ugcuccuccc ucccgcagag acuggggccu ggacuggaca    840
ugagagcccc uuggugccac agagggcugu gucuuacuag aaacaacgca aaccucuccu    900
uccucagaau agugaugugu ucgacguuuu aucaaaggcc cccuuucuau guucauguua    960 guuugcucc uucuguguuu uuuucugaac cauauccaug uugcugacuu uccaaauaa      1020 agguuuucac uccucuc                                                   1037

<210> SEQ ID NO 57
<211> LENGTH: 577
<212> TYPE: RNA
<213> ORGANISM: Artificial Sequence
<220> FEATURE:
<223> OTHER INFORMATION: Calr; calreticulin (3UTR-013)

<400> SEQUENCE: 57
agaggccugc cuccagggcu ggacugaggc cugagcgcuc cugccgcaga gcuggccgcg     60
ccaaauaaug ucucgugag acugagaac uuucauuuuu uuccaggcug guucggauuu      120
ggggguggau uugguuugu uccccuccuc cacucucccc caccccccucc ccgcccuuuu   180 uuuuuuuuu uuuuaaacug guauuuuauc uuugauucuc cuucagcccu caccccuggu    240
ucucaucuuu cuugaucaac aucuuuucuu gccucugucc ccuucucuca ucucuuagcu   300
ccccuccaac cuggggggca gugugugga gaagccacag gccugagauu caucgcuc      360 uccuuccugg agcccagagg agggcagcag aaggggugg ugucuccaac ccccagcac    420 ugaggaagaa cggggcucuu ucauuuuac ccccuccuuu ucccccugcc ccaggacug     480 ggccacuucu gggugggggca gugggucca gauuggcuca cacugagaau guaagaacua   540
caaacaaaau uucuauaaa uuaaauuuug ugucucc                             577

<210> SEQ ID NO 58
<211> LENGTH: 2212
<212> TYPE: RNA
<213> ORGANISM: Artificial Sequence
<220> FEATURE:
<223> OTHER INFORMATION: Col1a1; collagen, type I, alpha 1 (3UTR-014)

<400> SEQUENCE: 58
cucccuccau cccaaccugg cucccuccca cccaaccaac uuucccccca acccggaaac    60
agacaagcaa cccaaacuga accccccucaa aagccaaaaaa augggagaca auuucacaug  120
gacuuuggaa aauauuuuuu uccuuugcau ucaucucuca aacuuaguuu uuaucuuuga   180
ccaaccgaac augaccaaaa accaaaagug cauucaaccu uaccaaaaaa aaaaaaaaaa   240
aaagaauaaa uaauaacuu uuuaaaaaag gaagcuuggu ccacuugcuu gaagacccau    300
gcggggguaa gucccuuucu gcccguuggg cuuaugaaac cccaaugcug cccuuucugc   360
uccuuucucc acaccccccu uggggccucc cuccacuccc uucccaaauc ugucucccca   420
gaagacacag gaaacaaugu auugucgcc cagcaaucaa aggcaaugcu caaacaccca    480 aguggcccc acccucagcc cgcuccugcc cgcccagcac cccaggcccc uggggaccu    540 ggguucuca gacugccaaa gaagccuugc caucuggcgc ucccauggcu cuugcaacau   600
cuccccuucg uuuugaggg ggucaugccg gggagccac cagccccuca cugggucgg    660 aggagaguca ggaagggcca cgacaaagca gaaacaucgg auuuggggaa cgcgugucaa   720
ucccuugugc cgcagggcug ggcgggagag acguucugu uccuugugua acuguuugc    780 ugaaagacua cccucguucu ugucuugaugu gucaccgggg caacugccug ggggcgggga  840
```

```
ugggggcagg gguggaagcgg cuccccauuu uauaccaaag gugcuacauc uaugugaugg    900
gugggguggg gagggaauca cuggugcuau agaaauugag augccccccc aggccagcaa    960
auguuccuuu uuguucaaag ucuauuuuua uuccuugaua uuuuucuuuu uuuuuuuuu    1020 uuuuugugga uggggacuug ugaauuuuuc uaaaggugcu auuuaacaug ggaggagagc   1080
gugugcggcu ccagcccagc ccgcugcuca cuuuccaccc ucucuccacc ugccucuggc   1140
uucucaggcc ucugcucucc gaccucucuc cucugaaacc cuccuccaca gcugcagccc   1200
auccucccgg cucccuccua gucugaccug cguccucugu cccgggguuu cagagacaac   1260 ucccaaagc acaaagcagu uuuuccccu aggggguggga ggaagcaaaa gacucuguac    1320
cuauuuugua uguguauaau aauuugagau guuuuuaauu auuugauug cuggaauaaa    1380 gcaugugaaa augacccaaa cauaauccgc aguggccucc uaauuuccuu cuuuggaguu   1440 ggggagggg uagacauggg gaaggggcuu uggggugaug ggcuugccuu ccauccugc    1500 ccuuccccuc cccacuauuc ucuuucugauu cccuccauaa ccccacuccc cuuucucuca   1560
cccuucuuau accgcaaacc uuucuacuuc cucuuucauu uucuauucuu gcaauuuccu   1620
ugcaccuuuu ccaaauccuc uuccccccug caauaccaua caggcaauccc acgugcacaa   1680 cacacacaca cacucuuucac aucugggguu guccaaaccu cauacccacu ccccuucaag   1740
cccauccacu cuccacccccc uggaugcccu gcacuuggug gcgguggau gcucauggau   1800 acugggaggg ugagggaguu ggaacccgug aggaggaccu gggggccucu ccuugaacug   1860
acaugaaggg ucaucuggcc ucugcccccu cucacccac gcugaccucc ugccgaagga   1920
gcaacgcaac aggagagggg ucugcugagc cuggcgaggg ucuggagggg accaggagga   1980
aggcgugcuc ccugcucgcu guccuggccc ugggggagug agggagacag acaccuggga   2040
gagcuguggg gaaggcacuc gcaccgugcu cuuugggaagg aaggagaccu ggcccugcuc   2100
accacggacu gggugccucg accuccugaa uccccagaac acaacccccc ugggcugggg   2160
uggucugggg aaccaucgug ccccccgcccu ccgccuacuc cuuuuaagc uu           2212
```

<210> SEQ ID NO 59
<211> LENGTH: 729
<212> TYPE: RNA
<213> ORGANISM: Artificial Sequence
<220> FEATURE:
<223> OTHER INFORMATION: Plod1; procollagen-lysine, 2-oxoglutarate
      5-dioxygenase 1 (3UTR-015)

<400> SEQUENCE: 59

```
uuggccaggc cugacccucu uggaccuuuc uucuuugccg acaaccacug cccagcagcc     60
ucugggaccu cggggucccca gggaacccag uccagccucc uggcuguuga cuucccauug   120
cucuuggagc caccaaucaa agagauucaa agagauuccu gcaggccaga ggcggaacac   180
accuuuaugg cuggggcucu ccguggguguu cuggacccag ccccuggaga caccauucac   240
uuuuacugcu uuguagugac ucugcucucu caaccugucu uccugaaaaa ccaaggcccc   300
cuucccccac cucuuccaug ggugagacu ugagcagaac aggggcuucc ccaaguugcc    360
cagaaagacu gucugggguga gaagccaugg ccagagcuuc ucccaggcac aggguugca   420 ccagggacuu cugcuucaag uuuuggggua aagacaccug gaucagacuc caagggcugc   480
ccugagucug gacuucugc cuccauggcu ggucaugaga gcaaaccgua guccccugga   540
gacagcgacu ccagagaacc ucuugggaga cagaagaggc aucugugcac agcucgaucu   600
ucuacuugcc uguggggagg ggagugacag guccacacac cacacugggu cacccugucc   660
```

```
uggaugccuc ugaagagagg gacagaccgu cagaaacugg agaguuucua uuaaagguca    720
uuuaaacca                                                           729

<210> SEQ ID NO 60
<211> LENGTH: 847
<212> TYPE: RNA
<213> ORGANISM: Artificial Sequence
<220> FEATURE:
<223> OTHER INFORMATION: Nucb1; nucleobindin 1 (3UTR-016)

<400> SEQUENCE: 60
uccuccggga ccccagcccu caggauuccu gaugcuccaa ggcgacugau gggcgcugga    60
ugaaguggca cagucagcuu cccuggggc uggugucaug uugggcuccu ggggcggggg    120
cacggccugg cauuucacgc auugcugcca ccccaggucc accugucucc acuuucacag   180
ccuccaaguc uguggcucuu cccucugug cuccgagggg cuugccuucu cucgugucca    240
gugaggugcu cagugaucgg cuuaacuuag agaagcccgc ccccucccu ucuccgucug    300 ucccaagagg gucugcucug agccugcguu ccuagguggc ucggcucag cugccugggu    360 uguggccgcc cuagcauccu guaugcccac agcuacugga aucccgcug cugcuccggg    420 ccaagcuucu gguugauuaa ugagggcaug ggguggucccc ucaagaccuu ccccuaccuu   480
uuguggaacc agugaugccu caaagacagu uccccucca cagcugggug ccaggggcag    540
gggauccuca guauagccgg ugaacccuga uaccaggagc cugggccucc cugaaccccu   600
ggcuuccagc caucucaucg ccagccuccu ccuggaccuc uuggccccca gccccuuccc   660
cacacagccc cagaaggguc ccagagcuga ccccacucca ggaccuaggc ccagccccuc   720
agccucaucu ggagccccug aagaccaguc ccacccaccu uucuggcccu aucugacacu   780
gcuccgcauc cugcugugug uccuguucca uguccgguu ccauccaaau acacuuucug    840
gaacaaa                                                             847

<210> SEQ ID NO 61
<211> LENGTH: 110
<212> TYPE: RNA
<213> ORGANISM: Artificial Sequence
<220> FEATURE:
<223> OTHER INFORMATION: alpha-globin (3UTR-017)

<400> SEQUENCE: 61
gcuggagccu cgguggccau gcuucuugcc ccuugggccu cccccagcc ccuccucccc    60 uuccugcacc cguaccccg uggucuuuga auaaagucug agugggcggc                110

<210> SEQ ID NO 62
<211> LENGTH: 116
<212> TYPE: RNA
<213> ORGANISM: Artificial Sequence
<220> FEATURE:
<223> OTHER INFORMATION: Downstream UTR (3UTR-018)

<400> SEQUENCE: 62
uaauaggcug gagccucggu ggccaugcuu cuugcccuu gggccucccc ccagccccuc    60
cuccccuucc ugcacccgua ccccgugu cuugaauaa agucugagug ggcggc          116

<210> SEQ ID NO 63
<211> LENGTH: 138
<212> TYPE: RNA
<213> ORGANISM: Artificial Sequence
<220> FEATURE:
<223> OTHER INFORMATION: Downstream UTR (3UTR-018 + miR-122-5p binding
``` site)

<400> SEQUENCE: 63
uaauaggcug agccucggu ggccaugcuu cuugccccuu gggccucccc ccagccccuc    60
cuccccuucc ugcacccgua cccccaaac accauguca cacccagug gucuuugaau     120 aaagucugag ugggcggc                                                138

<210> SEQ ID NO 64
<211> LENGTH: 138
<212> TYPE: RNA
<213> ORGANISM: Artificial Sequence
<220> FEATURE:
<223> OTHER INFORMATION: Downstream UTR (3UTR-018 + miR-122-3p binding
      site)

<400> SEQUENCE: 64
uaauaggcug agccucggu ggccaugcuu cuugccccuu gggccucccc ccagccccuc    60
cuccccuucc ugcacccgua ccccuauuu agugugauaa uggcguugug gucuuugaau   120
aaagucugag ugggcggc                                                138

<210> SEQ ID NO 65
<211> LENGTH: 737
<212> TYPE: RNA
<213> ORGANISM: Artificial Sequence
<220> FEATURE:
<223> OTHER INFORMATION: Human OX40L with 5'-UTR, 3'-UTR and miR-122
      binding site

<400> SEQUENCE: 65
gggaaauaag agagaaaaga agaguaagaa gaaauauaag agccaccaug gaaagggucc    60
aaccccugga agagaaugug ggaaaugcag ccaggccaag auucgagagg aacaagcuau   120 ugcuggugc cucuguaauu cagggacugg ggcugcuccu gugcuucacc uacaucugcc    180
ugcacuucuc ugcucuucag guaucacauc gguauccucg aauucaaagu aucaaaguac   240
aauuuaccga auauaagaag gagaaagguu ucauccucac uucccaaaag gaggaugaaa   300
ucaugaaggu gcagaacaac ucagucauca ucaacugugu uggguuuau cucaucuccc    360 ugaagggcua cuucucccag gaagucaaca uuagccuuca uuaccagaag gaugaggagc   420
cccucuucca acugaagaag gucaggucug ucaacuccuu gauggugcc ucucugacuu    480 acaaagacaa agucuacuug aaugugacca cugacaauac cucccuggau gacuuccaug   540
ugaauggcgg agaacugauu cuuauccauc aaaauccugg ugaauucugu guccuuugau   600
aauaggcugg agccucggug gccaugcuuc uugccccuug ggccucccc cagccccucc    660 uccccuuccu gcacccguac ccccaaaca ccauguca cucccagugg ucuuugaaua      720
aagucugagu gggcggc                                                  737

<210> SEQ ID NO 66
<211> LENGTH: 782
<212> TYPE: RNA
<213> ORGANISM: Artificial Sequence
<220> FEATURE:
<223> OTHER INFORMATION: Murine OX40L with 5'-UTR, 3'-UTR and miR-122
      binding site

<400> SEQUENCE: 66
gggaaauaag agagaaaaga agaguaagaa gaaauauaag agccaccaug gaagggaag     60 ggguucaacc ccuggaugag aaucuggaaa acggaucaag gccaagauuc aaguggaaga   120

| | |
|---|---|
| agacgcuaag gcuggugguc ucugggauca agggagcagg gaugcuucug ugcuucaucu | 180 |
| augucugccu gcaacucucu uccucuccgg caaaggaccc uccaauccaa agacucagag | 240 |
| gagcaguuac cagaugugag gaugggcaac uauucaucag cucauacaag aaugaguauc | 300 |
| aaacuaugga ggugcagaac aauucgguug ucaucaagug cgaugggcuu uauaucaucu | 360 |
| accugaaggg cuccuuuuuc caggagguca agauugaccu ucauuccgg gaggaucaua | 420 |
| aucccaucuc uauuccaaug cugaacgaug gucgaaggau ugucuucacu guggugccu | 480 |
| cuuuggcuuu caaagauaaa guuuaccuga cuguaaaugc uccugauacu cucugcgaac | 540 |
| accuccagau aaaugauggg gagcugauug uguccagcu aacgccugga uacugugcuc | 600 |
| cugaaggauc uuaccacagc acugugaacc aaguaccacu gugauaauag gcuggagccu | 660 |
| cgguggccau gcuucuugcc ccuugggccu cccccagcc ccuccuccc uuccugcacc | 720 |
| cguaccccc aaacaccauu gucacacucc aguggucuuu gaauaaaguc ugaguggcg | 780 |
| gc | 782 |

<210> SEQ ID NO 67
<211> LENGTH: 1363
<212> TYPE: RNA
<213> ORGANISM: Artificial Sequence
<220> FEATURE:
<223> OTHER INFORMATION: Non-translatable FIX with 5'-UTR, 3'UTR and
      miR-122 binding site

<400> SEQUENCE: 67

| | |
|---|---|
| gggaaauaag agagaaaaga agaguaagaa gaaauauaag acagcgcguc aacauugccg | 60 |
| aaucgccggg acucaucaca aucugccucu uggguuaucu cuugucggca gauaccuucu | 120 |
| uggaucacga aaacgcgaac aaaauucuua aucgcccgaa gcgguauaac uccgggaaac | 180 |
| uugaggaguu ucagggcaau cuugaacgag acgaggagaa cuccuuugag gaggcgaggg | 240 |
| aauuugaaaa cacagagcga acaacggagu uuuggaagca auacuagggg accagucga | 300 |
| aucccucag gggaucuaaa gacaucaaua gcuacugccc guuggguuu gaagggaaga | 360 |
| acuagcugac caacaucaaa aacgacgcu agcaguuuug uaagaacucg gcugacaaua | 420 |
| agguagucuc cacagaggga uaccggcugg cggagaacca aaaauccgag cccgcaguec | 480 |
| cguucccuug gaggagcuca cagacuagca aguugacgag agcggagacu guauucccg | 540 |
| acgacuacgu caacagcacc gaagccgaaa caauccucga uaacaucacg cagagcacuc | 600 |
| aguccuucaa cuuuacgagg gucuagagg acgcgaaacc cggucaguuc cccuggcagg | 660 |
| uauugaacgg aaaagucgcc uuuugagguu ccauugucaa cgagaagauu ucacagcgg | 720 |
| cacacugcgu agaaacagga aaaaucacgg uagcgggaga gcauaacauu gaagagacag | 780 |
| agcacacgga acaaaagcga aucaucgaaa ucauuccaca ccauaacuau aacgcggcaa | 840 |
| ucaauaagua caaucacgac aucgcacuuu ggagcuuga cgaaccuuug cuuaauucgu | 900 |
| acgucaccccc uauuuguauu gccgacaaag aguauacaaa caucuucuug aaauucggcu | 960 |
| ccggguacgu aucgggcugg ggcagauucc auaagguag auccgcacug uugcaauacc | 1020 |
| ucaggcccu cgaucgagcc acuugucugc gguccaccaa auucacaauc uacaacaauu | 1080 |
| ucucgggauu ccaagggaga gauagcugcc agggagacuc aggggucccc cacacggaag | 1140 |
| ucgaggggac gucauuucug acgggaauua ucucgggaga ggcgaagggg aacaucuaca | 1200 |
| cuaaaucacg guucauugg aucaaggaaa agacgaaacu cacgugauaa uaggcuggag | 1260 |
| ccucggugc caugcuucuu gcccuuggg ccucccccca gccccuccuc cccuuccugc | 1320 | acccguaccc ccguggucuu ugaauaaagu cugagugggc ggc            1363

<210> SEQ ID NO 68
<211> LENGTH: 782
<212> TYPE: RNA
<213> ORGANISM: Artificial Sequence
<220> FEATURE:
<223> OTHER INFORMATION: Non-translatable OX40L with 5'-UTR, 3'UTR and
      miR-122 binding site

<400> SEQUENCE: 68
gggaauuaag agagaaaaga agaguaagaa gaaauauaag aacccgcaag gaagggaag            60
ggguucaacc ccuggaagag aaucuggaaa acggaucaag gccaagauuc aagaggaaga         120
agacgcuaag gcuggagguc ucugggauca agggagcagg gaagcuucug agcuucaucu         180
aagucugccu gcaacucucu uccucuccgg caaaggaccc uccaauccaa agacucagag         240
gagcaguuac cagaagagag gaagggcaac uauucaucag cucauacaag aaagaguauc         300
aaacuaagga ggagcagaac aauucgguug ucaucaagag cgaagggcuu uauaucaucu         360
accugaaggg ucccuuuuuc caggaggucaa agauugaccu ucauuccgg gaggaucaua         420
aucccaucuc uauuccaaag cugaacgaag gucgaaggau ugucuucacu gaggaggccu         480
cuuuggcuuu caaagauaaa guuuaccuga cuguaaaagc uccugauacu cucugcgaac         540
accuccagau aaaagaaggg gagcugauug uuguccagcu aacgccugga uacugagcuc         600
cugaaggauc uuaccacagc acugagaacc aaguaccacu gugauaauag gcuggagccu         660
cgguggccaa gcuucuugcc ccuugggccu cccccccagcc ccuccuccccc uuccugcacc      720
cguacccccc aaacaccauu gucacacucc aguggucuuu gaauaaaguc ugagugggcg         780
gc                                                                        782

<210> SEQ ID NO 69
<211> LENGTH: 1838
<212> TYPE: RNA
<213> ORGANISM: Artificial Sequence
<220> FEATURE:
<223> OTHER INFORMATION: Firefly luciferase with 5'-UTR, 3'-UTR and
      miR-122 binding site

<400> SEQUENCE: 69
gggaauuaag agagaaaaga agaguaagaa gaaauauaag agccaccaug gaagaugcga         60
agaacaucaa gaagggaccu gccccgguuu acccuuugga ggacgguaca gcaggagaac        120
agcuccacaa ggcgaugaaa cgcuacgccc ugguccccgg aacgauugcg uuuaccgaug        180
cacauauuga gguagacauc acauacgcag aauacuucga aaugucggug aggcuggcgg        240
aagcgaugaa gagauauggu cuuaacacua ucaccgcau cguggugugu ucggagaacu         300
cauugcaguu uuucaugccg guccuuggag cacuuuucau cggggucgca gucgcgccag        360
cgaacgacau cuacaaugag cgggaacucu ugaauagcau gggaaucccc agccgacgg         420
ucguguuugu cuccaaaaag gggcugcaga aaauccucaa cgugcagaag aagcuccccca       480
uuauucaaaa gaucaucauu auggauagca agacagauua ccaagggguuc cagucgaugu      540
auaccuuugu gacaucgcau uugccgccag gguuaacga guaugacuuc gucccgagu         600
cauugacag agauaaaacc aucgcgcuga uuaugaauuc cucggguagc accgguuugc         660
caaaggggu ggcguugccc caccgcacug cuugugugcg uucucgcac gcuagggauc         720
cuacucuuug uaaucagauc auucccgaca cagcaauccu guccgguggua ccuuuucauc      780
acgguuuugg cauguucacg acucucggcu auuugauuug cgguucagg gucguacuua         840

```
uguaucgguu cgaggaagaa cuguuuuuga gauccuugca agauuacaag auccagucgg    900
cccuccuugu gccaacgcuu uucucauucu uugcgaaauc gacacuuauu gauaaguaug    960
accuuuccaa ucugcaugag auugccucag ggggagcgcc gcuuagcaag gaagucgggg   1020 aggcagugqc caagcgcuuc caccuucccg gaauucggca gggauacggg cucacggaga   1080
caacauccgc gauccuuauc acgcccgagg gugacgauaa gccgggagcc gucggaaaag   1140 uggucccuu cuuugaagcc aaggucguag accucgacac gggaaaaacc cucggaguga    1200
accagagggg cgagcucugc gugagagggc cgaugaucau gucagguuac gugaauaacc   1260
cugaagcgac gaaugcgcug aucgacaagg auggguggu gcauucggga gacauugccu    1320
auugggauga ggaugagcac uucuuuaucg uagaucgacu uaagagcuug aucaaauaca   1380
aaggcuauca gguagcgccu gccgagcucg agucaauccu gcuccagcac cccaacauuu   1440
ucgacgccgg aguggccggg uugcccgaug acgacgcggg ugagcugcca gcggccgugg   1500
uaguccucga acaugggaaa acaaugaccg aaaaggagau cguggacuac guagcaucac   1560
aagugacgac ugcgaagaaa cugaggggag ggguagucuu uguggacgag gucccgaaag   1620
gcuugacugg gaagcuugac gcucgcaaaa uccgggaaau ccugauuaag gcaaagaaag   1680
gcgggaaaau cgcugucuga uaauaggcug gagccucggu ggccaugcuu cuugcccuu    1740 gggccucccc ccagcccuc cuccccuucc ugcacccgua cccccaaac accauuguca    1800 cacuccagug gucuuugaau aaagucugag ugggcggc                          1838
```